(12) United States Patent
Shimizu et al.

(10) Patent No.: US 7,170,078 B2
(45) Date of Patent: Jan. 30, 2007

(54) BIOCHEMICAL ANALYSIS DATA PRODUCING METHOD AND SCANNER USED THEREFOR

(75) Inventors: Hitoshi Shimizu, Kanagawa (JP); Keiko Neriishi, Kanagawa (JP); Nobuhiko Ogura, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/141,555

(22) Filed: May 9, 2002

(65) Prior Publication Data
US 2006/0266958 A1 Nov. 30, 2006

(30) Foreign Application Priority Data

| May 11, 2001 | (JP) | ............................. 2001-140873 |
| Jun. 14, 2001 | (JP) | ............................. 2001-180207 |
| Jun. 22, 2001 | (JP) | ............................. 2001-189107 |
| Jun. 28, 2001 | (JP) | ............................. 2001-196115 |

(51) Int. Cl.
G03B 42/08 (2006.01)

(52) U.S. Cl. .................................. 250/583
(58) Field of Classification Search ................ 250/583, 250/484.4, 585; 422/71
See application file for complete search history.

(56) References Cited

U.S. PATENT DOCUMENTS

| 5,534,702 | A | * | 7/1996 | Trutna et al. ............. 250/484.4 |
| 5,780,857 | A | * | 7/1998 | Harju et al. ................. 250/583 |
| 5,864,362 | A | * | 1/1999 | Cutler ........................... 348/96 |
| 6,861,214 | B1 | * | 3/2005 | Rampal et al. ................. 435/6 |

FOREIGN PATENT DOCUMENTS

| JP | 58-69281 A | | 4/1983 |
| JP | 59-56479 A | | 3/1984 |
| JP | 2-276997 A | | 11/1990 |
| JP | 3-91734 A | * | 4/1991 |
| JP | 2001-123162 A | | 5/2001 |
| JP | 2001-131545 A | | 5/2001 |

* cited by examiner

Primary Examiner—Constantine Hannaher
(74) Attorney, Agent, or Firm—Sughrue Mion, PLLC

(57) ABSTRACT

A biochemical analysis data producing method includes the steps of selectively storing one of radiation energy and light energy in a plurality of stimulable phosphor layer regions two-dimensionally formed in a support of a stimulable phosphor sheet and spaced apart from each other, moving the stimulable phosphor sheet and a stimulating ray relative to each other in a main scanning direction and a sub-scanning direction, sequentially irradiating the plurality of stimulable phosphor layer regions so that energy of the stimulating ray projected onto the plurality of stimulable phosphor layer regions per unit area is higher than that projected on regions other than the plurality of stimulable phosphor layer regions, thereby exciting stimulable phosphor contained in the plurality of stimulable phosphor layer regions, and photoelectrically detecting stimulated emission released from the stimulable phosphor layer to produce biochemical analysis data. According to this method, it is possible to effectively prevent the stimulating ray from entering a neighboring stimulable phosphor layer region to be next stimulated as the stimulating ray is scanned and thus prevent stimulable phosphor contained in the neighboring stimulable phosphor layer region from being excited to release radiation energy or light energy stored therein, and, therefore, biochemical analysis data having an excellent quantitative characteristic can be produced in a desired manner.

105 Claims, 38 Drawing Sheets

BIOCHEMICAL ANALYSIS DATA PRODUCING METHOD AND SCANNER USED THEREFOR

BACKGROUND OF THE INVENTION

The present invention relates to a biochemical analysis data producing method and a scanner therefor and, particularly, to a biochemical analysis data producing method and a scanner therefor, which can produce biochemical analysis data having excellent quantitative characteristics with high resolution even in the case of forming at a high density on the surface of a carrier such as a membrane filter a plurality of spot-like regions containing specific binding substances which can specifically bind with a substance derived from a living organism and whose sequence, base length, composition and the like are known, selectively labeling the plurality of spot-like regions with a radioactive labeling substance, thereby recording radiation data therein, exposing the stimulable phosphor layer of a stimulable phosphor sheet to the radioactive labeling substance selectively contained in the plurality of spot-like regions and recording radiation data in the stimulable phosphor layer of the stimulable phosphor sheet or in the case of forming at a high density on the surface of a carrier such as a membrane filter a plurality of spot-like regions containing specific binding substances which can specifically bind with a substance derived from a living organism and whose sequence, base length, composition and the like are known, selectively labeling the plurality of spot-like regions with a labeling substance which generates chemiluminescent emission when it contacts a chemiluminescent substrate, thereby recording chemiluminescent data therein, causing the plurality of spot-like regions to come into contact with a chemiluminescent substrate and to release chemiluminescent emission, exposing the stimulable phosphor layer of a stimulable phosphor sheet to the chemiluminescent emission selectively released from the plurality of spot-like regions and recording chemiluminescent data in the stimulable phosphor layer of the stimulable phosphor sheet.

DESCRIPTION OF THE PRIOR ART

An autoradiographic analyzing system using as a detecting material for detecting radiation a stimulable phosphor which can absorb, store and record the energy of radiation when it is irradiated with radiation and which, when it is then stimulated by an electromagnetic wave having a specified wavelength, can release stimulated emission whose light amount corresponds to the amount of radiation with which it was irradiated is known, which comprises the steps of introducing a radioactively labeled substance into an organism, using the organism or a part of the tissue of the organism as a specimen, superposing the specimen and a stimulable phosphor sheet formed with a stimulable phosphor layer for a certain period of time, storing and recording radiation energy in a stimulable phosphor contained in the stimulable phosphor layer, scanning the stimulable phosphor layer with an electromagnetic wave to excite the stimulable phosphor, photoelectrically detecting the stimulated emission released from the stimulable phosphor to produce digital image signals, effecting image processing on the obtained digital image signals, and reproducing an image on displaying means such as a CRT or the like or a photographic film (see, for example, Japanese Patent Publication No. 1-60784, Japanese Patent Publication No. 1-60782, Japanese Patent Publication No. 4-3952 and the like).

There is further known chemiluminescence analysis system comprising the steps of employing, as a detecting material for light, a stimulable phosphor which can absorb and store the energy of light upon being irradiated therewith and release a stimulated emission whose amount is proportional to that of the received light upon being stimulated with an electromagnetic wave having a specific wavelength range, selectively labeling a fixed high molecular substance such as a protein or a nucleic acid sequence with a labeling substance which generates chemiluminescent emission when it contacts a chemiluminescent substance, contacting the high molecular substance selectively labeled with the labeling substance and the chemiluminescent substance, storing and recording the chemiluminescent emission in the wavelength of visible light generated by the contact of the chemiluminescent substance and the labeling substance in the stimulable phosphor contained in a stimulable phosphor layer formed on a stimulable phosphor sheet, scanning the stimulable phosphor layer with an electromagnetic wave to excite the stimulable phosphor, photoelectrically detecting the stimulated emission released from the stimulable phosphor to produce digital signals, effecting data processing on the obtained digital signals, and reproducing data on displaying means such as a CRT or a recording material such as a photographic film (see for example, U.S. Pat. No. 5,028,793, UK Patent Application 2,246,197 A and the like).

Unlike the system using a photographic film, according to these systems using the stimulable phosphor as a detecting material, development, which is chemical processing, becomes unnecessary. Further, it is possible reproduce a desired image by effecting image processing on the obtained image data and effect quantitative analysis using a computer. Use of a stimulable phosphor in these processes is therefore advantageous.

On the other hand, a fluorescence analyzing system using a fluorescent substance as a labeling substance instead of a radioactive labeling substance in the autoradiographic analyzing system is known. According to this system, it is possible to study a genetic sequence, study the expression level of a gene, and to effect separation or identification of protein or estimation of the molecular weight or properties of protein or the like. For example, this system can perform a process including the steps of distributing a plurality of DNA fragments on a gel support by means of electrophoresis after a fluorescent dye was added to a solution containing a plurality of DNA fragments to be distributed, or distributing a plurality of DNA fragments on a gel support containing a fluorescent dye, or dipping a gel support on which a plurality of DNA fragments have been distributed by means of electrophoresis in a solution containing a fluorescent dye, thereby labeling the electrophoresed DNA fragments, exciting the fluorescent dye by a stimulating ray to cause it to release fluorescent light, detecting the released fluorescent light to produce an image and detecting the distribution of the DNA fragments on the gel support. This system can also perform a process including the steps of distributing a plurality of DNA fragments on a gel support by means of electrophoresis, denaturing the DNA fragments, transferring at least a part of the denatured DNA fragments onto a transfer support such as a nitrocellulose support by the Southern-blotting method, hybridizing a probe prepared by labeling target DNA and DNA or RNA complementary thereto with the denatured DNA fragments, thereby selectively labeling only the DNA fragments complementary to the probe DNA or probe RNA, exciting the fluorescent dye by a stimulating ray to cause it to release fluorescent light, detecting the released fluorescent light to produce an image and detecting the distribution of the target DNA on the transfer support. This system can further perform a process including the steps of preparing a DNA probe complementary to DNA containing a target gene labeled by a labeling substance, hybridizing it with DNA on a transfer support, combining an enzyme with the complementary DNA labeled by a labeling substance, causing the enzyme to contact a fluorescent substance, transforming the fluorescent substance to a fluorescent substance having fluorescent light releasing property, exciting the thus produced fluorescent substance by a stimulating ray to release fluorescent light, detecting the fluorescent light to produce an image and detecting the distribution of the target DNA on the transfer support. This fluorescence detecting system is advantageous in that a genetic sequence or the like can be easily detected without using a radioactive substance.

Similarly, there is known a chemiluminescence detecting system comprising the steps of fixing a substance derived from a living organism such as a protein or a nucleic acid sequence on a support, selectively labeling the substance derived from a living organism with a labeling substance which generates chemiluminescent emission when it contacts a chemiluminescent substrate, contacting the substance derived from a living organism and selectively labeled with the labeling substance and the chemiluminescent substrate, photoelectrically detecting the chemiluminescent emission in the wavelength of visible light generated by the contact of the chemiluminescent substrate and the labeling substance to produce digital image signals, effecting image processing thereon, and reproducing a chemiluminescent image on a display means such as a CRT or a recording material such as a photographic film, thereby obtaining information relating to the high molecular substance such as genetic information.

Further, a micro-array analyzing system has been recently developed, which comprises the steps of using a spotting device to drop at different positions on the surface of a carrier such as a slide glass plate, a membrane filter or the like specific binding substances, which can specifically bind with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substances using a hybridization method or the like with a substance derived from a living organism such as a cell, virus, hormone, tumor marker, enzyme, antibody, antigen, abzyme, other protein, a nuclear acid, cDNA, DNA or mRNA by extraction, isolation or the like and optionally further subjected to chemical processing, chemical modification or the like and which is labeled with a labeling substance such as a fluorescent substance, dye or the like, thereby forming a micro-array, irradiating the micro-array with a stimulating ray, photoelectrically detecting light such as fluorescence emission released from a labeling substance such as a fluorescent substance, dye or the like, and analyzing the substance derived from a living organism. This micro-array analyzing system is advantageous in that a substance derived from a living organism can be analyzed in a short time period by forming a number of spots of specific binding substances at different positions of the surface of a carrier such as a slide glass plate at high density and hybridizing them with a substance derived from a living organism and labeled with a labeling substance.

In addition, a macro-array analyzing system using a radioactive labeling substance as a labeling substance has been further developed, which comprises the steps of using a spotting device to drop at different positions on the surface of a carrier such as a membrane filter or the like specific binding substances, which can specifically bind with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substance using a hybridization method or the like with a substance derived from a living organism such as a cell, virus, hormone, tumor marker, enzyme, antibody, antigen, abzyme, other protein, a nuclear acid, cDNA, DNA or mRNA by extraction, isolation or the like and optionally further subjected to chemical processing, chemical modification or the like and which is labeled with a radioactive labeling substance, thereby forming a macro-array, superposing the macro-array and a stimulable phosphor sheet formed with a stimulable phosphor layer, exposing the stimulable phosphor layer to a radioactive labeling substance, irradiating the stimulable phosphor layer with a stimulating ray to excite the stimulable phosphor, photoelectrically detecting the stimulated emission released from the stimulable phosphor to produce biochemical analysis data, and analyzing the substance derived from a living organism.

However, in the macro-array analyzing system using a radioactive labeling substance as a labeling substance, when the stimulable phosphor layer is exposed to a radioactive labeling substance, since the radiation energy of the radioactive labeling substance contained in spot-like regions formed on the surface of a carrier such as a membrane filter is very large, electron beams ($\beta$ rays) released from the radioactive labeling substance contained in the individual spot-like regions are scattered in the carrier such as a membrane filter, thereby impinging on regions of the stimulable phosphor layer that should be exposed only to the radioactive labeling substance contained in neighboring spot-like regions, or electron beams released from the radioactive labeling substance adhering to the surface of the carrier such as a membrane filter between neighboring spot-like regions impinge on the stimulable phosphor layer, to generate noise in biochemical analysis data produced by photoelectrically detecting stimulated emission, thus making data of neighboring spot-like regions hard to separate and lowering resolution, and to lower the accuracy of biochemical analysis when a substance derived from a living organism is analyzed by quantifying the radiation amount of each spot. The degradation of the resolution and accuracy of biochemical analysis is particularly pronounced when spots are formed close to each other at high density.

Furthermore, in the field of biochemical analysis, it is often required to analyze a substance derived from a living organism by forming a plurality of spot-like regions containing specific binding substances at different positions on the surface of a carrier such as a membrane filter or the like, which can specifically bind with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, specifically binding, using a hybridization method or the like, the specific binding substances contained in the plurality of spot-like regions with a substance derived from a living organism labeled with a labeling substance which generates chemiluminescent emission when it contacts a chemiluminescent substrate, thereby selectively labeling the plurality of spot-like regions, causing the plurality of spot-like regions to come into contact with a chemiluminescent substrate, exposing the stimulable phosphor layer of a stimulable phosphor sheet to chemiluminescent emission in the wavelength of visible light generated by the contact of the chemiluminescent substance and the labeling substance, thereby storing the energy of chemiluminescent emission in the stimulable phosphor layer, irradiating the stimulable phosphor layer with a stimulating ray, and photoelectrically detecting stimulated emission released from the stimulable phosphor layer, thereby effecting biochemical analysis. In this case, chemiluminescent emission released from any particular spot-like region is scattered in the carrier such as a membrane filter and mixed with chemiluminescent emission released from neighboring spot-like regions, thereby generating noise in biochemical analysis data produced by photoelectrically detecting chemiluminescent emission.

Further, when the stimulable phosphor layer of a stimulable phosphor sheet is scanned using a scanner with a stimulating ray to excite stimulable phosphor contained in the stimulable phosphor layer and stimulated emission released from the stimulable phosphor layer is photoelectrically detected, thereby producing biochemical analysis data, since stimulable phosphor contained in a neighboring region of the stimulable phosphor layer to be next stimulated is excited by the stimulating ray as the stimulating ray is scanned and releases stimulated emission, whereby radiation energy or light energy is released, it is impossible to perform quantitative analysis with high quantitative accuracy based on biochemical analysis data produced by a conventional scanner.

SUMMARY OF THE INVENTION

It is therefore an object of the present invention to provide a biochemical analysis data producing method and a scanner therefor, which can produce biochemical analysis data having excellent quantitative characteristics with high resolution even in the case of forming at a high density on the surface of a carrier such as a membrane filter a plurality of spot-like regions containing specific binding substances which can specifically bind with a substance derived from a living organism and whose sequence, base length, composition and the like are known, selectively labeling the plurality of spot-like regions with a radioactive labeling substance, thereby recording radiation data therein, exposing the stimulable phosphor layer of a stimulable phosphor sheet to the radioactive labeling substance selectively contained in the plurality of spot-like regions and recording radiation data in the stimulable phosphor layer of the stimulable phosphor sheet or in the case of forming at a high density on the surface of a carrier such as a membrane filter a plurality of spot-like regions containing specific binding substances which can specifically bind with a substance derived from a living organism and whose sequence, base length, composition and the like are known, selectively labeling the plurality of spot-like regions with a labeling substance which generates chemiluminescent emission when it contacts a chemiluminescent substrate, thereby recording chemiluminescent data therein, causing the plurality of spot-like regions to come into contact with a chemiluminescent substrate and to release chemiluminescent emission, exposing the stimulable phosphor layer of a stimulable phosphor sheet to the chemiluminescent emission selectively released from the plurality of spot-like regions and recording chemiluminescent data in the stimulable phosphor layer of the stimulable phosphor sheet.

The above other objects of the present invention can be accomplished by a biochemical analysis data producing method comprising the steps of selectively storing one of radiation energy and light energy in a plurality of stimulable phosphor layer regions at least one-dimensionally formed in a support of a stimulable phosphor sheet and spaced apart from each other, moving the stimulable phosphor sheet and a stimulating ray relative to each other at least in a main scanning direction, sequentially irradiating the plurality of stimulable phosphor layer regions so that energy of the stimulating ray projected onto the plurality of stimulable phosphor layer regions per unit area is higher than that projected on regions other than the plurality of stimulable phosphor layer regions, thereby exciting stimulable phosphor contained in the plurality of stimulable phosphor layer regions, and photoelectrically detecting stimulated emission released from the stimulable phosphor layer to produce biochemical analysis data.

According to the present invention, since the stimulable phosphor includes the support with which the plurality of stimulable phosphor layer regions are at least one-dimensionally formed so as to be spaced apart from each other, even in the case of forming at a high density in a biochemical analysis unit a plurality of spot-like regions containing specific binding substances which can specifically bind with a substance derived from a living organism and whose sequence, base length, composition and the like are known, selectively labeling the plurality of spot-like regions with a radioactive labeling substance, thereby recording radiation data therein, if the plurality of stimulable phosphor layer regions are formed in the support in the same pattern as that of the plurality of spot-like regions formed in the biochemical analysis unit, electron beams (β rays) released from the radioactive labeling substance contained in the individual spot-like regions when the stimulable phosphor sheet is superposed on the biochemical analysis unit to expose the plurality of stimulable phosphor layer regions of the stimulable phosphor sheet to the radioactive labeling substance selectively contained in the plurality of spot-like regions of the biochemical analysis unit can be effectively prevented from entering stimulable phosphor layer regions other than that to be exposed to electron beams (β rays) released from the radioactive labeling substance contained in the spot-like region and, therefore, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

Further, according the present invention, since the stimulable phosphor includes the support with which the plurality of stimulable phosphor layer regions are at least one-dimensionally formed so as to be spaced apart from each other, even in the case of forming at a high density in a biochemical analysis unit a plurality of spot-like regions containing specific binding substances which can specifically bind with a substance derived from a living organism and whose sequence, base length, composition and the like are known, selectively labeling the plurality of spot-like regions with a labeling substance which generates chemiluminescent emission when it contacts a chemiluminescent substrate, thereby recording chemiluminescent data therein, if the plurality of stimulable phosphor layer regions are formed in the support in the same pattern as that of the plurality of spot-like regions formed in the biochemical analysis unit, chemiluminescent emission released from the individual spot-like regions of the biochemical analysis unit by the contact of the chemiluminescent substance and the labeling substance when the stimulable phosphor sheet is superposed on the biochemical analysis unit to expose the plurality of stimulable phosphor layer regions of the stimulable phosphor sheet to the chemiluminescent emission released from the plurality of spot-like regions of the biochemical analysis unit can be effectively prevented from entering stimulable phosphor layer regions other than that to be exposed to chemiluminescent emission released from the spot-like region and, therefore, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

Furthermore, according the present invention, when biochemical analysis data are produced by moving the stimulable phosphor sheet and a stimulating ray relative to each other at least in a main scanning direction, sequentially irradiating the plurality of stimulable phosphor layer regions and photoelectrically detecting stimulated emission released from the stimulable phosphor layer, since the plurality of stimulable phosphor layer regions are irradiated by the stimulating ray so that energy of the stimulating ray projected onto the plurality of stimulable phosphor layer regions per unit area is higher than that projected on regions other than the plurality of stimulable phosphor layer regions, it is possible to effectively prevent the stimulating ray from entering a neighboring stimulable phosphor layer region to be next stimulated as the stimulating ray is scanned and thus prevent stimulable phosphor contained in the neighboring stimulable phosphor layer region from being excited to release radiation energy or light energy stored therein, and, therefore, biochemical analysis data having an excellent quantitative characteristic can be produced in a desired manner.

In a preferred aspect of the present invention, the stimulable phosphor sheet and the stimulating ray are intermittently moved relative to each other in the main scanning direction and the individual stimulable phosphor regions are irradiated with the stimulating ray for a predetermined time.

According to this preferred aspect of the present invention, since the stimulable phosphor sheet and the stimulating ray are intermittently moved relative to each other in the main scanning direction and the individual stimulable phosphor regions are irradiated with the stimulating ray for a predetermined time, it is possible to effectively prevent the stimulating ray from entering a neighboring stimulable phosphor layer region to be next stimulated as the stimulating ray is scanned and thus prevent stimulable phosphor contained in the neighboring stimulable phosphor layer region from being excited to release radiation energy or light energy stored therein, and, therefore, biochemical analysis data having an excellent quantitative characteristic can be produced in a desired manner.

In a preferred aspect of the present invention, biochemical analysis data are produced by producing analog data by photoelectrically detecting stimulated emission, integrating the thus produced analog data and digitizing the integrated value of the analog data.

According to this preferred aspect of the present invention, since biochemical analysis data are produced by producing analog data by photoelectrically detecting stimulated emission released from stimulable phosphor contained in the plurality of stimulable phosphor layer regions in response to the excitation with the stimulating ray, integrating the thus produced analog data and digitizing the integrated value of the analog data, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced with high sensitivity.

In a preferred aspect of the present invention, biochemical analysis data are produced by producing analog data by photoelectrically detecting stimulated emission, digitizing the analog data to produce digital data and summing the digital data.

According to this preferred aspect of the present invention, since biochemical analysis data are produced by producing analog data by photoelectrically detecting stimulated emission released from stimulable phosphor contained in the plurality of stimulable phosphor layer regions in response to the excitation with the stimulating ray, digitizing the analog data to produce digital data and summing the digital data, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced with high sensitivity.

In a preferred aspect of the present invention, the biochemical analysis data producing method further comprises the steps of intermittently moving the stimulable phosphor sheet and the stimulating ray relative to each other at least one-dimensionally, sequentially irradiating the plurality of stimulable phosphor layer regions with a stimulating ray having reference excitation power which is relatively low to excite stimulable phosphor contained in the individual stimulable phosphor layer regions, photoelectrically detecting stimulated emission released from the individual stimulable phosphor layer regions to produce analog data, digitizing the analog data to produce digital data, comparing signal intensity of the digital data with a threshold value, irradiating, when the signal intensity of the digital data is lower than the threshold value, the stimulable phosphor layer region from which the digital data were obtained with a stimulating ray having excitation power higher than the reference excitation power to excite stimulable phosphor contained therein, and photoelectirically detecting stimulated emission released from the stimulable phosphor layer region.

According to this preferred aspect of the present invention, since the biochemical analysis data producing method further comprises the steps of intermittently moving the stimulable phosphor sheet and the stimulating ray relative to each other at least one-dimensionally, sequentially irradiating the plurality of stimulable phosphor layer regions with a stimulating ray having reference excitation power which is relatively low to excite stimulable phosphor contained in the individual stimulable phosphor layer regions, photoelectrically detecting stimulated emission released from the individual stimulable phosphor layer regions to produce analog data, digitizing the analog data to produce digital data, comparing signal intensity of the digital data with a threshold value, irradiating, when the signal intensity of the digital data is lower than the threshold value, the stimulable phosphor layer region from which the digital data were obtained with a stimulating ray having excitation power higher than the reference excitation power to excite stimulable phosphor contained therein, and photoelectirically detecting stimulated emission released from the stimulable phosphor layer region, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced with high sensitivity.

In a further preferred aspect of the present invention, when the signal intensity of the digital data produced by irradiating the stimulable phosphor layer region with the stimulating ray having the reference excitation power is equal to or higher than the threshold value, the thus produced digital data are adopted as biochemical analysis data of the stimulable phosphor layer region.

According to this preferred aspect of the present invention, when the signal intensity of the digital data produced by irradiating the stimulable phosphor layer region with the stimulating ray having the reference excitation power is equal to or higher than the threshold value, since the thus produced digital data are adopted as biochemical analysis data of the stimulable phosphor layer region, even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data.

In a further preferred aspect of the present invention, when the signal intensity of the digital data produced by irradiating the stimulable phosphor layer region with the stimulating ray having the reference excitation power is lower than the threshold value, digital data produced by irradiating the stimulable phosphor layer region from which the digital data were obtained with the stimulating ray having excitation power higher than the reference excitation power to excite stimulable phosphor contained therein, photoelectirically detecting stimulated emission released from the stimulable phosphor layer region to produce analog data and digitizing the analog data are adopted as biochemical analysis data of the stimulable phosphor layer region.

According to this preferred aspect of the present invention, when the signal intensity of the digital data produced by irradiating the stimulable phosphor layer region with the stimulating ray having the reference excitation power is lower than the threshold value, since digital data produced by irradiating the stimulable phosphor layer region from which the digital data were obtained with the stimulating ray having excitation power higher than the reference excitation power to excite stimulable phosphor contained therein, photoelectirically detecting stimulated emission released from the stimulable phosphor layer region to produce analog data and digitizing the analog data are adopted as biochemical analysis data of the stimulable phosphor layer region, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced with high sensitivity.

In another preferred aspect of the present invention, when the signal intensity of the digital data produced by irradiating the stimulable phosphor layer region with the stimulating ray having the reference excitation power is lower than the threshold value, the biochemical analysis data producing method further conducts the steps of irradiating the stimulable phosphor layer region from which the digital data were obtained with a stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, and adopting the digital data as biochemical analysis data of the stimulable phosphor layer region when the signal intensity of the digital data is equal to or higher than the threshold value.

According to this preferred aspect of the present invention, when the signal intensity of the digital data produced by irradiating the stimulable phosphor layer region with the stimulating ray having the reference excitation power is lower than the threshold value, since the biochemical analysis data producing method further comprises the steps of irradiating the stimulable phosphor layer region from which the digital data were obtained with the stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, and adopting the digital data as biochemical analysis data of the stimulable phosphor layer region when the signal intensity of the digital data is equal to or higher than the threshold value, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be reliably produced by detecting the stimulated emission with high sensitivity.

In a further preferred aspect of the present invention, when the signal intensity of the digital data produced by irradiating the stimulable phosphor layer region with the stimulating ray having the reference excitation power is lower than the threshold value, the biochemical analysis data producing method further conducts the steps of irradiating the stimulable phosphor layer region from which the digital data were obtained with a stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, sequentially increasing, when the signal intensity of the digital data is lower than the threshold value, the excitation power of the stimulating ray I times at maximum where I is a positive integer, irradiating the stimulable phosphor layer region from which the digital data were obtained with the stimulating ray to excite stimulable phosphor contained therein, photoelectrically detecting the stimulated emission released from the stimulable phosphor by the light detector, and adopting the digital data as biochemical analysis data of the stimulable phosphor layer region when the signal intensity of the digital data is equal to or higher than the threshold value, or determining biochemical analysis data of the stimulable phosphor layer region to be zero when the signal intensity of the digital data is still lower than the threshold value even though the excitation power of the stimulating ray was sequentially increased I times in total to irradiate the stimulable phosphor layer region from which the digital data were obtained with the stimulating ray and stimulated emission released from the stimulable phosphor layer region was photoelectrically detected by the light detector.

According to this preferred aspect of the present invention, when the signal intensity of the digital data produced by irradiating the stimulable phosphor layer region with the stimulating ray having the reference excitation power is lower than the threshold value, since the biochemical analysis data producing method further comprises the steps of irradiating the stimulable phosphor layer region from which the digital data were obtained with the stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, sequentially increasing, when the signal intensity of the digital data is lower than the threshold value, the excitation power of the stimulating ray I times at maximum where I is a positive integer, irradiating the stimulable phosphor layer region from which the digital data were obtained with the stimulating ray to excite stimulable phosphor contained therein, photoelectrically detecting the stimulated emission released from the stimulable phosphor by the light detector, and adopting the digital data as biochemical analysis data of the stimulable phosphor layer region to be zero, when the signal intensity of the digital data is equal to or higher than the threshold value, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be reliably produced by detecting the stimulated emission with high sensitivity and even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data.

Furthermore, according to this preferred aspect of the present invention, when the signal intensity of the digital data is still lower than the threshold value even though the excitation power of the stimulating ray was sequentially increased I times in total to irradiate the stimulable phosphor layer region from which the digital data were obtained with the stimulating ray and stimulated emission released from the stimulable phosphor layer region was photoelectrically detected by the light detector, since the biochemical analysis data of the stimulable phosphor layer region is determined to be zero, it is possible to prevent, by appropriately selecting I, unnecessary exciting operation from being repeated when no radiation energy or light energy is stored in the stimulable phosphor layer region, while biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small and it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large.

In a further preferred aspect of the present invention, when the signal intensity of the digital data produced by irradiating the stimulable phosphor layer region with the stimulating ray having the reference excitation power is equal to or higher than the threshold value, the biochemical analysis data producing method further conducts the steps of continuing to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value and adopting the summed digital data as biochemical analysis data of the stimulable phosphor layer region.

According to this preferred aspect of the present invention, when the signal intensity of the digital data produced by irradiating the stimulable phosphor layer region with the stimulating ray having the reference excitation power is equal to or higher than the threshold value, since the biochemical analysis data producing method further comprises the steps of continuing to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value and adopting the summed digital data as biochemical analysis data of the stimulable phosphor layer region, radiation energy or light energy stored in the stimulable phosphor layer region can be sufficiently released and, therefore, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be reliably produced by detecting the stimulated emission with high sensitivity.

In a further preferred aspect of the present invention, when the signal intensity of the digital data produced by irradiating the stimulable phosphor layer region with the stimulating ray having the reference excitation power is lower than the threshold value, the biochemical analysis data producing method further conducts the steps of irradiating the stimulable phosphor layer region from which the digital data were obtained with a stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, sequentially increasing, when the signal intensity of the digital data is lower than the threshold value, the excitation power of the stimulating ray j times at maximum where j is a positive integer, irradiating the stimulable phosphor layer region from which the digital data were obtained with the stimulating ray to excite stimulable phosphor contained therein, photoelectrically detecting the stimulated emission released from the stimulable phosphor by the light detector to produce analog data, digitizing the analog data to produce digital data, continuing, when the signal intensity of the thus obtained digital data has come to be equal to or higher than the threshold value, to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value and adopting the summed digital data as biochemical analysis data of the stimulable phosphor layer region, or determining biochemical analysis data of the stimulable phosphor layer region to be zero when the signal intensity of the digital data is still lower than the threshold value even though the excitation power of the stimulating ray was sequentially increased j times in total to irradiate the stimulable phosphor layer region from which the digital data were obtained with the stimulating ray and stimulated emission released from the stimulable phosphor layer region was photoelectrically detected by the light detector.

According to this preferred aspect of the present invention, when the signal intensity of the digital data produced by irradiating the stimulable phosphor layer region with the stimulating ray having the reference excitation power is lower than the threshold value, since the biochemical analysis data producing method further comprises the steps of irradiating the stimulable phosphor layer region from which the digital data were obtained with the stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, sequentially increasing, when the signal intensity of the digital data is lower than the threshold value, the excitation power of the stimulating ray j times at maximum where j is a positive integer, irradiating the stimulable phosphor layer region from which the digital data were obtained with the stimulating ray to excite stimulable phosphor contained therein, photoelectrically detecting the stimulated emission released from the stimulable phosphor by the light detector to produce analog data, digitizing the analog data to produce digital data, continuing, when the signal intensity of the thus obtained digital data has come to be equal to or higher than the threshold value, to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value and adopting the summed digital data as biochemical analysis data of the stimulable phosphor layer region, radiation energy or light energy stored in the stimulable phosphor layer region can be sufficiently released and, therefore, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be reliably produced by detecting the stimulated emission with high sensitivity.

Furthermore, according to this preferred aspect of the present invention, when the signal intensity of the digital data is still lower than the threshold value even though the excitation power of the stimulating ray was sequentially increased j times in total to irradiate the stimulable phosphor layer region from which the digital data were obtained with the stimulating ray and stimulated emission released from the stimulable phosphor layer region was photoelectrically detected by the light detector, since biochemical analysis data of the stimulable phosphor layer region is determined to be zero, it is possible to prevent, by appropriately selecting j, unnecessary exciting operation from being repeated when no radiation energy or light energy is stored in the stimulable phosphor layer region, while biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small and it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large.

In a further preferred aspect of the present invention, when the signal intensity of the digital data produced by irradiating the stimulable phosphor layer region with the stimulating ray having the reference excitation power is equal to or higher than the threshold value, the biochemical analysis data producing method further conducts the steps of continuing to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value, irradiating, when the signal intensity of digital data produced by photoelectrically detecting stimulated emission released from stimulable phosphor contained in the stimulable phosphor layer region to produce analog data and digitizing the analog data has come to be lower than the threshold value, the stimulable phosphor layer region from which the digital data were obtained with a stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, continuing to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data become to be lower than the threshold value, further sequentially increasing the excitation power of the stimulating ray k times at maximum where k is a positive integer, irradiating the stimulable phosphor layer region from which the digital data were obtained with the stimulating ray to excite stimulable phosphor contained therein, photoelectrically detecting the Stimulated emission released from the stimulable phosphor by the light detector to produce analog data, digitizing the analog data to produce digital data, summing the digital data, storing the summed digital data in the digital memory, calculating a total of the summed digital value, and adopting the thus calculated total of the summed digital value as biochemical analysis data of the stimulable phosphor layer region.

According to this preferred aspect of the present invention, when the signal intensity of the digital data produced by irradiating the stimulable phosphor layer region with the stimulating ray having the reference excitation power is equal to or higher than the threshold value, since the biochemical analysis data producing method further comprises the steps of continuing to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value, irradiating, when the signal intensity of digital data produced by photoelectrically detecting stimulated emission released from stimulable phosphor contained in the stimulable phosphor layer region to produce analog data and digitizing the analog data has come to be lower than the threshold value, the stimulable phosphor layer region from which the digital data were obtained with the stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, continuing to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data become to be lower than the threshold value, further sequentially increasing the excitation power of the stimulating ray k times at maximum where k is a positive integer, irradiating the stimulable phosphor layer region from which the digital data were obtained with the stimulating ray to excite stimulable phosphor contained therein, photoelectrically detecting the stimulated emission released from the stimulable phosphor by the light detector to produce analog data, digitizing the analog data to produce digital data, summing the digital data, storing the summed digital data in the digital memory, calculating a total of the summed digital value, and adopting the thus calculated total of the summed digital value as biochemical analysis data of the stimulable phosphor layer region, even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data and even in the case where radiation energy or light energy stored in a stimulable phosphor layer region is small, it is possible to produce biochemical analysis data having high quantitative characteristics by substantially completely releasing radiation energy or light energy stored in a stimulable phosphor layer region in the form of stimulated emission and detecting the stimulated emission with very high sensitivity.

In a further preferred aspect of the present invention, when the signal intensity of the digital data produced by irradiating the stimulable phosphor layer region with the stimulating ray having the reference excitation power is lower than the threshold value, the biochemical analysis data producing method further conducts the steps of irradiating the stimulable phosphor layer region from which the digital data were obtained with a stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, sequentially increasing, when the signal intensity of the digital data is lower than the threshold value, the excitation power of the stimulating ray m times at maximum where m is a positive integer, irradiating the stimulable phosphor layer region from which the digital data were obtained with the stimulating ray to excite stimulable phosphor contained therein, photoelectrically detecting the stimulated emission released from the stimulable phosphor by the light detector to produce analog data, digitizing the analog data to produce digital data, continuing, when the signal intensity of the thus obtained digital data has come to be equal to or higher than the threshold value, to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value, further sequentially increasing the excitation power of the stimulating ray m times at maximum, irradiating the stimulable phosphor layer region from which the digital data were obtained with the stimulating ray to excite stimulable phosphor contained therein, photoelectrically detecting the stimulated emission released from the stimulable phosphor by the light detector to produce analog data, digitizing the analog data to produce digital data, summing the digital data, storing the summed digital data in the digital memory, calculating a total of the summed digital value, and adopting the thus calculated total of the digital data as biochemical analysis data of the stimulable phosphor layer region, or determining biochemical analysis data of the stimulable phosphor layer region to be zero when the signal intensity of the digital data is still lower than the threshold value even though the excitation power of the stimulating ray was sequentially increased m times in total to irradiate the stimulable phosphor layer region from which the digital data were obtained with the stimulating ray and stimulated emission released from the stimulable phosphor layer region was photoelectrically detected by the light detector.

According to this preferred aspect of the present invention, when the signal intensity of the digital data produced by irradiating the stimulable phosphor layer region with the stimulating ray having the reference excitation power is lower than the threshold value, since the biochemical analysis data producing method further comprises the steps of irradiating the stimulable phosphor layer region from which the digital data were obtained with the stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, sequentially increasing, when the signal intensity of the digital data is lower than the threshold value, the excitation power of the stimulating ray m times at maximum where m is a positive integer, irradiating the stimulable phosphor layer region from which the digital data were obtained with the stimulating ray to excite stimulable phosphor contained therein, photoelectrically detecting the stimulated emission released from the stimulable phosphor by the light detector to produce analog data, digitizing the analog data to produce digital data, continuing, when the signal intensity of the thus obtained digital data has come to be equal to or higher than the threshold value, to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be reliably produced by detecting the stimulated emission with high sensitivity.

Furthermore, according to this aspect of the present invention, since the biochemical analysis data producing method comprises the steps of further sequentially increasing the excitation power of the stimulating ray m times at maximum, irradiating the stimulable phosphor layer region from which the digital data were obtained with the stimulating ray to excite stimulable phosphor contained therein, photoelectrically detecting the stimulated emission released from the stimulable phosphor by the light detector to produce analog data, digitizing the analog data to produce digital data, summing the digital data, storing the summed digital data in the digital memory, calculating a total of the summed digital value, and adopting the thus calculated total of the digital data as biochemical analysis data of the stimulable phosphor layer region, even in the case where radiation energy or light energy stored in a stimulable phosphor layer region is small, it is possible to produce biochemical analysis data having high quantitative characteristics by substantially completely releasing radiation energy or light energy stored in a stimulable phosphor layer region in the form of stimulated emission and detecting the stimulated emission with very high sensitivity.

Moreover, according to this aspect of the present invention, since the biochemical analysis data producing method further comprises the steps of determining biochemical analysis data of the stimulable phosphor layer region to be zero when the signal intensity of the digital data is still lower than the threshold value even though the excitation power of the stimulating ray was sequentially increased m times in total to irradiate the stimulable phosphor layer region from which the digital data were obtained with the stimulating ray and stimulated emission released from the stimulable phosphor layer region was photoelectrically detected by the light detector, it is possible to prevent, by appropriately selecting m, unnecessary exciting operation from being repeated when no radiation energy or light energy is stored in the stimulable phosphor layer region, while biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small and it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large.

In a further preferred aspect of the present invention, when the signal intensity of the digital data produced by irradiating the stimulable phosphor layer region with the stimulating ray having the reference excitation power is equal to or higher than the threshold value, the biochemical analysis data producing method further conducts the steps of continuing to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value, irradiating, when the signal intensity of digital data produced by photoelectrically detecting stimulated emission released from stimulable phosphor contained in the stimulable phosphor layer region to produce analog data and digitizing the analog data has come to be lower than the threshold value, the stimulable phosphor layer region from which the digital data were obtained with a stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, continuing to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data comes to be lower than the threshold value, calculating, when the signal intensity of digital data cannot come to be equal to or higher than the threshold value even if the excitation power of the stimulating ray is increased, a total of the summed digital data stored in the digital memory so far, and adopting it as the biochemical analysis data of the stimulable phosphor layer region.

According to this preferred aspect of the present invention, when the signal intensity of the digital data produced by irradiating the stimulable phosphor layer region with the stimulating ray having the reference excitation power is equal to or higher than the threshold value, since the biochemical analysis data producing method further comprises the steps of continuing to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value, irradiating, when the signal intensity of digital data produced by photoelectrically detecting stimulated emission released from stimulable phosphor contained in the stimulable phosphor layer region to produce analog data and digitizing the analog data has come to be lower than the threshold value, the stimulable phosphor layer region from which the digital data were obtained with the stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, continuing to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data come to be lower than the threshold value, calculating, when the signal intensity of digital data cannot come to be equal to or higher than the threshold value even if the excitation power of the stimulating ray is increased, a total of the summed digital data stored in the digital memory so far, and adopting it as the biochemical analysis data of the stimulable phosphor layer region, even in the case where radiation energy or light energy stored in a stimulable phosphor layer region is small, it is possible to produce biochemical analysis data having high quantitative characteristics by substantially completely releasing radiation energy or light energy stored in a stimulable phosphor layer region in the form of stimulated emission and detecting the stimulated emission with very high sensitivity.

In a further preferred aspect of the present invention, when the signal intensity of the digital-data produced by irradiating the stimulable phosphor layer region with the stimulating ray having the reference excitation power is lower than the threshold value, the biochemical analysis data producing method further conducts the steps of irradiating the stimulable phosphor layer region from which the digital data were obtained with a stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, sequentially increasing, when the signal intensity of the digital data is lower than the threshold value, the excitation power of the stimulating ray n times at maximum where n is a positive integer, irradiating the stimulable phosphor layer region from which the digital data were obtained with the stimulating ray to excite stimulable phosphor contained therein, photoelectrically detecting the stimulated emission released from the stimulable phosphor by the light detector to produce analog data, digitizing the analog data to produce digital data, continuing, when the signal intensity of the thus obtained digital data has come to be equal to or higher than the threshold value, to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value, further sequentially increasing the excitation power of the stimulating ray n times at maximum, irradiating the stimulable phosphor layer region from which the digital data were obtained with the stimulating ray to excite stimulable phosphor contained therein, photoelectrically detecting the stimulated emission released from the stimulable phosphor by the light detector to produce analog data, digitizing the analog data to produce digital data, summing the digital data, storing the summed digital data in the digital memory, calculating, when the signal intensity of digital data cannot come to be equal to or higher than the threshold value even if the excitation power of the stimulating ray is increased, a total of the summed digital data stored in the digital memory so far, and adopting it as the biochemical analysis data of the stimulable phosphor layer region, or determining biochemical analysis data of the stimulable phosphor layer region to be zero when the signal intensity of the digital data is still lower than the threshold value even though the excitation power of the stimulating ray was sequentially increased n times in total to irradiate the stimulable phosphor layer region from which the digital data were obtained with the stimulating ray and stimulated emission released from the stimulable phosphor layer region was photoelectrically detected by the light detector.

According to this preferred aspect of the present invention, when the signal intensity of the digital data produced by irradiating the stimulable phosphor layer region with the stimulating ray having the reference excitation power is lower than the threshold value, since the biochemical analysis data producing method further comprises the steps of irradiating the stimulable phosphor layer region from which the digital data were obtained with the stimulating ray having excitation power higher than the reference excitation power to excite stimulable phosphor contained therein, photoelectirically detecting stimulated emission released from the stimulable phosphor layer region to produce analog data, digitizing the analog data to produce digital data, comparing signal intensity of the thus obtained digital data with the threshold value, sequentially increasing, when the signal intensity of the digital data is lower than the threshold value, the excitation power of the stimulating ray n times at maximum where n is a positive integer, irradiating the stimulable phosphor layer region from which the digital data were obtained with the stimulating ray to excite stimulable phosphor contained therein, photoelectrically detecting the stimulated emission released from the stimulable phosphor by the light detector to produce analog data, digitizing the analog data to produce digital data, continuing, when the signal intensity of the thus obtained digital data has come to be equal to or higher than the threshold value, to irradiate the stimulable phosphor layer region with the stimulating ray, summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value, further sequentially increasing the excitation power of the stimulating ray n times at maximum, irradiating the stimulable phosphor layer region from which the digital data were obtained with the stimulating ray to excite stimulable phosphor contained therein, photoelectrically detecting the stimulated emission released from the stimulable phosphor by the light detector to produce analog data, digitizing the analog data to produce digital data, summing the digital data, storing the summed digital data in the digital memory, calculating, when the signal intensity of digital data cannot come to be equal to or higher than the threshold value even if the excitation power of the stimulating ray is increased, a total of the summed digital data stored in the digital memory so far, and adopting it as the biochemical analysis data of the stimulable phosphor layer region, even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, and even in the case where radiation energy or light energy stored in a stimulable phosphor layer region is small, it is possible to produce biochemical analysis data having high quantitative characteristics by substantially completely releasing radiation energy or light energy stored in a stimulable phosphor layer region in the form of stimulated emission.

Moreover, according to this preferred aspect of the present invention, since the biochemical analysis data producing method further comprises the steps of determining biochemical analysis data of the stimulable phosphor layer region to be zero when the signal intensity of the digital data is still lower than the threshold value even though the excitation power of the stimulating ray was sequentially increased n times in total to irradiate the stimulable phosphor layer region from which the digital data were obtained with the stimulating ray and stimulated emission released from the stimulable phosphor layer region was photoelectrically detected by the light detector, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be reliably produced by detecting the stimulated emission with high sensitivity and even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data.

In a further preferred aspect of the present invention, digital data produced by irradiating the stimulable phosphor layer region with the stimulating ray having different excitation power to excite stimulable phosphor contained in the stimulable phosphor layer region, photoelectrically detecting stimulated emission released from the stimulable phosphor to produce analog data, and digitizing the analog data is multiplied by a correction coefficient determined in accordance with the excitation power of the stimulating ray projected onto the stimulable phosphor layer region, thereby producing biochemical analysis data of the stimulable phosphor layer region.

According to this preferred aspect of the present invention, since digital data produced by irradiating the stimulable phosphor layer region with the stimulating ray having different excitation power to excite stimulable phosphor contained in the stimulable phosphor layer region, photoelectrically detecting stimulated emission released from the stimulable phosphor to produce analog data, and digitizing the analog data is multiplied by a correction coefficient determined in accordance with the excitation power of the stimulating ray projected onto the stimulable phosphor layer region, thereby producing biochemical analysis data of the stimulable phosphor layer region, even if the excitation power of the stimulating ray is increased to be greater than the reference excitation power and stimulable phosphor contained in the stimulable phosphor layer region is excited in order to detect stimulated emission with high sensitivity or release all detectable radiation energy or light energy stored in the stimulable phosphor layer region in the form of stimulated emission and detect stimulated emission, it is possible to produce biochemical analysis data having signal intensity corresponding to radiation energy or light energy stored in the stimulable phosphor layer region.

In a further preferred aspect of the present invention, the correction coefficient for each excitation power is determined so that digital data corresponding to the excitation power can be corrected to have the same level as that of digital data to be produced using the stimulating ray having the reference excitation power.

In a further preferred aspect of the present invention, the summed digital data produced by irradiating the stimulable phosphor layer region with the stimulating ray having different excitation power to excite stimulable phosphor contained in the stimulable phosphor layer region, photoelectrically detecting stimulated emission released from the stimulable phosphor to produce analog data, digitizing the analog data to produce digital data and summing the digital data is multiplied by a correction coefficient determined in accordance with the excitation power of the stimulating ray projected onto the stimulable phosphor layer region to correct the summed digital data and biochemical analysis data of the stimulable phosphor layer region are produced by calculating a total of the thus corrected summed digital data.

According to this preferred aspect of the present invention, since the summed digital data produced by irradiating the stimulable phosphor layer region with the stimulating ray having different excitation power to excite stimulable phosphor contained in the stimulable phosphor layer region, photoelectrically detecting stimulated emission released from the stimulable phosphor to produce analog data, digitizing the analog data to produce digital data and summing the digital data is multiplied by a correction coefficient determined in accordance with the excitation power of the stimulating ray projected onto the stimulable phosphor layer region to correct the summed digital data and biochemical analysis data of the stimulable phosphor layer region are produced by calculating a total of the thus corrected summed digital data, even if the excitation power of the stimulating ray is increased to be greater than the reference excitation power and stimulable phosphor contained in the stimulable phosphor layer region is excited in order to detect stimulated emission with high sensitivity or release all detectable radiation energy or light energy stored in the stimulable phosphor layer region in the form of stimulated emission and detect stimulated emission, it is possible to produce biochemical analysis data having signal intensity corresponding to radiation energy or light energy stored in the stimulable phosphor layer region.

In a further preferred aspect of the present invention, the correction coefficient for each excitation power is determined so that the summed digital data corresponding to the excitation power are corrected to have the same level as that of summed digital data to be produced using the stimulating ray having the reference excitation power.

In a preferred aspect of the present invention, the biochemical analysis data producing method further comprises the steps of intermittently moving the stimulable phosphor sheet and the stimulating ray relative to each other at least one-dimensionally, sequentially irradiating the plurality of stimulable phosphor layer regions with a stimulating ray having reference excitation power which is relatively low for a predetermined time to excite stimulable phosphor contained in the individual stimulable phosphor layer regions, photoelectrically detecting stimulated emission released from the individual stimulable phosphor layer regions to produce analog data, integrating the analog data to produce an integrated value of the analog data, digitizing the integrated value of the analog data to produce digital data, comparing signal intensity of the thus produced digital data with a threshold value, irradiating, when the signal intensity of the digital data is lower than the threshold value, the stimulable phosphor layer region from which the digital data were obtained with the stimulating ray having excitation power higher than the reference excitation power to excite stimulable phosphor contained therein, and photoelectirically detecting stimulated emission released from the stimulable phosphor layer region.

According to this preferred aspect of the present invention, since the biochemical analysis data producing method further comprises the steps of intermittently moving the stimulable phosphor sheet and the stimulating ray relative to each other at least one-dimensionally, sequentially irradiating the plurality of stimulable phosphor layer regions with the stimulating ray having reference excitation power which is relatively low to excite stimulable phosphor contained in the individual stimulable phosphor layer regions, photoelectrically detecting stimulated emission released from the individual stimulable phosphor layer regions to produce analog data, integrating the analog data to produce an integrated value of the analog data, digitizing the integrated value of the analog data to produce digital data, comparing signal intensity of the thus produced digital data with a threshold value, irradiating, when the signal intensity of the digital data is lower than the threshold value, the stimulable phosphor layer region from which the digital data were obtained with the stimulating ray having excitation power higher than the reference excitation power to excite stimulable phosphor contained therein, and photoelectirically detecting stimulated emission released from the stimulable phosphor layer region, even in the case where radiation energy or light energy stored in the stimulable phosphor layer region is small and the intensity of stimulated emission released from the stimulable phosphor layer region when stimulable phosphor contained therein is excited with the stimulating ray is small, biochemical analysis data having high quantitative characteristics can be produced detecting stimulated emission with high sensitivity.

In a further preferred aspect of the present invention, when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is equal to or higher than the threshold value, the thus produced digital data are adopted as biochemical analysis data of the stimulable phosphor layer region.

According to this preferred aspect of the present invention, since when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is equal to or higher than the threshold value, the thus produced digital data are adopted as biochemical analysis data of the stimulable phosphor layer region, even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data.

In a further preferred aspect of the present invention, when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is lower than the threshold value, digital data produced by irradiating the stimulable phosphor layer region from which the digital data were obtained with a stimulating ray having excitation power higher than the reference excitation power to excite stimulable phosphor contained therein, photoelectirically detecting stimulated emission released from the stimulable phosphor layer region to produce analog data, integrating the analog data to produce an integrated value of the analog data and digitizing the integrated value of the analog data and the thus produced digital data are adopted as biochemical analysis data of the stimulable phosphor layer region.

According to this preferred aspect of the present invention, when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is lower than the threshold value, since digital data produced by irradiating the stimulable phosphor layer region from which the digital data were obtained with the stimulating ray having excitation power higher than the reference excitation power to excite stimulable phosphor contained therein, photoelectirically detecting stimulated emission released from the stimulable phosphor layer region to produce analog data, integrating the analog data to produce an integrated value of the analog data and digitizing the integrated value of the analog data and the thus produced digital data are adopted as biochemical analysis data of the stimulable phosphor layer region, even in the case where radiation energy or light energy stored in the stimulable phosphor layer region is small and the intensity of stimulated emission released from the stimulable phosphor layer region when stimulable phosphor contained therein is excited with the stimulating ray is small, biochemical analysis data having high quantitative characteristics can be produced detecting stimulated emission with high sensitivity.

In another preferred aspect of the present invention, when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is lower than the threshold value, the biochemical analysis data producing method further conducts the steps of irradiating the stimulable phosphor layer region from which the digital data were obtained with a stimulating ray having excitation power higher than the reference excitation power to excite stimulable phosphor contained therein, photoelectirically detecting stimulated emission released from the stimulable phosphor layer region to produce analog data, integrating the analog data to produce an integrated value of the analog data, digitizing the integrated value of the analog data to produce digital data, comparing signal intensity of the thus obtained digital data with the threshold value, and adopting the digital data as biochemical analysis data of the stimulable phosphor layer region when the signal intensity of the digital data is equal to or higher than the threshold value.

According to this preferred aspect of the present invention, when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is lower than the threshold value, since the biochemical analysis data producing method further comprises the steps of irradiating the stimulable phosphor layer region from which the digital data were obtained with the stimulating ray having excitation power higher than the reference excitation power to excite stimulable phosphor contained therein, photoelectirically detecting stimulated emission released from the stimulable phosphor layer region to produce analog data, integrating the analog data to produce an integrated value of the analog data, digitizing the integrated value of the analog data to produce digital data, comparing signal intensity of the thus obtained digital data with the threshold value, and adopting the digital data as biochemical analysis data of the stimulable phosphor layer region when the signal intensity of the digital data is equal to or higher than the threshold value, even in the case where radiation energy or light energy stored in the stimulable phosphor layer region is small and the intensity of stimulated emission released from the stimulable phosphor layer region when stimulable phosphor contained therein is excited with the stimulating ray is small, biochemical analysis data having high quantitative characteristics can be produced detecting stimulated emission with high sensitivity.

In a further preferred aspect of the present invention, when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is lower than the threshold value, the biochemical analysis data producing method further conducts the steps of irradiating the stimulable phosphor layer region from which the digital data were obtained with a stimulating ray having excitation power higher than the reference excitation power to excite stimulable phosphor contained therein, photoelectirically detecting stimulated emission released from the stimulable phosphor layer region to produce analog data, integrating the analog data to produce an integrated value of the analog data, digitizing the integrated value of the analog data to produce digital data, comparing signal intensity of the thus obtained digital data with the threshold value, sequentially increasing, when the signal intensity of the digital data is lower than the threshold value, the excitation power of the stimulating ray I times at maximum where I is a positive integer, irradiating the stimulable phosphor layer region from which the digital data were obtained with the stimulating ray to excite stimulable phosphor contained therein, photoelectrically detecting the stimulated emission released from the stimulable phosphor by the light detector to produce analog data, integrating the analog data to produce an integrated value of the analog data, digitizing the integrated value of the analog data, and adopting the thus produced digital data as biochemical analysis data of the stimulable phosphor layer region when the signal intensity of the digital data is equal to or higher than the threshold value, or determining biochemical analysis data of the stimulable phosphor layer region to be zero when the signal intensity of the digital data is still lower than the threshold value even though the digital data were produced by sequentially increasing the excitation power of the stimulating ray I times in total, irradiating the stimulable phosphor layer region from which the digital data were obtained with the stimulating ray, photoelectrically detecting stimulated emission released from the stimulable phosphor layer region by the light detector to produce analog data, integrating the analog data to produce an integrated value of the analog data, and digitizing the integrated value of the analog data.

According to this preferred aspect of the present invention, when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is lower than the threshold value, since the biochemical analysis data producing method further comprises the steps of irradiating the stimulable phosphor layer region from which the digital data were obtained with the stimulating ray having excitation power higher than the reference excitation power to excite stimulable phosphor contained therein, photoelectirically detecting stimulated emission released from the stimulable phosphor layer region to produce analog data, integrating the analog data to produce an integrated value of the analog data, digitizing the integrated value of the analog data to produce digital data, comparing signal intensity of the thus obtained digital data with the threshold value, sequentially increasing, when the signal intensity of the digital data is lower than the threshold value, the excitation power of the stimulating ray I times at maximum where I is a positive integer, irradiating the stimulable phosphor layer region from which the digital data were obtained with the stimulating ray to excite stimulable phosphor contained therein, photoelectrically detecting the stimulated emission released from the stimulable phosphor by the light detector to produce analog data, integrating the analog data to produce an integrated value of the analog data, digitizing the integrated value of the analog data, and adopting the thus produced digital data as biochemical analysis data of the stimulable phosphor layer region when the signal intensity of the digital data is equal to or higher than the threshold value, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be reliably produced by detecting the stimulated emission with high sensitivity and even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data.

Moreover, according to this preferred aspect of the present invention, the biochemical analysis data further comprises the step of determining biochemical analysis data of the stimulable phosphor layer region to be zero when the signal intensity of the digital data is still lower than the threshold value even though the digital data were produced by sequentially increasing the excitation power of the stimulating ray I times in total, irradiating the stimulable phosphor layer region from which the digital data were obtained with the stimulating ray, photoelectrically detecting stimulated emission released from the stimulable phosphor layer region by the light detector to produce analog data, integrating the analog data to produce an integrated value of the analog data, digitizing the integrated value of the analog data, it is possible to prevent, by appropriately selecting I, unnecessary exciting operation from being repeated when no radiation energy or light energy is stored in the stimulable phosphor layer region, while biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small and it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large.

In a further preferred aspect of the present invention, when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is equal to or higher than the threshold value, the biochemical analysis data producing method further conducts the steps of storing the thus produced digital data in a digital memory, irradiating the stimulable phosphor layer region from which the digital data were obtained with a stimulating ray having excitation power greater than the reference excitation power to excite stimulable phosphor contained therein, photoelectrically detecting stimulated emission to produce analog data, integrating the analog data to produce an integrated value of the analog data and digitizing the integrated value of the analog data to produce digital data, storing the thus produced digital data in the digital memory, sequentially increasing the excitation power of the stimulating ray K times in total where K is a positive integer, irradiating the stimulable phosphor layer region from which the digital data were obtained with the stimulating ray having excitation power greater than the reference excitation power to excite stimulable phosphor contained therein, photoelectrically detecting stimulated emission to produce analog data, integrating the analog data to produce an integrated value of the analog data and digitizing the integrated value of the analog data to produce digital data, storing the thus produced digital data in the digital memory, summing the digital data stored in the digital memory to produce summed digital data, and adopting the summed digital data as biochemical analysis data of the stimulable phosphor layer region.

According to this preferred aspect of the present invention, when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is equal to or higher than the threshold value, since the biochemical analysis data producing method further comprises the steps of storing the thus produced digital data in a digital memory, irradiating the stimulable phosphor layer region from which the digital data were obtained with the stimulating ray having excitation power greater than the reference excitation power to excite stimulable phosphor contained therein, photoelectrically detecting stimulated emission to produce analog data, integrating the analog data to produce an integrated value of the analog data and digitizing the integrated value of the analog data to produce digital data, storing the thus produced digital data in the digital memory, sequentially increasing the excitation power of the stimulating ray K times in total where K is a positive integer, irradiating the stimulable phosphor layer region from which the digital data were obtained with the stimulating ray having excitation power greater than the reference excitation power to excite stimulable phosphor contained therein, photoelectrically detecting stimulated emission to produce analog data, integrating the analog data to produce an integrated value of the analog data and digitizing the integrated value of the analog data to produce digital data, storing the thus produced digital data in the digital memory, summing the digital data stored in the digital memory to produce summed digital data, and adopting the summed digital data as biochemical analysis data of the stimulable phosphor layer region, even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data and even in the case where radiation energy or light energy stored in a stimulable phosphor layer region is small and the intensity of stimulated emission released from the stimulable phosphor layer region when stimulable phosphor contained therein is excited with the stimulating ray is small, it is possible to produce biochemical analysis data having high quantitative characteristics by substantially completely releasing radiation energy or light energy stored in a stimulable phosphor layer region in the form of stimulated emission and detecting the stimulated emission with very high sensitivity.

In a further preferred aspect of the present invention, the biochemical analysis data producing method further conducts the steps of, when the signal intensity of digital data produced by irradiating the stimulable phosphor layer region with the stimulating ray having the reference excitation power to excite stimulable phosphor contained therein, photoelectrically detecting stimulated emission released from the stimulable phosphor layer region to produce analog data, integrating the analog data to produce an integrated value of the analog data and digitizing the integrated value of the analog data is lower than the threshold value, irradiating the stimulable phosphor layer region from which the digital data were obtained with a stimulating ray having excitation power greater than the reference excitation power to excite stimulable phosphor contained therein, photoelectrically detecting stimulated emission released from the stimulable phosphor layer region to produce analog data, integrating the analog data to produce an integrated value of the analog data, digitizing the analog data to produce digital data, comparing the signal intensity of the thus produced digital data with the threshold value, sequentially increasing, when the signal intensity of the digital data is lower than the threshold value, the excitation power of the stimulating ray M times at maximum where M is a positive integer, irradiating the stimulable phosphor layer region from which the digital data were obtained with the stimulating ray to excite stimulable phosphor contained therein, photoelectrically detecting stimulated emission released from the stimulable phosphor layer region to produce analog data, integrating the analog data to produce an integrated value of the analog data, digitizing the analog data to produce digital data, comparing the signal intensity of the thus produced digital data with the threshold value, storing the digital data in the digital memory when the signal intensity of the digital data has become to be equal to or higher than the threshold value, further sequentially increasing the excitation power of the stimulating ray K times in total, irradiating the stimulable phosphor layer region from which the digital data were obtained with the stimulating ray to excite stimulable phosphor contained therein, photoelectrically detecting stimulated emission released from the stimulable phosphor layer region to produce analog data, integrating the analog data to produce an integrated value of the analog data, digitizing the analog data to produce digital data, storing the thus produced digital data in the digital memory, summing the digital data stored in the digital data, and adopting the thus summed digital data as biochemical analysis data of the stimulable phosphor layer region, or determining biochemical analysis data of the stimulable phosphor layer region to be zero when the signal intensity of the digital data is still lower than the threshold value even though the digital data were produced by sequentially increasing the excitation power of the stimulating ray M times in total, irradiating the stimulable phosphor layer region from which the digital data were obtained with the stimulating ray, photoelectrically detecting stimulated emission released from the stimulable phosphor layer region to produce analog data, integrating the analog data to produce an integrated value of the analog data and digitizing the integrated value of the analog data.

According to this preferred aspect of the present invention, since the biochemical analysis data producing method further conducts the steps of, when the signal intensity of digital data produced by irradiating the stimulable phosphor layer region with the stimulating ray having the reference excitation power to excite stimulable phosphor contained therein, photoelectrically detecting stimulated emission released from the stimulable phosphor layer region to produce analog data, integrating the analog data to produce an integrated value of the analog data and digitizing the integrated value of the analog data is lower than the threshold value, irradiating the stimulable phosphor layer region from which the digital data were obtained with a stimulating ray having excitation power greater than the reference excitation power to excite stimulable phosphor contained therein, photoelectrically detecting stimulated emission released from the stimulable phosphor layer region to produce analog data, integrating the analog data to produce an integrated value of the analog data, digitizing the analog data to produce digital data, comparing the signal intensity of the thus produced digital data with the threshold value, sequentially increasing, when the signal intensity of the digital data is lower than the threshold value, the excitation power of the stimulating ray M times at maximum where M is a positive integer, irradiating the stimulable phosphor layer region from which the digital data were obtained with the stimulating ray to excite stimulable phosphor contained therein, photoelectrically detecting stimulated emission released from the stimulable phosphor layer region to produce analog data, integrating the analog data to produce an integrated value of the analog data, digitizing the analog data to produce digital data, comparing the signal intensity of the thus produced digital data with the threshold value, storing the digital data in the digital memory when the signal intensity of the digital data has become to be equal to or higher than the threshold value, further sequentially increasing the excitation power of the stimulating ray K times in total, irradiating the stimulable phosphor layer region from which the digital data were obtained with the stimulating ray to excite stimulable phosphor contained therein, photoelectrically detecting stimulated emission released from the stimulable phosphor layer region to produce analog data, integrating the analog data to produce an integrated value of the analog data, digitizing the analog data to produce digital data, storing the thus produced digital data in the digital memory, summing the digital data stored in the digital data, and adopting the thus summed digital data as biochemical analysis data of the stimulable phosphor layer region, even in the case where radiation energy or light energy stored in a stimulable phosphor layer region is small and the intensity of stimulated emission released from the stimulable phosphor layer region when stimulable phosphor contained therein is excited with the stimulating ray is small, it is possible to produce biochemical analysis data having high quantitative characteristics by completely releasing radiation energy or light energy stored in a stimulable phosphor layer region in the form of stimulated emission and detecting the stimulated emission with very high sensitivity.

Moreover, according to this aspect of the present invention, since the biochemical analysis data producing method further conducts the step of determining biochemical analysis data of the stimulable phosphor layer region to be zero when the signal intensity of the digital data is still lower than the threshold value even though the digital data were produced by sequentially increasing the excitation power of the stimulating ray M times in total, irradiating the stimulable phosphor layer region from which the digital data were obtained with the stimulating ray, photoelectrically detecting stimulated emission released from the stimulable phosphor layer region to produce analog data, integrating the analog data to produce an integrated value of the analog data and digitizing the integrated value of the analog data, it is possible to prevent, by appropriately selecting M, unnecessary exciting operation from being repeated when no radiation energy or light energy is stored in the stimulable phosphor layer region, while biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small and it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large.

In a further preferred aspect of the present invention, the biochemical analysis data producing method further conducts the steps of, when the signal intensity of digital data produced by irradiating the stimulable phosphor layer region with the stimulating ray having the reference excitation power to excite stimulable phosphor contained therein, photoelectrically detecting stimulated emission released from the stimulable phosphor layer region to produce analog data, integrating the analog data to produce an integrated value of the analog data and digitizing the integrated value of the analog data is equal to or higher than the threshold value, storing the thus produced digital data in the digital memory, irradiating the stimulable phosphor layer region from which the digital data were obtained with a stimulating ray having excitation power greater than the reference excitation power to excite stimulable phosphor contained therein, photoelectrically detecting stimulated emission released from the stimulable phosphor layer region to produce analog data, integrating the analog data to produce an integrated value of the analog data, digitizing the analog data to produce digital data, storing the thus produced digital data in the digital memory, sequentially increasing the excitation power of the stimulating ray, irradiating the stimulable phosphor layer region from which the digital data were obtained with the stimulating ray having excitation power greater than the reference excitation power to excite stimulable phosphor contained therein, photoelectrically detecting stimulated emission released from the stimulable phosphor layer region to produce analog data, integrating the analog data to produce an integrated value of the analog data, digitizing the analog data to produce digital data, storing the thus produced digital data in the digital memory, summing the digital data stored in the digital memory so far to calculate summed digital data when the signal intensity of digital data produced by irradiating the stimulable phosphor layer region from which the digital data were obtained with the stimulating ray to excite stimulable phosphor contained therein, photoelectrically detecting stimulated emission released from the stimulable phosphor layer region to produce analog data, integrating the analog data to produce an integrated value of the analog data and digitizing the analog data cannot come to be equal to or higher than the threshold value even if the excitation power of the stimulating ray is increased, and adopting the summed digital data as biochemical analysis data of the stimulable phosphor layer region.

According to this preferred aspect of the present invention, since the biochemical analysis data producing method further conducts the steps of, when the signal intensity of digital data produced by irradiating the stimulable phosphor layer region with the stimulating ray having the reference excitation power to excite stimulable phosphor contained therein, photoelectrically detecting stimulated emission released from the stimulable phosphor layer region to produce analog data, integrating the analog data to produce an integrated value of the analog data and digitizing the integrated value of the analog data is equal to or higher than the threshold value, storing the thus produced digital data in the digital memory, irradiating the stimulable phosphor layer region from which the digital data were obtained with a stimulating ray having excitation power greater than the reference excitation power to excite stimulable phosphor contained therein, photoelectrically detecting stimulated emission released from the stimulable phosphor layer region to produce analog data, integrating the analog data to produce an integrated value of the analog data, digitizing the analog data to produce digital data, storing the thus produced digital data in the digital memory, sequentially increasing the excitation power of the stimulating ray, irradiating the stimulable phosphor layer region from which the digital data were obtained with the stimulating ray having excitation power greater than the reference excitation power to excite stimulable phosphor contained therein, photoelectrically detecting stimulated emission released from the stimulable phosphor layer region to produce analog data, integrating the analog data to produce an integrated value of the analog data, digitizing the analog data to produce digital data, storing the thus produced digital data in the digital memory, summing the digital data stored in the digital memory so far to calculate summed digital data when the signal intensity of digital data produced by irradiating the stimulable phosphor layer region from which the digital data were obtained with the stimulating ray to excite stimulable phosphor contained therein, photoelectrically detecting stimulated emission released from the stimulable phosphor layer region to produce analog data, integrating the analog data to produce an integrated value of the analog data and digitizing the analog data cannot come to be equal to or higher than the threshold value even if the excitation power of the stimulating ray is increased, and adopting the summed digital data as biochemical analysis data of the stimulable phosphor layer region, even in the case where radiation energy or light energy stored in a stimulable phosphor layer region is small and the intensity of stimulated emission released from the stimulable phosphor layer region when stimulable phosphor contained therein is excited with the stimulating ray is small, it is possible to produce biochemical analysis data having high quantitative characteristics by completely releasing radiation energy or light energy stored in a stimulable phosphor layer region in the form of stimulated emission and detecting the stimulated emission with very high sensitivity.

In a further preferred aspect of the present invention, when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is equal to or higher than the threshold value, the biochemical analysis data producing method further conducts the steps of storing the thus produced digital data in a digital memory, irradiating the stimulable phosphor layer region from which the digital data were obtained with a stimulating ray having excitation power greater than the reference excitation power to excite stimulable phosphor contained therein, photoelectrically detecting stimulated emission to produce analog data, integrating the analog data to produce an integrated value of the analog data and digitizing the integrated value of the analog data to produce digital data, comparing the signal intensity of the thus produced digital data with the threshold value, sequentially increasing, when the signal intensity of the digital data is lower than the threshold value, the excitation power of the stimulating ray N times at maximum where N is a positive integer, irradiating the stimulable phosphor layer region from which the digital data were obtained with the stimulating ray having excitation power greater than the reference excitation power to excite stimulable phosphor contained therein, photoelectrically detecting stimulated emission to produce analog data, integrating the analog data to produce an integrated value of the analog data and digitizing the integrated value of the analog data to produce digital data, storing, when the signal intensity of the thus produced digital data has come to be equal to or higher than the threshold value, the digital data in a digital memory, further sequentially increasing the excitation power of the stimulating ray, irradiating the stimulable phosphor layer region from which the digital data were obtained with the stimulating ray, to excite stimulable phosphor contained therein, photoelectrically detecting stimulated emission to produce analog data, integrating the analog data to produce an integrated value of the analog data and digitizing the integrated value of the analog data to produce digital data, summing the digital data to produce summed digital data, storing the thus summed digital data in the digital memory, calculating, when the signal intensity of the thus produced digital data cannot come to be equal to or higher than the threshold value even if the excitation power of the stimulating ray is increased, a total of the summed digital data stored in the digital memory so far to produce the total of the summed digital dada, and adopting the thus calculated total of the summed digital data as biochemical analysis data of the stimulable phosphor layer region, or determining digital data of the stimulable phosphor layer region to be zero when the signal intensity of the digital data is still lower than the threshold value even though the excitation power of the stimulating ray was sequentially increased N times in total to irradiate the stimulable phosphor layer region from which the digital data were obtained with the stimulating ray and stimulated emission released from the stimulable phosphor layer region was photoelectrically detected by the light detector.

According to this preferred aspect of the present invention, when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is equal to or higher than the threshold value, since the biochemical analysis data producing method further comprises the steps of storing the thus produced digital data in a digital memory, irradiating the stimulable phosphor layer region from which the digital data were obtained with the stimulating ray having excitation power greater than the reference excitation power to excite stimulable phosphor contained therein, photoelectrically detecting stimulated emission to produce analog data, integrating the analog data to produce an integrated value of the analog data and digitizing the integrated value of the analog data to produce digital data, comparing the signal intensity of the thus produced digital data with the threshold value, sequentially increasing, when the signal intensity of the digital data is lower than the threshold value, the excitation power of the stimulating ray N times at maximum where N is a positive integer, irradiating the stimulable phosphor layer region from which the digital data were obtained with the stimulating ray having excitation power greater than the reference excitation power to excite stimulable phosphor contained therein, photoelectrically detecting stimulated emission to produce analog data, integrating the analog data to produce an integrated value of the analog data and digitizing the integrated value of the analog data to produce digital data, storing, when the signal intensity of the thus produced digital data has come to be equal to or higher than the threshold value, the digital data in a digital memory, further sequentially increasing the excitation power of the stimulating ray, irradiating the stimulable phosphor layer region from which the digital data were obtained with the stimulating ray, to excite stimulable phosphor contained therein, photoelectrically detecting stimulated emission to produce analog data, integrating the analog data to produce an integrated value of the analog data and digitizing the integrated value of the analog data to produce digital data, summing the digital data to produce summed digital data, storing the thus summed digital data in the digital memory, calculating, when the signal intensity of the thus produced digital data cannot come to be equal to or higher than the threshold value even if the excitation power of the stimulating ray is increased, a total of the summed digital data stored in the digital memory so far to produce the total of the summed digital dada, and adopting the thus calculated total of the summed digital data as biochemical analysis data of the stimulable phosphor layer region, even in the case where radiation energy or light energy stored in a stimulable phosphor layer region is small and the intensity of stimulated emission released from the stimulable phosphor layer region when stimulable phosphor contained therein is excited with the stimulating ray is small, it is possible to produce biochemical analysis data having high quantitative characteristics by substantially completely releasing radiation energy or light energy stored in a stimulable phosphor layer region in the form of stimulated emission and detecting the stimulated emission with very high sensitivity.

Moreover, according to this preferred aspect of the present invention, since the biochemical analysis data producing method further comprises the step of determining digital data of the stimulable phosphor layer region to be zero when the signal intensity of the digital data is still lower than the threshold value even though the excitation power of the stimulating ray was sequentially increased N times in total to irradiate the stimulable phosphor layer region from which the digital data were obtained with the stimulating ray and stimulated emission released from the stimulable phosphor layer region was photoelectrically detected by the light detector, it is possible to prevent, by appropriately selecting N, unnecessary exciting operation from being repeated when no radiation energy or light energy is stored in the stimulable phosphor layer region, while biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small and it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large.

In a further preferred aspect of the present invention, digital data produced by irradiating the stimulable phosphor layer region with the stimulating ray having different excitation power to excite stimulable phosphor contained in the stimulable phosphor layer region, photoelectrically detecting stimulated emission released from the stimulable phosphor to produce analog data, integrating the analog data to produce an integrated value of the analog data and digitizing the integrated value of the analog data is multiplied by a correction coefficient determined in accordance with the excitation power of the stimulating ray projected onto the stimulable phosphor layer region, thereby producing biochemical analysis data of the stimulable phosphor layer region.

According to this preferred aspect of the present invention, since digital data produced by irradiating the stimulable phosphor layer region with the stimulating ray having different excitation power to excite stimulable phosphor contained in the stimulable phosphor layer region, photoelectrically detecting stimulated emission released from the stimulable phosphor to produce analog data, integrating the analog data to produce an integrated value of the analog data and digitizing the integrated value of the analog data is multiplied by a correction coefficient determined in accordance with the excitation power of the stimulating ray projected onto the stimulable phosphor layer region, thereby producing biochemical analysis data of the stimulable phosphor layer region, even if the excitation power of the stimulating ray is increased to be greater than the reference excitation power and stimulable phosphor contained in the stimulable phosphor layer region is excited in order to detect stimulated emission with high sensitivity or release all detectable radiation energy or light energy stored in the stimulable phosphor layer region in the form of stimulated emission and detect stimulated emission, it is possible to produce biochemical analysis data having signal intensity corresponding to radiation energy or light energy stored in the stimulable phosphor layer region.

In a further preferred aspect of the present invention, the correction coefficient for each excitation power is determined so that digital data corresponding to the excitation power can be corrected to have the same level as that of digital data to be produced using the stimulating ray having the reference excitation power.

In a further preferred aspect of the present invention, the summed digital data produced by irradiating the stimulable phosphor layer region with a stimulating ray having different excitation power to excite stimulable phosphor contained in the stimulable phosphor layer region, photoelectrically detecting stimulated emission released from the stimulable phosphor to produce analog data, integrating the analog data to produce an integrated value of the analog data, digitizing the integrated value of the analog data to produce digital data and summing the digital data is multiplied by a correction coefficient determined in accordance with the excitation power of the stimulating ray projected onto the stimulable phosphor layer region to correct the summed digital data and biochemical analysis data of the stimulable phosphor layer region are produced by calculating a total of the thus corrected summed digital data.

According to this preferred aspect of the present invention, since the summed digital data produced by irradiating the stimulable phosphor layer region with the stimulating ray having different excitation power to excite stimulable phosphor contained in the stimulable phosphor layer region, photoelectrically detecting stimulated emission released from the stimulable phosphor to produce analog data, integrating the analog data to produce an integrated value of the analog data, digitizing the integrated value of the analog data to produce digital data and summing the digital data is multiplied by a correction coefficient determined in accordance with the excitation power of the stimulating ray projected onto the stimulable phosphor layer region to correct the summed digital data and biochemical analysis data of the stimulable phosphor layer region are produced by calculating a total of the thus corrected summed digital data, even if the excitation power of the stimulating ray is increased to be greater than the reference excitation power and stimulable phosphor contained in the stimulable phosphor layer region in order to detect stimulated emission with high sensitivity or release all detectable radiation energy or light energy stored in the stimulable phosphor layer region in the form of stimulated emission and detect stimulated emission, it is possible to produce biochemical analysis data having signal intensity corresponding to radiation energy or light energy stored in the stimulable phosphor layer region.

In a further preferred aspect of the present invention, the correction coefficient for each excitation power is determined so that the summed digital data corresponding to the excitation power are corrected to have the same level as that of summed digital data to be produced using the stimulating ray having the reference excitation power.

In a preferred aspect of the present invention, the excitation power of the stimulating ray is increased by an increment $\Delta P$ when the excitation power of the stimulating ray is to be increased.

In another preferred aspect of the present invention, the excitation power of the stimulating ray is increased by an increment $\Delta P$ when the excitation power of the stimulating ray is to be increased and the increment $\Delta P$ is controlled to be increased every time the excitation power of the stimulating ray is to be increased.

In another preferred aspect of the present invention, the excitation power of the stimulating ray is increased by an increment $\Delta P$ when the excitation power of the stimulating ray is to be increased and the increment $\Delta P$ is controlled to be decreased every time the excitation power of the stimulating ray is to be increased.

In a preferred aspect of the present invention, the biochemical analysis data producing method further comprises the steps of intermittently moving the stimulable phosphor sheet and the stimulating ray relative to each other at least one-dimensionally, sequentially irradiating the plurality of stimulable phosphor layer regions with the stimulating ray for a predetermined time and increasing the excitation power of the stimulating ray with the lapse of time to excite stimulable phosphor contained in the individual stimulable phosphor layer regions.

In the case where stimulable phosphor contained in the stimulable phosphor layer region formed in the support of the stimulable phosphor sheet is excited with a stimulating ray whose excitation power is held constant, since an amount of stimulated emission detected by the light detector is too large and exceeds the upper limit of the dynamic range of the light detector immediately after the stimulable phosphor layer region is irradiated with the stimulating ray and, on the other hand, the amount of stimulated emission released from the stimulable phosphor layer region drastically decreases with the lapse of time, it is extremely difficult to photoelectrically detect stimulated emission with high sensitivity. However, according to this preferred aspect of the present invention, since the excitation power of the stimulating ray is controlled so as to be increased with the lapse of time, it is possible to reliably prevent the amount of stimulated emission released from stimulable phosphor contained in the stimulable phosphor layer region in response to the excitation with the stimulating ray from exceeding the upper limit of the dynamic range of the light detector and biochemical analysis data having high quantitative characteristics can be produced by photoelectrically detecting stimulated emission with high sensitivity.

In a further preferred aspect of the present invention, the excitation power of the stimulating ray is controlled so as to be increased with the lapse of time in accordance with an exponential function.

In the case where stimulable phosphor contained in the stimulable phosphor layer region formed in the support of the stimulable phosphor sheet is excited with a stimulating ray whose excitation power is held constant, since the amount of stimulated emission detected by the light detector is too large and exceeds the upper limit of the dynamic range of the light detector immediately after the stimulable phosphor layer region is irradiated with the stimulating ray and, on the other hand, the amount of stimulated emission released from the stimulable phosphor layer region drastically decreases with the lapse of time, it is extremely difficult to photoelectrically detect stimulated emission with high sensitivity. However, according to this preferred aspect of the present invention, since the excitation power of the stimulating ray is controlled so as to be increased with the lapse of time in accordance with an exponential function, it is possible to reliably prevent an amount of stimulated emission released from stimulable phosphor contained in the stimulable phosphor layer region in response to the excitation with the stimulating ray from exceeding the upper limit of the dynamic range of the light detector and biochemical analysis data having high quantitative characteristics can be produced by photoelectrically detecting stimulated emission with high sensitivity.

In a further preferred aspect of the present invention, the biochemical analysis data producing method further conducts the steps of photoelectrically detecting stimulated emission released from the stimulable phosphor layer region to produce analog data and counting the number of photons contained in the stimulated emission based on the thus produced analog data, thereby producing biochemical analysis data of the stimulable phosphor layer region.

In a further preferred aspect of the present invention, the stimulating ray is on and off controlled in such a manner that only the plurality of stimulable phosphor layer regions are irradiated with the stimulating ray and regions other than the plurality of stimulable phosphor layer regions are not irradiated with the stimulating ray.

According to this preferred aspect of the present invention, since the stimulating ray is on and off controlled in such a manner that only the plurality of stimulable phosphor layer regions are irradiated with the stimulating ray and regions other than the plurality of stimulable phosphor layer regions are not irradiated with the stimulating ray, it is possible to reliably prevent the stimulating ray from entering a neighboring stimulable phosphor layer region to be next stimulated as the stimulating ray is scanned and thus prevent stimulable phosphor contained in the neighboring stimulable phosphor layer region from being excited to release radiation energy or light energy stored therein, and, therefore, biochemical analysis data having an excellent quantitative characteristic can be produced in a desired manner.

In a further preferred aspect of the present invention, the stimulable phosphor sheet and the stimulating ray are intermittently moved relative to each other in the main scanning direction by a pitch equal to a distance between neighboring stimulable phosphor layer regions in the main scanning direction.

In another preferred aspect of the present invention, the stimulable phosphor sheet is constantly irradiated with the stimulating ray while the stimulable phosphor sheet and the stimulating ray are intermittently moved relative to each other in the main scanning direction.

According to this preferred aspect of the present invention, although the stimulable phosphor sheet is constantly irradiated with the stimulating ray, since the stimulable phosphor sheet and the stimulating ray are intermittently moved relative to each other in the main scanning direction, it is possible to reliably prevent the stimulating ray from entering a neighboring stimulable phosphor layer region to be next stimulated as the stimulating ray is scanned and thus prevent stimulable phosphor contained in the neighboring stimulable phosphor layer region from being excited to release radiation energy or light energy stored therein, and, therefore, biochemical analysis data having an excellent quantitative characteristic can be produced in a desired manner.

In another preferred aspect of the present invention, the stimulable phosphor sheet and the stimulating ray are continuously moved relative to each other in the main scanning direction and the stimulating ray is on and off controlled in such a manner that substantially only the plurality of stimulable phosphor layer regions are irradiated with the stimulating ray and regions other than the plurality of stimulable phosphor layer regions are not irradiated with the stimulating ray.

According to this preferred aspect of the present invention, although the stimulable phosphor sheet and the stimulating ray are continuously moved relative to each other in the main scanning direction, since the stimulating ray is on and off controlled in such a manner that substantially only the plurality of stimulable phosphor layer regions are irradiated with the stimulating ray and regions other than the plurality of stimulable phosphor layer regions are not irradiated with the stimulating ray, it is possible to reliably prevent the stimulating ray from entering a neighboring stimulable phosphor layer region to be next stimulated as the stimulating ray is scanned and thus prevent stimulable phosphor contained in the neighboring stimulable phosphor layer region from being excited to release radiation energy or light energy stored therein, and, therefore, biochemical analysis data having an excellent quantitative characteristic can be produced in a desired manner.

In a preferred aspect of the present invention, the plurality of stimulable phosphor layer regions of the stimulable phosphor sheet are two-dimensionally formed in the support so as to be spaced apart from each other and the biochemical analysis data producing method comprises the steps of moving the stimulable phosphor sheet and the stimulating ray relative to each other in the main scanning direction and a sub-scanning direction perpendicular to the main scanning direction, sequentially irradiating the plurality of stimulable phosphor layer regions with the stimulating ray to excite stimulable phosphor contained in the individual stimulable phosphor layer regions, and photoelectrically detecting stimulated emission released from the individual stimulable phosphor layer regions, thereby producing biochemical analysis data.

According to this preferred aspect of the present invention, the plurality of stimulable phosphor layer regions can be formed in the stimulable phosphor sheet at high density and biochemical analysis data can be efficiently produced.

In a further preferred aspect of the present invention, a laser beam is used as the stimulating ray and the stimulable phosphor sheet and the laser beam are moved relative to each other in the main scanning direction and a sub-scanning direction perpendicular to the main scanning direction so that the plurality of stimulable phosphor layer regions are sequentially irradiated with the laser beam, thereby exciting stimulable phosphor contained in the plurality of stimulable phosphor layer regions.

In a further preferred aspect of the present invention, the stimulable phosphor sheet is moved in the main scanning direction.

In another preferred aspect of the present invention, the stimulating ray is moved in the main scanning direction.

The above and other objects of the present invention can be also accomplished by a scanner comprising a stimulating ray source for emitting a stimulating ray, a sample stage on which a stimulable phosphor sheet including a plurality of stimulable phosphor layer regions formed spaced apart from each other and selectively storing radiation energy or light energy is to be placed, an irradiation optical system for directing the stimulating ray emitted from the stimulating ray source toward the sample stage, a scanning mechanism for moving the irradiation optical system and the sample stage relative to each other in at least a main scanning direction so that the plurality of stimulable phosphor layer regions are sequentially irradiated with the stimulating ray emitted from the stimulating ray source, a light detector for photoelectrically detecting stimulated emission released from the plurality of stimulable phosphor layer regions of the stimulable phosphor sheet upon being stimulated by the stimulating ray emitted from the stimulating ray source and directed toward the sample stage by the scanning mechanism, stimulation control means for controlling the stimulating ray source and the scanning mechanism, and position detecting means for detecting relative positional relationship in the main scanning direction between the irradiation optical system and the sample stage, the stimulation control means being constituted so as to control the irradiation optical system and the stimulating ray source based on the relative positional relationship in the main scanning direction between the irradiation optical system and the sample stage so that energy of the stimulating ray projected onto the plurality of stimulable phosphor layer regions per unit area is higher than that projected on regions other than the plurality of stimulable phosphor layer regions.

According to this aspect of the present invention, since a scanner includes a stimulating ray source for emitting a stimulating ray, a sample stage on which a stimulable phosphor sheet including a plurality of stimulable phosphor layer regions formed spaced apart from each other and selectively storing radiation energy or light energy is to be placed, an irradiation optical system for directing the stimulating ray emitted from the stimulating ray source toward the sample stage, a scanning mechanism for moving the irradiation optical system and the sample stage relative to each other in at least a main scanning direction so that the plurality of stimulable phosphor layer regions are sequentially irradiated with the stimulating ray emitted from the stimulating ray source, a light detector for photoelectrically detecting stimulated emission released from the plurality of stimulable phosphor layer regions of the stimulable phosphor sheet upon being stimulated by the stimulating ray emitted from the stimulating ray source and directed toward the sample stage by the scanning mechanism, stimulation control means for controlling the stimulating ray source and the scanning mechanism, and position detecting means for detecting relative positional relationship in the main scanning direction between the irradiation optical system and the sample stage, and the stimulation control means is constituted so as to control the irradiation optical system and the stimulating ray source based on the relative positional relationship in the main scanning direction between the irradiation optical system and the sample stage so that energy of the stimulating ray projected onto the plurality of stimulable phosphor layer regions per unit area is higher than that projected on regions other than the plurality of stimulable phosphor layer regions, it is possible to effectively prevent the stimulating ray from entering a neighboring stimulable phosphor layer region to be next stimulated as the stimulating ray is scanned and thus prevent stimulable phosphor contained in the neighboring stimulable phosphor layer region from being excited to release radiation energy or light energy stored therein, and, therefore, biochemical analysis data having an excellent quantitative characteristic can be produced in a desired manner.

In a preferred aspect of the present invention, the scanning mechanism is constituted so as to move the irradiation optical system and the sample stage relative to each other in the main scanning direction and a sub-scanning direction perpendicular to the main scanning direction.

According to this preferred aspect of the present invention, since the scanning mechanism is constituted so as to move the irradiation optical system and the sample stage relative to each other in the main scanning direction and a sub-scanning direction perpendicular to the main scanning direction, biochemical analysis data can be efficiently produced.

In a preferred aspect of the present invention, the stimulation control means is constituted so as to control the scanning mechanism so that it intermittently moves the irradiation optical system and the sample stage relative to each other in the main scanning direction and to control the stimulating ray source so that each of the plurality of stimulable phosphor layer regions is irradiated with the stimulating ray for a predetermined time.

According to this preferred aspect of the present invention, since the stimulation control means is constituted so as to control the scanning mechanism so that it intermittently moves the irradiation optical system and the sample stage relative to each other in the main scanning direction and to control the stimulating ray source so that each of the plurality of stimulable phosphor layer regions is irradiated with the stimulating ray for a predetermined time, it is possible to effectively prevent the stimulating ray from entering a neighboring stimulable phosphor layer region to be next stimulated as the stimulating ray is scanned and thus prevent stimulable phosphor contained in the neighboring stimulable phosphor layer region from being excited to release radiation energy or light energy stored therein, and, therefore, biochemical analysis data having an excellent quantitative characteristic can be produced in a desired manner.

In a preferred aspect of the present invention, the scanner further comprises an integrating amplifier for integrating analog data produced by photoelectrically detecting stimulated emission by the light detector and an A/D converter for digitizing an integrated value of the analog data produced by the integrating amplifier to produce digital data.

According to this preferred aspect of the present invention, since the scanner further comprises an integrating amplifier for integrating analog data produced by photoelectrically detecting stimulated emission by the light detector and an A/D converter for digitizing an integrated value of the analog data produced by the integrating amplifier to produce digital data, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced with high sensitivity.

In another preferred aspect of the present invention, the scanner further comprises an A/D converter for digitizing analog data produced by photoelectrically detecting stimulated emission by the light detector to produce digital data and a summing means for summing the digital data produced by the A/D converter.

According to this preferred aspect of the present invention, since the scanner further comprises an A/D converter for digitizing analog data produced by photoelectrically detecting stimulated emission by the light detector to produce digital data and a summing means for summing the digital data produced by the A/D converter, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced with high sensitivity.

In a preferred aspect of the present invention, the scanner further comprises an A/D converter for digitizing analog data produced by the light detector to produce digital data and a signal intensity determining means for comparing signal intensity of digital data produced by the A/D converter with a threshold value and adopting the digital data as biochemical analysis data of the stimulable phosphor layer region in accordance with the result of the comparison, the stimulation control means being adapted for controlling the stimulating ray source so as to first emit a stimulating ray having reference excitation power which is relatively low and increasing the excitation power of the stimulating ray emitted from the stimulating ray source when an excitation power increasing signal is input from the signal intensity determining means, the signal intensity determining means being constituted so as to output the excitation power increasing signal to the stimulating controlling means when it determines that the signal intensity of digital data produced by photoelectrically detecting stimulated emission released from stimulable phosphor contained in the stimulable phosphor layer region in response to the excitation with the stimulating ray by the light detector to produce analog data and digitizing the analog data by the A/D converter is lower than the threshold value.

According to this preferred aspect of the present invention, since the scanner further comprises an A/D converter for digitizing analog data produced by the light detector to produce digital data and a signal intensity determining means for comparing signal intensity of digital data produced by the A/D converter with a threshold value and adopting the digital data as biochemical analysis data of the stimulable phosphor layer region in accordance with the result of the comparison, the stimulation control means being adapted for controlling the stimulating ray source so as to first emit a stimulating ray having reference excitation power which is relatively low and increasing excitation power of a stimulating ray emitted from the stimulating ray source when an excitation power increasing signal is input from the signal intensity determining means, the signal intensity determining means being constituted so as to output the excitation power increasing signal to the stimulating controlling means when it determines that the signal intensity of digital data produced by photoelectrically detecting stimulated emission released from stimulable phosphor contained in the stimulable phosphor layer region in response to the excitation with the stimulating ray by the light detector to produce analog data and digitizing the analog data by the A/D converter is lower than the threshold value, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced by detecting stimulated emission with high sensitivity.

In a further preferred aspect of the present invention, the signal intensity determining means is constituted so as to adopt digital data as biochemical analysis data of the stimulable phosphor layer region when it determines that the signal intensity of the digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is equal to or higher than the threshold value.

According to this preferred aspect of the present invention, since the signal intensity determining means is constituted so as to adopt digital data as biochemical analysis data of the stimulable phosphor layer region when it determines that the signal intensity of the digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is equal to or higher than the threshold value, even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data.

In a further preferred aspect of the present invention, when the excitation power increasing signal is output from the signal intensity determining means to the stimulating controlling means, the signal intensity determining means adopts as biochemical analysis data of the stimulable phosphor layer region digital data produced by exciting stimulable phosphor contained in the stimulable phosphor layer region from which the digital data were obtained with the stimulating ray having excitation power greater than the reference excitation power, photoelectrically detecting stimulated emission released from the stimulable phosphor to produce analog data and digitizing the analog data by the A/D converter.

According to this preferred aspect of the present invention, when the excitation power increasing signal is output from the signal intensity determining means to the stimulating controlling means, since the signal intensity determining means is constituted so as to adopt as biochemical analysis data of the stimulable phosphor layer region digital data produced by exciting stimulable phosphor contained in the stimulable phosphor layer region with the stimulating ray having excitation power greater than the reference excitation power, photoelectrically detecting stimulated emission released from the stimulable phosphor to produce analog data and digitizing the analog data by the A/D converter, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced by detecting stimulated emission with high sensitivity.

In a further preferred aspect of the present invention, when the excitation power increasing signal is output from the signal intensity determining means to the stimulating controlling means and the signal intensity determining means determines that the signal intensity of digital data produced by exciting stimulable phosphor contained in the stimulable phosphor layer region from which the digital data were obtained with the stimulating ray having excitation power greater than the reference excitation power, photoelectrically detecting stimulated emission released from the stimulable phosphor to produce analog data and digitizing the analog data by the A/D converter is equal to or higher than the threshold value, the signal intensity determining means adopts the digital data as biochemical analysis data of the stimulable phosphor layer region.

According to this preferred aspect of the present invention, when the excitation power increasing signal is output from the signal intensity determining means to the stimulating controlling means and the signal intensity determining means determines that the signal intensity of digital data produced by exciting stimulable phosphor contained in the stimulable phosphor layer region from which the digital data were obtained with the stimulating ray having excitation power greater than the reference excitation power, photoelectrically detecting stimulated emission released from the stimulable phosphor to produce analog data and digitizing the analog data by the A/D converter is equal to or higher than the threshold value, since the signal intensity determining means is constituted so as to adopt the digital data as biochemical analysis data of the stimulable phosphor layer region, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced by detecting stimulated emission with high sensitivity.

In a further preferred aspect of the present invention, when the excitation power increasing signal is output from the signal intensity determining means to the stimulating controlling means and the signal intensity determining means determines that the signal intensity of digital data produced by exciting stimulable phosphor contained in the stimulable phosphor layer region from which the digital data were obtained with the stimulating ray having excitation power greater than the reference excitation power, photoelectrically detecting stimulated emission released from the stimulable phosphor to produce analog data and digitizing the analog data by the A/D converter is lower than the threshold value, the signal intensity determining means sequentially outputs the excitation power increasing signal to the stimulation control means i times at maximum where i is a positive integer, thereby sequentially increasing the excitation power of the stimulating ray emitted from the stimulating ray source and adopts, when it determines that digital data produced by exciting stimulable phosphor contained in the stimulable phosphor layer region from which the digital data were obtained with the stimulating ray having excitation power greater than the reference excitation power, photoelectrically detecting stimulated emission released from the stimulable phosphor to produce analog data and digitizing the analog data by the A/D converter has come to be equal to or higher than the threshold value, the digital data as biochemical analysis data of the stimulable phosphor layer region, or determines biochemical analysis data of the stimulable phosphor layer region to be zero when it determines that the signal intensity of the digital data is still lower than the threshold value even though it output the excitation power increasing signal to the stimulation control means i times in total, thereby sequentially increasing the excitation power of the stimulating ray to irradiate the stimulable phosphor layer region from which the digital data were obtained with the stimulating ray and stimulated emission released from the stimulable phosphor layer region was photoelectrically detected by the light detector.

According to this preferred aspect of the present invention, when the excitation power increasing signal is output from the signal intensity determining means to the stimulating controlling means and the signal intensity determining means determines that the signal intensity of digital data produced by exciting stimulable phosphor contained in the stimulable phosphor layer region from which the digital data were obtained with the stimulating ray having excitation power greater than the reference excitation power, photoelectrically detecting stimulated emission released from the stimulable phosphor to produce analog data and digitizing the analog data by the A/D converter is lower than the threshold value, since the signal intensity determining means is constituted so as to sequentially output the excitation power increasing signal to the stimulation control means i times at maximum where i is a positive integer, thereby sequentially increasing the excitation power of the stimulating ray emitted from the stimulating ray source and adopt, when it determines that digital data produced by exciting stimulable phosphor contained in the stimulable phosphor layer region from which the digital data were obtained with the stimulating ray having excitation power greater than the reference excitation power, photoelectrically detecting stimulated emission released from the stimulable phosphor to produce analog data and digitizing the analog data by the A/D converter has come to be equal to or higher than the threshold value, the digital data as biochemical analysis data of the stimulable phosphor layer region, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be reliably produced by detecting the stimulated emission with high sensitivity and even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data.

Moreover, according to this preferred aspect of the present invention, since the signal intensity determining means is further constituted so as to determine biochemical analysis data of the stimulable phosphor layer region to be zero when it determines that the signal intensity of the digital data is still lower than the threshold value even though it output the excitation power increasing signal to the stimulation control means i times in total, thereby sequentially increasing the excitation power of the stimulating ray to irradiate the stimulable phosphor layer region from which the digital data were obtained with the stimulating ray and stimulated emission released from the stimulable phosphor layer region was photoelectrically detected by the light detector, it is possible to prevent, by appropriately selecting I, unnecessary exciting operation from being repeated when no radiation energy or light energy is stored in the stimulable phosphor layer region, while biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small and it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large.

In a further preferred aspect of the present invention, the scanner further comprises a digital memory and when the signal intensity determining means determines that the signal intensity of digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is equal to or higher than the threshold value, the stimulation control means continues to drive the stimulating ray source until the signal intensity of digital data produced by exciting the stimulable phosphor contained in the stimulable phosphor layer region with the stimulating ray having the reference excitation power, photoelectrically detecting stimulated emission released from stimulable phosphor contained in the stimulable phosphor layer region to produce analog data and digitizing the analog data has come to be lower than the threshold value and the signal intensity determining means sums digital data produced by exciting the stimulable phosphor contained in the stimulable phosphor layer region with the stimulating ray having the reference excitation power, photoelectrically detecting stimulated emission released from stimulable phosphor contained in the stimulable phosphor layer region to produce analog data and digitizing the analog data, stores the summed digital data in the digital memory and adopts the summed digital data stored in the digital memory as biochemical analysis data of the stimulable phosphor layer region when it determines that the signal intensity of digital data has come to be lower than the threshold value.

According to this preferred aspect of the present invention, since the scanner further comprises a digital memory and when the signal intensity determining means determines that the signal intensity of digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is equal to or higher than the threshold value, the stimulation control means continues to drive the stimulating ray source until the signal intensity of digital data produced by exciting the stimulable phosphor contained in the stimulable phosphor layer region with the stimulating ray having the reference excitation power, photoelectrically detecting stimulated emission released from stimulable phosphor contained in the stimulable phosphor layer region to produce analog data and digitizing the analog data has come to be lower than the threshold value and the signal intensity determining means is constituted so as to sum digital data produced by exciting the stimulable phosphor contained in the stimulable phosphor layer region with the stimulating ray having the reference excitation power, photoelectrically detecting stimulated emission released from stimulable phosphor contained in the stimulable phosphor layer region to produce analog data and digitizing the analog data, stores the summed digital data in the digital memory and adopts the summed digital data stored in the digital memory as biochemical analysis data of the stimulable phosphor layer region when it determines that the signal intensity of digital data has come to be lower than the threshold value, radiation energy or light energy stored in the stimulable phosphor layer region can be sufficiently released and even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be reliably produced by detecting the stimulated emission with high sensitivity.

In a further preferred aspect of the present invention, when the excitation power increasing signal is output from the signal intensity determining means to the stimulating controlling means and the signal intensity determining means determines that the signal intensity of digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is lower than the threshold value, the signal intensity determining means sequentially outputs the excitation power increasing signal to the stimulation control means j times at maximum where j is a positive integer, thereby sequentially increasing the excitation power of the stimulating ray emitted from the stimulating ray source, to cause, when it determines that the signal intensity of digital data produced by exciting stimulable phosphor contained in the stimulable phosphor layer region from which the digital data were obtained with the stimulating ray having excitation power greater than the reference excitation power, photoelectrically detecting stimulated emission released from the stimulable phosphor to produce analog data and digitizing the analog data by the A/D converter has come to be equal to or higher than the threshold value, the stimulating controlling means to continue to drive the stimulating ray source until it determines that the signal intensity of digital data produced by exciting stimulable phosphor contained in the stimulable phosphor layer region from which the digital data were obtained with the stimulating ray having excitation power greater than the reference excitation power, photoelectrically detecting stimulated emission released from the stimulable phosphor to produce analog data and digitizing the analog data by the A/D converter has come to be lower than the threshold value, to sum digital data produced by exciting stimulable phosphor contained in the stimulable phosphor layer region with the stimulating ray, photoelectrically detecting stimulated emission released from the stimulable phosphor to produce analog data and digitizing the analog data to produce summed digital data, to store the summed digital data in the digital memory, and to adopt the summed digital data stored in the digital memory as biochemical analysis data of the stimulable phosphor layer region when it determines that the signal intensity of digital data has come to be lower than the threshold value, or to determine biochemical analysis data of the stimulable phosphor layer region to be zero when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data cannot be equal to or higher than the threshold value even though it output the exciting power increasing signal to the stimulation control means j times to cause the stimulation control means to increase the excitation power of the stimulating ray emitted from the stimulating ray source.

According to this preferred aspect of the present invention, when the excitation power increasing signal is output from the signal intensity determining means to the stimulating controlling means and the signal intensity determining means determines that the signal intensity of digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is lower than the threshold value, since the signal intensity determining means is constituted so as to sequentially output the excitation power increasing signal to the stimulation control means j times at maximum where j is a positive integer, thereby sequentially increasing the excitation power of the stimulating ray emitted from the stimulating ray source, to cause, when it determines that the signal intensity of digital data produced by exciting stimulable phosphor contained in the stimulable phosphor layer region from which the digital data were obtained with the stimulating ray having excitation power greater than the reference excitation power, photoelectrically detecting stimulated emission released from the stimulable phosphor to produce analog data and digitizing the analog data by the A/D converter has come to be equal to or higher than the threshold value, the stimulating controlling means to continue to drive the stimulating ray source until it determines that the signal intensity of digital data produced by exciting stimulable phosphor contained in the stimulable phosphor layer region from which the digital data were obtained with the stimulating ray having excitation power greater than the reference excitation power, photoelectrically detecting stimulated emission released from the stimulable phosphor to produce analog data and digitizing the analog data by the A/D converter has come to be lower than the threshold value, to sum digital data produced by exciting stimulable phosphor contained in the stimulable phosphor layer region with the stimulating ray, photoelectrically detecting stimulated emission released from the stimulable phosphor to produce analog data and digitizing the analog data to produce summed digital data, to store the summed digital data in the digital memory, and to adopt the summed digital data stored in the digital memory as biochemical analysis data of the stimulable phosphor layer region when it determines that the signal intensity of digital data has come to be lower than the threshold value, radiation energy or light energy stored in the stimulable phosphor layer region can be sufficiently released and even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be reliably produced by detecting the stimulated emission with high sensitivity.

Moreover, according to this preferred aspect of the present invention, since the signal intensity determining means is further constituted so as to determine biochemical analysis data of the stimulable phosphor layer region to be zero when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data cannot be equal to or higher than the threshold value even though it output the exciting power increasing signal to the stimulation control means j times to cause the stimulation control means to increase the excitation power of the stimulating ray emitted from the stimulating ray source, it is possible to prevent, by appropriately selecting j, unnecessary exciting operation from being repeated when no radiation energy or light energy is stored in the stimulable phosphor layer region, while biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small and it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large.

In a further preferred aspect of the present invention, the signal intensity determining means is constituted so as to cause, when it determines that the signal intensity of the digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is equal to or higher than the threshold value, the stimulation control means to continue to drive the stimulating ray source until the signal intensity of the digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter has come to be lower than the threshold value, to sum digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter to produce summed digital data, to store the summed digital data in the digital memory, to output, when it determines that the signal intensity of the digital data has come to be lower than the threshold value, the excitation power increasing signal to the stimulation control means k times at maximum where k is a positive integer, thereby increasing the excitation power of the stimulating ray emitted from the stimulating ray source, to sum digital data produced by exciting stimulable phosphor contained in the stimulable phosphor layer region with the stimulating ray having the respective excitation powers, photoelectrically detecting stimulated emission released from the stimulable phosphor to produce analog data and digitizing the analog data by the A/D converter to produce summed digital data and store the summed digital data in the digital memory until it determines that the signal intensity of the digital data has come to be lower than the threshold value, to calculate a total of the summed digital data stored in the digital memory, and to adopt the thus calculated total of the summed digital data as biochemical analysis data of the stimulable phosphor layer region.

According to this preferred aspect of the present invention, since the signal intensity determining means is constituted so as to cause, when it determines that the signal intensity of the digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is equal to or higher than the threshold value, the stimulation control means to continue to drive the stimulating ray source until the signal intensity of the digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter has come to be lower than the threshold value, to sum digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter to produce summed digital data, to store the summed digital data in the digital memory, to output, when it determines that the signal intensity of the digital data has come to be lower than the threshold value, the excitation power increasing signal to the stimulation control means k times at maximum where k is a positive integer, thereby increasing the excitation power of the stimulating ray emitted from the stimulating ray source, to sum digital data produced by exciting stimulable phosphor contained in the stimulable phosphor layer region with the stimulating ray having the respective excitation powers, photoelectrically detecting stimulated emission released from the stimulable phosphor to produce analog data and digitizing the analog data by the A/D converter to produce summed digital data and store the summed digital data in the digital memory until it determines that the signal intensity of the digital data has come to be lower than the threshold value, to calculate a total of the summed digital data stored in the digital memory, and to adopt the thus calculated total of the summed digital data as biochemical analysis data of the stimulable phosphor layer region, even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data and even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced by detecting stimulated emission with high sensitivity.

In a further preferred aspect of the present invention, when the excitation power increasing signal is output from the signal intensity determining means to the stimulating controlling means and the signal intensity determining means determines that the signal intensity of digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is lower than the threshold value, the signal intensity determining means sequentially outputs the excitation power increasing signal to the stimulation control means m times at maximum where m is a positive integer, thereby sequentially increasing the excitation power of the stimulating ray emitted from the stimulating ray source, to cause, when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data by the A/D converter has come to be equal to or higher than the threshold value, the stimulating controlling means to continue to drive the stimulating ray source until it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data by the A/D converter has come to be lower than the threshold value, to sum digital data produced by exciting stimulable phosphor contained in the stimulable phosphor layer region with the stimulating ray, photoelectrically detecting stimulated emission released from the stimulable phosphor to produce analog data and digitizing the analog data to produce summed digital data, to store the summed digital data in the digital memory, to output, when it determines that the signal intensity of digital data has come to be lower than the threshold value, the excitation power increasing signal to the stimulation control means k times in total, thereby increasing the excitation power of the stimulating ray emitted from the stimulating ray source, to sum digital data produced by exciting stimulable phosphor contained in the stimulable phosphor layer region with the stimulating ray, photoelectrically detecting stimulated emission released from the stimulable phosphor to produce analog data and digitizing the analog data to produce summed digital data and store the summed digital data in the digital memory until the signal intensity of the digital data has come to be lower than the threshold value, to calculate a total of the summed digital data stored in the digital memory and to adopt the thus calculated total of the summed digital data as biochemical analysis data of the stimulable phosphor layer region, or to determine biochemical analysis data of the stimulable phosphor layer region to be zero when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data cannot be equal to or higher than the threshold value even though it output the exciting power increasing signal to the stimulation control means m times in total to cause the stimulation control means to increase the excitation power of the stimulating ray emitted from the stimulating ray source.

According to this preferred aspect of the present invention, when the excitation power increasing signal is output from the signal intensity determining means to the stimulating controlling means and the signal intensity determining means determines that the signal intensity of digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is lower than the threshold value, since the signal intensity determining means sequentially outputs the excitation power increasing signal to the stimulation control means m times at maximum where m is a positive integer, thereby sequentially increasing the excitation power of the stimulating ray emitted from the stimulating ray source, to cause, when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data by the A/D converter has come to be equal to or higher than the threshold value, the stimulating controlling means to continue to drive the stimulating ray source until it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data by the A/D converter has come to be lower than the threshold value, to sum digital data produced by exciting stimulable phosphor contained in the stimulable phosphor layer region with the stimulating ray, photoelectrically detecting stimulated emission released from the stimulable phosphor to produce analog data and digitizing the analog data to produce summed digital data, and to store the summed digital data in the digital memory, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced by detecting stimulated emission with high sensitivity.

Furthermore, according to this preferred aspect of the present invention, since the signal intensity determining means is further constituted so as to output, when it determines that the signal intensity of digital data has come to be lower than the threshold value, the excitation power increasing signal to the stimulation control means k times in total, thereby increasing the excitation power of the stimulating ray emitted from the stimulating ray source, to sum digital data produced by exciting stimulable phosphor contained in the stimulable phosphor layer region with the stimulating ray, photoelectrically detecting stimulated emission released from the stimulable phosphor to produce analog data and digitizing the analog data to produce summed digital data and store the summed digital data in the digital memory until the signal intensity of the digital data has come to be lower than the threshold value, to calculate a total of the summed digital data stored in the digital memory and to adopt the thus calculated total of the summed digital data as biochemical analysis data of the stimulable phosphor layer region, even in the case where radiation energy or light energy stored in a stimulable phosphor layer region is small and the intensity of the stimulated emission released from the stimulable phosphor layer region when stimulable phosphor contained therein is excited with the stimulating ray is small, it is possible to produce biochemical analysis data having high quantitative characteristics by substantially completely releasing radiation energy or light energy stored in a stimulable phosphor layer region in the form of stimulated emission and detecting the stimulated emission with very high sensitivity.

Moreover according to this preferred aspect of the present invention, since the signal intensity determining means is further constituted so as to determine biochemical analysis data of the stimulable phosphor layer region to be zero when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data cannot be equal to or higher than the threshold value even though it output the exciting power increasing signal to the stimulation control means m times to cause the stimulation control means to increase the excitation power of the stimulating ray emitted from the stimulating ray source, it is possible to prevent, by appropriately selecting m, unnecessary exciting operation from being repeated when no radiation energy or light energy is stored in the stimulable phosphor layer region, while biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small and it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large.

In a further preferred aspect of the present invention, the signal intensity determining means is constituted so as to cause, when it determines that the signal intensity of the digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is equal to or higher than the threshold value, the stimulation control means to continue to drive the stimulating ray source until the signal intensity of the digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter has come to be lower than the threshold value, to sum digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter to produce summed digital data, to store the summed digital data in the digital memory, to sequentially output, when it determines that the signal intensity of the digital data has come to be lower than the threshold value, the excitation power increasing signal to the stimulation control means, thereby sequentially increasing the excitation power of the stimulating ray emitted from the stimulating ray source, to sum digital data produced by exciting stimulable phosphor contained in the stimulable phosphor layer region with the stimulating ray having the respective excitation powers, photoelectrically detecting stimulated emission released from the stimulable phosphor to produce analog data and digitizing the analog data by the A/D converter to produce summed digital data and store the summed digital data in the digital memory until it determines that the signal intensity of the digital data has come to be lower than the threshold value, to calculate a total of the summed digital data stored in the digital memory so far when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data by the A/D converter cannot come to be equal to or higher than the threshold value even if the excitation power of the stimulating ray emitted from the stimulating ray source is increased, and to adopt the thus calculated total of the digital data as biochemical analysis data of the stimulable phosphor layer region.

According to this preferred aspect of the present invention, since the signal intensity determining means is constituted so as to cause, when it determines that the signal intensity of the digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is equal to or higher than the threshold value, the stimulation control means to continue to drive the stimulating ray source until the signal intensity of the digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter has come to be lower than the threshold value, to sum digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter to produce summed digital data, to store the summed digital data in the digital memory, to sequentially output, when it determines that the signal intensity of the digital data has come to be lower than the threshold value, the excitation power increasing signal to the stimulation control means, thereby sequentially increasing the excitation power of the stimulating ray emitted from the stimulating ray source, to sum digital data produced by exciting stimulable phosphor contained in the stimulable phosphor layer region with the stimulating ray having the respective excitation powers, photoelectrically detecting stimulated emission released from the stimulable phosphor to produce analog data and digitizing the analog data by the A/D converter to produce summed digital data and store the summed digital data in the digital memory until it determines that the signal intensity of the digital data has come to be lower than the threshold value, to calculate a total of the summed digital data stored in the digital memory so far when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data by the A/D converter cannot come to be equal to or higher than the threshold value even if the excitation power of the stimulating ray emitted from the stimulating ray source is increased, and to adopt the thus calculated total of the digital data as biochemical analysis data of the stimulable phosphor layer region, even in the case where radiation energy or light energy stored in a stimulable phosphor layer region is small and the intensity of stimulated emission released from the stimulable phosphor layer region when stimulable phosphor contained therein is excited with the stimulating ray is small, it is possible to produce biochemical analysis data having high quantitative characteristics by substantially completely releasing radiation energy or light energy stored in a stimulable phosphor layer region in the form of stimulated emission and detecting the stimulated emission with very high sensitivity.

In a further preferred aspect of the present invention, when the excitation power increasing signal is output from the signal intensity determining means to the stimulating controlling means and the signal intensity determining means determines that the signal intensity of digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is lower than the threshold value, the signal intensity determining means sequentially outputs the excitation power increasing signal to the stimulation control means n times at maximum where n is a positive integer, thereby sequentially increasing the excitation power of the stimulating ray emitted from the stimulating ray source, to cause, when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data by the A/D converter has come to be equal to or higher than the threshold value, the stimulating controlling means to continue to drive the stimulating ray source until it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data by the A/D converter has come to be lower than the threshold value, to sum digital data produced by exciting stimulable phosphor contained in the stimulable phosphor layer region with the stimulating ray, photoelectrically detecting stimulated emission released from the stimulable phosphor to produce analog data and digitizing the analog data to produce summed digital data, to store the summed digital data in the digital memory, to sequentially output, when it determines that the signal intensity of digital data has come to be lower than the threshold value, the excitation power increasing signal to the stimulation control means, thereby sequentially increasing the excitation power of the stimulating ray emitted from the stimulating ray source, to sum digital data digital data produced by exciting stimulable phosphor contained in the stimulable phosphor layer region with the stimulating ray having the respective excitation powers, photoelectrically detecting stimulated emission released from the stimulable phosphor to produce analog data and digitizing the analog data by the A/D converter to produce summed digital data and store the summed digital data in the digital memory until it determines that the signal intensity of the digital data has come to be lower than the threshold value, to calculate a total of the summed digital data stored in the digital memory so far when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data by the A/D converter cannot come to be equal to or higher than the threshold value even if the excitation power of the stimulating ray emitted from the stimulating ray source is increased, and to adopt the thus calculated total of the digital data as biochemical analysis data of the stimulable phosphor layer region, or to determine biochemical analysis data of the stimulable phosphor layer region to be zero when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data cannot be equal to or higher than the threshold value even though it outputs the exciting power increasing signal to the stimulation control means n times in total to cause the stimulation control means to increase the excitation power of the stimulating ray emitted from the stimulating ray source.

According to this preferred aspect of the present invention, when the excitation power increasing signal is output from the signal intensity determining means to the stimulating controlling means and the signal intensity determining means determines that the signal intensity of digital data produced by exciting stimulable phosphor contained in the stimulable phosphor layer region with the stimulating ray having the reference excitation power, photoelectrically detecting stimulated emission released from the stimulable phosphor to produce analog data and digitizing the analog data by the A/D converter is lower than the threshold value, since the signal intensity determining means is constituted so as to sequentially output the excitation power increasing signal to the stimulation control means n times at maximum where n is a positive integer, thereby sequentially increasing the excitation power of the stimulating ray emitted from the stimulating ray source, to cause, when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data by the A/D converter has come to be equal to or higher than the threshold value, the stimulating controlling means to continue to drive the stimulating ray source until it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data by the A/D converter has come to be lower than the threshold value, to sum digital data produced by exciting stimulable phosphor contained in the stimulable phosphor layer region with the stimulating ray, photoelectrically detecting stimulated emission released from the stimulable phosphor to produce analog data and digitizing the analog data to produce summed digital data, to store the summed digital data in the digital memory, to sequentially output, when it determines that the signal intensity of digital data has come to be lower than the threshold value, the excitation power increasing signal to the stimulation control means, thereby sequentially increasing the excitation power of the stimulating ray emitted from the stimulating ray source, to sum digital data digital data produced by exciting stimulable phosphor contained in the stimulable phosphor layer region with the stimulating ray having the respective excitation powers, photoelectrically detecting stimulated emission released from the stimulable phosphor to produce analog data and digitizing the analog data by the A/D converter to produce summed digital data and store the summed digital data in the digital memory until it determines that the signal intensity of the digital data has come to be lower than the threshold value, to calculate a total of the summed digital data stored in the digital memory so far when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data by the A/D converter cannot come to be equal to or higher than the threshold value even if the excitation power of the stimulating ray emitted from the stimulating ray source is increased, and to adopt the thus calculated total of the digital data as biochemical analysis data of the stimulable phosphor layer region, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large and biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small.

Moreover, according to this preferred aspect of the present invention, since the signal intensity determining means is further constituted so as to determine biochemical analysis data of the stimulable phosphor layer region to be zero when it determines that the signal intensity of digital data produced by exciting stimulable phosphor contained in the stimulable phosphor layer region with the stimulating ray, photoelectrically detecting stimulated emission released from the stimulable phosphor to produce analog data and digitizing the analog data cannot be equal to or higher than the threshold value even though it output the exciting power increasing signal to the stimulation control means n times in total to cause the stimulation control means to increase the excitation power of the stimulating ray emitted from the stimulating ray source, it is possible to prevent, by appropriately selecting n, unnecessary exciting operation from being repeated when no radiation energy or light energy is stored in the stimulable phosphor layer region, while biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small and it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large.

In a further preferred aspect of the present invention, the signal intensity determining means is constituted so as to correct digital data produced by irradiating the stimulable phosphor layer region with the stimulating ray having different excitation power to excite stimulable phosphor contained in the stimulable phosphor layer region, photoelectrically detecting stimulated emission released from the stimulable phosphor to produce analog data, and digitizing the analog data by multiplying them by a correction coefficient determined in accordance with the excitation power of the stimulating ray projected onto the stimulable phosphor layer region, thereby producing biochemical analysis data of the stimulable phosphor layer region.

According to this preferred aspect of the present invention, since the signal intensity determining means is constituted so as to correct digital data produced by irradiating the stimulable phosphor layer region with the stimulating ray having different excitation power to excite stimulable phosphor contained in the stimulable phosphor layer region, photoelectrically detecting stimulated emission released from the stimulable phosphor to produce analog data, and digitizing the analog data by multiplying them by a correction coefficient determined in accordance with the excitation power of the stimulating ray projected onto the stimulable phosphor layer region, thereby producing biochemical analysis data of the stimulable phosphor layer region, even if the excitation power of the stimulating ray is increased to be greater than the reference excitation power and stimulable phosphor contained in the stimulable phosphor layer region in order to detect stimulated emission with high sensitivity or release all detectable radiation energy or light energy stored in the stimulable phosphor layer region in the form of stimulated emission and detect stimulated emission, it is possible to produce biochemical analysis data having signal intensity corresponding to radiation energy or light energy stored in the stimulable phosphor layer region.

In a further preferred aspect of the present invention, the correction coefficient for each excitation power is determined so that digital data corresponding to the excitation power can be corrected to have the same level as that of digital data to be produced using the stimulating ray having the reference excitation power.

In a further preferred aspect of the present invention, the signal intensity determining means is constituted so as to correct the summed digital data produced by irradiating the stimulable phosphor layer region with the stimulating ray having different excitation power to excite stimulable phosphor contained in the stimulable phosphor layer region, photoelectrically detecting stimulated emission released from the stimulable phosphor to produce analog data, digitizing the analog data to produce digital data and summing the digital data by multiplying them by a correction coefficient determined in accordance with the excitation power of the stimulating ray projected onto the stimulable phosphor layer region and to calculate a total of the thus corrected summed digital data, thereby producing biochemical analysis data of the stimulable phosphor layer region.

According to this preferred aspect of the present invention, since the signal intensity determining means is constituted so as to correct the summed digital data produced by irradiating the stimulable phosphor layer region with the stimulating ray having different excitation power to excite stimulable phosphor contained in the stimulable phosphor layer region, photoelectrically detecting stimulated emission released from the stimulable phosphor to produce analog data, digitizing the analog data to produce digital data and summing the digital data by multiplying them by a correction coefficient determined in accordance with the excitation power of the stimulating ray projected onto the stimulable phosphor layer region and to calculate a total of the thus corrected summed digital data, thereby producing biochemical analysis data of the stimulable phosphor layer region, even if the excitation power of the stimulating ray is increased to be greater than the reference excitation power and stimulable phosphor contained in the stimulable phosphor layer region in order to detect stimulated emission with high sensitivity or release all detectable radiation energy or light energy stored in the stimulable phosphor layer region in the form of stimulated emission and detect stimulated emission, it is possible to produce biochemical analysis data having signal intensity corresponding to radiation energy or light energy stored in the stimulable phosphor layer region.

In a further preferred aspect of the present invention, the correction coefficient for each excitation power is determined so that the summed digital data corresponding to the excitation power are corrected to have the same level as that of summed digital data to be produced using the stimulating ray having the reference excitation power.

In a preferred aspect of the present invention, the scanner further comprises an integrating amplifier for integrating analog data produced by the light detector, an A/D converter for digitizing an integrated value of the analog data produced by the integrating amplifier to produce digital data, and a signal intensity determining means for comparing signal intensity of digital data produced by the A/D converter with a threshold value and adopting the digital data as biochemical analysis data of the stimulable phosphor layer region in accordance with the result of the comparison, the stimulation control means being adapted for controlling the stimulating ray source so as to first emit a stimulating ray having reference excitation power which is relatively low and increasing excitation power of a stimulating ray emitted from the stimulating ray source when an excitation power increasing signal is input from the signal intensity determining means, the signal intensity determining means being constituted so as to output the excitation power increasing signal to the stimulating controlling means when it determines that the signal intensity of digital data produced by integrating analog data by the integrating amplifier and digitizing the integrated value of the analog data by the A/D converter is lower than the threshold value.

According to this preferred aspect of the present invention, since the scanner further comprises an integrating amplifier for integrating analog data produced by the light detector, an A/D converter for digitizing an integrated value of the analog data produced by the integrating amplifier to produce digital data, and a signal intensity determining means for comparing signal intensity of digital data produced by the A/D converter with a threshold value and adopting the digital data as biochemical analysis data of the stimulable phosphor layer region in accordance with the result of the comparison, the stimulation control means being adapted for controlling the stimulating ray source so as to first emit a stimulating ray having reference excitation power which is relatively low and increasing excitation power of a stimulating ray emitted from the stimulating ray source when an excitation power increasing signal is input from the signal intensity determining means, the signal intensity determining means being constituted so as to output the excitation power increasing signal to the stimulating controlling means when it determines that the signal intensity of digital data produced by integrating analog data by the integrating amplifier and digitizing the integrated value of the analog data by the A/D converter is lower than the threshold value, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced by detecting stimulated emission with high sensitivity.

In a further preferred aspect of the present invention, the signal intensity determining means is constituted so as to adopt digital data produced by exciting stimulable phosphor contained in the stimulable phosphor layer region with the stimulating ray having the reference excitation power, photoelectrically detecting stimulated emission released from the stimulable phosphor by the light detector to produce analog data, integrating the analog data by the integrating amplifier and digitizing an integrated value of the analog data by the A/D converter as biochemical analysis data of the stimulable phosphor layer region when it determines that the signal intensity of the digital data is equal to or higher than the threshold value.

According to this preferred aspect of the present invention, since the signal intensity determining means is constituted so as to adopt digital data produced by exciting stimulable phosphor contained in the stimulable phosphor layer region with the stimulating ray having the reference excitation power, photoelectrically detecting stimulated emission released from the stimulable phosphor by the light detector to produce analog data, integrating the analog data by the integrating amplifier and digitizing an integrated value of the analog data by the A/D converter as biochemical analysis data of the stimulable phosphor layer region when it determines that the signal intensity of the digital data is equal to or higher than the threshold value, even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data.

In a further preferred aspect of the present invention, the signal intensity determining means is constituted so as to adopt digital data produced by exciting stimulable phosphor contained in the stimulable phosphor layer region with the stimulating ray having exciting power greater than the reference excitation power emitted from the stimulating ray source by outputting the excitation power increasing signal to the stimulation control means therefrom, photoelectrically detecting stimulated emission released from the stimulable phosphor by the light detector to produce analog data, integrating the analog data by the integrating amplifier and digitizing an integrated value of the analog data by the A/D converter as biochemical analysis data of the stimulable phosphor layer region.

According to this preferred aspect of the present invention, since the signal intensity determining means is constituted so as to adopt digital data produced by exciting stimulable phosphor contained in the stimulable phosphor layer region with the stimulating ray having exciting power greater than the reference excitation power emitted from the stimulating ray source by outputting the excitation power increasing signal to the stimulation control means therefrom, photoelectrically detecting stimulated emission released from the stimulable phosphor by the light detector to produce analog data, integrating the analog data by the integrating amplifier and digitizing an integrated value of the analog data by the A/D converter as biochemical analysis data of the stimulable phosphor layer region, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced by detecting stimulated emission with high sensitivity.

In another preferred aspect of the present invention, the signal intensity determining means is constituted so as to adopt digital data produced by exciting stimulable phosphor contained in the stimulable phosphor layer region with the stimulating ray having exciting power greater than the reference excitation power emitted from the stimulating ray source by outputting the excitation power increasing signal to the stimulation control means therefrom, photoelectrically detecting stimulated emission released from the stimulable phosphor by the light detector to produce analog data, integrating the analog data by the integrating amplifier and digitizing an integrated value of the analog data by the A/D converter as biochemical analysis data of the stimulable phosphor layer region According to this preferred aspect of the present invention, since the signal intensity determining means is constituted so as to adopt digital data produced by exciting stimulable phosphor contained in the stimulable phosphor layer region with the stimulating ray having exciting power greater than the reference excitation power emitted from the stimulating ray source by outputting the excitation power increasing signal to the stimulation control means therefrom, photoelectrically detecting stimulated emission released from the stimulable phosphor by the light detector to produce analog data, integrating the analog data by the integrating amplifier and digitizing an integrated value of the analog data by the A/D converter as biochemical analysis data of the stimulable phosphor layer region, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced by detecting stimulated emission with high sensitivity, when it determines that the signal intensity of the digital data is equal to or higher than the threshold value, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be produced by detecting stimulated emission with high sensitivity.

In a further preferred aspect of the present invention, the signal intensity determining means is constituted so as to output, when it determines that the signal intensity of digital data produced by exciting stimulable phosphor contained in the stimulable phosphor layer region with the stimulating ray having exciting power greater than the reference excitation power emitted from the stimulating ray source by outputting the excitation power increasing signal to the stimulation control means therefrom, photoelectrically detecting stimulated emission released from the stimulable phosphor by the light detector to produce analog data, integrating the analog data by the integrating amplifier and digitizing an integrated value of the analog data by the A/D converter is lower than the threshold value, the excitation power increasing signal to the stimulation control means I times where I is a positive integer, thereby sequentially increasing the excitation power of the stimulating ray emitted from the stimulating ray source to be greater than the reference excitation power, and to adopt, when the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter has come to be equal to or higher than the threshold value, the digital data as biochemical analysis data of the stimulable phosphor layer region, or to determine biochemical analysis data of the stimulable phosphor layer region to be zero when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter is still lower than the threshold value even though it output the excitation power increasing signal to the stimulation control means I times in total, thereby increasing the excitation power of the stimulating ray emitted from the stimulating ray source to be greater than the reference excitation power.

According to this preferred aspect of the present invention, since the signal intensity determining means is constituted so as to output, when it determines that the signal intensity of digital data produced by exciting stimulable phosphor contained in the stimulable phosphor layer region with the stimulating ray having exciting power greater than the reference excitation power emitted from the stimulating ray source by outputting the excitation power increasing signal to the stimulation control means therefrom, photoelectrically detecting stimulated emission released from the stimulable phosphor by the light detector to produce analog data, integrating the analog data by the integrating amplifier and digitizing an integrated value of the analog data by the A/D converter is lower than the threshold value, the excitation power increasing signal to the stimulation control means I times where I is a positive integer, thereby sequentially increasing the excitation power of the stimulating ray emitted from the stimulating ray source to be greater than the reference excitation power, and to adopt, when the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter has come to be equal to or higher than the threshold value, the digital data as biochemical analysis data of the stimulable phosphor layer region, even in the case where radiation energy or light energy stored in a stimulable phosphor layer region is small and the intensity of stimulated emission released from the stimulable phosphor layer region when stimulable phosphor contained therein is excited with the stimulating ray is small, biochemical analysis data having high quantitative characteristics can be reliably produced by detecting the stimulated emission with high sensitivity and even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data.

Moreover, according to this preferred aspect of the present invention, since the signal intensity determining means is further constituted so as to determine biochemical analysis data of the stimulable phosphor layer region to be zero when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter is still lower than the threshold value even though it output the excitation power increasing signal to the stimulation control means I times in total, thereby increasing the excitation power of the stimulating ray emitted from the stimulating ray source to be greater than the reference excitation power, it is possible to prevent, by appropriately selecting I, unnecessary exciting operation from being repeated when no radiation energy or light energy is stored in the stimulable phosphor layer region, while biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small and it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large.

In a further preferred aspect of the present invention, the scanner further comprises a digital memory and the signal intensity determining means is constituted so as to sum digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter to produce summed digital data, when it determines that the signal intensity of the digital data is equal to or higher than the threshold value, to store the summed digital data in the digital memory, to further output the excitation power increasing signal to the stimulation control means K times at maximum where K is a positive integer, thereby increasing the excitation power of the stimulating ray emitted from the stimulating ray source to be greater than the reference excitation power, to sum digital data produced by exciting stimulable phosphor contained in the stimulable phosphor layer region with the stimulating ray having respective excitation powers, photoelectrically detecting stimulated emission released from the stimulable phosphor by the light detector to produce analog data, integrating the analog data by the integrating amplifier and digitizing an integrated value of the analog data by the A/D converter to produce summed digital data, to store the summed digital data in the digital memory, to calculate a total of the summed digital data stored in the digital memory and to adopt the thus calculated total of the summed digital data as biochemical analysis data of the stimulable phosphor layer region.

According to this preferred aspect of the present invention, since the scanner further comprises a digital memory and the signal intensity determining means is constituted so as to sum digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter to produce summed digital data, when it determines that the signal intensity of the digital data is equal to or higher than the threshold value, to store the summed digital data in the digital memory, to further output the excitation power increasing signal to the stimulation control means K times at maximum where K is a positive integer, thereby increasing the excitation power of the stimulating ray emitted from the stimulating ray source to be greater than the reference excitation power, to sum digital data produced by exciting stimulable phosphor contained in the stimulable phosphor layer region with the stimulating ray having respective excitation powers, photoelectrically detecting stimulated emission released from the stimulable phosphor by the light detector to produce analog data, integrating the analog data by the integrating amplifier and digitizing an integrated value of the analog data by the A/D converter to produce summed digital data, to store the summed digital data in the digital memory, to calculate a total of the summed digital data stored in the digital memory and to adopt the thus calculated total of the summed digital data as biochemical analysis data of the stimulable phosphor layer region, even in the case where radiation energy or light energy stored in a stimulable phosphor layer region is large, it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data and even in the case where radiation energy or light energy stored in a stimulable phosphor layer region is small, it is possible to produce biochemical analysis data having high quantitative characteristics by substantially completely releasing radiation energy or light energy stored in a stimulable phosphor layer region in the form of stimulated emission and detecting the stimulated emission with very high sensitivity.

In a further preferred aspect of the present invention, the signal intensity determining means is constituted so as to output, when it determines that the signal intensity of digital data produced by exciting stimulable phosphor contained in the stimulable phosphor layer region with the stimulating ray having exciting power greater than the reference excitation power emitted from the stimulating ray source by outputting the excitation power increasing signal to the stimulation control means therefrom, photoelectrically detecting stimulated emission released from the stimulable phosphor by the light detector to produce analog data, integrating the analog data by the integrating amplifier and digitizing an integrated value of the analog data by the A/D converter is lower than the threshold value, the excitation power increasing signal to the stimulation control means M times at maximum where M is a positive integer, thereby increasing the excitation power of the stimulating ray emitted from the stimulating ray source to be greater than the reference excitation power, to further output, when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter has come to be equal to or higher than the threshold value, the excitation power increasing signal to the stimulation control means K times in total, thereby increasing the excitation power of the stimulating ray emitted from the stimulating ray source, to sum digital data produced by exciting stimulable phosphor contained in the stimulable phosphor layer region with the stimulating ray having respective excitation powers, photoelectrically detecting stimulated emission released from the stimulable phosphor by the light detector to produce analog data, integrating the analog data by the integrating amplifier and digitizing an integrated value of the analog data by the A/D converter to produce summed digital data, to store the summed digital data in the digital memory, to calculate a total of the summed digital data stored in the digital memory and to adopt the thus calculated total of the summed digital data as biochemical analysis data of the stimulable phosphor layer region, or to determine biochemical analysis data of the stimulable phosphor layer region to be zero when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter cannot come to be equal to or higher than the threshold value even though it output the excitation power increasing signal to the stimulation control means M times in total, thereby increasing the excitation power of the stimulating ray emitted from the stimulating ray source.

According to this preferred aspect of the present invention, since the signal intensity determining means is constituted so as to output, when it determines that the signal intensity of digital data produced by exciting stimulable phosphor contained in the stimulable phosphor layer region with the stimulating ray having exciting power greater than the reference excitation power emitted from the stimulating ray source by outputting the excitation power increasing signal to the stimulation control means therefrom, photoelectrically detecting stimulated emission released from the stimulable phosphor by the light detector to produce analog data, integrating the analog data by the integrating amplifier and digitizing an integrated value of the analog data by the A/D converter is lower than the threshold value, the excitation power increasing signal to the stimulation control means M times at maximum where M is a positive integer, thereby increasing the excitation power of the stimulating ray emitted from the stimulating ray source to be greater than the reference excitation power, to further output, when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter has come to be equal to or higher than the threshold value, the excitation power increasing signal to the stimulation control means K times in total, thereby increasing the excitation power of the stimulating ray emitted from the stimulating ray source, to sum digital data produced by exciting stimulable phosphor contained in the stimulable phosphor layer region with the stimulating ray having respective excitation powers, photoelectrically detecting stimulated emission released from the stimulable phosphor by the light detector to produce analog data, integrating the analog data by the integrating amplifier and digitizing an integrated value of the analog data by the A/D converter to produce summed digital data, to store the summed digital data in the digital memory, to calculate a total of the summed digital data stored in the digital memory and to adopt the thus calculated total of the summed digital data as biochemical analysis data of the stimulable phosphor layer region, even in the case where radiation energy or light energy stored in a stimulable phosphor layer region is small and the intensity of the stimulated emission released from the stimulable phosphor layer region when stimulable phosphor contained therein is excited with the stimulating ray is small, it is possible to produce biochemical analysis data having high quantitative characteristics by substantially completely releasing radiation energy or light energy stored in a stimulable phosphor layer region in the form of stimulated emission and detecting the stimulated emission with very high sensitivity.

Moreover, according to this preferred aspect of the present invention, since the signal intensity determining means is further constituted so as to determine biochemical analysis data of the stimulable phosphor layer region to be zero when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter cannot come to be equal to or higher than the threshold value even though it output the excitation power increasing signal to the stimulation control means M times in total, thereby increasing the excitation power of the stimulating ray emitted from the stimulating ray source, it is possible to prevent, by appropriately selecting M, unnecessary exciting operation from being repeated when no radiation energy or light energy is stored in the stimulable phosphor layer region, while biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small and it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large.

In a further preferred aspect of the present invention, the scanner further comprises a digital memory and the signal intensity determining means is constituted so as to sum, when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter is equal to or higher than the threshold value, the digital data to produce summed digital data, to store the summed digital data in the digital memory, to further sequentially output the excitation power increasing signal to the stimulation control means, thereby sequentially increasing the excitation power of the stimulating ray emitted from the stimulating ray source to be greater than the reference excitation power, to sum digital data produced by exciting stimulable phosphor contained in the stimulable phosphor layer region with the stimulating ray having respective exciting powers, photoelectrically detecting stimulated emission released from the stimulable phosphor by the light detector to produce analog data, integrating the analog data by the integrating amplifier and digitizing an integrated value of the analog data by the A/D converter to produce summed digital data, to store the summed digital data in the digital memory, to calculate, when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter cannot come to be equal to or higher than the threshold value even though it output the excitation power increasing signal to the stimulation control means, thereby increasing the excitation power of the stimulating ray emitted from the stimulating ray source, a total of the summed digital data stored in the digital memory so far and to adopt the thus calculated total of the summed digital data.

According to this preferred aspect of the present invention since the scanner further comprises a digital memory and the signal intensity determining means is constituted so as to sum, when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter is equal to or higher than the threshold value, the digital data to produce summed digital data, to store the summed digital data in the digital memory, to further sequentially output the excitation power increasing signal to the stimulation control means, thereby sequentially increasing the excitation power of the stimulating ray emitted from the stimulating ray source to be greater than the reference excitation power, to sum digital data produced by exciting stimulable phosphor contained in the stimulable phosphor layer region with the stimulating ray having respective exciting powers, photoelectrically detecting stimulated emission released from the stimulable phosphor by the light detector to produce analog data, integrating the analog data by the integrating amplifier and digitizing an integrated value of the analog data by the A/D converter to produce summed digital data, to store the summed digital data in the digital memory, to calculate, when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter cannot come to be equal to or higher than the threshold value even though it output the excitation power increasing signal to the stimulation control means, thereby increasing the excitation power of the stimulating ray emitted from the stimulating ray source, a total of the summed digital data stored in the digital memory so far and to adopt the thus calculated total of the summed digital data, even in the case where radiation energy or light energy stored in a stimulable phosphor layer region is small and the intensity of stimulated emission released from the stimulable phosphor layer region when stimulable phosphor contained therein is excited with the stimulating ray is small, it is possible to produce biochemical analysis data having high quantitative characteristics by substantially completely releasing radiation energy or light energy stored in a stimulable phosphor layer region in the form of stimulated emission.

In a further preferred aspect of the present invention, the signal intensity determining means is constituted so as to output, when it determines that the signal intensity of digital data produced by exciting stimulable phosphor contained in the stimulable phosphor layer region with the stimulating ray having exciting power greater than the reference excitation power emitted from the stimulating ray source by outputting the excitation power increasing signal to the stimulation control means therefrom, photoelectrically detecting stimulated emission released from the stimulable phosphor by the light detector to produce analog data, integrating the analog data by the integrating amplifier and digitizing an integrated value of the analog data by the A/D converter is lower than the threshold value, the excitation power increasing signal to the stimulation control means N times at maximum where N is a positive integer, thereby sequentially increasing the excitation power of the stimulating ray emitted from the stimulating ray source to be greater than the reference excitation power, to compare the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter with the threshold value, to store the digital data in the digital memory when it determines that the signal intensity of the digital data has come to be equal to or higher than the threshold value, to further sequentially output the excitation power increasing signal to the stimulation control means, thereby sequentially increasing the excitation power of the stimulating ray emitted from the stimulating ray source, to sum digital data produced by exciting stimulable phosphor contained in the stimulable phosphor layer region with the stimulating ray having respective excitation powers, photoelectrically detecting stimulated emission released from the stimulable phosphor by the light detector to produce analog data, integrating the analog data by the integrating amplifier and digitizing an integrated value of the analog data by the A/D converter to produce summed digital data, to store the summed digital data in the digital memory, to calculate, when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter cannot come to be equal to or higher than the threshold value even if it further outputs the excitation power increasing signal to the stimulation control means, thereby further increasing the excitation power of the stimulating ray emitted from the stimulating ray source, a total of the summed digital data stored in the digital memory so far and to adopt the thus calculated total of the summed digital data as biochemical analysis data of the stimulable phosphor layer region, or to determine biochemical analysis data of the stimulable phosphor layer region to be zero when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter cannot come to be equal to or higher than the threshold value even though it output the excitation power increasing signal to the stimulation control means N times in total, thereby sequentially increasing the excitation power of the stimulating ray emitted from the stimulating ray source.

According to this preferred aspect of the present invention, since the signal intensity determining means is constituted so as to output, when it determines that the signal intensity of digital data produced by exciting stimulable phosphor contained in the stimulable phosphor layer region with the stimulating ray having exciting power greater than the reference excitation power emitted from the stimulating ray source by outputting the excitation power increasing signal to the stimulation control means therefrom, photoelectrically detecting stimulated emission released from the stimulable phosphor by the light detector to produce analog data, integrating the analog data by the integrating amplifier and digitizing an integrated value of the analog data by the A/D converter is lower than the threshold value, the excitation power increasing signal to the stimulation control means N times at maximum where N is a positive integer, thereby sequentially increasing the excitation power of the stimulating ray emitted from the stimulating ray source to be greater than the reference excitation power, to compare the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter with the threshold value, to store the digital data in the digital memory when it determines that the signal intensity of the digital data has come to be equal to or higher than the threshold value, to further sequentially output the excitation power increasing signal to the stimulation control means, thereby sequentially increasing the excitation power of the stimulating ray emitted from the stimulating ray source, to sum digital data produced by exciting stimulable phosphor contained in the stimulable phosphor layer region with the stimulating ray having respective excitation powers, photoelectrically detecting stimulated emission released from the stimulable phosphor by the light detector to produce analog data, integrating the analog data by the integrating amplifier and digitizing an integrated value of the analog data by the A/D converter to produce summed digital data, to store the summed digital data in the digital memory, to calculate, when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter cannot come to be equal to or higher than the threshold value even if it further outputs the excitation power increasing signal to the stimulation control means, thereby further increasing the excitation power of the stimulating ray emitted from the stimulating ray source, a total of the summed digital data stored in the digital memory so far and to adopt the thus calculated total of the summed digital data as biochemical analysis data of the stimulable phosphor layer region, even in the case where radiation energy or light energy stored in a stimulable phosphor layer region is small and the intensity of stimulated emission released from the stimulable phosphor layer region when stimulable phosphor contained therein is excited with the stimulating ray is small, it is possible to produce biochemical analysis data having high quantitative characteristics by substantially completely releasing radiation energy or light energy stored in a stimulable phosphor layer region in the form of stimulated emission.

Moreover, according to this preferred aspect of the present invention, since the signal intensity determining means is further constituted so as to determine biochemical analysis data of the stimulable phosphor layer region to be zero when it determines that the signal intensity of digital data produced by exciting stimulable phosphor contained in the stimulable phosphor layer region with the stimulating ray, photoelectrically detecting stimulated emission released from the stimulable phosphor by the light detector to produce analog data, integrating the analog data by the integrating amplifier and digitizing an integrated value of the analog data by the A/D converter cannot come to be equal to or higher than the threshold value even though it output the excitation power increasing signal to the stimulation control means N times in total, thereby sequentially increasing the excitation power of the stimulating ray emitted from the stimulating ray source, it is possible to prevent, by appropriately selecting N, unnecessary exciting operation from being repeated when no radiation energy or light energy is stored in the stimulable phosphor layer region, while biochemical analysis data having high quantitative characteristics can be reliably produced by detecting stimulated emission with high sensitivity, even in the case where radiation energy or light energy stored in a stimulable phosphor layer region is small and the intensity of the stimulated emission released from the stimulable phosphor layer region when stimulable phosphor contained therein is excited with the stimulating ray is small and it is possible to reliably prevent the intensity of stimulated emission released from the stimulable phosphor layer region in response to the excitation with the stimulating ray from becoming excessively high and exceeding the upper limit of the dynamic range of the light detector, and to reliably prevent the signal intensity of digital data produced by detecting the stimulated emission from being saturated, thereby degrading the quantitative characteristics of biochemical analysis data, even in the case where radiation energy or light energy stored in a stimulable phosphor layer region is large.

In a further preferred aspect of the present invention, the signal intensity determining means is constituted so as to multiply digital data produced by irradiating the stimulable phosphor layer region with the stimulating ray having different excitation power to excite stimulable phosphor contained in the stimulable phosphor layer region, photoelectrically detecting stimulated emission released from the stimulable phosphor by the light detector to produce analog data, integrating the analog data by the integrating amplifier and digitizing an integrated value of the analog data by the A/D converter by a correction coefficient determined in accordance with the excitation power of the stimulating ray projected onto the stimulable phosphor layer region, thereby correcting the digital data and producing biochemical analysis data of the stimulable phosphor layer region.

According to this preferred aspect of the present invention, since the signal intensity determining means is constituted so as to multiply digital data produced by irradiating the stimulable phosphor layer region with the stimulating ray having different excitation power to excite stimulable phosphor contained in the stimulable phosphor layer region, photoelectrically detecting stimulated emission released from the stimulable phosphor by the light detector to produce analog data, integrating the analog data by the integrating amplifier and digitizing an integrated value of the analog data by the A/D converter by a correction coefficient determined in accordance with the excitation power of the stimulating ray projected onto the stimulable phosphor layer region, thereby correcting the digital data and producing biochemical analysis data of the stimulable phosphor layer region, even if the excitation power of the stimulating ray is increased to be greater than the reference excitation power and stimulable phosphor contained in the stimulable phosphor layer region in order to detect stimulated emission with high sensitivity or release all detectable radiation energy or light energy stored in the stimulable phosphor layer region in the form of stimulated emission and detect stimulated emission, it is possible to produce biochemical analysis data having signal intensity corresponding to radiation energy or light energy stored in the stimulable phosphor layer region.

In a further preferred aspect of the present invention, the correction coefficient for each excitation power is determined so that digital data corresponding to the excitation power can be corrected to have the same level as that of digital data to be produced using the stimulating ray having the reference excitation power.

In a further preferred aspect of the present invention, the signal intensity determining means is constituted so as to multiply the summed digital data produced by irradiating the stimulable phosphor layer region with the stimulating ray having different excitation power to excite stimulable phosphor contained in the stimulable phosphor layer region, photoelectrically detecting stimulated emission released from the stimulable phosphor by the light detector to produce analog data, integrating the analog data by the integrating amplifier and digitizing an integrated value of the analog data by the A/D converter by a correction coefficient determined in accordance with the excitation power of the stimulating ray projected onto the stimulable phosphor layer region, thereby correcting the summed digital data and to calculate a total of the thus corrected summed digital data, thereby producing biochemical analysis data of the stimulable phosphor layer region.

According to this preferred aspect of the present invention, since the signal intensity determining means is constituted so as to multiply the summed digital data produced by irradiating the stimulable phosphor layer region with the stimulating ray having different excitation power to excite stimulable phosphor contained in the stimulable phosphor layer region, photoelectrically detecting stimulated emission released from the stimulable phosphor by the light detector to produce analog data, integrating the analog data by the integrating amplifier and digitizing an integrated value of the analog data by the A/D converter by a correction coefficient determined in accordance with the excitation power of the stimulating ray projected onto the stimulable phosphor layer region, thereby correcting the summed digital data and to calculate a total of the thus corrected summed digital data, thereby producing biochemical analysis data of the stimulable phosphor layer region, even if the excitation power of the stimulating ray is increased to be greater than the reference excitation power and stimulable phosphor contained in the stimulable phosphor layer region in order to detect stimulated emission with high sensitivity or release all detectable radiation energy or light energy stored in the stimulable phosphor layer region in the form of stimulated emission and detect stimulated emission, it is possible to produce biochemical analysis data having signal intensity corresponding to radiation energy or light energy stored in the stimulable phosphor layer region.

In a further preferred aspect of the present invention, the correction coefficient for each excitation power is determined so that the summed digital data corresponding to the excitation power are corrected to have the same level as that of summed digital data to be produced using the stimulating ray having the reference excitation power.

In a further preferred aspect of the present invention, the stimulation control means is constituted so as to increase the excitation power of the stimulating ray emitted from the stimulating ray source by an increment $\Delta P$ when it receives an excitation power increasing signal from the signal intensity determining means.

In another preferred aspect of the present invention, the stimulation control means is constituted so as to increase the excitation power of the stimulating ray emitted from the stimulating ray source by an increment $\Delta P$ when it receives an excitation power increasing signal from the signal intensity determining means and to control the increment $\Delta P$ to be increased every time it receives the excitation power increasing signal.

In another preferred aspect of the present invention, the stimulation control means is constituted so as to increase the excitation power of the stimulating ray emitted from the stimulating ray source by an increment $\Delta P$ when it receives an excitation power increasing signal from the signal intensity determining means and to control the increment $\Delta P$ to be decreased every time it receives the excitation power increasing signal.

In a preferred aspect of the present invention, the stimulation control means is constituted so as to control the stimulating ray source based on the relative positional relationship between the irradiation optical system and the sample stage detected by the position detecting means so that the stimulable phosphor layer region is irradiated with the stimulating ray for a predetermined time and that the excitation power of the stimulating ray emitted from the stimulating ray source is increased with the lapse of time.

In the case where stimulable phosphor contained in the stimulable phosphor layer region formed in the support of the stimulable phosphor sheet is excited with a stimulating ray whose excitation power is held constant, since the amount of stimulated emission detected by the light detector is too large and exceeds the upper limit of the dynamic range of the light detector immediately after the stimulable phosphor layer region is irradiated with the stimulating ray and, on the other hand, an amount of stimulated emission released from the stimulable phosphor layer region drastically decreases with the lapse of time, it is extremely difficult to photoelectrically detect stimulated emission with high sensitivity. However, according to this preferred aspect of the present invention, since the stimulation control means is constituted so as to control the stimulating ray source based on the relative positional relationship between the irradiation optical system and the sample stage detected by the position detecting means so that the stimulable phosphor layer region is irradiated with the stimulating ray for a predetermined time and that the excitation power of the stimulating ray emitted from the stimulating ray source is increased with the lapse of time, it is possible to reliably prevent the amount of stimulated emission released from stimulable phosphor contained in the stimulable phosphor layer region in response to the excitation with the stimulating ray from exceeding the upper limit of the dynamic range of the light detector and biochemical analysis data having high quantitative characteristics can be produced by photoelectrically detecting stimulated emission with high sensitivity.

In a further preferred aspect of the present invention, the stimulation control means is constituted so as to control the stimulating ray source so that the excitation power of the stimulating ray emitted from the stimulating ray source is increased in accordance with an exponential function with the lapse of time.

In the case where stimulable phosphor contained in the stimulable phosphor layer region formed in the support of the stimulable phosphor sheet is excited with a stimulating ray whose excitation power is held constant, since the amount of stimulated emission detected by the light detector is too large and exceeds the upper limit of the dynamic range of the light detector immediately after the stimulable phosphor layer region is irradiated with the stimulating ray and, on the other hand, the amount of stimulated emission released from the stimulable phosphor layer region drastically decreases with the lapse of time, it is extremely difficult to photoelectrically detect stimulated emission with high sensitivity. However, according to this preferred aspect of the present invention, since the stimulation control means is constituted so as to control the stimulating ray source so that the excitation power of the stimulating ray emitted from the stimulating ray source is increased in accordance with an exponential function with the lapse of time, it is possible to reliably prevent an amount of stimulated emission released from stimulable phosphor contained in the stimulable phosphor layer region in response to the excitation with the stimulating ray from exceeding the upper limit of the dynamic range of the light detector and biochemical analysis data having high quantitative characteristics can be produced by photoelectrically detecting stimulated emission with high sensitivity.

In a further preferred aspect of the present invention, the scanner further comprises a photon counter for counting the number of photons contained in stimulated emission released from the stimulable phosphor layer region and detected by the light detector based on analog data produced by photoelectrically detecting the stimulated emission by the light detector.

According to this preferred aspect of the present invention, since the scanner further comprises a photon counter for counting the number of photons contained in stimulated emission released from the stimulable phosphor layer region and detected by the light detector based on analog data produced by photoelectrically detecting the stimulated emission by the light detector and the stimulating ray source is controlled by the stimulation control means so that the excitation power of the stimulating ray emitted from the stimulating ray source is increased in accordance with an exponential function with the lapse of time, the number of photons detected by the light detector can be controlled so as to be substantially constant and it is therefore possible to read radiation data or chemiluminescent data recorded in the stimulable phosphor layer region with high accuracy to produce biochemical analysis data having excellent quantitative characteristics.

In a preferred aspect of the present invention, the stimulation control means is constituted so as to control the on and off operation of the stimulating ray source in such a manner that only the plurality of stimulable phosphor layer regions are irradiated with the stimulating ray and regions other than the plurality of stimulable phosphor layer regions are not irradiated with the stimulating ray.

In a preferred aspect of the present invention, the scanning mechanism is constituted so as to intermittently move the irradiation optical system and the sample stage relative to each other in the main scanning direction by a pitch equal to a distance between neighboring stimulable phosphor layer regions in the main scanning direction.

In a preferred aspect of the present invention, the stimulation control means is constituted so as to control the stimulating ray source so that the stimulable phosphor sheet is constantly irradiated with the stimulating ray while the stimulable phosphor sheet and the stimulating ray are intermittently moved relative to each other in the main scanning direction.

In a preferred aspect of the present invention, the scanning mechanism is constituted so as to continuously move the irradiation optical system and the sample stage relative to each other and the stimulation control means is constituted so as to on and off control the stimulating ray source and control the scanning mechanism in such a manner that only the plurality of stimulable phosphor layer regions are irradiated with the stimulating ray and regions other than the plurality of stimulable phosphor layer regions other than the plurality of stimulable phosphor layer regions are not irradiated with the stimulating ray.

In a further preferred aspect of the present invention, the stimulation control means is constituted so as to control the stimulating ray source so as to be turned off when the scanning mechanism intermittently moves the irradiation optical system and the sample stage relative to each other in the main scanning direction.

In a further preferred aspect of the present invention, the scanning mechanism is constituted so as to intermittently move the sample stage in the main scanning direction.

In another preferred aspect of the present invention, the scanning mechanism is constituted so as to intermittently move the irradiation optical system in the main scanning direction.

In a further preferred aspect of the present invention, the stimulating ray source is constituted by a laser stimulating ray source.

In another preferred aspect of the present invention, the stimulating ray source is constituted by an LED (light emitting diode) stimulating ray source.

In a preferred aspect of the present invention, a plurality of holes are formed in the support of the stimulable phosphor sheet so as to be spaced apart from each other and the plurality of stimulable phosphor layer regions of the stimulable phosphor sheet are formed by charging stimulable phosphor in the holes.

In a further preferred aspect of the present invention, a plurality of through-holes are formed in the support of the stimulable phosphor sheet so as to be spaced apart from each other and the plurality of stimulable phosphor layer regions of the stimulable phosphor sheet are formed by embedding stimulable phosphor in the through-holes.

In a further preferred aspect of the present invention, a plurality of through-holes are formed in the support of the stimulable phosphor sheet so as to be spaced apart from each other and the plurality of stimulable phosphor layer regions of the stimulable phosphor sheet are formed by pressing a stimulable phosphor membrane containing stimulable phosphor in the through-holes.

In another preferred aspect of the present invention, a plurality of recesses are formed in the support of the stimulable phosphor sheet so as to be spaced apart from each other and the plurality of stimulable phosphor layer regions of the stimulable phosphor sheet are formed by embedding stimulable phosphor in the recesses.

In another preferred aspect of the present invention, the plurality of stimulable phosphor layer regions of the stimulable phosphor sheet are formed on the surface of the support.

In a preferred aspect of the present invention, the plurality of stimulable phosphor layer regions of the stimulable phosphor sheet are formed in a regular pattern.

In a preferred aspect of the present invention, each of the plurality of stimulable phosphor layer regions of the stimulable phosphor sheet is formed substantially circular.

In another preferred aspect of the present invention, each of the plurality of stimulable phosphor layer regions of the stimulable phosphor sheet is formed substantially rectangular.

In a preferred aspect of the present invention, the support of the stimulable phosphor sheet is formed with 10 or more stimulable phosphor layer regions.

In a further preferred aspect of the present invention, the support of the stimulable phosphor sheet is formed with 50 or more stimulable phosphor layer regions.

In a further preferred aspect of the present invention, the support of the stimulable phosphor sheet is formed with 100 or more stimulable phosphor layer regions.

In a further preferred aspect of the present invention, the support of the stimulable phosphor sheet is formed with 500 or more stimulable phosphor layer regions.

In a further preferred aspect of the present invention, the support of the stimulable phosphor sheet is formed with 1,000 or more stimulable phosphor layer regions.

In a further preferred aspect of the present invention, the support of the stimulable phosphor sheet is formed with 5,000 or more stimulable phosphor layer regions.

In a further preferred aspect of the present invention, the support of the stimulable phosphor sheet is formed with 10,000 or more stimulable phosphor layer regions.

In a further preferred aspect of the present invention, the support of the stimulable phosphor sheet is formed with 50,000 or more stimulable phosphor layer regions.

In a further preferred aspect of the present invention, the support of the stimulable phosphor sheet is formed with 10,0000 or more stimulable phosphor layer regions.

In a preferred aspect of the present invention, each of the plurality of stimulable phosphor layer regions is formed in the stimulable phosphor sheet to have a size of less than 5 $mm^2$.

In a further preferred aspect of the present invention, each of the plurality of stimulable phosphor layer regions is formed in the stimulable phosphor sheet to have a size of less than 1 $mm^2$.

In a further preferred aspect of the present invention, each of the plurality of stimulable phosphor layer regions is formed in the stimulable phosphor sheet to have a size of less than 0.5 $mm^2$.

In a further preferred aspect of the present invention, each of the plurality of stimulable phosphor layer regions is formed in the stimulable phosphor sheet to have a size of less than 0.1 $mm^2$.

In a further preferred aspect of the present invention, each of the plurality of stimulable phosphor layer regions is formed in the stimulable phosphor sheet to have a size of less than 0.05 $mm^2$.

In a further preferred aspect of the present invention, each of the plurality of stimulable phosphor layer regions is formed in the stimulable phosphor sheet to have a size of less than 0.01 $mm^2$.

In the present invention, the density of the stimulable phosphor layer regions formed in the stimulable phosphor sheet can be determined based upon the material of the support, the kind of electron beam released from the radioactive labeling substance and the like.

In a preferred aspect of the present invention, the plurality of stimulable phosphor layer regions are formed in the stimulable phosphor sheet at a density of 10 or more per $cm^2$.

In a further preferred aspect of the present invention, the plurality of stimulable phosphor layer regions are formed in the stimulable phosphor sheet at a density of 50 or more per $cm^2$.

In a further preferred aspect of the present invention, the plurality of stimulable phosphor layer regions are formed in the stimulable phosphor sheet at a density of 100 or more per $cm^2$.

In a further preferred aspect of the present invention, the plurality of stimulable phosphor layer regions are formed in the stimulable phosphor sheet at a density of 500 or more per $cm^2$.

In a further preferred aspect of the present invention, the plurality of stimulable phosphor layer regions are formed in the stimulable phosphor sheet at a density of 1,000 or more per $cm^2$.

In a further preferred aspect of the present invention, the plurality of stimulable phosphor layer regions are formed in the stimulable phosphor sheet at a density of 5,000 or more per $cm^2$.

In a further preferred aspect of the present invention, the plurality of stimulable phosphor layer regions are formed in the stimulable phosphor sheet at a density of 10,000 or more per $cm^2$.

In a further preferred aspect of the present invention, the plurality of stimulable phosphor layer regions are formed in the stimulable phosphor sheet at a density of 50,000 or more per $cm^2$.

In a further preferred aspect of the present invention, the plurality of stimulable phosphor layer regions are formed in the stimulable phosphor sheet at a density of 100,000 or more per $cm^2$.

In a preferred aspect of the present invention, the support of the stimulable phosphor sheet has a property of attenuating radiation energy.

According to this preferred aspect of the present invention, since the support of the stimulable phosphor sheet has a property of attenuating radiation energy, even in the case where a plurality of spot-like regions labeled with a radioactive labeling substance are formed at a high density in a biochemical analysis unit such as a membrane filter, if the plurality of stimulable phosphor layer regions are formed in the support in the same pattern as that of the plurality of spot-like regions formed in the biochemical analysis unit, electron beams (β rays) released from the radioactive labeling substance contained in the individual spot-like regions can be effectively prevented from entering stimulable phosphor layer regions other than that to be exposed to electron beams (β rays) released from the radioactive labeling substance contained in the spot-like region and, therefore, it is possible to produce biochemical analysis data having an excellent quantitative characteristic with high resolution by scanning the plurality of the stimulable phosphor layer regions with a stimulating ray and photoelectrically detecting stimulated emission released from the plurality of stimulable phosphor layer regions.

In a preferred aspect of the present invention, the support of the stimulable phosphor sheet has a property of reducing the energy of radiation to ⅕ or less when the radiation travels in the support by a distance equal to that between neighboring stimulable phosphor layer regions.

In a further preferred aspect of the present invention, the support of the stimulable phosphor sheet has a property of reducing the energy of radiation to 1/10 or less when the radiation travels in the support by a distance equal to that between neighboring stimulable phosphor layer regions.

In a further preferred aspect of the present invention, the support of the stimulable phosphor sheet has a property of reducing the energy of radiation to $1/50$ or less when the radiation travels in the support by a distance equal to that between neighboring stimulable phosphor layer regions.

In a further preferred aspect of the present invention, the support of the stimulable phosphor sheet has a property of reducing the energy of radiation to $1/100$ or less when the radiation travels in the support by a distance equal to that between neighboring stimulable phosphor layer regions.

In a further preferred aspect of the present invention, the support of the stimulable phosphor sheet has a property of reducing the energy of radiation to $1/500$ or less when the radiation travels in the support by a distance equal to that between neighboring stimulable phosphor layer regions.

In a further preferred aspect of the present invention, the support of the stimulable phosphor sheet has a property of reducing the energy of radiation to $1/1000$ or less when the radiation travels in the support by a distance equal to that between neighboring stimulable phosphor layer regions.

In a preferred aspect of the present invention, the support of the stimulable phosphor sheet has a property of attenuating light energy.

According to this preferred aspect of the present invention, since the support of the stimulable phosphor sheet has a property of attenuating radiation energy, even in the case where a plurality of spot-like regions labeled with a labeling substance which generates chemiluminescent emission when it contacts a chemiluminescent substrate are formed at a high density in a biochemical analysis unit such as a membrane filter, if the plurality of stimulable phosphor layer regions are formed in the support in the same pattern as that of the plurality of spot-like regions formed in the biochemical analysis unit, chemiluminescent emission in the wavelength of visible light released from the individual spot-like regions of a biochemical analysis unit when the stimulable phosphor sheet is superposed on the biochemical analysis unit formed with the plurality of spot-like regions releasing chemiluminescent emission generated by the contact of the chemiluminescent substance and the labeling substance to expose the plurality of stimulable phosphor layer regions of the stimulable phosphor sheet to the chemiluminescent emission can be effectively prevented from entering stimulable phosphor layer regions other than that to be exposed to chemiluminescent emission released from the spot-like region and, therefore, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

In the present invention, the plurality of spot-like regions of the biochemical analysis unit may be selectively labeled with a labeling substance which generates chemiluminescent emission when it contacts a chemiluminescent substrate by selectively binding a substance derived from a living organism and labeled with a labeling substance which generates chemiluminescent emission when it contacts a chemiluminescent substrate or selectively binding a substance derived from a living organism and labeled with a hapten, and binding an antibody for the hapten labeled with an enzyme which generates chemiluminescent emission when it contacts a chemiluminescent substrate with the hapten by an antigen-antibody reaction.

In the present invention, illustrative examples of the combination of hapten and antibody include digoxigenin and anti-digoxigenin antibody, theophylline and anti-theophylline antibody, fluorosein and anti-fluorosein antibody, and the like. Further, the combination of biotin and avidin, antigen and antibody may be utilized instead of the combination of hapten and antibody.

In a preferred aspect of the present invention, the support of the stimulable phosphor sheet has a property of reducing the energy of light to $1/5$ or less when the light travels in the support by a distance equal to that between neighboring stimulable phosphor layer regions.

In a further preferred aspect of the present invention, the support of the stimulable phosphor sheet has a property of reducing the energy of light to $1/10$ or less when the light travels in the support by a distance equal to that between neighboring stimulable phosphor layer regions.

In a further preferred aspect of the present invention, the support of the stimulable phosphor sheet has a property of reducing the energy of light to $1/50$ or less when the light travels in the support by a distance equal to that between neighboring stimulable phosphor layer regions.

In a further preferred aspect of the present invention, the support of the stimulable phosphor sheet has a property of reducing the energy of light to $1/100$ or less when the light travels in the support by a distance equal to that between neighboring stimulable phosphor layer regions.

In a further preferred aspect of the present invention, the support of the stimulable phosphor sheet has a property of reducing the energy of light to $1/500$ or less when the light travels in the support by a distance equal to that between neighboring stimulable phosphor layer regions.

In a further preferred aspect of the present invention, the support of the stimulable phosphor sheet has a property of reducing the energy of light to $1/1000$ or less when the light travels in the support by a distance equal to that between neighboring stimulable phosphor layer regions.

In the present invention, the material for forming the support of the stimulable phosphor sheet is preferably capable of attenuating radiation energy and/or light energy but is not particularly limited. The material for forming the support of the stimulable phosphor sheet may be any type of inorganic compound material or organic compound material and the support of the stimulable phosphor sheet can preferably be formed of metal material, ceramic material or plastic material.

Illustrative examples of inorganic compound materials preferably usable for forming the support of the stimulable phosphor sheet and capable of attenuating radiation energy and/or light energy in the present invention include metals such as gold, silver, copper, zinc, aluminum, titanium, tantalum, chromium, iron, nickel, cobalt, lead, tin, selenium and the like; alloys such as brass, stainless steel, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. These may have either a monocrystal structure or a polycrystal sintered structure such as amorphous, ceramic or the like.

In the present invention, a high molecular compound can preferably be used as an organic compound material preferably usable for forming the support of the stimulable phosphor sheet and capable of attenuating radiation energy and/or light energy. Illustrative examples of high molecular compounds preferably usable for forming the support of the stimulable phosphor sheet in the present invention include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifuluoroethylene; polycarbonate; polyesters such as polyethylene naphthalate, polyethylene terephthalate and the like; nylons such as nylon-6, nylon-6,6, nylon-4,10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Since the capability of attenuating radiation energy generally increases as specific gravity increases, the support of the stimulable phosphor sheet is preferably formed of a compound material or a composite material having specific gravity of 1.0 g/cm$^3$ or more and more preferably formed of a compound material or a composite material having specific gravity of 1.5 g/cm$^3$ to 23 g/cm$^3$.

Since the capability of attenuating light energy generally increases as scattering and/or absorption of light increases, the support of the stimulable phosphor sheet preferably has absorbance of 0.3 per cm (thickness) or more and more preferably has absorbance of 1 per cm (thickness) or more. The absorbance can be determined by placing an integrating sphere immediately behind a plate-like member having a thickness of T cm, measuring an amount A of transmitted light at a wavelength of probe light or emission light used for measurement by a spectrophotometer, and calculating A/T. In the present invention, a light scattering substance or a light absorbing substance may be added to the support of the stimulable phosphor sheet in order to improve the capability of attenuating light energy. Particles of a material different from a material forming the support of the stimulable phosphor sheet may be preferably used as a light scattering substance and a pigment or dye may be preferably used as a light absorbing substance.

In the present invention, the stimulable phosphor usable for storing radiation energy may be of any type insofar as it can store radiation energy or electron beam energy and can be stimulated by an electromagnetic wave to release the radiation energy or the electron beam energy stored therein in the form of light. More specifically, preferably employed stimulable phosphors include alkaline earth metal fluorohalide phosphors $(Ba_{1-x}, M^{2+}_x)FX:yA$ (where $M^{2+}$ is at least one alkaline earth metal selected from the group consisting of Mg, Ca, Sr, Zn and Cd; X is at least one element selected from the group consisting of Cl, Br and I, A is at least one element selected from the group consisting of Eu, Tb, Ce, Tm, Dy, Pr, Ho, Nd, Yb and Er; x is equal to or greater than 0 and equal to or less than 0.6 and y is equal to or greater than 0 and equal to or less than 0.2) disclosed in U.S. Pat. No. 4,239,968, alkaline earth metal fluorohalide phosphors SrFX:Z (where X is at least one halogen selected from the group consisting of Cl, Br and I; Z is at least one of Eu and Ce) disclosed in Japanese Patent Application Laid Open No. 2-276997, europium activated complex halide phosphors BaFXxNaX':aEu$^{2+}$ (where each of X or X' is at least one halogen selected from the group consisting of Cl, Br and I; x is greater than 0 and equal to or less than 2; and y is greater than 0 and equal to or less than 0.2) disclosed in Japanese Patent Application Laid Open No. 59-56479, cerium activated trivalent metal oxyhalide phosphors MOX:xCe (where M is at least one trivalent metal selected from the group consisting of Pr, Nd, Pm, Sm, Eu, Tb, Dy, Ho, Er, Tm, Yb and Bi; X is at least one halogen selected from the group consisting of Br and I; and x is greater than 0 and less than 0.1) disclosed in Japanese Patent Application laid Open No. 58-69281, cerium activated rare earth oxyhalide phosphors LnOX:xCe (where Ln is at least one rare earth element selected from the group consisting of Y, La, Gd and Lu; X is at least one halogen selected from the group consisting of Cl, Br and I; and x is greater than 0 and equal to or less than 0.1) disclosed in U.S. Pat. No. 4,539,137, and europium activated complex halide phosphors $M^{II}FXaM^IX'bM^{II}X''_2cM^{III}X'''_3xA:yEu^{2+}$ (where $M^{II}$ is at least one alkaline earth metal selected from the group consisting of Ba, Sr and Ca; $M^I$ is at least one alkaline metal selected from the group consisting of Li, Na, K, Rb and Cs; $M^{II}$ is at least one divalent metal selected from the group consisting of Be and Mg; $M^{III}$ is at least one trivalent metal selected from the group consisting of Al, Ga, In and Ti; A is at least one metal oxide; X is at least one halogen selected from the group consisting of Cl, Br and I; each of X', X" and X'" is at least one halogen selected from the group consisting of F, Cl, Br and I; a is equal to or greater than 0 and equal to or less than 2; b is equal to or greater than 0 and equal to or less than $10^{-2}$; c is equal to or greater than 0 and equal to or less than $10^{-2}$; a+b+c is equal to or greater than $10^{-2}$; x is greater than 0 and equal to or less than 0.5; and y is greater than 0 and equal to or less than 0.2) disclosed in U.S. Pat. No. 4,962,047.

In the present invention, the stimulable phosphor usable for storing light energy may be of any type insofar as it can store the energy of light in the wavelength band of visible light and can be stimulated by an electromagnetic wave to release in the form of light the energy of light in the wavelength band of visible light stored therein. More specifically, preferably employed stimulable phosphors include at least one selected from the group consisting of metal halophosphates, rare-earth-activated sulfide-host phosphors, aluminate-host phosphors, silicate-host phosphors, fluoride-host phosphors and mixtures of two, three or more of these phosphors. Among them, rare-earth-activated sulfide-host phosphors are more preferable and, particularly, rare-earth-activated alkaline earth metal sulfide-host phosphors disclosed in U.S. Pat. Nos. 5,029,253 and 4,983,834, zinc germanate such as $Zn_2GeO_4$:Mn, V; $Zn_2GeO_4$:Mn disclosed in Japanese Patent Application Laid Open No. 2001-131545, alkaline-earth aluminate such as $Sr_4Al_{14}O_{25}$:Ln (where Ln is a rare-earth element) disclosed in Japanese Patent Application Laid Open No. 2001-123162, $Y_{0.8}Lu_{1.2}SiO_5$:Ce, Zr; GdOCl:Ce disclosed in Japanese Patent Publication No. 6-31904 and the like are most preferable.

The above and other objects and features of the present invention will become apparent from the following description made with reference to the accompanying drawings.

DESCRIPTION OF THE PREFERRED EMBODIMENTS

Figure 1:
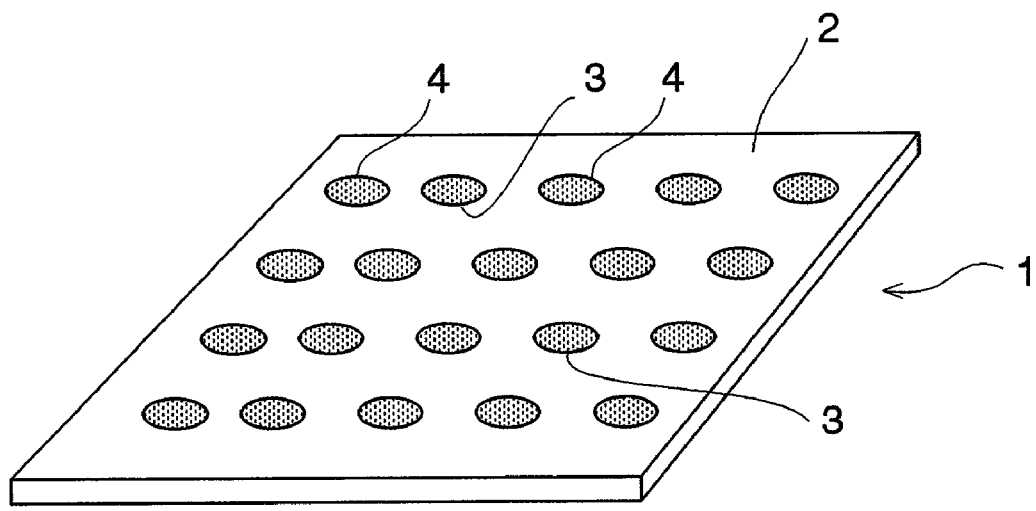
FIG. 1 is a schematic perspective view showing a biochemical analysis unit used in a biochemical analysis data producing method which is a preferred embodiment of the present invention.

FIG. 1 is a schematic perspective view showing a biochemical analysis unit used in a biochemical analysis data producing method which is a preferred embodiment of the present invention.

As shown in FIG. 1, a biochemical analysis unit 1 according to this embodiment includes a substrate 2 formed of stainless steel and formed with a number of substantially circular through-holes 3 at a high density, and a number of absorptive regions 4 are dot-like formed spaced apart from each other by charging nylon-6 in the through-holes 3.

Although not accurately shown in FIG. 1, in this embodiment, the through-holes 3 are formed in the substrate 2 so that substantially circular absorptive regions 4 having a size of about 0.07 cm$^2$ are regularly formed in the manner of a matrix of 120 columns×160 lines and, therefore, 19,200 absorptive regions 4 are formed.

A number of absorptive regions 4 are formed by charging nylon-6 in the through-holes 3 formed in the substrate in such a manner that the surfaces of the absorptive regions 4 lie below the surface of the substrate 2.

Figure 2:
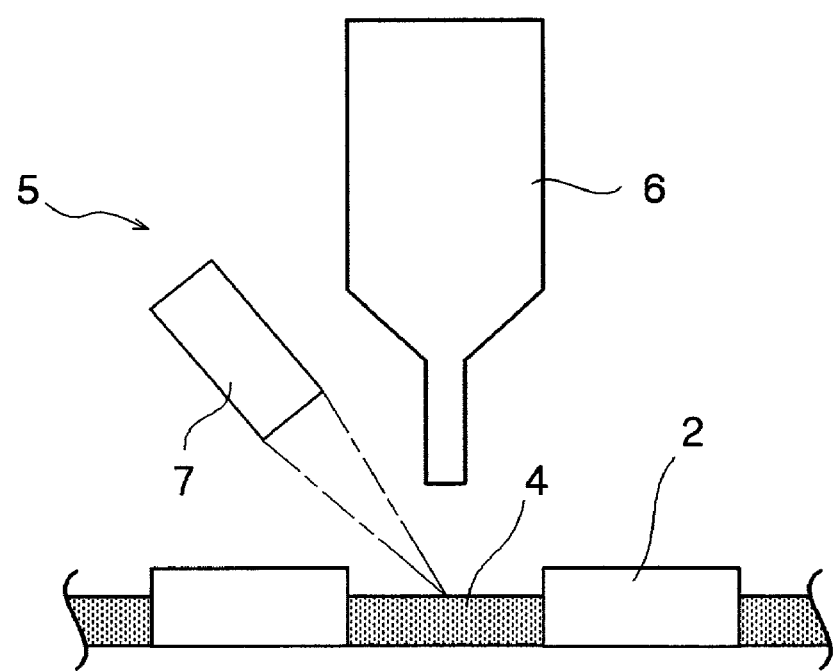
FIG. 2 is a schematic front view showing a spotting device.

FIG. 2 is a schematic front view showing a spotting device.

As shown in FIG. 2, when biochemical analysis is performed, a solution containing specific binding substances such as a plurality of cDNAs whose sequences are known but differ from each other are spotted using a spotting device 5 onto a number of the absorptive regions 4 of the biochemical analysis unit 1 and the specific binding substances are fixed therein.

As shown in FIG. 2, the spotting device 5 includes an injector 6 for ejecting a solution of specific binding substances toward the biochemical analysis unit 1 and a CCD camera 7 and is constituted so that the solution of specific binding substances such as cDNAs are spotted from the injector 6 when the tip end portion of the injector 6 and the center of the absorptive region 4 into which the solution containing specific binding substances is to be spotted are determined to coincide with each other as a result of viewing them using the CCD camera, thereby ensuring that the solution of specific binding substances can be accurately spotted into a number of the absorptive regions 4 of the biochemical analysis unit 1.

Figure 3:
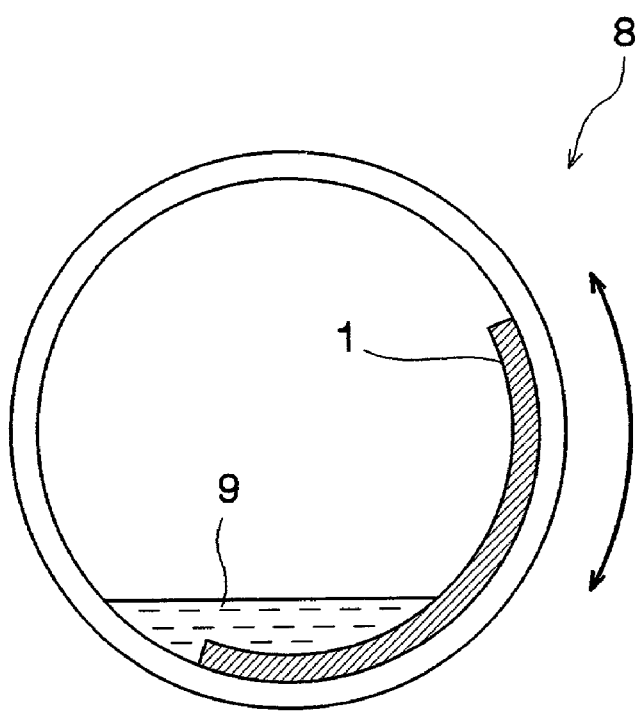
FIG. 3 is a schematic longitudinal cross sectional view showing a hybridization reaction vessel.

FIG. 3 is a schematic longitudinal cross sectional view showing a hybridization reaction vessel.

As shown in FIG. 3, a hybridization reaction vessel 8 is formed cylindrically and accommodates a hybridization reaction solution 9 containing a substance derived from a living organism and labeled with a labeling substance therein.

In the case where a specific binding substance such as cDNA is to be labeled with a radioactive labeling substance, a hybridization reaction solution 9 containing a substance derived from a living organism and labeled with a radioactive labeling substance as a probe is prepared and is accommodated in the hybridization reaction vessel 8.

On the other hand, in the case where a specific binding substance such as cDNA is to be labeled with a labeling substance which generates chemiluminescent emission when it contacts a chemiluminescent substrate, a hybridization reaction solution 9 containing a substance derived from a living organism and labeled with a labeling substance which generates chemiluminescent emission when it contacts a chemiluminescent substrate as a probe is prepared and is accommodated in the hybridization reaction vessel 8.

Further, in the case where a specific binding substance such as cDNA is to be labeled with a fluorescent substance such as a fluorescent dye, a hybridization reaction solution 9 containing a substance derived from a living organism and labeled with a fluorescent substance such as a fluorescent dye as a probe is prepared and is accommodated in the hybridization reaction vessel 8.

It is possible to prepare a hybridization reaction solution 9 containing two or more substances derived from a living organism among a substance derived from a living organism and labeled with a radioactive labeling substance, a substance derived from a living organism and labeled with a labeling substance which generates chemiluminescent emission when it contacts a chemiluminescent substrate, and a substance derived from a living organism and labeled with a fluorescent substance such as a fluorescent dye and accommodate it in the hybridization reaction vessel 8. In this embodiment, a hybridization reaction solution 9 containing a substance derived from a living organism and labeled with a radioactive labeling substance, a substance derived from a living organism and labeled with a fluorescent substance such as a fluorescent dye, and a substance derived from a living organism and labeled with a labeling substance which generates chemiluminescent emission when it contacts a chemiluminescent substrate is prepared and accommodated in the hybridization reaction vessel 8.

When hybridization is to be performed, the biochemical analysis unit 1 containing specific binding substances such as a plurality of cDNAs spotted into a number of the absorptive regions 4 is accommodated in the hybridization reaction vessel 8. In this embodiment, since the substrate 2 is formed of stainless steel having flexibility, the biochemical analysis unit 140 can, as shown in FIG. 3, be bent and accommodated in the hybridization reaction vessel 8 along the inner wall surface thereof.

As indicated by the arrows in FIG. 3, the hybridization reaction vessel 8 is constituted so as to be rotatable about a shaft by a drive means (not shown) and since the biochemical analysis unit 1 is bent and accommodated in the hybridization vessel 8 along the inner wall surface thereof, even when the hybridization vessel 8 accommodates only a small amount of hybridization reaction solution 9, specific binding substances spotted in a number of the absorptive regions 4 can be selectively hybridized with a substance derived from a living organism labeled with a radioactive labeling substance and a substance derived from a living organism labeled with a fluorescent substance and contained in the hybridization reaction solution 9 by rotating the hybridization reaction vessel 8.

In this manner, specific binding substances spotted in a number of the absorptive regions 4 of the biochemical analysis unit 1 are selectively hybridized with a substance derived from a living organism, labeled with a radioactive labeling substance and contained in the hybridization reaction solution 9, a substance derived from a living organism, labeled with a fluorescent substance such as a fluorescent dye and contained in the hybridization reaction solution 9 and a substance derived from a living organism, labeled with a labeling substance which generates chemiluminescent emission when it contacts a chemiluminescent substrate and contained in the hybridization reaction solution 9, whereby radiation data of a radioactive labeling substance, fluorescence data of a fluorescent substance such as a fluorescent dye and chemilumminescent data are recorded in a number of absorptive regions 4 formed in the biochemical analysis unit 1.

Fluorescence data recorded in the biochemical analysis unit 1 are read by a first scanner described later, thereby producing biochemical analysis data.

On the other hand, radiation data of the radioactive labeling substance recorded in a number of absorptive regions 4 formed in the biochemical analysis unit 1 are transferred onto a stimulable phosphor layer of a stimulable phosphor sheet and read by the first scanner described later, thereby producing biochemical analysis data.

Further, chemiluminescent data recorded in a number of absorptive regions 4 formed in the biochemical analysis unit 1 are transferred onto a stimulable phosphor layer of another stimulable phosphor sheet and read by a second scanner described later, thereby producing biochemical analysis data.

Figure 4:
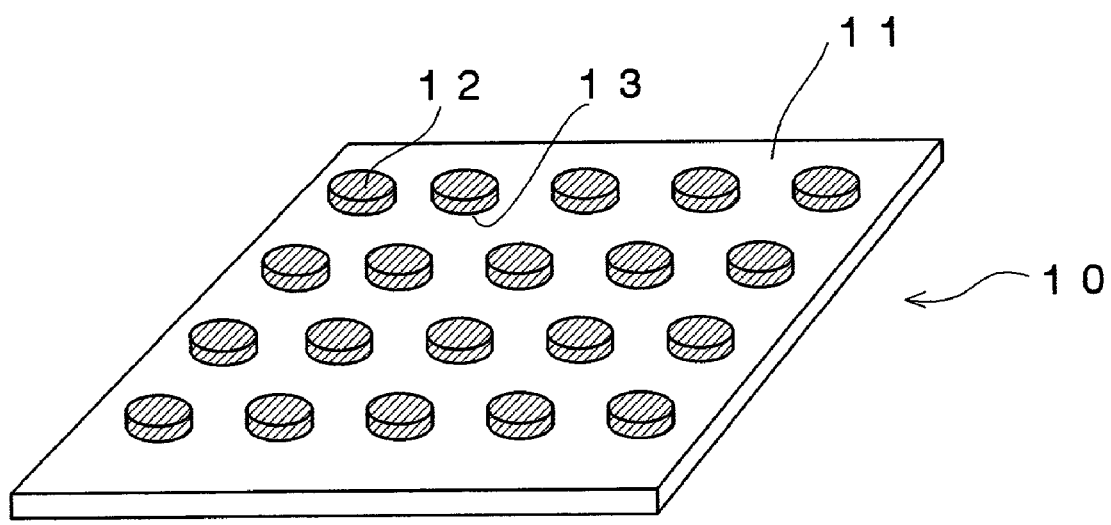
FIG. 4 is a schematic perspective view showing a stimulable phosphor sheet used for a biochemical analysis data producing method which is a preferred embodiment of the present invention.

FIG. 4 is a schematic perspective view showing a stimulable phosphor sheet used for a biochemical analysis data producing method which is a preferred embodiment of the present invention.

As shown in FIG. 4, a stimulable phosphor sheet 10 according to this embodiment includes a support 11 made of oxygen free copper and regularly formed with a number of substantially circular recesses 13 and a number of stimulable phosphor layer regions 12 are dot-like formed by embedding BaFX system stimulable phosphor (where X is at least one halogen atom selected from the group consisting of Cl, Br and I) capable of absorbing and storing radiation energy in the recesses 13.

In this embodiment, stimulable phosphor is embedding in a number of the recesses 13 in such a manner that the surfaces of the stimulable phosphor layer regions 12 lie above the surface of the support 11.

A number of the recesses 13 are formed in the support 11 in the same pattern as that of a number of the absorptive regions 4 formed in the substrate 2 of the biochemical analysis unit 1 and each of them has the same size as that of the absorptive region 4 formed in the substrate 2 of the biochemical analysis unit 1.

Therefore, although not accurately shown in FIG. 4, in this embodiment, substantially circular stimulable phosphor layer regions 12 having a size of about 0.07 cm$^2$ are regularly formed in the manner of a matrix of 120 columns× 160 lines in the support 11 and, therefore, 19,200 stimulable phosphor layer regions 12 are dot-like formed.

Figure 5:
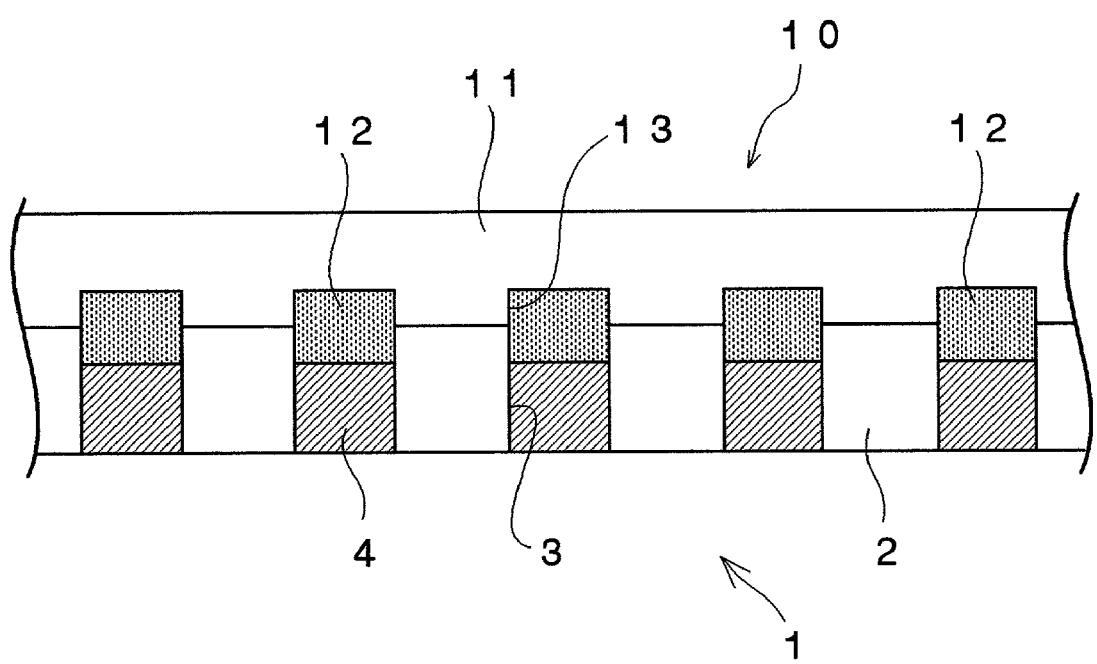
FIG. 5 is a schematic cross-sectional view showing a method for exposing a number of stimulable phosphor layer regions formed in a stimulable phosphor sheet to a radioactive labeling substance contained in a number of absorptive regions formed in the biochemical analysis unit.

FIG. 5 is a schematic cross-sectional view showing a method for exposing a number of the stimulable phosphor layer regions 12 formed in the stimulable phosphor sheet 10 to a radioactive labeling substance contained in a number of the absorptive regions 4 formed in the biochemical analysis unit 1.

As shown in FIG. 5, when the stimulable phosphor layer regions 12 of a stimulable phosphor sheet 10 are to be exposed, the stimulable phosphor sheet 10 is superposed on the biochemical analysis unit 1 in such a manner that a number of the stimulable phosphor layer regions 12 formed in the support 11 of the stimulable phosphor sheet 10 are located in the corresponding through-holes 3 formed in the substrate 2 of the biochemical analysis unit 1 and face the corresponding absorptive regions 4 formed in the through-holes 3.

In this embodiment, since the biochemical analysis unit 1 is formed by embedding nylon-6 in a number of the through-holes 3 formed in the substrate 2 made of stainless steel, the biochemical analysis unit 1 hardly stretches or shrinks even when it is subjected to liquid processing such as hybridization and, therefore, it is possible to easily and accurately superpose the stimulable phosphor sheet 10 on the biochemical analysis unit 1 so that each of the stimulable phosphor layer regions 12 formed in the support 11 of the stimulable phosphor sheet 10 accurately faces the corresponding absorptive region 4 formed in the substrate 2 of the biochemical analysis unit 1, thereby exposing the stimulable phosphor layer regions 12.

In this manner, each of the stimulable phosphor layer regions 12 formed in the support 11 of the stimulable phosphor sheet 10 is kept to face the corresponding absorptive region 4 formed in the substrate 2 of the biochemical analysis unit 1 for a predetermined time period, whereby a number of the stimulable phosphor layer regions 12 formed in the support 11 of the stimulable phosphor sheet 10 are exposed to the radioactive labeling substance contained in a number of the absorptive regions 4 formed in the substrate 2 of the biochemical analysis unit 1.

During the exposure operation, electron beams (β rays) are released from the radioactive labeling substance contained in the absorptive regions 4 of the biochemical analysis unit 1. However, since a number of the absorptive regions 4 of the biochemical analysis unit 1 are formed spaced apart from each other in the substrate 2 made of stainless steel and the substrate 2 made of stainless steel capable of attenuating radiation energy is present around each of the absorptive regions 4, electron beams (β rays) released from the radioactive labeling substance contained in the absorptive regions 4 of the biochemical analysis unit 1 can be efficiently prevented from scattering in the substrate 2 of the biochemical analysis unit 1. Further, since a number of the stimulable phosphor layer regions 12 of the stimulable phosphor sheet 10 are formed by embedding stimulable phosphor in a number of the recesses 13 formed in the support 11 made of oxygen free copper and the support 11 made of oxygen free copper capable of attenuating radiation energy is present around each of the stimulable phosphor layer regions 12, electron beams (β rays) released from the radioactive labeling substance contained in the absorptive regions 4 of the biochemical analysis unit 1 can be efficiently prevented from scattering in the support 11 of the stimulable phosphor sheet 10. Therefore, it is possible to selectively expose only the stimulable phosphor layer region 12 each of the absorptive regions 4 faces to the electron beams (β rays) released from the radioactive labeling substance contained in each of the absorptive regions 4.

In this manner, radiation data of a radioactive labeling substance are recorded in a number of the stimulable phosphor layer regions 12 formed in the support 11 of the stimulable phosphor sheet 10.

Figure 6:
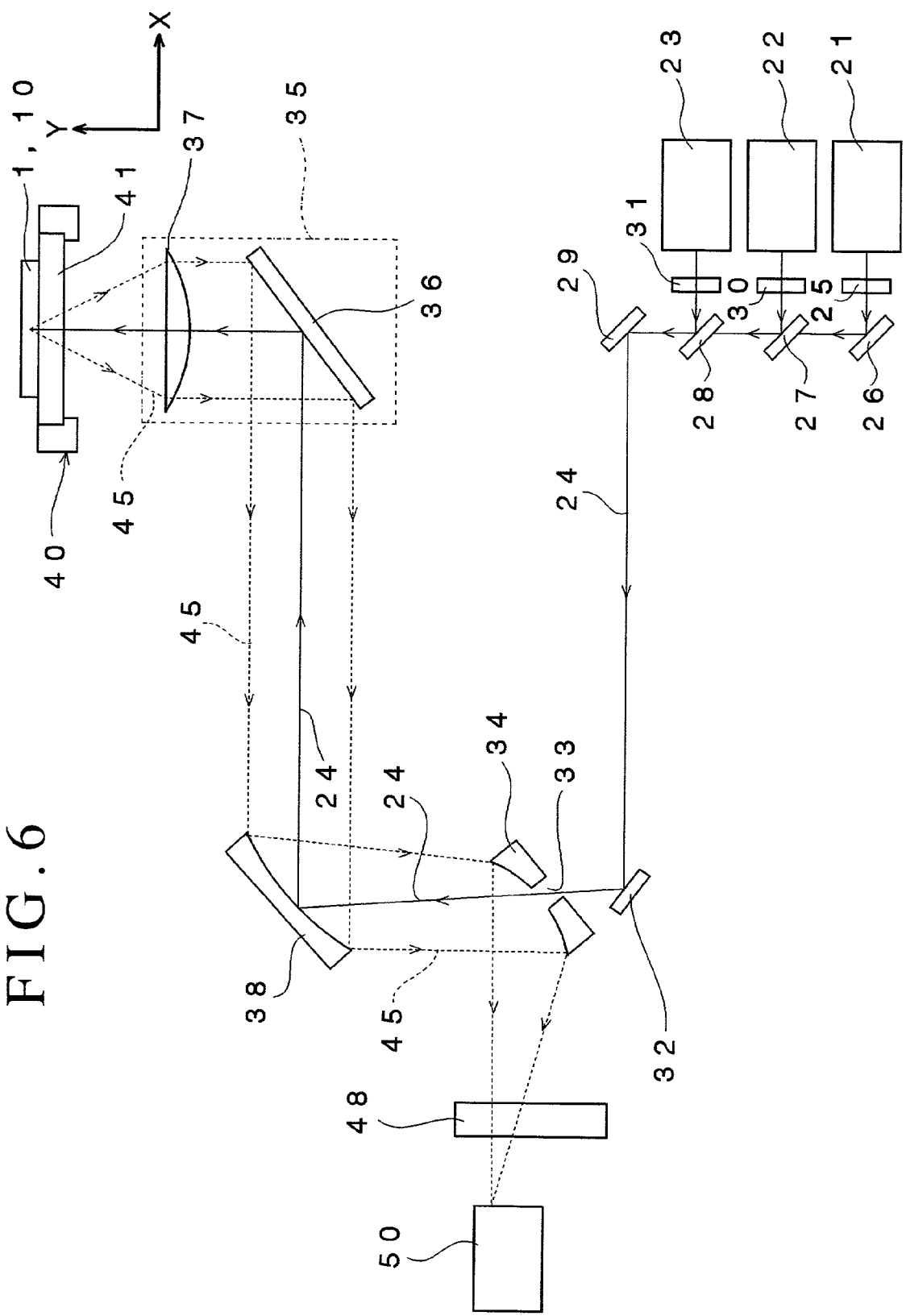
FIG. 6 is a schematic perspective view showing a first scanner for reading radiation data of a radioactive labeling substance recorded in a number of the stimulable phosphor layer regions 12 formed in the support 11 of the stimulable phosphor sheet 10 and fluorescence data recorded in a number of the absorptive regions 4 formed in the biochemical analysis unit 1 and producing biochemical analysis data.
Figure 7:
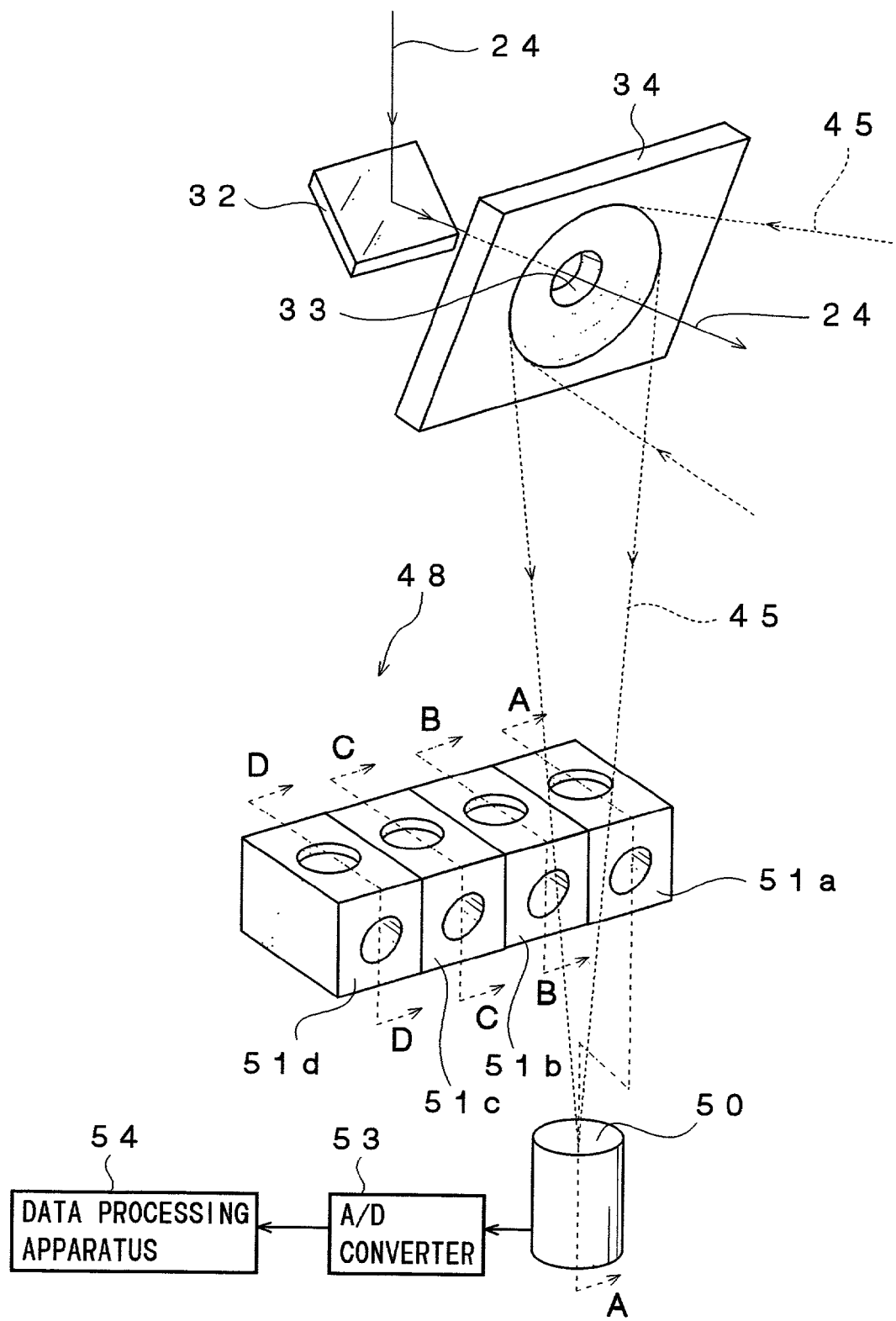
FIG. 7 is a schematic perspective view showing details in the vicinity of a photomultiplier of a first scanner shown in FIG. 6.

FIG. 6 is a schematic view showing a first scanner for reading radiation data of a radioactive labeling substance recorded in a number of the stimulable phosphor layer regions 12 formed in the support 11 of the stimulable phosphor sheet 10 and fluorescence data recorded in a number of the absorptive regions 4 formed in the biochemical analysis unit 1 and producing biochemical analysis data, and FIG. 7 is a schematic perspective view showing details in the vicinity of a photomultiplier of the first scanner.

The first scanner shown according to this embodiment is constituted so as to read radiation data of a radioactive labeling substance recorded in a number of the stimulable phosphor layer regions 12 formed in the support 11 of the stimulable phosphor sheet 10 and fluorescence data recorded in a number of the absorptive regions 4 of the biochemical analysis unit 1 to produce biochemical analysis data and includes a first laser stimulating ray source 21 for emitting a laser beam having a wavelength of 640 nm, a second laser stimulating ray source 22 for emitting a laser beam having a wavelength of 532 nm and a third laser stimulating ray source 23 for emitting a laser beam having a wavelength of 473 nm.

In this embodiment, the first laser stimulating ray source 21 is constituted by a semiconductor laser beam source and the second laser stimulating ray source 22 and the third laser stimulating ray source 23 are constituted by a second harmonic generation element.

A laser beam 24 emitted from the first laser stimulating source 21 passes through a collimator lens 25, thereby being made a parallel beam, and is reflected by a mirror 26. A first dichroic mirror 27 for transmitting light having a wavelength of 640 nm but reflecting light having a wavelength of 532 nm and a second dichroic mirror 28 for transmitting light having a wavelength equal to and longer than 532 nm but reflecting light having a wavelength of 473 nm are provided in the optical path of the laser beam 24 emitted from the first laser stimulating ray source 21. The laser beam 24 emitted from the first laser stimulating ray source 21 and reflected by the mirror 26 passes through the first dichroic mirror 27 and the second dichroic mirror 28 and advances to a mirror 29.

On the other hand, the laser beam 24 emitted from the second laser stimulating ray source 22 passes through a collimator lens 30, thereby being made a parallel beam, and is reflected by the first dichroic mirror 27, thereby changing its direction by 90 degrees. The laser beam 24 then passes through the second dichroic mirror 28 and advances to the mirror 29.

Further, the laser beam 24 emitted from the third laser stimulating ray source 23 passes through a collimator lens 31, thereby being made a parallel beam, and is reflected by the second dichroic mirror 28, thereby changing its direction by 90 degrees. The laser beam 24 then advances to the mirror 29.

The laser beam 24 advancing to the mirror 29 is reflected by the mirror 29 and advances to a mirror 32 to be reflected thereby.

A perforated mirror 34 formed with a hole 33 at the center portion thereof is provided in the optical path of the laser beam 24 reflected by the mirror 32. The laser beam 24 reflected by the mirror 32 passes through the hole 33 of the perforated mirror 34 and advances to a concave mirror 38.

The laser beam 24 advancing to the concave mirror 38 is reflected by the concave mirror 38 and enters an optical head 35.

The optical head 35 includes a mirror 36 and an aspherical lens 37. The laser beam 24 entering the optical head 35 is reflected by the mirror 36 and condensed by the aspherical lens 37 onto the stimulable phosphor sheet 10 or the biochemical analysis unit 1 placed on the glass plate 41 of a stage 40.

When the laser beam 24 impinges on the stimulable phosphor layer region 12 of the stimulable phosphor sheet 10, stimulable phosphor contained in the stimulable phosphor layer region 12 formed in the support 11 of the stimulable phosphor 10 is excited, thereby releasing stimulated emission 45. On the other hand, when the laser beam 24 impinges on the absorptive region 4 formed in the substrate 2 of the biochemical analysis unit 1, a fluorescent dye or the like contained in the absorptive region 4 is excited, thereby releasing fluorescence emission 45.

The stimulated emission 45 released from the stimulable phosphor layer region 12 of the stimulable phosphor 10 or the fluorescence emission 45 released from the absorptive region 4 of the biochemical analysis unit 1 is condensed onto the mirror 36 by the aspherical lens 37 provided in the optical head 35 and reflected by the mirror 36 on the side of the optical path of the laser beam 24, thereby being made a parallel beam to advance to the concave mirror 38.

The stimulated emission 45 or the fluorescence emission 45 advancing to the concave mirror 38 is reflected by the concave mirror 38 and advances to the perforated mirror 34.

As shown in FIG. 7, the stimulated emission 45 or the fluorescence emission 45 advancing to the perforated mirror 34 is reflected downward by the perforated mirror 34 formed as a concave mirror and advances to a filter unit 48, whereby light having a predetermined wavelength is cut. The stimulated emission 45 or the fluorescence emission 45 then impinges on a photomultiplier 50, thereby being photoelectrically detected.

As shown in FIG. 7, the filter unit 48 is provided with four filter members 51a, 51b, 51c and 51d and is constituted to be laterally movable in FIG. 7 by a motor (not shown).

Figure 8:
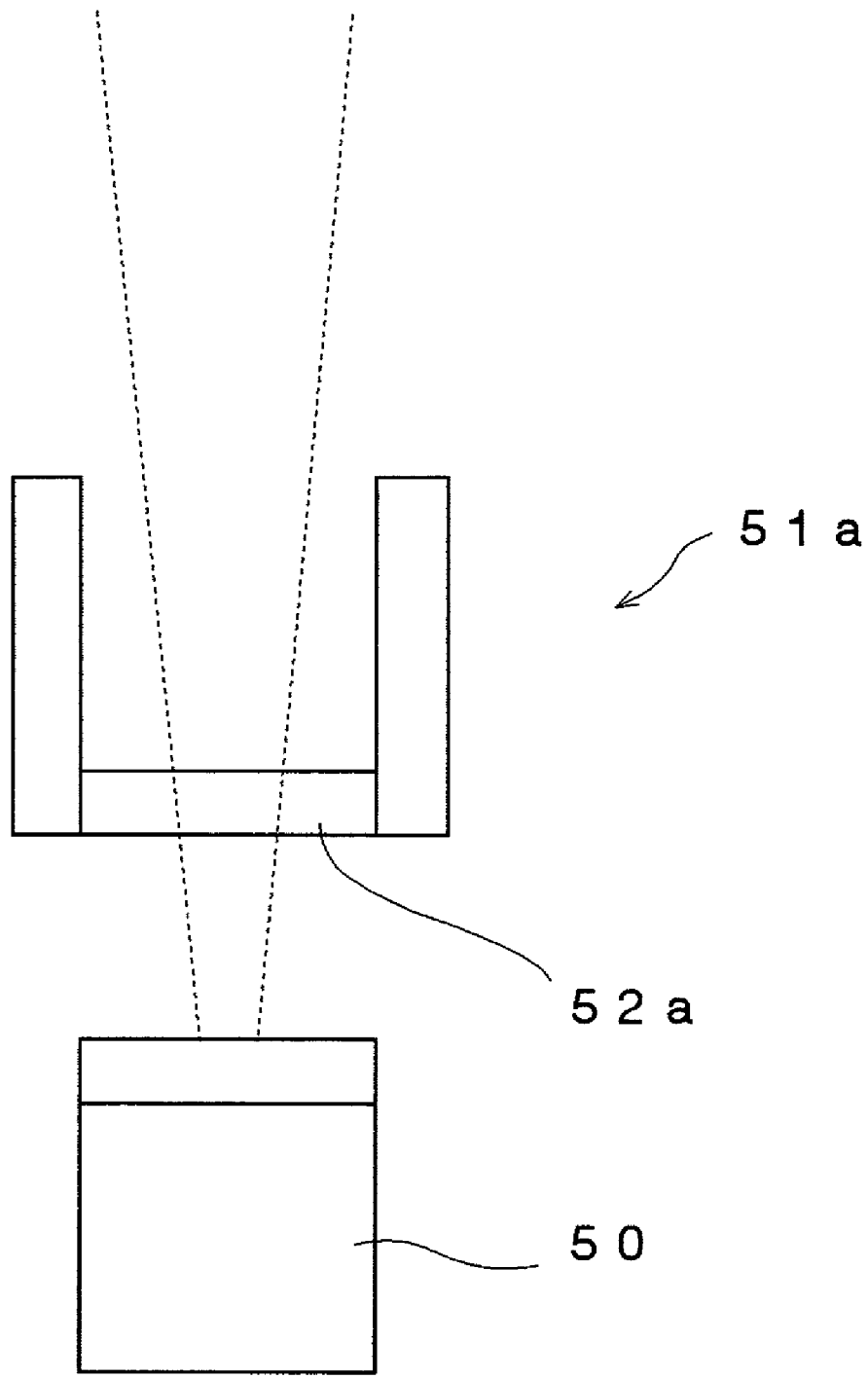
FIG. 8 is a schematic cross-sectional view taken along a line A—A in FIG. 7.

FIG. 8 is a schematic cross-sectional view taken along a line A—A in FIG. 7.

As shown in FIG. 8, the filter member 51a includes a filter 52a and the filter 52a is used for reading fluorescence emission 45 by stimulating a fluorescent substance such as a fluorescent dye contained in a number of the absorptive regions 4 formed in the substrate 2 of the biochemical analysis unit 1 using the first laser stimulating ray source 21 and has a property of cutting off light having a wavelength of 640 nm but transmitting light having a wavelength longer than 640 nm.

Figure 9:
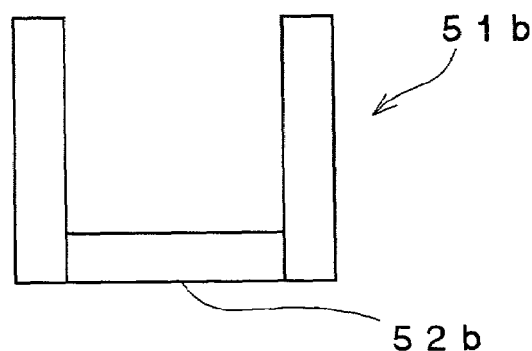
FIG. 9 is a schematic cross-sectional view taken along a line B—B in FIG. 7.

FIG. 9 is a schematic cross-sectional view taken along a line B—B in FIG. 7.

As shown in FIG. 9, the filter member 51b includes a filter 52b and the filter 52b is used for reading fluorescence emission 45 by stimulating a fluorescent substance such as a fluorescent dye contained in a number of the absorptive regions 4 formed in the substrate 2 of the biochemical analysis unit 1 using the second laser stimulating ray source 22 and has a property of cutting off light having a wavelength of 532 nm but transmitting light having a wavelength longer than 532 nm.

Figure 10:
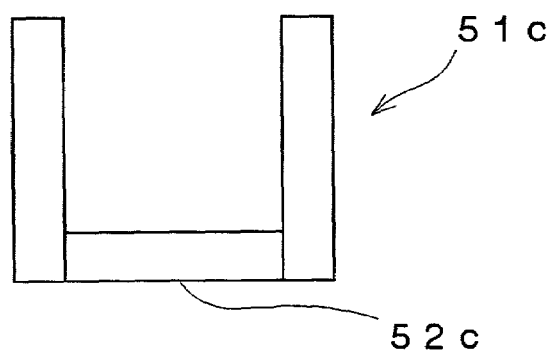
FIG. 10 is a schematic cross-sectional view taken along a line C—C in FIG. 7.

FIG. 10 is a schematic cross-sectional view taken along a line C—C in FIG. 7.

As shown in FIG. 10, the filter member 51c includes a filter 52c and the filter 52c is used for reading fluorescence emission 45 by stimulating a fluorescent substance such as a fluorescent dye contained in in a number of the absorptive regions 4 formed in the substrate 2 of the biochemical analysis unit 1 using the third laser stimulating ray source 23 and has a property of cutting off light having a wavelength of 473 nm but transmitting light having a wavelength longer than 473 nm.

Figure 11:
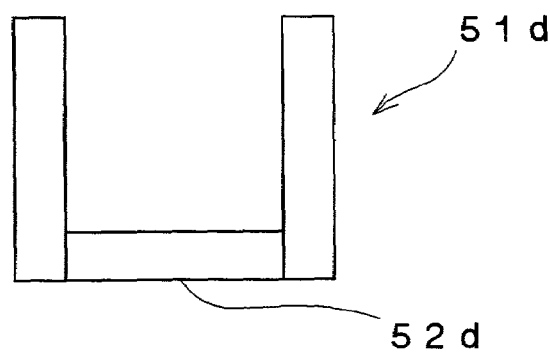
FIG. 11 is a schematic cross-sectional view taken along a line D—D in FIG. 7.

FIG. 11 is a schematic cross-sectional view taken along a line D—D in FIG. 7.

As shown in FIG. 11, the filter member 51d includes a filter 52d and the filter 52d is used for reading stimulated emission released from stimulable phosphor contained in the stimulable phosphor layer 12 formed in the support 11 of the stimulable phosphor sheet 10 upon being stimulated using the first laser stimulating ray source 1 and has a property of transmitting only light having a wavelength corresponding to that of stimulated emission emitted from stimulable phosphor and cutting off light having a wavelength of 640 nm.

Therefore, in accordance with the kind of a stimulating ray source to be used, one of these filter members 51a, 51b, 51c, 51d is selectively positioned in front of the photomultiplier 50, thereby enabling the photomultiplier 50 to photoelectrically detect only light to be detected.

The analog data produced by photoelectrically detecting light with the photomultiplier 50 are converted by an A/D converter 53 into digital data and the digital data are fed to a data processing apparatus 54.

Although not shown in FIG. 6, the optical head 35 is constituted to be movable by a scanning mechanism in a main scanning direction indicated by an arrow X and a sub-scanning direction indicated by an arrow Y in FIG. 6 so that all of the stimulable phosphor layer regions 12 formed in the support 11 of the stimulable phosphor sheet 10 or all of the absorptive regions 4 formed in the substrate 2 of the biochemical analysis unit 1 can be scanned by the laser beam 24.

Figure 12:
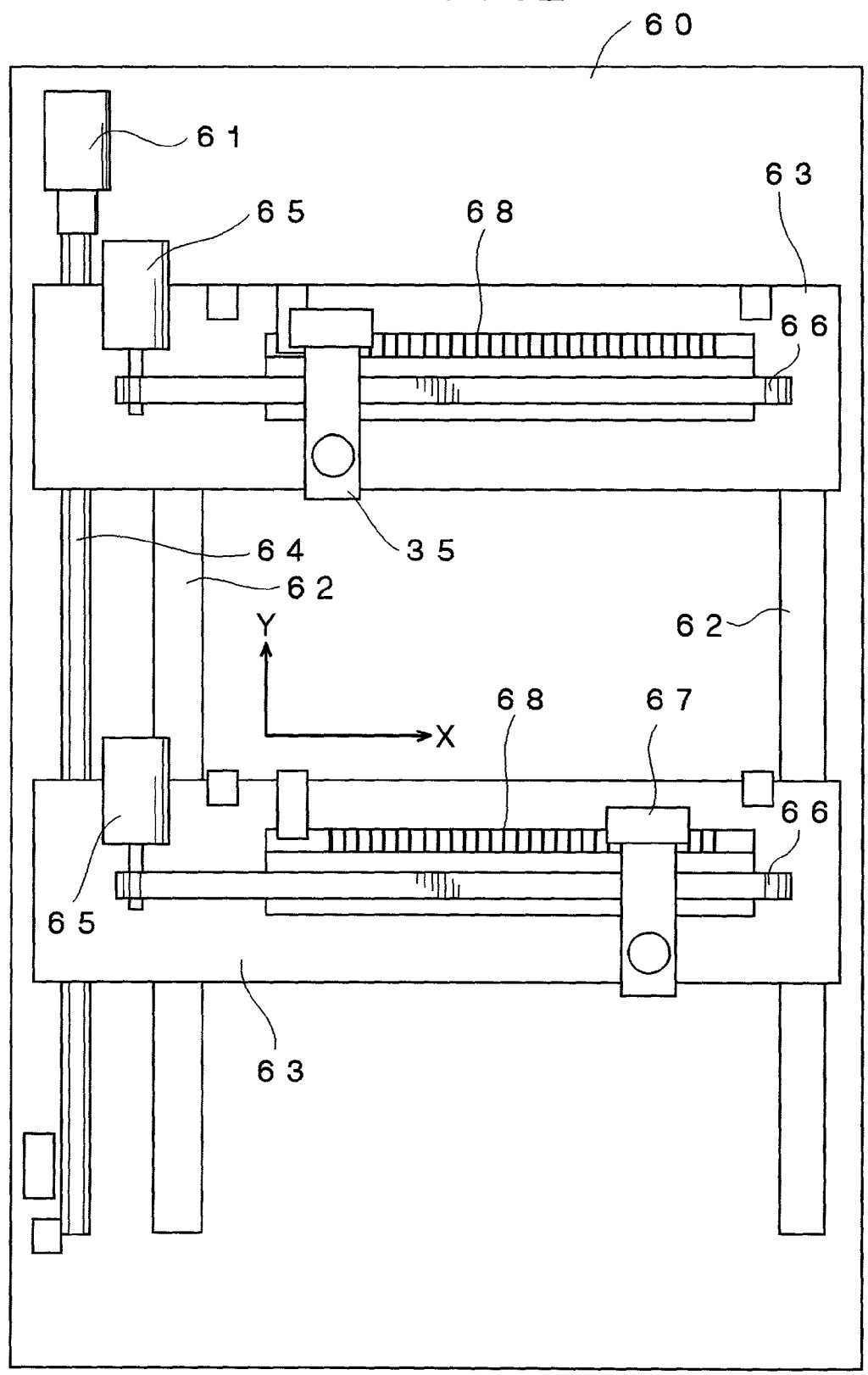
FIG. 12 is a schematic plan view of a scanning mechanism of an optical head.

FIG. 12 is a schematic plan view showing the scanning mechanism of the optical head 35.

In FIG. 12, optical systems other than the optical head 35 and the paths of the laser beam 24 and stimulated emission 45 or fluorescence emission 45 are omitted for simplification.

As shown in FIG. 12, the scanning mechanism of the optical head 35 includes a base plate 60, and a sub-scanning pulse motor 61 and a pair of rails 62, 62 are fixed on the base plate 60. A movable base plate 63 is further provided so as to be movable in the sub-scanning direction indicated by an arrow Y in FIG. 12.

The movable base plate 63 is formed with a threaded hole (not shown) and a threaded rod 64 rotated by the sub-scanning pulse motor 61 is engaged with the inside of the hole.

A main scanning stepping motor 65 is provided on the movable base plate 63. The main scanning stepping motor 65 is adapted for intermittently driving an endless belt 66 by a pitch equal to the distance between neighboring absorptive regions 4 formed in the biochemical analysis unit 1, namely, the distance between neighboring stimulable phosphor layer regions 12 formed in the stimulable phosphor sheet 10.

The optical head 35 is fixed to the endless belt 66 and when the endless belt 66 is driven by the main scanning stepping motor 65, the optical head 35 is moved in the main scanning direction indicated by an arrow X in FIG. 12. In FIG. 12, the reference numeral 67 designates a linear encoder for detecting the position of the optical head 35 in the main scanning direction and the reference numeral 68 designates slits of the linear encoder 67.

Therefore, the optical head 35 is moved in the main scanning direction indicated by the arrow X and the sub-scanning direction indicated by the arrow Y in FIG. 12 by driving the endless belt 66 in the main scanning direction by the main scanning stepping motor 65 and intermittently moving the movable base plate 63 in the sub-scanning direction by the sub-scanning pulse motor 61, thereby scanning all of the stimulable phosphor layer regions 12 formed in the support 11 of the stimulable phosphor sheet 10 or all of the absorptive regions 4 formed in the substrate 2 of the biochemical analysis unit 1 with the laser beam 24.

Figure 13:
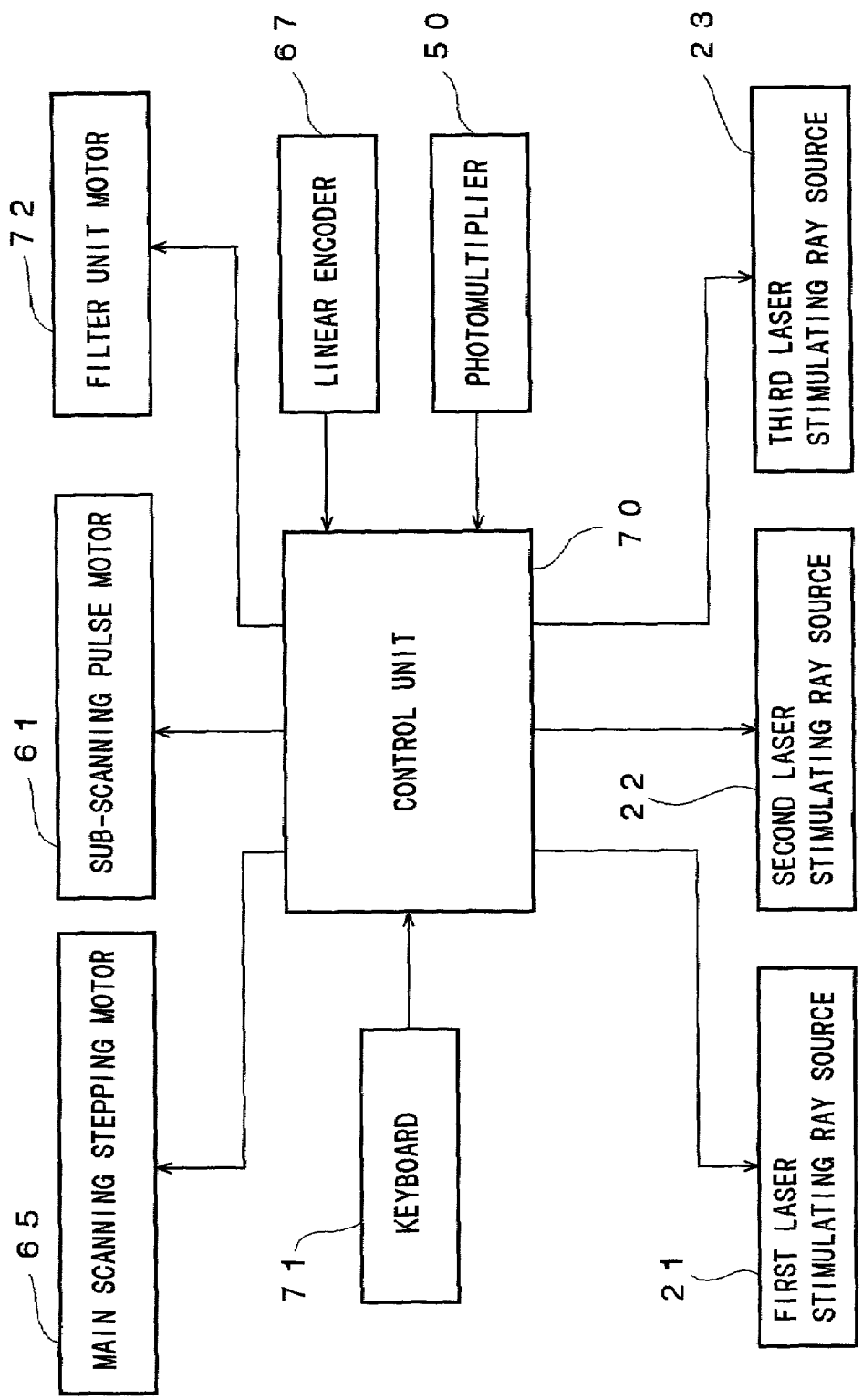
FIG. 13 is a block diagram of a control system, an input system, a drive system and a detection system of the first scanner which is a preferred embodiment of the present invention.

FIG. 13 is a block diagram of a control system, an input system, a drive system and a detection system of the first scanner which is a preferred embodiment of the present invention.

As shown in FIG. 13, the control system of the first scanner includes a control unit 70 for controlling the overall operation of the first scanner and the data processing apparatus 54, and the input system of the first scanner includes a keyboard 71 which can be operated by a user and through which various instruction signals can be input.

As shown in FIG. 13, the drive system of the first scanner includes the main scanning stepping motor 65 for intermittently moving the optical head 35 in the main scanning direction, the sub-scanning pulse motor 61 for moving the optical head 35 in the sub-scanning direction and a filter unit motor 72 for moving the filter unit 48 provided with the four filter members 51a, 51b, 51c and 51d.

The control unit 70 is adapted for selectively outputting a drive signal to the first laser stimulating ray source 21, the second laser stimulating ray source 22 or the third laser stimulating ray source 23 and outputting a drive signal to the filter unit motor 72.

As shown in FIG. 13, the detection system of the first scanner includes the photomultiplier 50 and the linear encoder 67.

In this embodiment, the control unit 70 is adapted to control the on and off operation of the first laser stimulating ray source 21, the second laser stimulating ray source 22 or the third laser stimulating ray source 23 in accordance with a detection signal indicating the position of the optical head 35 input from the linear encoder 67.

The thus constituted first scanner reads radiation data recorded in a stimulable phosphor sheet 10 by exposing a number of the stimulable phosphor layer regions 12 to a radioactive labeling substance contained in a number of the absorptive regions 4 formed in the biochemical analysis unit 1 and produces biochemical analysis data in the following manner.

A stimulable phosphor sheet 10 is first set on the glass plate 41 of the stage 40 by a user.

An instruction signal indicating that radiation data recorded in the stimulable phosphor layer 12 formed in the support 11 of the stimulable phosphor sheet 10 are to be read is then input through the keyboard 71.

The instruction signal input through the keyboard 71 is input to the control unit 70 and the control unit 70 outputs a drive signal to the filter unit motor 72 in accordance with the instruction signal, thereby moving the filter unit 48 so as to locate the filter member 51d provided with the filter 52d having a property of transmitting only light having a wavelength corresponding to that of stimulated emission emitted from stimulable phosphor but cutting off light having a wavelength of 640 nm in the optical path of stimulated emission 45.

The control unit 70 further outputs a drive signal to the main scanning stepping motor 65 to move the optical head 35 in the main scanning direction and when it determines based on a detection signal indicating the position of the optical head 35 input from the linear encoder 67 that the optical head 35 has reached a position where a laser beam 24 can be projected onto a first stimulable phosphor layer region 12 among a number of the stimulable phosphor layer regions 12 formed in the support 11 of the stimulable phosphor sheet 10, it outputs a drive stop signal to the main scanning stepping motor 65 and a drive signal to the first stimulating ray source 21, thereby actuating it to emit a laser beam 24 having a wavelength of 640 nm.

A laser beam 24 emitted from the first laser stimulating source 21 passes through the collimator lens 25, thereby being made a parallel beam, and is reflected by the mirror 26.

The laser beam 24 reflected by the mirror 26 passes through the first dichroic mirror 27 and the second dichroic mirror 28 and advances to the mirror 29.

The laser beam 24 advancing to the mirror 29 is reflected by the mirror 29 and advances to the mirror 32 to be reflected thereby.

The laser beam 24 reflected by the mirror 32 passes through the hole 33 of the perforated mirror 34 and advances to the concave mirror 38.

The laser beam 24 advancing to the concave mirror 38 is reflected by the concave mirror 38 and enters the optical head 35.

The laser beam 24 entering the optical head 35 is reflected by the mirror 36 and condensed by the aspherical lens 37 onto the first stimulable phosphor layer region 12 of the stimulable phosphor sheet 10 placed on the glass plate 41 of a stage 40.

In this embodiment, since the stimulable phosphor layer regions 12 are formed by embedding stimulable phosphor in the recesses 13 formed in the support 11 made of oxygen free copper capable of attenuating light energy, it is possible to effectively prevent the laser beam 24 from scattering in each of the stimulable phosphor layer regions 12 and entering the neighboring stimulable phosphor layer regions 12 to excite stimulable phosphor contained in the neighboring stimulable phosphor layer regions 12.

When the laser beam 24 impinges onto the first stimulable phosphor layer region 12 formed in the support 11 of the stimulable phosphor sheet 10, stimulable phosphor contained in the first stimulable phosphor layer region 12 formed in the stimulable phosphor sheet 10 is excited by the laser beam 24, thereby releasing stimulated emission 45 from the first stimulable phosphor layer region 12.

The stimulated emission 45 released from the first stimulable phosphor layer region 12 is condensed onto the mirror 36 by the aspherical lens 37 provided in the optical head 35 and reflected by the mirror 36 on the side of the optical path of the laser beam 24, thereby being made a parallel beam to advance to the concave mirror 38.

The stimulated emission 45 advancing to the concave mirror 38 is reflected by the concave mirror 38 and advances to the perforated mirror 34.

As shown in FIG. 7, the stimulated emission 45 advancing to the perforated mirror 34 is reflected downward by the perforated mirror 34 formed as a concave mirror and advances to the filter 52d of the filter unit 48.

Since the filter 52d has a property of transmitting only light having a wavelength corresponding to that of stimulated emission emitted from stimulable phosphor and cutting off light having a wavelength of 640 nm, light having a wavelength of 640 nm corresponding to that of the stimulating ray is cut off by the filter 52d and only light having a wavelength corresponding to that of stimulated emission passes through the filter 52d to be photoelectrically detected by the photomultiplier 50.

Analog data produced by photoelectrically detecting stimulated emission 45 with the photomultiplier 50 are converted by an A/D converter 53 into digital data and the digital data are fed to a data processing apparatus 54.

When a predetermined time, for example, several microseconds, has passed after the first stimulating ray source 21 was turned on, the control unit 70 outputs a drive stop signal to the first stimulating ray source 21, thereby turning it off and outputs a drive signal to the main scanning stepping motor 65, thereby moving the optical head 35 by one pitch equal to the distance between neighboring stimulable phosphor layer regions 12 of the stimulable phosphor sheet 10.

When the control unit 70 determines based on a detection signal indicating the position of the optical head 35 input from the linear encoder 67 that the optical head 35 has been moved by one pitch equal to the distance between neighboring stimulable phosphor layer regions 12, it outputs a drive signal to the first stimulating ray source 21 to turn it on, thereby causing the laser beam 24 to excite stimulable phosphor contained in a second stimulable phosphor layer region 12 formed in the support 11 of the stimulable phosphor sheet 10 next to the first stimulable phosphor layer region 12.

Similarly to the above, the second stimulable phosphor layer region 12 formed in the support 11 of the stimulable phosphor sheet 10 is irradiated with the laser beam 24 for a predetermined time and when stimulated emission 45 released from the second stimulable phosphor layer region 12 is photoelectrically detected by the photomultiplier 50, the control unit 70 outputs a drive stop signal to the first stimulating ray source 21, thereby turning it off and outputs a drive signal to the main scanning stepping motor 65, thereby moving the optical head 35 by one pitch equal to the distance between neighboring stimulable phosphor layer regions 12.

In this manner, the on and off operation of the first stimulating ray source 21 is repeated in synchronism with the intermittent movement of the optical head 35 and when the control unit 70 determines based on a detection signal indicating the position of the optical head 35 input from the linear encoder 67 that the optical head 35 has been moved by one scanning line in the main scanning direction and that the stimulable phosphor layer regions 12 included in a first line of the stimulable phosphor layer regions 12 formed in the support 11 of the stimulable phosphor sheet 10 have been scanned with the laser beam 24, it outputs a drive signal to the main scanning stepping motor 65, thereby returning the optical head 35 to its original position and outputs a drive signal to the sub-scanning pulse motor 61, thereby causing it to move the movable base plate 63 by one scanning line in the sub-scanning direction.

When the control unit 70 determines based on a detection signal indicating the position of the optical head 35 input from the linear encoder 67 that the optical head 35 has been returned to its original position and determines that the movable base plate 63 has been moved by one scanning line in the sub-scanning direction, similarly to the manner in which the stimulable phosphor layer regions 12 included in the first line of the stimulable phosphor layer regions 12 formed in the support 11 of the stimulable phosphor sheet 10 were sequentially irradiated with the laser beam 24 emitted from the first laser stimulating ray source 21, the stimulable phosphor layer regions 12 included in a second line of the stimulable phosphor layer regions 12 formed in the support 11 of the stimulable phosphor sheet 10 are sequentially irradiated with the laser beam 24 emitted from the first laser stimulating ray source 21, thereby exciting stimulable phosphor contained in the stimulable phosphor layer regions 12 included in the second line and stimulated emission 45 released from the stimulable phosphor layer regions 12 is sequentially and photoelectrically detected by the photomultiplier 50.

Analog data produced by photoelectrically detecting stimulated emission 45 with the photomultiplier 50 are converted by an A/D converter 53 into digital data and the digital data are fed to a data processing apparatus 54.

When all of the stimulable phosphor layer regions 12 formed in the support 11 of the stimulable phosphor sheet 10 have been scanned with the laser beam 24 to excite stimulable phosphor contained in the stimulable phosphor layer regions 12 and digital data produced by photoelectrically detecting stimulated emission 45 released from the stimulable phosphor layer regions 12 by the photomultiplier 50 to produce analog data and digitizing the analog data by the A/D converter 53 have been forwarded to the data processing apparatus 54, the control unit 70 outputs a drive stop signal to the first laser stimulating ray source 21, thereby turning it off.

As described above, radiation data of the radioactive labeling substance recorded in a number of the stimulable phosphor layer regions 12 of the stimulable phosphor sheet 10 are read by the first scanner to produce biochemical analysis data.

On the other hand, when fluorescence data of a fluorescent substance recorded in a number of the absorptive regions 4 formed in the substrate 2 of the biochemical analysis unit 1 are to be read to produce biochemical analysis data, the biochemical analysis unit 1 is first set by the user on the glass plate 41 of the stage 40.

An instruction signal identifying the kind of a fluorescent substance such as a fluorescent dye labeling a substance derived from a living organism is then input by the user through the keyboard 71.

When the kind of fluorescent substance is input by the user through the keyboard 71, the control unit 70 selects a laser stimulating ray source for emitting a laser beam 24 of a wavelength capable of efficiently stimulating the input fluorescent substance from among the first laser stimulating ray source 21, the second laser stimulating ray source 22 and the third laser stimulating ray source 23 and selects the filter member for cutting light having a wavelength of the laser beam 24 to be used for stimulating the input fluorescent substance and transmitting light having a longer wavelength than that of the laser beam to be used for stimulation from among the three filter members 51a, 51b and 51c.

Similarly to the case where radiation data recorded in a number of the stimulable phosphor layer regions 12 of the stimulable phosphor sheet 10 are read, all of the absorptive regions 4 formed in the substrate 2 of the biochemical analysis unit 1 are scanned by the laser beam 24, thereby stimulating a fluorescent substance contained in the absorptive regions 4, fluorescence emission 45 released from the fluorescent substance is photoelectrically detected by the photomultiplier 50 to produce analog data and the analog data are digitized by the A/D converter 53 to be forwarded to the data processing apparatus 54.

In this manner, fluorescent data of the fluorescent substance are read by the first scanner to produce biochemical analysis data.

Figure 14:
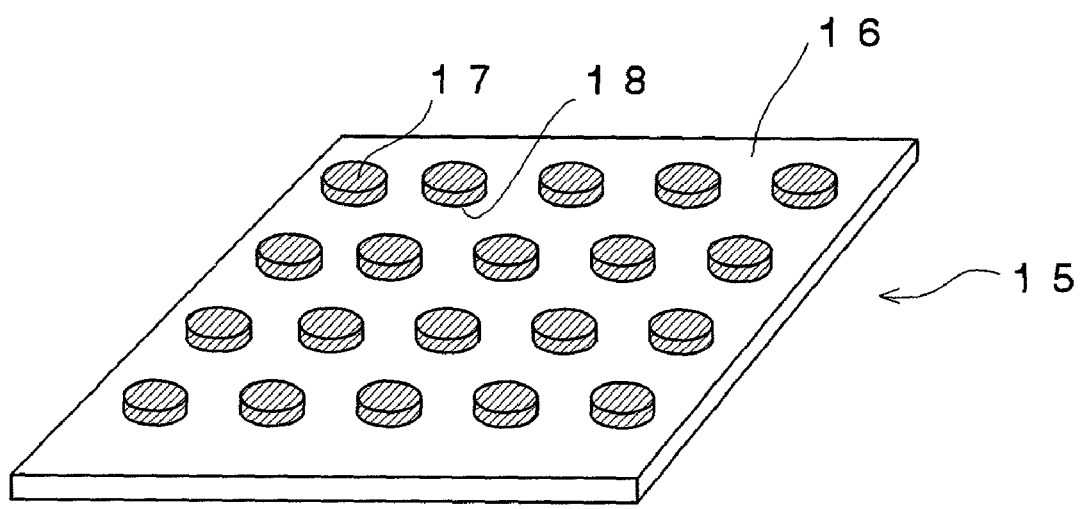
FIG. 14 is a schematic perspective view showing another stimulable phosphor sheet used for a biochemical analysis data producing method which is a preferred embodiment of the present invention.

FIG. 14 is a schematic perspective view showing another stimulable phosphor sheet used for a biochemical analysis data producing method which is a preferred embodiment of the present invention.

A stimulable phosphor sheet 15 shown in FIG. 14 has same configuration as that of the stimulable phosphor sheet 10 shown in FIG. 4 except that a support 16 is made of stainless steel and that a number of stimulable phosphor layer regions 17 are dot-like formed by charging SrS system stimulable phosphor capable of absorbing and storing light energy in a number of the recesses 18 formed in the support 16.

Chemiluminescent data recorded in a number of the absorptive regions 4 of the biochemical analysis unit 1 are transferred onto a number of the stimulable phosphor layer regions 17 of the stimulable phosphor 15 shown in FIG. 14.

When chemiluminescent data recorded in a number of the absorptive regions 4 of the biochemical analysis unit 1 are to be transferred onto a number of the stimulable phosphor layer regions 17 of the stimulable phosphor 15, a number of the absorptive regions 4 of the biochemical analysis unit 1 are first brought into contact with a chemiluminescent substrate.

As a result, chemiluminescent emission in a wavelength of visible light is selectively released from a number of the absorptive regions 4 of the biochemical analysis unit 1.

The stimulable phosphor sheet 15 is then superposed on the biochemical analysis unit 1 formed of a number of the absorptive regions 4 selectively releasing chemiluminescent emission in such a manner that a number of the stimulable phosphor layer regions 17 formed in the support 16 of the stimulable phosphor sheet 15 are located in the corresponding through-holes 3 formed in the substrate 2 of the biochemical analysis unit 1 and face the corresponding absorptive regions 4 formed in the through-holes 3.

In this manner, each of the stimulable phosphor layer regions 17 formed in the support 16 of the stimulable phosphor sheet 15 is kept to face the corresponding absorptive region 4 formed in the substrate 2 of the biochemical analysis unit 1 for a predetermined time period, whereby a number of the stimulable phosphor layer regions 17 formed in the support 16 of the stimulable phosphor sheet 15 are exposed to chemiluminescent emission released from a number of the absorptive regions 4 formed in the substrate 2 of the biochemical analysis unit 1.

In this embodiment, since a number of the absorptive regions 4 of the biochemical analysis unit 1 are formed spaced apart from each other in the substrate 2 made of stainless steel and the substrate 2 made of stainless steel capable of attenuating light energy is present around each of the absorptive regions 4, chemiluminescent emission released from the absorptive regions 4 of the biochemical analysis unit 1 during the exposure operation can be efficiently prevented from scattering in the substrate 2 of the biochemical analysis unit 1. Further, since a number of the stimulable phosphor layer regions 17 of the stimulable phosphor sheet 15 are formed by embedding stimulable phosphor in a number of the recesses 18 formed in the support 16 made of stainless steel and the support 16 made of stainless steel capable of attenuating light energy is present around each of the stimulable phosphor layer regions 17, chemiluminescent emission released from the absorptive regions 4 of the biochemical analysis unit 1 during the exposure operation can be efficiently prevented from scattering in the support 16 of the stimulable phosphor sheet 15. Therefore, it is possible to selectively expose only the stimulable phosphor layer region 17 each of the absorptive regions 4 faces to the chemiluminescent emission released from the absorptive regions 4 of the biochemical analysis unit 1.

In this manner, chemiluminescent data are recorded in a number of the stimulable phosphor layer regions 17 formed in the support 16 of the stimulable phosphor sheet 15.

Figure 15:
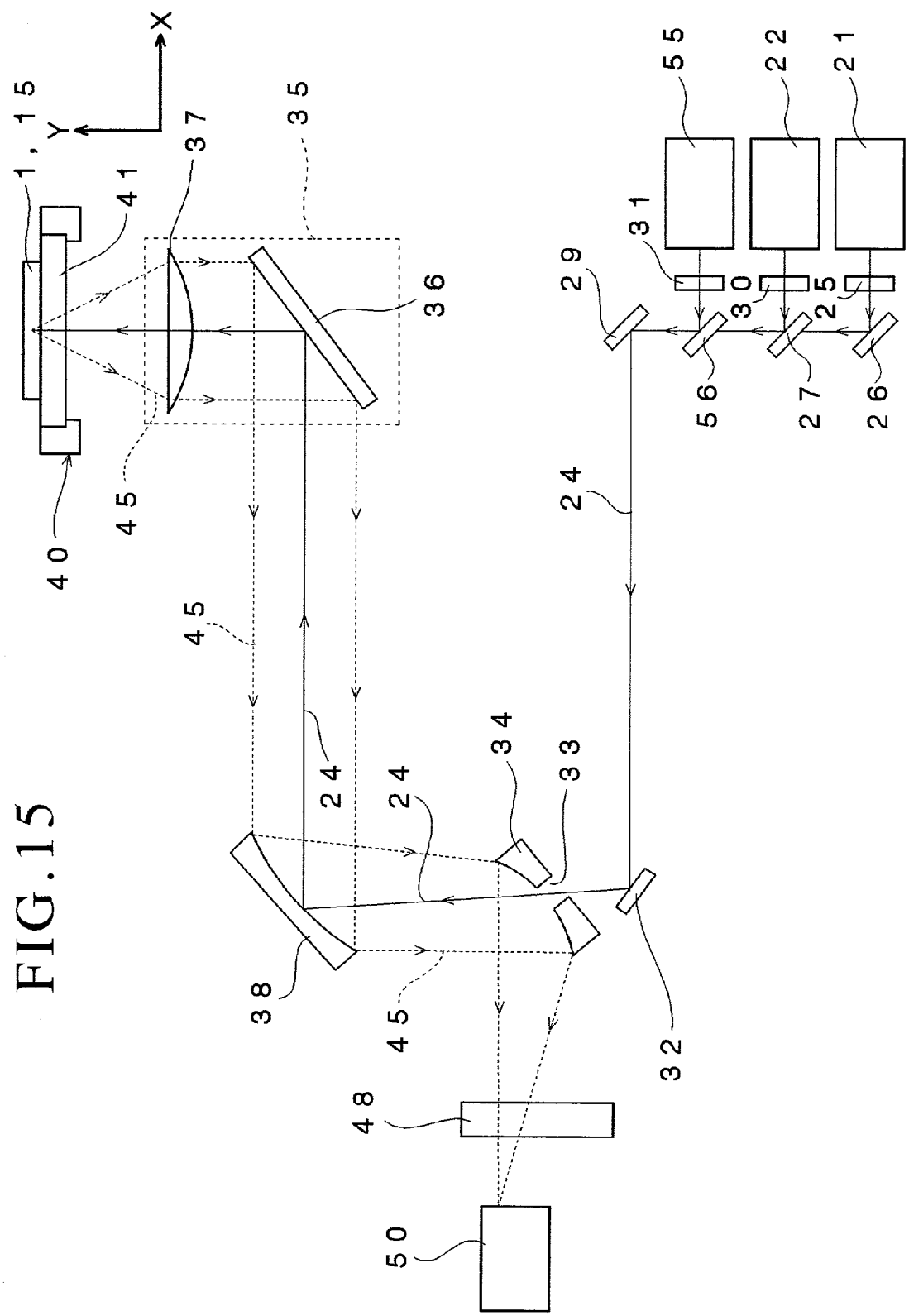
FIG. 15 is a schematic perspective view showing a second scanner for reading chemiluminescent data recorded in a number of the stimulable phosphor layer regions formed in the support of the stimulable phosphor sheet shown in FIG. 14 and producing biochemical analysis data.
Figure 16:
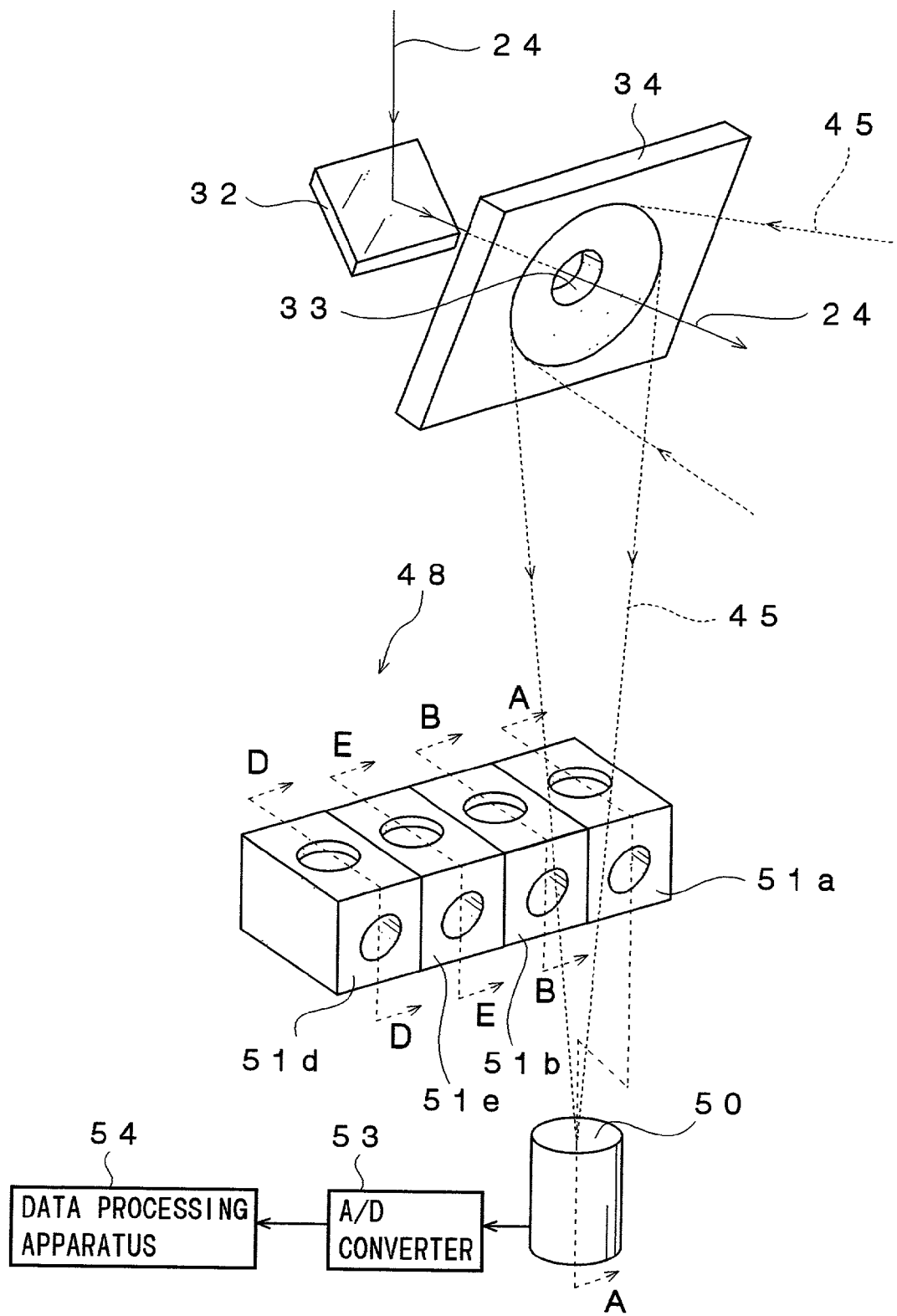
FIG. 16 is a schematic perspective view showing details in the vicinity of a photomultiplier of a second scanner shown in FIG. 15.

FIG. 15 is a schematic perspective view showing a second scanner for reading chemiluminescent data recorded in a number of the stimulable phosphor layer regions 17 formed in the support 16 of the stimulable phosphor sheet 15 and producing biochemical analysis data. FIG. 16 is a schematic perspective view showing details in the vicinity of a photomultiplier of a second scanner shown in FIG. 15 and FIG. 17 is a schematic cross-sectional view taken along a line E—E in FIG. 16.

Figure 17:
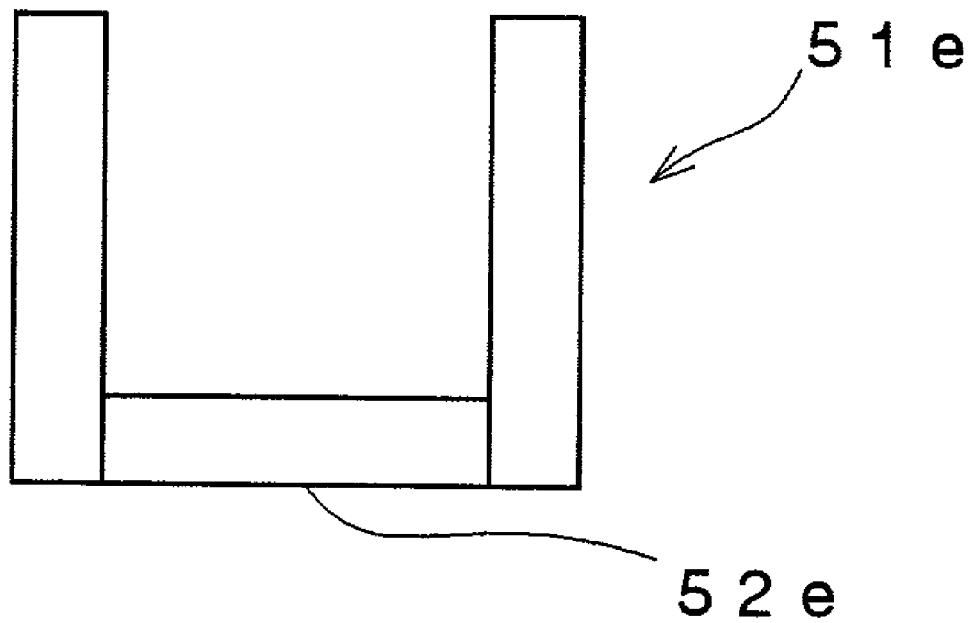
FIG. 17 is a schematic cross-sectional view taken along a line E—E in FIG. 16.

A second scanner shown in FIGS. 15 to 17 has the same configuration as that of the first scanner shown in FIGS. 6 and 7 except that it includes a fourth laser stimulating ray source 55 for emitting a laser beam 24 having a wavelength of 980 nm which can effectively stimulate SrS system stimulable phosphor instead of the third laser stimulating ray source 23 for emitting a laser beam 24 having a wavelength of 473 nm, includes a filter member 51e provided with a filter having a property of transmitting only light having a wavelength corresponding to that of stimulated emission emitted from stimulable phosphor and cutting off light having a wavelength of 980 nm, and includes a third dichroic mirror 56 for transmitting light having a wavelength equal to and shorter than 640 nm but reflecting light having a wavelength of 980 nm instead of the second dichroic mirror 28 for transmitting light having a wavelength equal to and longer than 532 nm but reflecting light having a wavelength of 473 nm.

The thus constituted second scanner reads chemiluminescent data recorded in a number of the stimulable phosphor layer regions 17 of the stimulable phosphor sheet 15 and produces biochemical analysis data in the following manner.

A stimulable phosphor sheet 15 is first set on the glass plate 41 of the stage 40 by a user.

An instruction signal indicating that radiation data recorded in the stimulable phosphor layer 17 formed in the support 16 of the stimulable phosphor sheet 15 are to be read is then input through the keyboard 71.

The instruction signal input through the keyboard 71 is input to the control unit 70 and the control unit 70 outputs a drive signal to the filter unit motor 72 in accordance with the instruction signal, thereby moving the filter unit 48 so as to locate the filter member 51e provided with the filter 52e having a property of transmitting only light having a wavelength corresponding to that of stimulated emission emitted from stimulable phosphor and cutting off light having a wavelength of 980 nm in the optical path of stimulated emission 45.

The control unit 70 further outputs a drive signal to the main scanning stepping motor 65 to move the optical head 35 in the main scanning direction and when it determines based on a detection signal indicating the position of the optical head 35 input from the linear encoder 67 that the optical head 35 has reached a position where a laser beam 24 can be projected onto a first stimulable phosphor layer region 17 among a number of the stimulable phosphor layer regions 17 formed in the support 16 of the stimulable phosphor sheet 15, it outputs a drive stop signal to the main scanning stepping motor 65 and a drive signal to the fourth stimulating ray source 55, thereby actuating it to emit a laser beam 24 having a wavelength of 980 nm.

A laser beam 24 emitted from the third laser stimulating ray source 23 passes through a collimator lens 31, thereby being made a parallel beam, and is reflected by the third dichroic mirror 56, thereby changing its direction by 90 degrees. The laser beam 24 then advances to the mirror 29.

The laser beam 24 advancing to the mirror 29 is reflected by the mirror 29 and advances to the mirror 32 to be reflected thereby.

The laser beam 24 reflected by the mirror 32 passes through the hole 33 of the perforated mirror 34 and advances to the concave mirror 38.

The laser beam 24 advancing to the concave mirror 38 is reflected by the concave mirror 38 and enters the optical head 35.

The laser beam 24 entering the optical head 35 is reflected by the mirror 36 and condensed by the aspherical lens 37 onto the first stimulable phosphor layer region 17 of the stimulable phosphor sheet 15 placed on the glass plate 41 of a stage 40.

In this embodiment, since the stimulable phosphor layer regions 17 are formed by embedding stimulable phosphor in the recesses 18 formed in the support 16 made of stainless steel, it is possible to effectively prevent the laser beam 24 from scattering in each of the stimulable phosphor layer regions 17 and entering the neighboring stimulable phosphor layer regions 17 to excite stimulable phosphor contained in the neighboring stimulable phosphor layer regions 17.

When the laser beam 24 impinges onto the first stimulable phosphor layer region 17 formed in the support 16 of the stimulable phosphor sheet 15, stimulable phosphor contained in the first stimulable phosphor layer region 17 formed in the stimulable phosphor sheet 15 is excited by the laser beam 24, thereby releasing stimulated emission 45 from the first stimulable phosphor layer region 17.

The stimulated emission 45 released from the first stimulable phosphor layer region 17 of the stimulable phosphor sheet 15 is condensed onto the mirror 36 by the aspherical lens 37 provided in the optical head 35 and reflected by the mirror 36 on the side of the optical path of the laser beam 24, thereby being made a parallel beam to advance to the concave mirror 38.

The stimulated emission 45 advancing to the concave mirror 38 is reflected by the concave mirror 38 and advances to the perforated mirror 34.

As shown in FIG. 7, the stimulated emission 45 advancing to the perforated mirror 34 is reflected downward by the perforated mirror 34 formed as a concave mirror and advances to the filter 52e of the filter unit 48.

Since the filter 52e has a property of transmitting only light having a wavelength corresponding to that of stimulated emission emitted from stimulable phosphor and cutting off light having a wavelength of 980 nm, light having a wavelength of 980 nm corresponding to that of the stimulating ray is cut off by the filter 52e and only light having a wavelength corresponding to that of stimulated emission passes through the filter 52e to be photoelectrically detected by the photomultiplier 50.

Analog data produced by photoelectrically detecting stimulated emission 45 with the photomultiplier 50 are converted by an A/D converter 53 into digital data and the digital data are fed to a data processing apparatus 54.

When a predetermined time has passed after the fourth stimulating ray source 55 was turned on, the control unit 70 outputs a drive stop signal to the fourth stimulating ray source 55, thereby turning it off and outputs a drive signal to the main scanning stepping motor 65, thereby moving the optical head 35 by one pitch equal to the distance between neighboring stimulable phosphor layer regions 17 of the stimulable phosphor sheet 15.

When the control unit 70 determines based on a detection signal indicating the position of the optical head 35 input from the linear encoder 67 that the optical head 35 has been moved by one pitch equal to the distance between neighboring stimulable phosphor layer regions 17, it outputs a drive signal to the fourth stimulating ray source 55 to turn it on, thereby causing the laser beam 24 to excite stimulable phosphor contained in a second stimulable phosphor layer region 17 formed in the support 16 of the stimulable phosphor sheet 15 next to the first stimulable phosphor layer region 17.

Similarly to the above, the second stimulable phosphor layer region 17 formed in the support 16 of the stimulable phosphor sheet 15 is irradiated with the laser beam 24 for a predetermined time and when stimulated emission 45 released from the second stimulable phosphor layer region 17 is photoelectrically detected by the photomultiplier 50, the control unit 70 outputs a drive stop signal to the fourth stimulating ray source 55, thereby turning it off and outputs a drive signal to the main scanning stepping motor 65, thereby moving the optical head 35 by one pitch equal to the distance between neighboring stimulable phosphor layer regions 17.

In this manner, the on and off operation of the fourth stimulating ray source 55 is repeated in synchronism with the intermittent movement of the optical head 35 and when the control unit 70 determines based on a detection signal indicating the position of the optical head 35 input from the linear encoder 67 that the optical head 35 has been moved by one scanning line in the main scanning direction and that the stimulable phosphor layer regions 17 included in a first line of the stimulable phosphor layer regions 17 formed in the support 16 of the stimulable phosphor sheet 15 have been scanned with the laser beam 24, it outputs a drive signal to the main scanning stepping motor 65, thereby returning the optical head 35 to its original position and outputs a drive signal to the sub-scanning pulse motor 61, thereby causing it to move the movable base plate 63 by one scanning line in the sub-scanning direction.

When the control unit 70 determines based on a detection signal indicating the position of the optical head 35 input from the linear encoder 67 that the optical head 35 has been returned to its original position and determines that the movable base plate 63 has been moved by one scanning line in the sub-scanning direction, similarly to the manner in which the stimulable phosphor layer regions 17 included in the first line of the stimulable phosphor layer regions 17 formed in the support 16 of the stimulable phosphor sheet 15 were sequentially irradiated with the laser beam 24 emitted from the fourth laser stimulating ray source 55, the stimulable phosphor layer regions 17 included in a second line of the stimulable phosphor layer regions 17 formed in the support 16 of the stimulable phosphor sheet 15 are sequentially irradiated with the laser beam 24 emitted from the fourth laser stimulating ray source 55, thereby exciting stimulable phosphor contained in the stimulable phosphor layer regions 17 included in the second line and stimulated emission 45 released from the stimulable phosphor layer regions 17 is sequentially and photoelectrically detected by the photomultiplier 50.

Analog data produced by photoelectrically detecting stimulated emission 45 with the photomultiplier 50 are converted by an A/D converter 53 into digital data and the digital data are fed to a data processing apparatus 54.

When all of the stimulable phosphor layer regions 17 formed in the support 16 of the stimulable phosphor sheet 15 have been scanned with the laser beam 24 to excite stimulable phosphor contained in the stimulable phosphor layer regions 17 and digital data produced by photoelectrically detecting stimulated emission 45 released from the stimulable phosphor layer regions 17 by the photomultiplier 50 to produce analog data and digitizing the analog data by the A/D converter 53 have been forwarded to the data processing apparatus 54, the control unit 70 outputs a drive stop signal to the fourth laser stimulating ray source 55, thereby turning it off.

As described above, chemiluminescent data recorded in a number of the stimulable phosphor layer regions 17 of the stimulable phosphor sheet 15 are read by the second scanner to produce biochemical analysis data.

According to this embodiment, when a number of the stimulable phosphor layer regions 12 formed in the support 11 of the stimulable phosphor sheet 10 are exposed to the radioactive labeling substance contained in a number of the absorptive regions 4 formed in the substrate 2 of the biochemical analysis unit 1, although electron beams (β rays) having high energy are released from the radioactive labeling substance contained in the absorptive regions 4 of the biochemical analysis unit 1, since the substrate 2 of the biochemical analysis unit 1 is made of stainless steel and capable of attenuating radiation energy, electron beams (β rays) released from the radioactive labeling substance contained in the absorptive regions 4 of the biochemical analysis unit 1 can be effectively prevented from scattering in the substrate 2 of the biochemical analysis unit 1. Further, since a number of the stimulable phosphor layer regions 12 of the stimulable phosphor sheet 10 are formed by embedding stimulable phosphor in a number of the recesses 13 formed in the support 11 made of oxygen free copper and the support 11 made of oxygen free copper capable of attenuating radiation energy in the same pattern as that of a number of the absorptive regions 4 formed in the substrate 2 of the biochemical analysis unit 1 and the stimulable phosphor 10 is superposed on the biochemical analysis unit 1 in such a manner that each of the stimulable phosphor layer regions 12 faces the corresponding absorptive region 4 formed in the substrate 2 of the biochemical analysis unit 1, electron beams (β rays) released from the radioactive labeling substance contained in the absorptive regions 4 of the biochemical analysis unit 1 can be effectively prevented from scattering in the support 11 of the stimulable phosphor sheet 10. Therefore, since it is possible to selectively expose only the stimulable phosphor layer region 12 each of the absorptive regions 4 faces to the electron beams (β rays) released from the radioactive labeling substance contained in each of the absorptive regions 4, it is possible to prevent noise from being generated in biochemical analysis data produced by photoelectrically detecting stimulated emission 45 released from the stimulable phosphor layer regions 12 of the stimulable phosphor sheet 10 in response to the stimulation with the laser beam 24 and to produce biochemical analysis data having a high quantitative accuracy.

Furthermore, according to this embodiment, since the substrate 2 of the biochemical analysis unit 1 is made of stainless steel and capable of attenuating light energy, when a number of the stimulable phosphor layer regions 17 formed in the support 16 of the stimulable phosphor sheet 15 are exposed to chemiluminescent emission selectively released from a number of the absorptive regions 4 formed in the substrate 2 of the biochemical analysis unit 1, chemiluminescent emission selectively released from a number of the absorptive regions 4 formed in the substrate 2 of the biochemical analysis unit 1 can be effectively prevented from scattering in the substrate 2 of the biochemical analysis unit 1. Moreover, since a number of the stimulable phosphor layer regions 17 of the stimulable phosphor sheet 15 are formed by embedding stimulable phosphor in a number of the recesses 18 formed in the support 16 made of stainless steel and the support 16 made of stainless steel capable of attenuating light energy in the same pattern as that of a number of the absorptive regions 4 formed in the substrate 2 of the biochemical analysis unit 1 and the stimulable phosphor 15 is superposed on the biochemical analysis unit 1 in such a manner that each of the stimulable phosphor layer regions 17 faces the corresponding absorptive region 4 formed in the substrate 2 of the biochemical analysis unit 1, chemiluminescent emission released from the absorptive regions 4 of the biochemical analysis unit 1 can be effectively prevented from scattering in the support 16 of the stimulable phosphor sheet 15. Therefore, since it is possible to selectively expose only the stimulable phosphor layer region 17 each of the absorptive regions 4 faces to the chemiluminescent emission released from each of the absorptive regions 4, it is possible to prevent noise from being generated in biochemical analysis data produced by photoelectrically detecting stimulated emission 45 released from the stimulable phosphor layer regions 17 of the stimulable phosphor sheet 15 in response to the stimulation with the laser beam 24 and to produce biochemical analysis data having a high quantitative accuracy.

Further, according to this embodiment, since the support 11 of the stimulable phosphor sheet 10 is made of oxygen free copper, it is possible to reliably prevent external light from entering the stimulable phosphor layer regions 12 of the stimulable phosphor sheet 10 when the stimulable phosphor layer regions 12 are to be exposed to the radioactive labeling substance. Therefore, since it is possible to reliably prevent radiation energy stored in the stimulable phosphor layer regions 12 of the stimulable phosphor sheet 10 by irradiating them to electron beams (β rays) released from the radioactive labeling substance contained in the absorptive regions 4 in the corresponding through-holes 3 formed in the substrate 2 of the biochemical analysis unit 1 they face from being released by incident external light, the quantitative accuracy of analysis can be markedly improved.

Moreover, according to this embodiment, since the support 16 of the stimulable phosphor sheet 15 is made of stainless steel, it is possible to reliably prevent external light from entering the stimulable phosphor layer regions 17 of the stimulable phosphor sheet 15 when the stimulable phosphor layer regions 17 are to be exposed to chemiluminescent emission. Therefore, since it is possible to reliably prevent light energy stored in the stimulable phosphor layer regions 17 of the stimulable phosphor sheet 15 by exposing them to chemiluminescent emission released from the absorptive regions 4 in the corresponding through-holes 3 formed in the substrate 2 of the biochemical analysis unit 1 they face from being released by incident external light, the quantitative accuracy of analysis can be markedly improved.

Even in the case where the support 11 of the stimulable phosphor sheet 10 is made of a material capable of attenuating radiation energy, if radiation is released from the support 11 of the stimulable phosphor sheet 10 when the support 11 is exposed to electron beams (β rays), a number of stimulable phosphor layer regions 12 are exposed to radiation released from the support 11 and fog is generated. However, according to this embodiment, since the support 11 of the stimulable phosphor sheet 10 is made of oxygen free copper which can attenuate radiation energy and does not substantially release radiation when it is exposed to electron beams (β rays), no radiation is released from the support 11 when the support 11 is irradiated with electron beams (β rays) released from the radioactive labeling substance and, therefore, it is possible to effectively prevent fog caused by radiation released from the support 11 in response to the irradiation with electron beams (β rays) released from the radioactive labeling substance.

Furthermore, in this embodiment, the optical head 35 is intermittently moved in the main scanning direction by the main scanning stepping motor 65 and when it is judged in accordance with a detection signal indicating the position of the optical head 35 input from the linear encoder 67 that the optical head 35 has reached a position where a laser beam 24 can be projected onto a first stimulable phosphor layer region 12 among a number of the stimulable phosphor layer regions 12 formed in the support 11 of the stimulable phosphor sheet 10 or a first stimulable phosphor layer region 17 among a number of the stimulable phosphor layer regions 17 formed in the support 16 of the stimulable phosphor sheet 15, the first laser stimulating ray source 21 or the fourth laser stimulating ray source 55 is activated to irradiate the first stimulable phosphor layer region 12 or the first stimulable phosphor layer region 17 with the laser beam 24 having a wavelength of 640 nm or the laser beam 24 having a wavelength of 980 nm, thereby exciting stimulable phosphor contained in the first stimulable phosphor layer region 12 or the first stimulable phosphor layer region 17 and stimulated emission 45 released from the first stimulable phosphor layer region 12 or the first stimulable phosphor layer region 17 is photoelectrically detected by the photomultiplier 50.

When a predetermined time has passed after the first stimulating ray source 21 or the fourth laser stimulating ray source 55 was turned on, the first stimulating ray source 21 is turned off and the optical head 35 is moved by one pitch equal to the distance between neighboring stimulable phosphor layer regions 12 formed in the support 11 of the stimulable phosphor sheet 10 or the distance between neighboring stimulable phosphor layer regions 17 formed in the support 16 of the stimulable phosphor sheet 15.

When it is judged based on a detection signal indicating the position of the optical head 35 input from the linear encoder 67 that the optical head 35 has been moved by one pitch equal to the distance between neighboring stimulable phosphor layer regions 12 or the distance between neighboring stimulable phosphor layer regions 17, the first laser stimulating ray source 21 or the fourth laser stimulating ray source 55 is activated to irradiate a second stimulable phosphor layer region 12 formed in the support 11 of the stimulable phosphor sheet 10 next to the first stimulable phosphor layer region 12 or a second stimulable phosphor layer region 17 formed in the support 16 of the stimulable phosphor sheet 15 next to the first stimulable phosphor layer region 17 with the laser beam 24 having a wavelength of 640 nm or the laser beam 24 having a wavelength of 980 nm, thereby exciting stimulable phosphor contained in the second stimulable phosphor layer region 12 or the second stimulable phosphor layer region 17 and stimulated emission 45 released from the second stimulable phosphor layer region 12 or the second stimulable phosphor layer region 17 is photoelectrically detected by the photomultiplier 50.

When a predetermined time has passed after the first stimulating ray source 21 or the fourth laser stimulating ray source 55 was turned on, the first stimulating ray source 21 or the fourth laser stimulating ray source 55 is turned off and the optical head 35 is moved by one pitch equal to the distance between neighboring stimulable phosphor layer regions 12 formed in the support 11 of the stimulable phosphor sheet 10 or the distance between neighboring stimulable phosphor layer regions 17 formed in the support 16 of the stimulable phosphor sheet 15.

In this manner, the on and off operation of the first stimulating ray source 21 or the fourth laser stimulating ray source 55 is repeated in synchronism with the intermittent movement of the optical head 35 and when it is judged based on a detection signal indicating the position of the optical head 35 input from the linear encoder 67 that the optical head 35 has been moved by one scanning line in the main scanning direction and that the stimulable phosphor layer regions 12 included in a first line of the stimulable phosphor layer regions 12 formed in the support 11 of the stimulable phosphor sheet 10 or the stimulable phosphor layer regions 17 included in a first line of the stimulable phosphor layer regions 17 formed in the support 16 of the stimulable phosphor sheet 15 have been scanned with the laser beam 24, the optical head 35 is returned to its original position and the movable base plate 63 is moved by the sub-scanning pulse motor 61 by one scanning line in the sub-scanning direction. Similarly to the manner in which the stimulable phosphor layer regions 12 included in the first line of the stimulable phosphor layer regions 12 formed in the support 11 of the stimulable phosphor sheet 10 or the stimulable phosphor layer regions 17 included in a first line of the stimulable phosphor layer regions 17 formed in the support 16 of the stimulable phosphor sheet 15 were sequentially irradiated with the laser beam 24 emitted from the first laser stimulating ray source 21 or the fourth laser stimulating ray source 55, the stimulable phosphor layer regions 12 included in a second line of the stimulable phosphor layer regions 12 formed in the support 11 of the stimulable phosphor sheet 10 or the stimulable phosphor layer regions 17 included in a second line of the stimulable phosphor layer regions 17 formed in the support 16 of the stimulable phosphor sheet 15 are sequentially irradiated with the laser beam 24 emitted from the first laser stimulating ray source 21 or the fourth laser stimulating ray source 55, thereby exciting stimulable phosphor contained in the stimulable phosphor layer regions 12 included in the second line or the stimulable phosphor layer regions 17 included in the second line and stimulated emission 45 released from the stimulable phosphor layer regions 12 or the stimulable phosphor layer regions 17 is sequentially and photoelectrically detected by the photomultiplier 50.

In this manner, when all of the stimulable phosphor layer regions 12 formed in the support 11 of the stimulable phosphor sheet 10 or all of the stimulable phosphor layer regions 17 formed in the support 16 of the stimulable phosphor sheet 15 have been scanned with the laser beam 24 emitted from the first laser stimulating ray source 21 or the fourth laser stimulating ray source 5, thereby exciting stimulable phosphor contained in the stimulable phosphor layer regions 12 or the stimulable phosphor layer regions 17, analog data produced by photoelectrically detecting stimulated emission 45 released from the stimulable phosphor by the photomultiplier 50 are converted to digital data by the A/D converter 53 to be forwarded to the data processing apparatus 54, the production of biochemical analysis data is completed.

Therefore, since the first scanner according to this embodiment is constituted so as to intermittently move the optical head 35, to stop the optical head when it is judged that the optical head 35 has reached a position where a laser beam 24 can be projected onto one of a number of the stimulable phosphor layer regions 12 formed in the support 11 of the stimulable phosphor sheet 10, to irradiate the one of the stimulable phosphor layer regions 12 with the laser beam 24 emitted from the first laser stimulating ray source 21 for a predetermined time period, to stop the driving of the first laser stimulating ray source 21 when a predetermined time period has passed, to move the optical head 35 to a position where a laser beam 24 can be projected onto a stimulable phosphor layer region 12 next to the stimulable phosphor layer region 12 irradiated with the laser beam 24, and to irradiate the stimulable phosphor layer region 12 next to the stimulable phosphor layer region 12 irradiated with the laser beam 24 with the laser beam 24 emitted from the first laser stimulating ray source 21 for a predetermined time period, it is possible to reliably prevent the laser beam 24 from entering a neighboring stimulable phosphor layer region 12 to be next stimulated as the laser beam 24 is scanned and thus prevent stimulable phosphor contained in the neighboring stimulable phosphor layer region 12 from being excited to release radiation energy stored therein and, therefore, biochemical analysis data having an excellent quantitative characteristic can be produced.

Further, since the second scanner according to this embodiment is constituted so as to intermittently move the optical head 35, to stop the optical head when it is judged that the optical head 35 has reached a position where a laser beam 24 can be projected onto one of a number of the stimulable phosphor layer regions 17 formed in the support 16 of the stimulable phosphor sheet 15, to irradiate the one of the stimulable phosphor layer regions 17 with the laser beam 24 emitted from the fourth laser stimulating ray source 55 for a predetermined time period, to stop the driving of the fourth laser stimulating ray source 55 when a predetermined time period has passed, to move the optical head 35 to a position where a laser beam 24 can be projected onto a stimulable phosphor layer region 17 next to the stimulable phosphor layer region 17 irradiated with the laser beam 24, and to irradiate the stimulable phosphor layer region 17 next to the stimulable phosphor layer region 17 irradiated with the laser beam 24 with the laser beam 24 emitted from the fourth laser stimulating ray source 55 for a predetermined time period, it is possible to reliably prevent the laser beam 24 from entering a neighboring stimulable phosphor layer region 17 to be next stimulated as the laser beam 24 is scanned and thus prevent stimulable phosphor contained in the neighboring stimulable phosphor layer region 17 from being excited to release radiation energy stored therein and, therefore, biochemical analysis data having an excellent quantitative characteristic can be produced.

Figure 18:
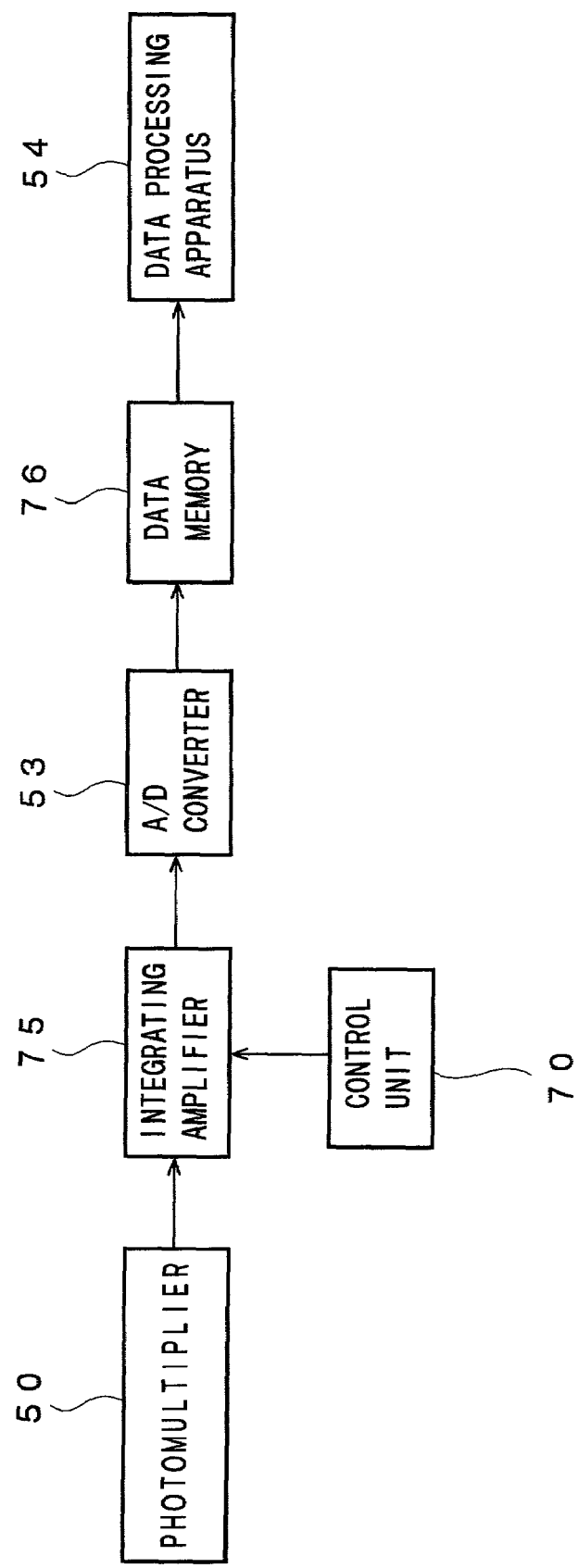
FIG. 18 is a block diagram showing the vicinity of a photomultiplier and a data processing apparatus of a scanner which is another preferred embodiment of the present invention.

FIG. 18 is block diagram showing the vicinity of the photomultiplier 50 and the data processing apparatus 54 of a scanner which is another preferred embodiment of the present invention.

As shown in FIG. 18, the scanner according to this embodiment includes an integrating amplifier 75 for integrating analog data produced by the photomultiplier 50 and an integrated value of analog data produced by the integrating amplifier 75 are digitized by the A/D converter 53 and stored in a data memory 76.

In this embodiment, each of a number of the stimulable phosphor layer regions 12 is irradiated with a laser beam 24 to excite stimulable phosphor contained therein, stimulated emission 45 released from the stimulable phosphor layer region 12 is photoelectrically detected by the photomultiplier 50, thereby producing analog data and the thus produced analog data are integrated by the integrating amplifier 75.

A first stimulable phosphor layer region 12 among a number of the stimulable phosphor layers 12 formed in the support 11 of the stimulable phosphor sheet 10 is irradiated a laser beam 24 emitted from the first laser stimulating ray source 21, thereby exciting stimulable phosphor and stimulated emission released from the first stimulable phosphor layer region 12 is photoelectrically detected by the photomultiplier 50 to produce analog data.

The analog data produced by the photomultiplier 50 are integrated by the integrating amplifier 75.

When a predetermined time has passed after the first stimulating ray source 21 was turned on, the control unit 70 outputs a drive stop signal to the first stimulating ray source 21, thereby turning it off and outputs the analog data produced by the integrating amplifier 75 to the A/D converter 53, thereby causing the A/D converter 53 to digitize the integrated value of the analog data and to output it as digital data of the first stimulable phosphor layer region 12 to the data memory 76 to be stored therein.

At the same time, the control unit 70 outputs a drive signal to the main scanning stepping motor 65, thereby moving the optical head 35 by one pitch equal to the distance between neighboring stimulable phosphor layer regions 12 and when the control unit 70 determines based on a detection signal indicating the position of the optical head 35 input from the linear encoder 67 that the optical head 35 has been moved by one pitch equal to the distance between neighboring stimulable phosphor layer regions 12, it outputs a drive signal to the first stimulating ray source 21 to turn it on, thereby causing the laser beam 24 to excite stimulable phosphor contained in a second stimulable phosphor layer region 12 formed in the support 11 of the stimulable phosphor sheet 10 next to the first stimulable phosphor layer region 12.

When a predetermined time has passed after the first stimulating ray source 21 was turned on, the control unit 70 outputs a drive stop signal to the first stimulating ray source 21, thereby turning it off and outputs the analog data produced by the integrating amplifier 75 to the A/D converter 53, thereby causing the A/D converter 53 to digitize the integrated value of the analog data and to output it as digital data of the second stimulable phosphor layer region 12 to the data memory 76 to be stored therein.

At the same time, the control unit 70 outputs a drive signal to the main scanning stepping motor 65, thereby moving the optical head 35 by one pitch equal to the distance between neighboring stimulable phosphor layer regions 12 and when the control unit 70 determines based on a detection signal indicating the position of the optical head 35 input from the linear encoder 67 that the optical head 35 has been moved by one pitch equal to the distance between neighboring stimulable phosphor layer regions 12, it outputs a drive signal to the first stimulating ray source 21 to turn it on.

Similarly, when all of the stimulable phosphor layer regions 12 formed in the support 11 of the stimulable phosphor sheet 10 are sequentially irradiated with the laser beam 24 emitted from the first stimulating ray source 21, stimulated emission 45 released from the stimulable phosphor layer regions 12 is photoelectrically detected by the photomultiplier 50 to produce analog data, the integrated value of the analog data produced by the integrating amplifier 75 is digitized by the A/D converter 53 and the thus produced digital data are output to the data memory 76 as digital data of the stimulable phosphor layer regions 12 to be stored therein, the reading operation of radiation data recorded in the stimulable phosphor layer regions 12 formed in the support 11 of the stimulable phosphor sheet 10 is completed.

According to this embodiment, digital data of each of the stimulable phosphor layer regions 12 are produced by irradiating each of the stimulable phosphor regions 12 with the laser beam 24 to excite stimulable phosphor contained in the stimulable phosphor layer region 12, photoelectrically detecting stimulated emission 45 released from the stimulable phosphor layer region 12 by the photomultiplier 50 to produce analog data, integrating the thus produced analog data by the integrating amplifier 75, and digitizing the thus produced integrated value of the analog data by the A/D converter 53. Therefore, even when the radiation energy stored in the stimulable phosphor layer region 12 is low and the intensity of stimulated emission released from the stimulable phosphor layer region 12 is low, it is possible to produce biochemical analysis data having high signal intensity with high sensitivity.

Figure 19:
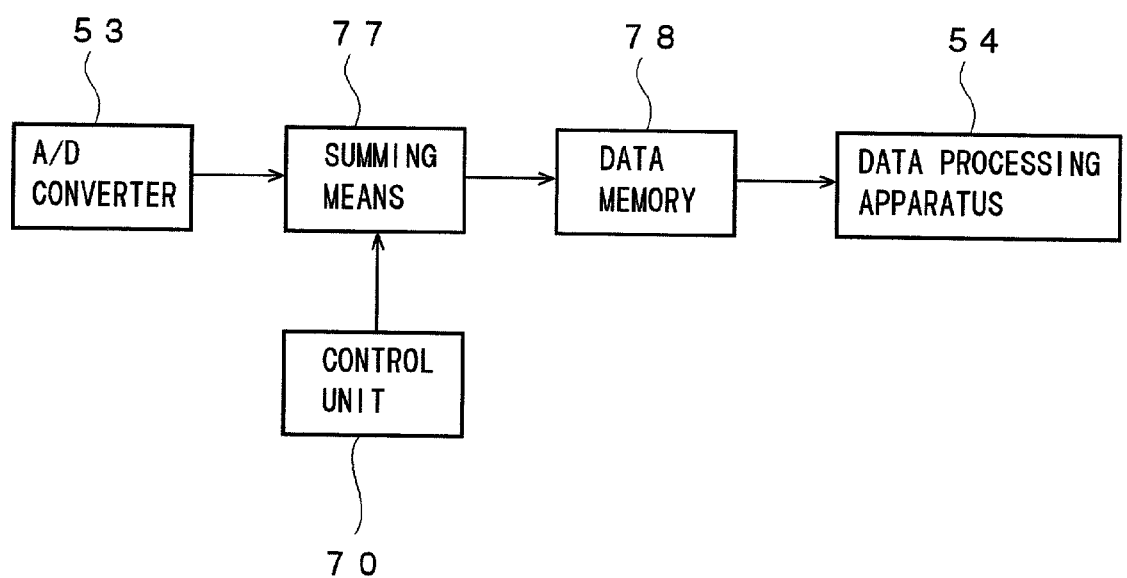
FIG. 19 is a block diagram showing the vicinity of the photomultiplier 50 and the data processing apparatus 54 of a scanner which is a further preferred embodiment of the present invention.

FIG. 19 is a block diagram showing the vicinity of the photomultiplier 50 and the data processing apparatus 54 of a scanner which is a further preferred embodiment of the present invention.

As shown in FIG. 19, the scanner according to this embodiment includes a summing means 77 for summing digital data produced by the A/D converter 53 and a data memory 78 for storing digital data summed by the summing means 77.

In this embodiment, the control unit 70 is constituted so as to output a summing operation effecting signal to the summing means 77 at the same time it outputs a drive signal to the first laser stimulating ray source 21. Each of a number of the stimulable phosphor layer regions 12 is irradiated with a laser beam 24 to excite stimulable phosphor contained therein, stimulated emission 45 released from the stimulable phosphor layer region 12 is photoelectrically detected by the photomultiplier 50, thereby producing analog data, the thus produced analog data are digitized by the A/D converter 53 to produce digital data and the thus produced digital data are summed by the summing means 77 to be stored in the data memory 78.

A first stimulable phosphor layer region 12 among a number of the stimulable phosphor layers 12 formed in the support 11 of the stimulable phosphor sheet 10 is irradiated a laser beam 24 emitted from the first laser stimulating ray source 21, thereby exciting stimulable phosphor and stimulated emission released from the first stimulable phosphor layer region 12 is photoelectrically detected by the photomultiplier 50 to produce analog data.

The analog data are digitized by the A/D converter 53 to produce digital data and the thus produced digital data are summed by the summing means 77 and stored in the data memory 78.

When a predetermined time has passed after the first stimulating ray source 21 was turned on, the control unit 70 outputs a drive stop signal to the first stimulating ray source 21, thereby turning it off and outputs a summing operation effecting signal to the summing means 77.

When the summing operation effecting signal is input from the control unit 70, the summing means 77 stores a summed value of digital data produced by summing digital data and stored in the data memory 78 so far in a predetermined memory area of the data memory 78 as digital data of the first stimulable phosphor layer region 12.

At the same time, the control unit 70 outputs a drive signal to the main scanning stepping motor 65, thereby moving the optical head 35 by one pitch equal to the distance between neighboring stimulable phosphor layer regions 12 and when the control unit 70 determines based on a detection signal indicating the position of the optical head 35 input from the linear encoder 67 that the optical head 35 has been moved by one pitch equal to the distance between neighboring stimulable phosphor layer regions 12, it outputs a drive signal to the first stimulating ray source 21 to turn it on, thereby causing the laser beam 24 to excite stimulable phosphor contained in a second stimulable phosphor layer region 12 formed in the support 11 of the stimulable phosphor sheet 10 next to the first stimulable phosphor layer region 12.

When a predetermined time has passed after the first stimulating ray source 21 was turned on, the control unit 70 outputs a drive stop signal to the first stimulating ray source 21, thereby turning it off and outputs a summing operation effecting signal to the summing means 77.

When the summing operation effecting signal is input from the control unit 70, the summing means 77 stores a summed value of digital data produced by summing digital data and stored in the data memory 78 so far in a predetermined memory area of the data memory 78 as digital data of the second stimulable phosphor layer region 12.

At the same time, the control unit 70 outputs a drive signal to the main scanning stepping motor 65, thereby moving the optical head 35 by one pitch equal to the distance between neighboring stimulable phosphor layer regions 12 and when the control unit 70 determines based on a detection signal indicating the position of the optical head 35 input from the linear encoder 67 that the optical head 35 has been moved by one pitch equal to the distance between neighboring stimulable phosphor layer regions 12, it outputs a drive signal to the first stimulating ray source 21 to turn it on.

Similarly, when all of the stimulable phosphor layer regions 12 formed in the support 11 of the stimulable phosphor sheet 10 are sequentially irradiated with the laser beam 24 emitted from the first stimulating ray source 21, stimulated emission 45 released from the stimulable phosphor layer regions 12 is photoelectrically detected by the photomultiplier 50 to produce analog data, the thus produced analog data are digitized by the A/D converter 53 to produce digital data and the thus produced digital data are summed by the summing means 77 and stored as digital data of each of the stimulable phosphor layer regions 12 in the data memory 78, the reading operation of radiation data recorded in the stimulable phosphor layer regions 12 formed in the support 11 of the stimulable phosphor sheet 10 is completed.

According to this embodiment, digital data of each of the stimulable phosphor layer regions 12 are produced by irradiating each of the stimulable phosphor regions 12 with the laser beam 24 to excite stimulable phosphor contained in the stimulable phosphor layer region 12, photoelectrically detecting stimulated emission 45 released from the stimulable phosphor layer region 12 by the photomultiplier 50 to produce analog data, digitizing the thus produced analog data by the A/D converter 53, and summing the thus produced digital data by the summing means 77. Therefore, even when the radiation energy stored in the stimulable phosphor layer region 12 is low and the intensity of stimulated emission released from the stimulable phosphor layer region 12 is low, it is possible to produce biochemical analysis data having high signal intensity with high sensitivity.

Figure 20:
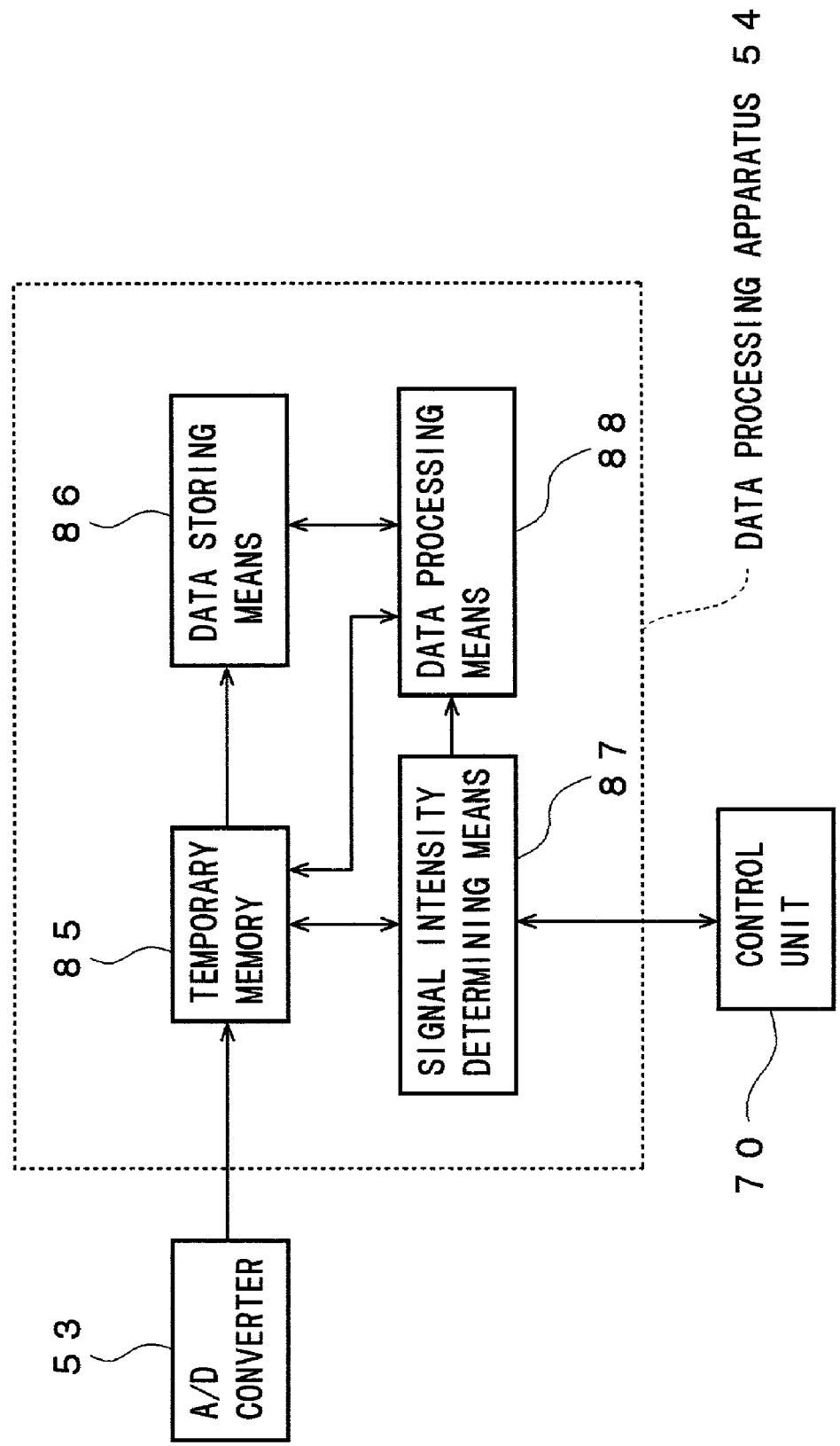
FIG. 20 is a block diagram of a data processing apparatus of a scanner which is a further preferred embodiment of the present invention.

FIG. 20 is a block diagram of a data processing apparatus 54 of a scanner which is a further preferred embodiment of the present invention.

As shown in FIG. 20, the data processing apparatus of the scanner according to this embodiment includes a temporary memory 85 for temporarily storing digital data produced by the A/D converter 53, a signal intensity determining means 87 for reading digital data temporarily stored in the temporary memory 85, comparing the signal intensity of the digital data with a threshold value T and outputting a laser power increasing signal to the control unit 70 when the signal intensity of the digital data is lower than the threshold value T, while transferring the digital data temporarily stored in the temporary memory 85 to a data storing means 86 to be stored therein when the signal intensity of the digital data is equal to or greater than the threshold value T and a data processing means 88.

In this embodiment, the control unit 70 is constituted so as to control the value of a drive current supplied to the first laser stimulating ray source 21, the second laser stimulating ray source 22 and the third laser stimulating ray source 23, thereby controlling the power of a laser beam 24 emitted from the first laser stimulating ray source 21, the second laser stimulating ray source 22 and the third laser stimulating ray source 23.

The thus constituted scanner according to this embodiment reads radiation data recorded in a stimulable phosphor sheet 10 by exposing a number of the stimulable phosphor layer regions 12 to a radioactive labeling substance contained in a number of the absorptive regions 4 formed in the biochemical analysis unit 1 and produces biochemical analysis data in the following manner.

A stimulable phosphor sheet 10 is first set on the glass plate 41 of the stage 40 by a user.

An instruction signal indicating that radiation data recorded in the stimulable phosphor layer 12 formed on the support 11 of the stimulable phosphor sheet 10 are to be read is then input through the keyboard 71.

The instruction signal input through the keyboard 71 is input to the control unit 70 and the control unit 70 outputs a drive signal to the filter unit motor 72 in accordance with the instruction signal, thereby moving the filter unit 48 so as to locate the filter member 51$d$ provided with the filter 52$d$ having a property of transmitting only light having a wavelength corresponding to that of stimulated emission emitted from stimulable phosphor but cutting off light having a wavelength of 640 nm in the optical path of stimulated emission 45.

The control unit 70 further outputs a drive signal to the main scanning stepping motor 65 to move the optical head 35 in the main scanning direction and when it determines based on a detection signal indicating the position of the optical head 35 input from the linear encoder 67 that the optical head 35 has reached a position where a laser beam 24 can be projected onto a first stimulable phosphor layer region 12 among a number of the stimulable phosphor layer regions 12 formed in the support 11 of the stimulable phosphor sheet 10, it outputs a drive stop signal to the main scanning stepping motor 65 and supplies a reference drive signal and reference drive current to the first stimulating ray source 21, thereby actuating it to emit a laser beam 24 having a wavelength of 640 nm.

In this embodiment, the value of the reference drive current first supplied to the first laser stimulating ray source 21 is selected so that when a stimulable phosphor layer region 12 storing the greatest amount of radiation energy is irradiated with a laser beam 24 and stimulated emission 45 released from the stimulable phosphor layer region 12 is photoelectrically detected by the photomultiplier 50, the intensity of stimulated emission 45 does not exceed the upper limit of the dynamic range of the photomultiplier 50 and a laser beam 24 having reference laser power P0 which is relatively low is first emitted from the first laser stimulating ray source 21.

A laser beam 24 emitted from the first laser stimulating source 21 passes through the collimator lens 25, thereby being made a parallel beam, and is reflected by the mirror 26.

The laser beam 24 reflected by the mirror 26 passes through the first dichroic mirror 27 and the second dichroic mirror 28 and advances to the mirror 29.

The laser beam 24 advancing to the mirror 29 is reflected by the mirror 29 and advances to the mirror 32 to be reflected thereby.

The laser beam 24 reflected by the mirror 32 passes through the hole 33 of the perforated mirror 34 and advances to the concave mirror 38.

The laser beam 24 advancing to the concave mirror 38 is reflected by the concave mirror 38 and enters the optical head 35.

The laser beam 24 entering the optical head 35 is reflected by the mirror 36 and condensed by the aspherical lens 37 onto the first stimulable phosphor layer region 12 of the stimulable phosphor sheet 10 placed on the glass plate 41 of a stage 40.

In this embodiment, since the stimulable phosphor layer regions 12 are formed by embedding stimulable phosphor in the recesses 13 formed in the support 11 made of oxygen free copper, it is possible to effectively prevent the laser beam 24 from scattering in each of the stimulable phosphor layer regions 12 and entering the neighboring stimulable phosphor layer regions 12 to excite stimulable phosphor contained in the neighboring stimulable phosphor layer regions 12.

When the laser beam 24 impinges onto the first stimulable phosphor layer region 12 formed in the support 11 of the stimulable phosphor sheet 10, stimulable phosphor contained in the first stimulable phosphor layer region 12 formed in the stimulable phosphor sheet 10 is excited by the laser beam 24, thereby releasing stimulated emission 45 from the first stimulable phosphor layer region 12.

The stimulated emission 45 released from the first stimulable phosphor layer region 12 is condensed onto the mirror 36 by the aspherical lens 37 provided in the optical head 35 and reflected by the mirror 36 on the side of the optical path of the laser beam 24, thereby being made a parallel beam to advance to the concave mirror 38.

The stimulated emission 45 advancing to the concave mirror 38 is reflected by the concave mirror 38 and advances to the perforated mirror 34.

As shown in FIG. 7, the stimulated emission 45 advancing to the perforated mirror 34 is reflected downward by the perforated mirror 34 formed as a concave mirror and advances to the filter 52d of the filter unit 48.

Since the filter 52d has a property of transmitting only light having a wavelength corresponding to that of stimulated emission emitted from stimulable phosphor and cutting off light having a wavelength of 640 nm, light having a wavelength of 640 nm corresponding to that of the stimulating ray is cut off by the filter 52d and only light having a wavelength corresponding to that of stimulated emission passes through the filter 52d to be photoelectrically detected by the photomultiplier 50.

Analog data produced by photoelectrically detecting stimulated emission 45 with the photomultiplier 50 are converted by an A/D converter 53 into digital data and the digital data are fed to a data processing apparatus 54.

In this embodiment, stimulable phosphor contained in a stimulable phosphor layer region 12 is first excited by the laser beam 24 having reference laser power P0 which is relatively low so that when a stimulable phosphor layer region 12 storing the greatest radiation energy is irradiated with a laser beam 24 and stimulated emission 45 released from the stimulable phosphor layer region 12 is photoelectrically detected by the photomultiplier 50, the intensity of stimulated emission 45 does not exceed the upper limit of the dynamic range of the photomultiplier 50. Therefore, since even in the case where the stimulable phosphor layer region 12 irradiated with the laser beam 24 stores a large amount of radiation energy, the intensity of stimulated emission 45 released from the stimulable phosphor layer region 12 is within the dynamic range of the photomultiplier 50 and the intensity of signals produced by the photomultiplier does no saturate, the stimulated emission 45 can be photoelectrically detected by the photomultiplier 50 with high sensitivity. On the other hand, however, in the case where the stimulable phosphor layer region 12 irradiated with the laser beam 24 stores small amount of radiation energy, since the intensity of stimulated emission 45 released from the stimulable phosphor layer region 12 is too low, it is extremely difficult for the photomultiplier 50 to photoelectrically detect the stimulated emission 45 with high sensitivity.

Therefore, in the scanner according to this embodiment, it is determined whether or not the signal intensity of digital data produced by exciting stimulable phosphor contained in a stimulable phosphor layer region 12 with a laser beam 24 having the reference laser power P0 which is relatively low and released from the first laser stimulating ray source 21 and photoelectrically detecting stimulated emission 45 released from the stimulable phosphor layer region 12 is lower than the threshold value T and when the signal intensity of the digital data is determined to be lower than the threshold value T, the laser power of the laser beam 24 released from the first laser stimulating ray source 21 is set to be higher than the reference laser power P0 and stimulable phosphor contained in the stimulable phosphor layer region 12 is again excited by the laser beam 24.

Analog data produced by photoelectrically detecting stimulated emission 45 released from the first stimulable phosphor layer region 12 formed in the support 11 of the stimulable phosphor sheet 10 by the photomultiplier 50 are digitized by the A/D converter 53 to produce digital data and the thus produced digital data are temporarily stored in the temporary memory 85 of the data processing apparatus 54.

When a predetermined time, for example, several microseconds, has passed after the first stimulating ray source 21 was turned on, the control unit 70 outputs a drive stop signal to the first stimulating ray source 21, thereby turning it off and outputs a signal intensity determination start signal to the signal intensity determining means 87 of the data processing apparatus 54.

Figure 21:
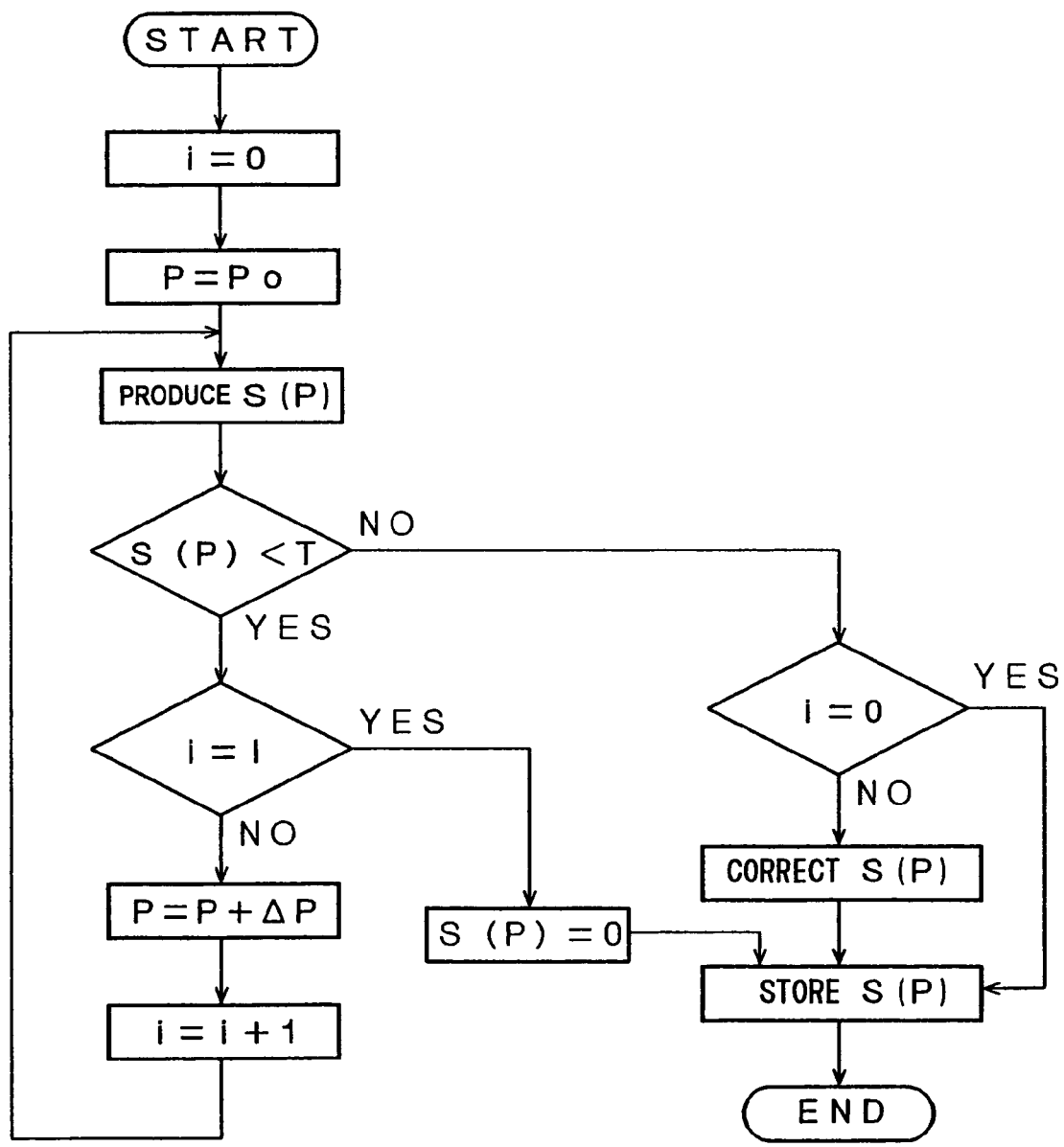
FIG. 21 is a flow chart showing a biochemical analysis data producing operation performed by a signal intensity determining means and a control unit of a scanner which is a further preferred embodiment of the present invention.

FIG. 21 is a flow chart showing a biochemical analysis data producing operation performed by the signal intensity determining means 87 and the control unit 70 of a scanner which is a further preferred embodiment of the present invention.

As shown in FIG. 21, when the signal intensity determining means 87 receives the signal intensity determination start signal from the control unit 70, it reads digital data S (P0) produced by photoelectrically detecting stimulated emission 45 released from the first stimulable phosphor layer region 12 and temporarily stored in the temporary memory 85 and compares the signal intensity of the digital data S (P0) with the threshold value T.

When the signal intensity determining means 87 determines that the signal intensity of the digital data S (P0) is equal to or higher than the threshold value T, it can be considered that the digital data S (P0) having sufficiently high signal intensity have been produced even though stimulable phosphor contained in the first stimulable phosphor layer region 12 was excited by the laser beam 24 having the reference laser power P0 which is relatively low and since it can be considered that a large amount of radiation energy is stored in the first stimulable phosphor layer region 12, if stimulable phosphor contained in the first stimulable phosphor layer region 12 is excited by the laser beam 24 having laser power higher than the reference laser power P0, there occurs a risk of the signal intensity of the digital data exceeding the upper limit of the dynamic range of the photomultiplier 50. Therefore, the signal intensity determining means 87 determines the digital data S (P0) produced by exciting stimulable phosphor contained in the first stimulable phosphor layer region 12 by the laser beam 24 having the reference laser power P0 which is relatively low and photoelectrically detecting stimulated emission 45 released from the first stimulable phosphor layer region 12 and temporarily stored in the temporary memory 85 as digital data of the first stimulable phosphor layer region 12 and transfers the digital data S (P0) temporarily stored in the temporary memory 85 to the data storing means 86 to be stored therein.

To the contrary, when the signal intensity determining means 87 determines that the signal intensity of the digital data S (P0) is lower than the threshold value T, it can be considered that since the amount of radiation energy stored in the first stimulable phosphor layer region 12 is small, the intensity of stimulated emission 45 released from the first stimulable phosphor layer region 12 in response to the stimulation with the laser beam 24 having the reference laser power P0 which is relatively low is too low and digital data S (P0) having sufficiently high signal intensity and high quantitative characteristic cannot be obtained. Therefore, the signal intensity determining means 87 outputs a laser power increasing signal to the control unit 70.

When the laser power increasing signal is input from the signal intensity determining means 87 of the data processing apparatus 54, the control unit 70 outputs a first drive signal and supplies first drive current whose value is higher than that of the reference drive current to the first laser stimulating ray source 21, thereby causing the first laser stimulating ray source 21 to emit a laser beam 24 having first laser power P1 higher than the reference laser power P0 where P1=P0+ΔP.

A laser beam 24 having a wavelength of 640 nm and the first laser power P1 emitted from the first laser stimulating source 21 passes through the collimator lens 25, thereby being made a parallel beam, and is reflected by the mirror 26.

The laser beam 24 reflected by the mirror 26 passes through the first dichroic mirror 27 and the second dichroic mirror 28 and advances to the mirror 29.

The laser beam 24 advancing to the mirror 29 is reflected by the mirror 29 and advances to the mirror 32 to be reflected thereby.

The laser beam 24 reflected by the mirror 32 passes through the hole 33 of the perforated mirror 34 and advances to the concave mirror 38.

The laser beam 24 advancing to the concave mirror 38 is reflected by the concave mirror 38 and enters the optical head 35.

The laser beam 24 entering the optical head 35 is reflected by the mirror 36 and condensed by the aspherical lens 37 onto the first stimulable phosphor layer region 12 of the stimulable phosphor sheet 10 placed on the glass plate 41 of a stage 40.

In this embodiment, since the stimulable phosphor layer regions 12 are formed by embedding stimulable phosphor in the recesses 13 formed in the support 11 made of oxygen free copper, it is possible to effectively prevent the laser beam 24 from scattering in each of the stimulable phosphor layer regions 12 and entering the neighboring stimulable phosphor layer regions 12 to excite stimulable phosphor contained in the neighboring stimulable phosphor layer regions 12.

When the laser beam 24 impinges onto the first stimulable phosphor layer region 12 formed in the support 11 of the stimulable phosphor sheet 10, stimulable phosphor contained in the first stimulable phosphor layer region 12 formed in the stimulable phosphor sheet 10 is excited by the laser beam 24, thereby releasing stimulated emission 45 from the first stimulable phosphor layer region 12.

Since the laser beam 24 projected on the first stimulable phosphor layer region 12 has the first laser power P1 higher than the reference laser power P0, even when the amount of radiation energy stored in the first stimulable phosphor layer region 12 is small, stimulated emission 45 having high intensity is emitted from the first stimulable phosphor layer region 12.

The stimulated emission 45 released from the first stimulable phosphor layer region 12 is condensed onto the mirror 36 by the aspherical lens 37 provided in the optical head 35 and reflected by the mirror 36 on the side of the optical path of the laser beam 24, thereby being made a parallel beam to advance to the concave mirror 38.

The stimulated emission 45 advancing to the concave mirror 38 is reflected by the concave mirror 38 and advances to the perforated mirror 34.

As shown in FIG. 7, the stimulated emission 45 advancing to the perforated mirror 34 is reflected downward by the perforated mirror 34 formed as a concave mirror and advances to the filter 52d of the filter unit 48.

Since the filter 52d has a property of transmitting only light having a wavelength corresponding to that of stimulated emission emitted from stimulable phosphor and cutting off light having a wavelength of 640 nm, light having a wavelength of 640 nm corresponding to that of the stimulating ray is cut off by the filter 52d and only light having a wavelength corresponding to that of stimulated emission passes through the filter 52d to be photoelectrically detected by the photomultiplier 50.

Analog data produced by photoelectrically detecting stimulating emission with the photomultiplier 50 are digitized by the A/D converter 53 to produce digital data and the digital data are temporarily stored in the temporary memory 85 of the data processing apparatus 54.

When a predetermined time, for example, several microseconds, has passed after the first stimulating ray source 21 was turned on, the control unit 70 outputs a drive stop signal to the first stimulating ray source 21, thereby turning it off and outputs a signal intensity determination start signal to the signal intensity determining means 87 of the data processing apparatus 54.

When the signal intensity determining means 87 receives the signal intensity determination start signal from the control unit 70, it reads digital data S (P1) produced by photoelectrically detecting stimulated emission 45 released from the first stimulable phosphor layer region 12 and temporarily stored in the temporary memory 85 and compares the signal intensity of the digital data S (P1) with the threshold value T.

When the signal intensity determining means 87 determines that the signal intensity of the digital data S (P1) is equal to or higher than the threshold value T, it can be considered that since the power of the laser beam 24 was set to be the first laser power P1 higher than the reference laser power P0 by ΔP and stimulable phosphor contained in the first stimulable phosphor layer region 12 was excited by the laser beam 24 having the first laser power P1, the intensity of stimulated emission 45 released from the first stimulable phosphor layer region 12 and photoelectrically detected by the photomultiplier 50 has become sufficiently higher and digital data S (P1) having sufficiently high signal intensity and high quantitative characteristic have been produced. Therefore, if stimulable phosphor contained in the first stimulable phosphor layer region 12 is excited by the laser beam 24 having laser power higher than the first laser power P1, since the intensity of stimulated emission 45 released from the first stimulable phosphor layer region 12 and to be photoelectrically detected by the photomultiplier 50 becomes too high and there occurs a risk of the signal intensity of the digital data exceeding the dynamic range of the photomultiplier 50, the signal intensity determining means 87 determines the digital data S (P1) produced by exciting stimulable phosphor contained in the first stimulable phosphor layer region 12 by the laser beam 24 having the first laser power P1 and photoelectrically detecting stimulated emission 45 released from the first stimulable phosphor layer region 12 and temporarily stored in the temporary memory 85 as digital data of the first stimulable phosphor layer region 12.

Since the digital data S (P1) temporarily stored in the temporary memory 85 have been produced by irradiating the first stimulable phosphor layer region 12 with the laser beam 24 having the first laser power P1 higher than the reference laser power P0 to excite stimulable phosphor contained in the first stimulable phosphor layer region 12 and photoelectrically detecting stimulated emission 45 released from the first stimulable phosphor layer region 12, the digital data S (P1) have apparently higher signal intensity than that of the digital data S (P0) produced by irradiating the first stimulable phosphor layer region 12 with the laser beam 24 having the reference laser power P0 to excite stimulable phosphor contained in the first stimulable phosphor layer region 12 and photoelectrically detecting stimulated emission 45 released from the first stimulable phosphor layer region 12 even if same radiation energy is released from the first stimulable phosphor layer region 12. Therefore, since it is necessary to correct the digital data S (P1) so as to become digital data that would be obtained by exciting stimulable phosphor contained in the first stimulable phosphor layer region 12 with the laser beam 24 having the reference laser power P0, the signal intensity determining means 87 outputs a correction effecting signal to the data processing means 88.

When the correction effecting signal is input from the signal intensity determining means 87, the data processing means 88 reads the digital data S (P1) temporarily stored in the temporary memory 85, correct the digital data S (P1) in accordance with the following formula so as to become digital data that would be obtained by exciting stimulable phosphor contained in the first stimulable phosphor layer region 12 with the laser beam 24 having the reference laser power P0 and stores the thus obtained digital data S in the data storing means 88.

$$S = S(P1) \times C1(P0/P1)$$

In this formula, S is digital data to be obtained by correcting the digital data S (P1) and C1 (P0/P1) is a correction coefficient and is a function of the reference laser power P0 and the first laser power P1.

To the contrary, when the signal intensity determining means 87 determines that the signal intensity of the digital data S (P1) is lower than the threshold value T, it can be considered that since the amount of radiation energy stored in the first stimulable phosphor layer region 12 is too small, even though the power of the laser beam 24 was increased from the reference laser power P0 to the first laser power P1 and stimulable phosphor contained in the first stimulable phosphor layer region 12 was excited by the laser beam 24 having the first laser power P1 higher than the reference laser power P0, the intensity of stimulated emission 45 released from the first stimulable phosphor layer region 12 and photoelectrically detected by the photomultiplier 50 is still too low and digital data S (P0) having sufficiently high signal intensity and high quantitative characteristic have not been obtained. Therefore, the signal intensity determining means 87 outputs a laser power increasing signal to the control unit 70.

When the laser power increasing signal is again input from the signal intensity determining means 87 of the data processing apparatus 54, the control unit 70 outputs a second drive signal and supplies second drive current whose value is higher than that of the first drive current to the first laser stimulating ray source 21, thereby causing the first laser stimulating ray source 21 to emit a laser beam 24 having second laser power P2 higher than the first laser power P1 where P2=P1+ΔP.

In this manner, the steps of increasing the power of the laser beam 24, exciting stimulable phosphor contained in the first stimulable phosphor layer region 12, photoelectrically detecting stimulated emission 45 released from the first stimulable phosphor layer region 12 by the photomultiplier 50 to produce analog data, digitizing the analog data to produce digital data and comparing the signal intensity of the digital data with the threshold value T are repeated up to I times at the maximum where I is an integer greater than 2.

In this embodiment, the step of increasing the power of the laser beam 24 is repeated only I times because some of the stimulable phosphor layer regions 12 store no radiation energy since a number of the stimulable phosphor layer regions 12 formed in the support 11 of the stimulable phosphor sheet 10 are selectively labeled with the radioactive labeling substance and even if the laser beam 24 whose power has been increased is repeatedly projected onto those stimulable phosphor layer regions 12, the signal intensity of digital data cannot become equal to or higher than the threshold value T. Therefore, when the signal intensity of the thus produced digital data is still lower than the threshold value T even though the power of the laser beam 24 was increased I times to produce digital data, the signal intensity determining means 87 determines that digital data of the first stimulable phosphor layer region 12 are zero and stores zero in the data storing means 88 as the digital data of the first stimulable phosphor layer region 12.

To the contrary, when, as the result of increasing the power of the laser beam 24 emitted from the first laser stimulating ray source 21 by ΔP i times where i is a positive integer less than I and exciting stimulable phosphor contained in the first stimulable phosphor layer region 12, the signal intensity determining means 87 determines that the signal intensity of digital data S (Pi) obtained by photoelectrically detecting stimulated emission 45 released from the first stimulable phosphor layer region 12 by the photomultiplier 50 to produce analog data and digitizing the analog data has become equal to or greater than the threshold value T, the signal intensity determining means 87 outputs a correction effecting signal to the data processing means 88 and causes it to correct the digital data S (Pi) similarly to the case of the digital data S (P1) produced using the laser beam 24 having the first laser power P1 and to store the thus corrected digital data in the data storing means 86.

Since radiation energy stored in the stimulable phosphor layer region 12 is released in the form of stimulated emission 45 when it is irradiated with the laser beam 24 and the amount of radiation energy stored in the stimulable phosphor layer region 12 is decreased, the reference laser power P0 and the increment ΔP are experimentally determined in advance so as to minimize the number of repetitions of the excitation with the laser beam 24 and are stored as set values of the laser power in a memory (not shown) of the control unit 70.

In the above described manner, when digital data have been produced by irradiating the first stimulable phosphor layer region 12 formed in the support 11 of the stimulable phosphor sheet 10 with the laser beam 24 to excite stimulable phosphor contained in the first stimulable phosphor layer region 12, photoelectrically detecting stimulated emission 45 released from the first stimulable phosphor layer region 12 to produce analog data and digitizing the analog data, and the digital data have been stored in the data storing means 86, the control unit 70 outputs a drive stop signal to the first laser stimulating ray source 21, thereby turning it off and outputs a drive signal to the main scanning stepping motor 65, thereby moving the optical head 35 by one pitch equal to the distance between neighboring stimulable phosphor layer regions 12 of the stimulable phosphor sheet 10 in the main scanning direction.

When the control unit 70 determines based on a detection signal indicating the position of the optical head 35 input from the linear encoder 67 that the optical head 35 has been moved by one pitch equal to the distance between neighboring stimulable phosphor layer regions 12 in the main scanning direction, it outputs a reference drive signal and supplies a reference drive current to the first stimulating ray source 21, thereby causing it to emit a laser beam 24 having the reference laser power P0. As a result, stimulable phosphor contained in a second stimulable phosphor layer region 12 formed in the support 11 of the stimulable phosphor sheet 10 next to the first stimulable phosphor layer region 12 is first excited by the laser beam 24 having the reference laser power P0.

Similarly to the above, the second stimulable phosphor layer region 12 formed in the support 11 of the stimulable phosphor sheet 10 is irradiated with the laser beam 24 for a predetermined time and when digital data S (P0) produced by photoelectrically detecting stimulated emission 45 released from the second stimulable phosphor layer region 12 by the photomultiplier 50 to produce analog data and digitizing the analog data by the A/D converter 53 have been temporarily stored in the temporary memory 85 of the data processing apparatus 54, the control unit 70 outputs a drive stop signal to the first stimulating ray source 21, thereby turning it off and outputs a signal intensity determination start signal to the signal intensity determining means 87 of the data processing apparatus 54.

When the signal intensity determining means 87 receives the signal intensity determination start signal from the control unit 70, it reads digital data S (P0) produced by photoelectrically detecting stimulated emission 45 released from the second stimulable phosphor layer region 12 and temporarily stored in the temporary memory 85 and compares the signal intensity of the digital data S (P0) with the threshold value T.

Similarly to the case of irradiating the first stimulable phosphor layer region 12 with the laser beam having the reference laser power P0 and producing digital data, when the signal intensity of digital data S (P0) is determined to be equal to or higher than the threshold value T, the digital data S (P0) stored in the temporary memory 85 are determined as digital data of the second stimulable phosphor layer region 12 and stored in the data storing means 86 of the data processing apparatus 54. On the other hand, when the signal intensity of digital data S (P0) is determined to be lower than the threshold value T, the power of the laser beam 24 is increased, whereby stimulable phosphor contained in the second stimulable phosphor layer region 12 second stimulable phosphor layer region 12 is excited by the laser beam and stimulated emission 45 released from the second stimulable phosphor layer region 12 is photoelectrically detected to produce digital data. When the signal intensity of digital data S (P0) is determined to have become equal to or higher than the threshold value T, the digital data are determined as digital data of the second stimulable phosphor layer region 12 and corrected by the data processing means 88 in accordance with the power of the laser beam 24 to be stored in the data storing means 86 of the data processing apparatus 54.

In this manner, the on and off operation of the first stimulating ray source 21 is repeated in synchronism with the intermittent movement of the optical head 35 and when the control unit 70 determines based on a detection signal indicating the position of the optical head 35 input from the linear encoder 67 that the optical head 35 has been moved by one scanning line in the main scanning direction and that the stimulable phosphor layer regions 12 included in a first line of the stimulable phosphor layer regions 12 formed in the support 11 of the stimulable phosphor sheet 10 have been scanned with the laser beam 24, it outputs a drive signal to the main scanning stepping motor 65, thereby returning the optical head 35 to its original position and outputs a drive signal to the sub-scanning pulse motor 61, thereby causing it to move the movable base plate 63 by one scanning line in the sub-scanning direction.

When the control unit 70 determines based on a detection signal indicating the position of the optical head 35 input from the linear encoder 67 that the optical head 35 has been returned to its original position and determines that the movable base plate 63 has been moved by one scanning line in the sub-scanning direction, similarly to the manner in which the stimulable phosphor layer regions 12 included in the first line of the stimulable phosphor layer regions 12 formed in the support 11 of the stimulable phosphor sheet 10 were sequentially irradiated with the laser beam 24 emitted from the first laser stimulating ray source 21, the stimulable phosphor layer regions 12 included in a second line of the stimulable phosphor layer regions 12 formed in the support 11 of the stimulable phosphor sheet 10 are sequentially irradiated with the laser beam 24 emitted from the first laser stimulating ray source 21, thereby exciting stimulable phosphor contained in the stimulable phosphor layer regions 12 included in the second line and stimulated emission 45 released from the stimulable phosphor layer regions 12 is sequentially and photoelectrically detected by the photomultiplier 50 to produce analog data. The analog data are digitized by the A/D converter 53 to produce digital data and the digital data are temporarily stored in the temporary memory 85. Then, in accordance with the signal intensity of the digital data stored in the temporary memory 85, the digital data stored in the temporary memory 85 are stored as the digital data of the stimulable phosphor layer region 12 in the data storing means 88 of the data processing apparatus 54, or, the steps of increasing the power of the laser beam 24, irradiating each of the stimulable phosphor layer regions 12 included in the second line to excite stimulable phosphor contained therein, photoelectrically detecting stimulated emission 45 from each of the stimulable phosphor layer regions 12 to produce analog data and digitizing the analog data to produce digital data are conducted, and when the signal intensity of the digital data is determined to be equal to or higher than the threshold value T, the digital data are stored as the digital data of the stimulable phosphor layer region 12 in the data storing means 88 of the data processing apparatus 54.

When all of the stimulable phosphor layer regions 12 formed in the support 11 of the stimulable phosphor sheet 10 have been scanned with the laser beam 24 in this manner, the first laser stimulating ray source 21 is turned off and the reading operation of radiation data stored in a number of the stimulable phosphor layer regions 12 of the stimulable phosphor sheet 10 is completed.

In this embodiment, digital data of each of the stimulable phosphor layer regions 12 of the stimulable phosphor sheet 10 are produced by first irradiating each of the stimulable phosphor layer regions 12 with the laser beam 24 having the reference laser power P0 which is relatively low and emitted from the first laser stimulating ray source 21 to excite stimulable phosphor contained therein, photoelectrically detecting stimulated emission 45 released from each of the stimulable phosphor layer regions 12 by the photomultiplier 50 to produce analog data and digitizing the analog data, and the signal intensity of the thus produced digital data S (P0) is compared with the threshold value T by the signal intensity determining means 87. When it is determined that the signal intensity of the digital data S (P0) is equal to or higher than the threshold value T, since it can be considered that large radiation energy is stored in the stimulable phosphor region 12 and if stimulable phosphor contained in the stimulable phosphor region 12 is excited by a laser beam 24 having a laser power higher than the reference laser power P0, there is a risk of the signal strength of digital data exceeding the upper limit of the dynamic range of the photomultiplier 50, the digital data S (P0) produced by exciting stimulable phosphor contained in the stimulable phosphor layer region 12 with the laser beam 24 having the reference laser power P0 which is relatively low and photoelectrically detecting stimulated emission 45 released from the stimulable phosphor layer region 12 and temporarily stored in the temporary memory 85 are determined as digital data of the stimulable phosphor layer region 12 and stored in the data storing means 88.

Therefore, according to this embodiment, even in the case where radiation energy stored in a stimulable phosphor layer region 12 is extremely large, it is possible to reliably prevent the intensity of stimulated emission 45 released from the stimulable phosphor layer region 12 from becoming too high and exceeding the upper limit of the dynamic range of the photomultiplier 50 and to photoelectrically detect stimulated emission 45 with high sensitivity by the photomultiplier 50, thereby producing biochemical analysis data.

On the other hand, in this embodiment, when it is determined that the signal intensity of the digital data S (P0) is lower than the threshold value T, since it can be considered that extremely small radiation energy is stored in the stimulable phosphor region 12 and it is extremely difficult for the photomultiplier 50 to photoelectrically detect stimulated emission 45 released from the stimulable phosphor region 12 with high intensity because the intensity of the stimulated emission 45 is too low and to produce digital data having high quantitative characteristics and high signal intensity, only when the signal intensity of digital data S (Pi) produced by increasing the power of a laser beam 24 emitted from the first laser stimulating ray source 21, causing the first laser stimulating ray source 21 to emit a laser beam 24 having laser power Pi higher than the reference power P0 where Pi=P0+ΔP×i and i is a positive integer, exciting stimulable phosphor contained in the stimulable phosphor region 12 by the laser beam 24 having the laser beam Pi, and photoelectrically detecting stimulated emission 45 released from the stimulable phosphor region 12 by the photomultiplier 50 is equal to or higher than the threshold value T, the digital data S (Pi) are determined as digital data of the stimulable phosphor region 12.

Therefore, according to this embodiment, even in the case where radiation energy stored in a stimulable phosphor region 12 is too small, so that the intensity of stimulated emission 45 released from the stimulable phosphor layer region 12 is too low to be photoelectrically detected by the photomultiplier 50 with high sensitivity when the stimulable phosphor layer region 12 is irradiated with a laser beam 24 whose power is selected in such a manner that the signal intensity of digital data produced by irradiating a stimulable phosphor layer regions 12 storing high radiation energy with the laser beam 24 to excite stimulable phosphor contained therein and photoelectrically detecting stimulated emission 45 released from the stimulable phosphor region 12 does not exceed the upper limit of the dynamic range of the photomultiplier 50, stimulated emission 45 released from the stimulable phosphor layer region 12 can be photoelectrically detected with high sensitivity to produce digital data S (Pi), thereby producing biochemical analysis data having high quantitative characteristics.

Further, in this embodiment, when the signal intensity of digital data S (Pi) is equal to or higher than the threshold value T and the digital data S (Pi) are determined as digital data of the stimulable phosphor region 12, the digital data S (Pi) are multiplied by Ci (P0/Pi) which is a function of the power of the laser beam 24 so that the digital data S (Pi) are corrected so as to become digital data that would be obtained by exciting stimulable phosphor contained in the stimulable phosphor layer region 12 with the laser beam 24 having the reference laser power P0 and the thus corrected digital data are stored in the data storing means 86. Therefore, even in the case of increasing the laser power of a laser beam 24 so as to become greater that the reference laser power P0 and exciting stimulable phosphor contained in a stimulable phosphor layer region 12 with the laser beam 24 in order to detect stimulated emission 45 with high sensitivity or release all detectable radiation energy stored in the stimulable phosphor layer region 12 in the form of stimulated emission 45 to be detected, it is possible to produce digital data having signal intensity corresponding to radiation energy stored in the stimulable phosphor layer region 12.

Moreover, according to this embodiment, when the signal intensity of digital data are lower than the threshold value T even if the increase in the power of a laser beam 24 is repeated I times at the maximum where I is an integer equal to or greater than 3, since it is judged that no radiation energy is stored in the stimulable phosphor layer region 12 and digital data S are stored in the data storing means 86 so that S equals 0, radiation data recorded in a number of the stimulable phosphor layer regions 12 by being selectively labeled with a radioactive labeling substance can be effectively read to produce biochemical analysis data.

Figure 22:
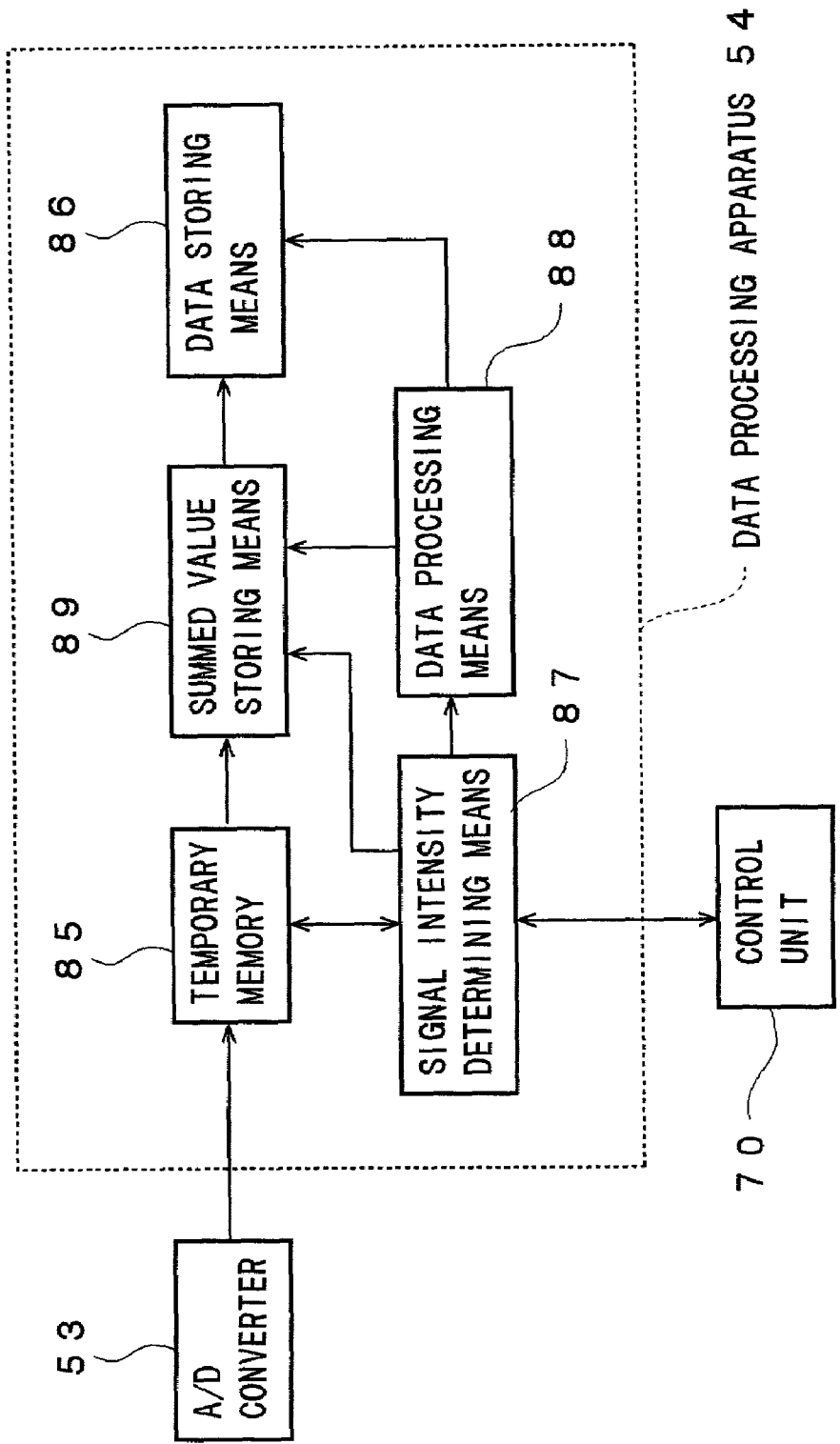
FIG. 22 is a block diagram of a data processing apparatus of a scanner which is a further preferred embodiment of the present invention.

FIG. 22 is a block diagram of a data processing apparatus of a scanner which is a further preferred embodiment of the present invention.

As shown in FIG. 22, a data processing apparatus 54 of a scanner according to this embodiment further includes a summed value storing means 89 for storing a summed value of digital data and the signal intensity determining means 87 of the data processing apparatus 54 is constituted so as to temporarily store digital data S (P0) produced by irradiating each of the stimulable phosphor layer regions 12 formed in the support 11 of the stimulable phosphor sheet 10 with a laser beam 24 having the reference laser power P0 to excite stimulable phosphor contained therein, to photoelectrically detect stimulated emission 45 released from each of the stimulable phosphor layer regions 12 by the photomultiplier 50 to produce analog data, and digitizing the analog data, to compare the digital data S (P0) temporarily stored in the temporary memory 85 with the threshold value T, to sample, when it determines that the signal intensity of the digital data S (P0) is equal to or higher than the threshold value T, digital data at a predetermined cycle until the signal intensity of the digital data S (P0) comes to be lower than the threshold value T, to sum the thus sampled digital data, and to store the summed digital data in the summed value storing means 89.

Furthermore, in this embodiment, the signal intensity determining means 87 of the data processing apparatus 54 is constituted so as to output, when it determines that the signal intensity of digital data S (P0) produced by irradiating each of the stimulable phosphor layer regions 12 formed in the support 11 of the stimulable phosphor sheet 10 with a laser beam 24 having the reference laser power P0 to excite stimulable phosphor contained therein, photoelectrically detecting stimulated emission 45 released from each of the stimulable phosphor layer regions 12 by the photomultiplier 50 to produce analog data, and digitizing the analog data is lower than the threshold value T, a laser power increasing signal to the control unit 70 up to I times at maximum where I is an integer equal to or greater than 3, thereby causing the control unit 70 to increase the power of a laser beam 24 emitted from the first laser stimulating ray source 21 by $\Delta Pr$ I times at maximum, to temporarily store in the temporary memory 85 digital data S (Pi) produced by irradiating stimulable phosphor contained in the stimulable phosphor layer region 12 from which that digital data S (P0) have been obtained with the laser beam 24 thereby exciting stimulable phosphor contained therein, photoelectrically detecting stimulated emission 45 released from the stimulable phosphor layer region 12 to produce analog data and digitizing the analog data to produce digital data, to compare the signal intensity of the digital data S (Pi) temporarily stored in the temporary memory 85 with the threshold value T, to sample, when it determines that the signal intensity of the digital data S (Pi) is equal to or higher than the threshold value T, digital data at a predetermined cycle until the signal intensity of the digital data S (Pi) becomes to be lower than the threshold value T, to sum the thus sampled digital data, and to store the summed digital data in the summed value storing means 89. Here, $Pi = P0 + \Delta P \times i$ and i is equal to or less than I.

Further, in this embodiment, the control unit 70 is constituted so as to hold the first laser stimulating ray source 21 on and to output a signal intensity determination start signal to the data processing apparatus 54 at a predetermined cycle.

When digital data S (P0) are produced by irradiating a stimulable phosphor layer region 12 with a laser beam 24 having the reference power P0 and emitted from the first laser stimulating ray source 21 to excite stimulable phosphor contained therein, photoelectrically detecting stimulated emission 45 released from each of the stimulable phosphor layer regions 12 by the photomultiplier 50 to produce analog data, and digitizing the analog data by the A/D converter 53 and temporarily stored in the temporary memory 85 and the signal intensity determination start signal is input from the control unit 70, the signal intensity determining means 87 reads the digital data S (P0) temporarily stored in the temporary memory 85 and compares the signal intensity thereof with the threshold value T.

When the signal intensity determining means 87 determines that the signal intensity of the digital data S (P0) is equal to or higher than the threshold value T, it samples the digital data S (P0) temporarily stored in the temporary memory 85 and stores them in the summed value storing means 89.

Then, each time the signal intensity determination start signal is input from the control unit 70, the signal intensity determining means 87 reads the digital data S (P0) temporarily stored in the temporary memory 85 and compares the signal intensity thereof with the threshold value T. When the signal intensity determining means 87 determines that the signal intensity of the digital data S (P0) is equal to or higher than the threshold value T, it samples the digital data S (P0) and adds them to the digital data S (P0) stored in the summed value storing means 89.

Figure 23:
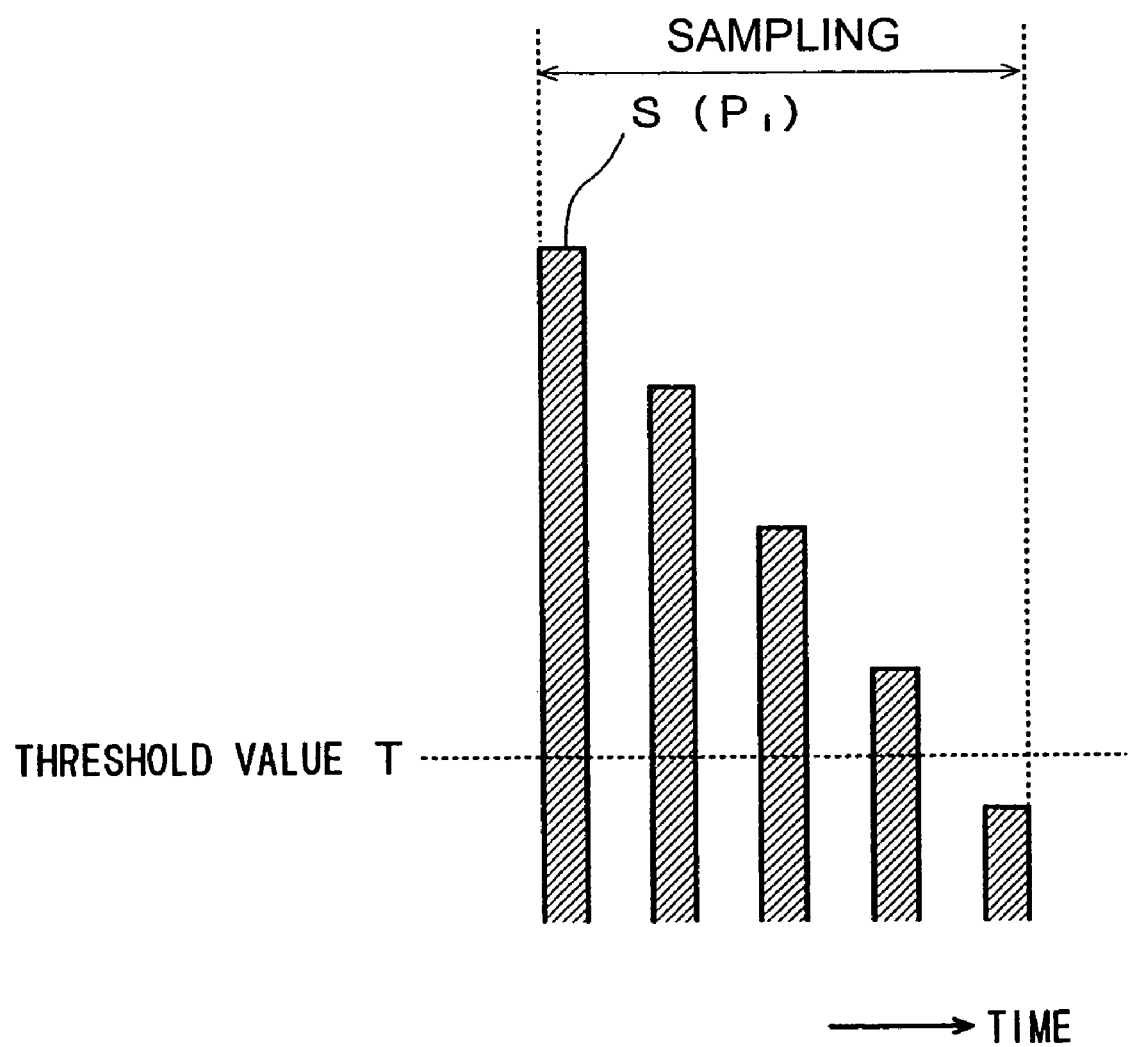
FIG. 23 is a notional view showing digital data S (Pi).

FIG. 23 is a notional view showing digital data S (Pi).

As shown in FIG. 23, since when a stimulable phosphor layer region 12 is irradiated with a laser beam 24 having laser power Pi, stimulable phosphor contained in the stimulable phosphor layer region 12 is excited and radiation energy stored in the stimulable phosphor is released in the form of light, thereby releasing stimulated emission 45 from the stimulable phosphor layer region 12, the intensity of stimulated emission 45 is lowered with lapse of time and, therefore, the signal intensity of digital data S (Pi) is also lowered with lapse of time.

When a result of receiving the signal intensity determination start signal from the control unit 70, reading digital data S (P0) temporarily stored in the temporary memory 85 and comparing the signal intensity of the digital data S (P0) with the threshold value T, the signal intensity determining means 87 determines that the signal intensity of the digital data S (P0) has become lower than the threshold value T because stimulated emission has been released from the stimulable phosphor layer region 12 and radiation energy stored in stimulable phosphor layer region 12 has been decreased, the signal intensity determining means 87 does not sample the digital data S (P0).

To the contrary, when the signal intensity determining means 87 determines that the signal intensity of the digital data S (P0) is lower than the threshold value T, similarly to the previous embodiment, it outputs a laser power increasing signal to the control unit 70.

As a result, a laser beam 24 having the laser power Pi higher than the reference laser power P0 is emitted from the first laser stimulating ray source 21, the stimulable phosphor layer region 12 from which the digital data S (P0) are obtained is irradiated with the laser beam 24 to excite stimulable phosphor contained therein, stimulated emission 45 released from the stimulable phosphor layer region 12 is photoelectrically detected by the photomultiplier 50 to produce analog data, the analog data are digitized by the A/D converter 53 to produce digital data S (Pi), and the digital data S (Pi) are temporarily stored in the temporary memory 85.

When the signal intensity determination start signal is input from the control unit 70, the signal intensity determining means 87 compares the signal intensity of the digital data S (Pi) with the threshold value T.

When the signal intensity determining means 87 determines that the signal intensity of the digital data S (Pi) is equal to or higher than the threshold value T, it samples the digital data S (Pi) and stores them in the summed value storing means 89.

Then, each time the signal intensity determination start signal is input from the control unit 70, the signal intensity determining means 87 reads the digital data S (Pi) temporarily stored in the temporary memory 85 and compares the signal intensity thereof with the threshold value T. When the signal intensity determining means 87 determines that the signal intensity of the digital data S (Pi) is equal to or higher than the threshold value T, it samples the digital data S (Pi) and adds them to the digital data S (Pi) stored in the summed value storing means 89.

In this manner, the signal intensity determining means 87 repeatedly receives the signal intensity determination start signal from the control unit 70, reads the digital data S (Pi) temporarily stored in the temporary memory 85 and compares the signal intensity of the digital data S (Pi) with the threshold value T. When the signal intensity determining means 87 determines that the signal intensity of the digital data S (Pi) has become lower than the threshold value T because stimulated emission has been released from the stimulable phosphor layer region 12 and radiation energy stored in stimulable phosphor layer region 12 has been decreased, the signal intensity determining means 87 outputs a correction effecting signal to the data processing means 88 without sampling the digital data S (Pi).

When the correction effecting signal is input from the signal intensity determining means 87, the data processing means 88 of the data processing apparatus 54 reads the summed value ΣS (Pi) of the digital data S (Pi) stored in the summed value storing means 89, corrects, in accordance with the following formula, the summed value ΣS (Pi) of the digital data S (Pi) so as to become a summed value ΣS of digital data S that would be obtained by exciting stimulable phosphor contained in the stimulable phosphor layer region 12 with the laser beam 24 having the reference laser power P0 and stored the thus corrected summed value ΣS in the data storing means 88.

$$\Sigma S = \Sigma S(Pi) \times C2(P0/Pi)$$

In the above formula, ΣS is the corrected summed value of digital data and C2 (P0/Pi) is a correction coefficient and a function of the reference laser power P0 and the laser power Pi.

According to this embodiment, digital data of each of the stimulable phosphor layer regions 12 of the stimulable phosphor sheet 10 are produced by first irradiating each of the stimulable phosphor layer regions 12 with the laser beam 24 having the reference laser power P0 which is relatively low and emitted from the first laser stimulating ray source 21 to excite stimulable phosphor contained therein, photoelectrically detecting stimulated emission 45 released from each of the stimulable phosphor layer regions 12 by the photomultiplier 50 to produce analog data and digitizing the analog data, and the signal intensity of the thus produced digital data S (P0) is compared with the threshold value T by the signal intensity determining means 87. When the signal intensity determining means 87 determines that the signal intensity of the digital data S (P0) is equal to or higher than the threshold value T, digital data S (P0) are sampled at a predetermined cycle and summed until the signal intensity of the digital data S (P0) comes to be lower than the threshold value T, thereby producing digital data of the stimulable phosphor layer region 12. Therefore, even in the case where radiation energy stored in a stimulable phosphor region 12 is too small, it is possible to produce digital data with high sensitivity by detecting stimulated emission 45 released from the stimulable phosphor region 12 and to produce biochemical analysis data having high quantitative characteristics. On the other hand, when the signal intensity of digital data S (P0) produced by exciting stimulable phosphor contained in a stimulable phosphor layer region 12 with a laser beam 24 having the reference laser power P0 which is relatively low is lower than the threshold value T, the power of the laser beam 24 is increased by ΔP and the stimulable phosphor contained in the stimulable phosphor layer region 12 is excited by the laser beam 24. Therefore, it is possible to prevent stimulated emission released from stimulable phosphor contained in the stimulable phosphor layer region 12 by exciting the stimulable phosphor with the laser beam 24 from becoming too great to exceed the upper limit of the dynamic range of the photomultiplier 50 and to prevent the signal intensity of digital data produced by detecting the stimulated emission 45 from being saturated, thereby degrading the quantitative characteristics of biochemical analysis data.

Further, according to this embodiment, digital data of each of the stimulable phosphor layer regions 12 of the stimulable phosphor sheet 10 are produced by first irradiating each of the stimulable phosphor layer regions 12 with the laser beam 24 having the reference laser power P0 which is relatively low and emitted from the first laser stimulating ray source 21 to excite stimulable phosphor contained therein, photoelectrically detecting stimulated emission 45 released from each of the stimulable phosphor layer regions 12 by the photomultiplier 50 to produce analog data and digitizing the analog data, and the signal intensity of the thus produced digital data S (P0) is compared with the threshold value T by the signal intensity determining means 87. When it is determined that the signal intensity of the digital data S (P0) is lower than the threshold value T, digital data S (Pi) are produced by repeating increase in the power of a laser beam 24 emitted from the first laser stimulating ray source 21 by ΔP I times at maximum, irradiating the stimulable phosphor layer region 12 with the laser beam 24 to excite stimulable phosphor contained therein, photoelectrically detecting stimulated emission 45 released from each of the stimulable phosphor layer regions 12 by the photomultiplier 50 to produce analog data and digitizing the analog data, and the signal intensity of the digital data S (Pi) is compared with the threshold value T. When the signal intensity of the digital data S (Pi) has come to be equal to or higher than the threshold value T, the digital data S (Pi) are sampled at a predetermined cycle until the signal intensity of the digital data S (Pi) comes to be lower than the threshold value T and summed, thereby producing digital data of the stimulable phosphor layer region 12. Therefore, even if radiation energy stored in a stimulable phosphor layer region 12 is too small, it is possible to detect stimulated emission 45 released from the stimulable phosphor layer region 12 with high sensitivity and to produce digital data of the stimulable phosphor layer region 12, thereby producing biochemical analysis data having high quantitative characteristics.

Figure 24:
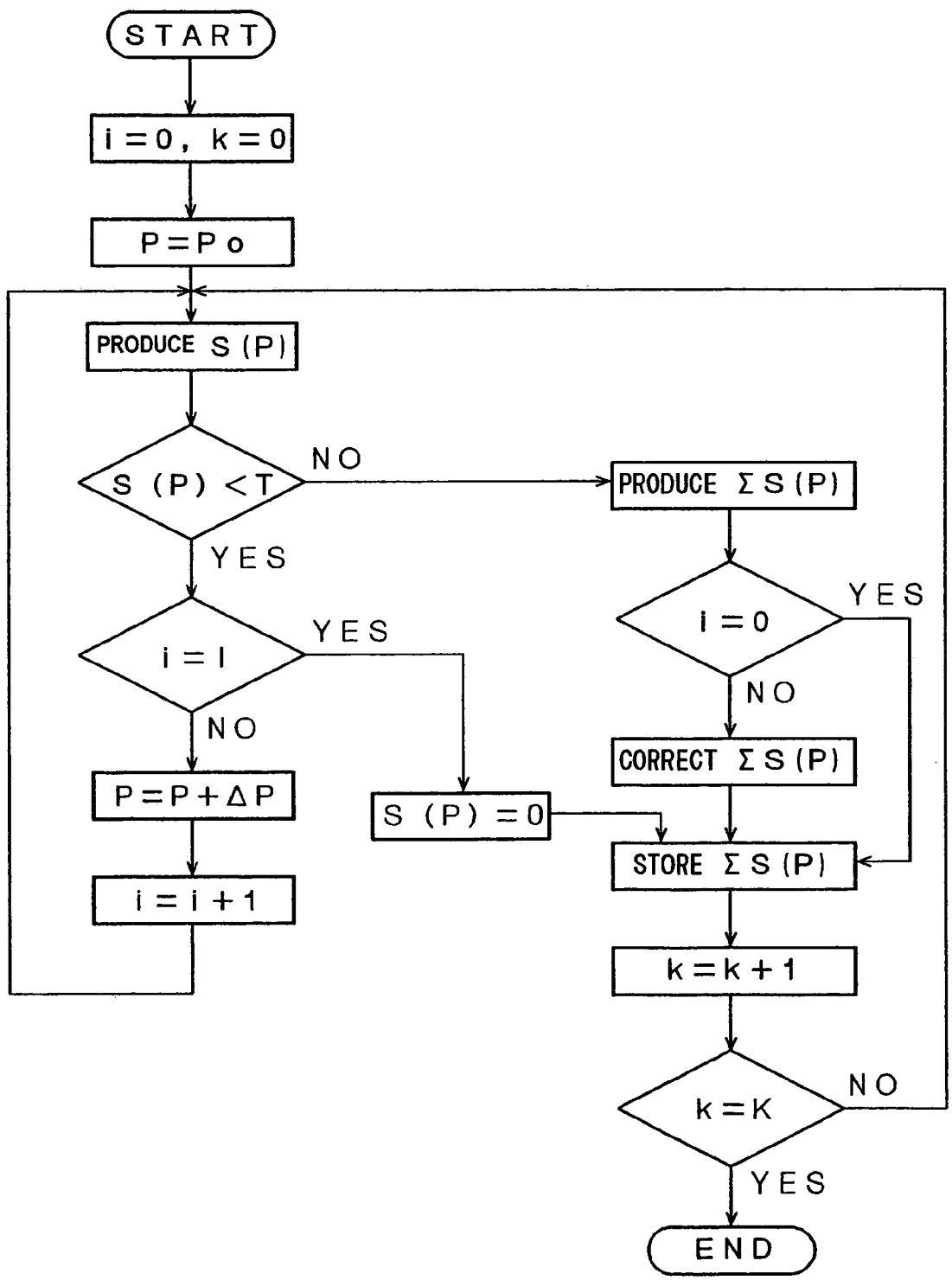
FIG. 24 is a flow chart showing a biochemical analysis data producing operation effected by a signal intensity determining means and a control unit of a scanner which is a further preferred embodiment of the present invention.

FIG. 24 is a flow chart showing a biochemical analysis data producing operation effected by a signal intensity determining means and a control unit of a scanner which is a further preferred embodiment of the present invention.

Similarly to the data processing apparatus 54 of the scanner shown in FIG. 22, a data processing apparatus 54 of a scanner according to this embodiment includes a summed value storing means 89 for storing a summed value of digital data and the signal intensity determining means 87 of the data processing apparatus 54 is constituted so as to temporarily store digital data S (P0) produced by irradiating each of the stimulable phosphor layer regions 12 formed in the support 11 of the stimulable phosphor sheet 10 with a laser beam 24 having the reference laser power P0 to excite stimulable phosphor contained therein, photoelectrically detecting stimulated emission 45 released from each of the stimulable phosphor layer regions 12 by the photomultiplier 50 to produce analog data, and digitizing the analog data, to compare the digital data S (P0) temporarily stored in the temporary memory 85 with the threshold value T, to sample, when it determines that the signal intensity of the digital data S (P0) is equal to or higher than the threshold value T, digital data at a predetermined cycle until the signal intensity of the digital data S (P0) comes to be lower than the threshold value T, to sum the thus sampled digital data, and to store the summed digital data in the summed value storing means 89.

Furthermore, in this embodiment, the signal intensity determining means 87 of the data processing apparatus 54 is constituted so as to output, when it determines that the signal intensity of digital data S (P0) produced by irradiating each of the stimulable phosphor layer regions 12 formed in the support 11 of the stimulable phosphor sheet 10 with a laser beam 24 having the reference laser power P0 to excite stimulable phosphor contained therein, photoelectrically detecting stimulated emission 45 released from each of the stimulable phosphor layer regions 12 by the photomultiplier 50 to produce analog data, and digitizing the analog data has come to be lower than the threshold value T, a laser power increasing signal to the control unit 70 up to K times at maximum where K is an integer equal to or greater than 2, thereby causing the first laser stimulating ray source 21 to emit a laser beam 24 having a higher laser power, to sample digital data at a predetermined cycle and sum them up until it determines that the signal intensity of digital data S (P0+k) comes to be lower than the threshold value T, thereby storing a summed value in the sunned value storing means 89. Here, Pi P0+$\Delta$P×k, i is equal to or less than I and k is equal to or less than K.

Moreover, in this embodiment, when the signal intensity determining means 87 of the data processing apparatus 54 determines that the signal intensity of digital data S (P0) produced by irradiating each of the stimulable phosphor layer regions 12 formed in the support 11 of the stimulable phosphor sheet 10 with a laser beam 24 having the reference laser power P0 to excite stimulable phosphor contained therein, photoelectrically detecting stimulated emission 45 released from each of the stimulable phosphor layer regions 12 by the photomultiplier 50 to produce analog data, and digitizing the analog data is lower than the threshold value T, the signal intensity determining means 87 outputs a laser power increasing signal to the control unit 70 up to I times at maximum where I is an integer equal to or greater than 3, thereby causing the control unit 70 to increase the power of a laser beam 24 emitted from the first laser stimulating ray source 21 by $\Delta$P I times at maximum, to temporarily store in the temporary memory 85 digital data S (Pi) produced by exciting stimulable phosphor contained in the stimulable phosphor layer region 12 from which that digital data S (P0) have been obtained with the laser beam 24 thereby exciting stimulable phosphor contained therein, photoelectrically detecting stimulated emission 45 released from the stimulable phosphor layer region 12 to produce analog data and digitizing the analog data to produce digital data, to compare the signal intensity of the digital data S (Pi) temporarily stored in the temporary memory 85 with the threshold value T, to sample, when it determines that the signal intensity of the digital data S (Pi) is equal to or higher than the threshold value T, digital data at a predetermined cycle until the signal intensity of the digital data S (Pi) comes to be lower than the threshold value T, to sum the thus sampled digital data, and to store the summed digital data in the summed value storing means 89. Further, when the signal intensity determining means 87 determines that the signal intensity of the digital data S (Pi) comes to be lower than the threshold value T, the signal intensity determining means 87 outputs a laser power increasing signal to the control unit 70 up to K times at maximum where K is an integer equal to or greater than 2, thereby causing the first laser stimulating ray source 21 to emit a laser beam 24 having higher laser power, to sample digital data at a predetermined cycle and sum them up until it determines that the signal intensity of digital data S (P0+k) comes to be lower than the threshold value T, thereby storing a summed value in the sunned value storing means 89. Here, Pi=P0+$\Delta$P×k, i is equal to or less than I and k is equal to or less than K.

In this embodiment, the control unit 70 is constituted so as to hold the first laser stimulating ray source 21 on and to output a signal intensity determination start signal to of the data processing apparatus 54 at a predetermined cycle.

When digital data S (P0) are produced by irradiating a stimulable phosphor layer region 12 with a laser beam 24 having the reference power P0 and emitted from the first laser stimulating ray source 21 to excite stimulable phosphor contained therein, photoelectrically detecting stimulated emission 45 released from each of the stimulable phosphor layer regions 12 by the photomultiplier 50 to produce analog data, and digitizing the analog data by the A/D converter 53 and temporarily stored in the temporary memory 85 and the signal intensity determination start signal is input from the control unit 70, the signal intensity determining means 87 reads the digital data S (P0) temporarily stored in the temporary memory 85 and compares the signal intensity thereof with the threshold value T.

When the signal intensity determining means 87 determines that the signal intensity of the digital data S (P0) is equal to or higher than the threshold value T, it samples the digital data S (P0) temporarily stored in the temporary memory 85 and stores them in a predetermined memory area of the summed value storing means 89.

Then, each time the signal intensity determination start signal is input from the control unit 70, the signal intensity determining means 87 reads the digital data S (P0) temporarily stored in the temporary memory 85 and compares the signal intensity thereof with the threshold value T. When the signal intensity determining means 87 determines that the signal intensity of the digital data S (P0) is equal to or higher than the threshold value T, it samples the digital data S (P0) and adds them to the digital data S (P0) stored in the predetermined memory area of the summed value storing means 89.

When, as a result of receiving the signal intensity determination start signal from the control unit 70, reading digital data S (P0) temporarily stored in the temporary memory 85 and comparing the signal intensity of the digital data S (P0) with the threshold value T, the signal intensity determining means 87 determines that the signal intensity of the digital data S (P0) has become lower than the threshold value T because stimulated emission has been released from the stimulable phosphor layer region 12 and radiation energy stored in stimulable phosphor layer region 12 has been decreased, the signal intensity determining means 87 outputs a laser power increasing signal to the control unit 70 without sampling the digital data S (P0).

As a result, a laser beam 24 having laser power P1 higher than the reference laser power P0 by $\Delta P$ is emitted from the first laser stimulating ray source 21 and the stimulable phosphor layer region 12 from which the digital data S (P0) were obtained is irradiated with the laser beam 24, thereby exciting stimulable phosphor contained therein. Here, $P1=P0+\Delta P$.

Since the stimulable phosphor layer region 12 is irradiated with the laser beam 24 having the laser power P1 higher than the reference laser power P0 by $\Delta P$ in this manner, even if the signal intensity of the digital data S (P0) obtained by irradiating the stimulable phosphor layer region 12 with the laser beam 24 having the reference laser power P0 and photoelectrically detecting stimulated emission 45 released from the stimulable phosphor layer region 12 is lower than the threshold value T, the signal intensity of digital data S (P1) obtained by irradiating the stimulable phosphor layer region 12 with the laser beam 24 having the laser power P1 and photoelectrically detecting stimulated emission 45 released from the stimulable phosphor layer region 12 and temporarily stored in the temporary memory 85 is normally equal to or higher than the threshold value T.

Therefore, the signal intensity determining means 87 samples the digital data S (P1) thus produced and temporarily stored in the temporary memory 85 and stores them in a predetermined memory area of the summed value storing means 89 other than the memory area in which the digital data S (P0) are stored.

Then, each time the signal intensity determination start signal is input from the control unit 70, the signal intensity determining means 87 reads the digital data S (P1) temporarily stored in the temporary memory 85 and compares the signal intensity thereof with the threshold value T. When the signal intensity determining means 87 determines that the signal intensity of the digital data S (P1) is equal to or higher than the threshold value T, it samples the digital data S (P1) and adds them to the digital data S (P1) stored in the predetermined memory area of the summed value storing means 89.

In this manner, the signal intensity determining means 87 repeatedly receives the signal intensity determination start signal from the control unit 70, reads the digital data S (P1) temporarily stored in the temporary memory 85 and compares the signal intensity of the digital data S (P1) with the threshold value T. When the signal intensity determining means 87 determines that the signal intensity of the digital data S (P1) is equal to or higher than the threshold value T, it adds the digital data S (P1) to the digital data S (P1) stored in the predetermined memory area of the summed value storing means 89. On the other hand, when the signal intensity determining means 87 determines that the signal intensity of the digital data S (P1) is lower than the threshold value T, it outputs a laser power increasing signal to the control unit 70 without sampling the digital data S (P1).

In the above described manner, the steps of increasing the laser power of a laser beam 24 emitted from the first laser stimulating ray source 21 and sampling digital data S (PK) whose signal intensity is equal to or higher than the threshold value T to add them to the digital data S (PK) stored in the predetermined memory area of the summed value storing means 89 for each laser power are repeated K times and at the time the signal intensity of digital data S (PK) obtained by exciting stimulable phosphor contained in the stimulable phosphor layer region 12 with a laser beam 24 having laser power PK and photoelectrically detecting stimulated emission 45 released from the stimulable phosphor layer region 12 has come to be lower than the threshold value T, the signal intensity determining means 87 outputs a correction effecting signal to the data processing means 88, thereby causing the data processing means 88 to correct the summed value of digital data stored in the predetermined memory area of the summed value storing means 89 for each laser power in accordance with the following formula similarly to the embodiment shown in FIGS. 22 and 23 and store the corrected value in the data storing means 86.

$$\Sigma S=\Sigma S(P0)+\Sigma S(P1)\times C2(P0/P1)+\cdots+\Sigma S(PK)\times C2(P0/PK)$$

In the above formula, $\Sigma S$ is the corrected summed value of digital data and C2 (P0/P1) and C2 (P0/PK) are correction coefficients and functions of the reference laser power P0, the laser power P1 and the laser power PK.

When the thus corrected summed value of the digital data $\Sigma S$ has been stored in the data storing means 86 in this manner, the control unit 70 completes the production of digital data of the stimulable phosphor layer region 12.

On the other hand, when the signal intensity determining means 87 determines that the signal intensity of the digital data S (P0) produced by exciting stimulable phosphor contained in the stimulable phosphor layer region 12 with the laser beam 24 having the reference laser power P0 and photoelectrically detecting stimulated emission released from the stimulable phosphor layer region 12 is lower than the threshold value T, it outputs a laser power increasing signal to the control unit 70 up to I times at maximum, thereby causing it to sequentially increase the laser power of a laser beam 24 emitted from the first laser stimulating ray source 21.

When, a result of increasing the laser power of the laser beam 24, the signal intensity determining means 87 determines that the signal intensity of digital data S (Pi) produced by exciting stimulable phosphor contained in the stimulable phosphor layer region 12 with the laser beam 24 having laser power Pi and photoelectrically detecting stimulated emission 45 released from the stimulable phosphor layer region 12 and temporarily stored in the temporary memory 85 has come to be equal to or higher than the threshold value T, it samples the digital data S (Pi) and stores them in a predetermined memory area of the summed value storing means 89.

Then, each time the signal intensity determination start signal is input from the control unit 70, the signal intensity determining means 87 reads the digital data S (Pi) temporarily stored in the temporary memory 85 and compares the signal intensity thereof with the threshold value T. When the signal intensity determining means 87 determines that the signal intensity of the digital data S (Pi) is equal to or higher than the threshold value T, it samples the digital data S (Pi) and adds them to the digital data S (Pi) stored in the predetermined memory area of the summed value storing means 89.

As described above, since the intensity of stimulated emission 45 released from the stimulable phosphor layer region 12 is lowered with lapse of time, when the signal intensity determining means 87 determines that the signal intensity of the digital data S (Pi) read from the temporary memory 85 has become lower than the threshold value T because stimulated emission has been released from the stimulable phosphor layer region 12 and radiation energy stored in stimulable phosphor layer region 12 has been decreased, the signal intensity determining means 87 outputs a laser power increasing signal to the control unit 70 without sampling the digital data S (Pi).

Similarly to the case of sampling the digital data S (P0) produced by exciting stimulable phosphor contained in the stimulable phosphor layer region 12 with the laser beam 24 having the reference laser power P0 and photoelectrically detecting stimulated emission 45 released from the stimulable phosphor layer region 12, the laser power of a laser beam 24 emitted from the first laser stimulating ray source 21 is increased K times and only digital data S (Pi+k) whose signal intensity is determined to be equal to or higher than the threshold value T are sampled by the signal intensity determining means 87 and added to digital data S (Pi+k) stored in a predetermined memory area of the summed value storing means 89.

At the time the signal intensity determining means 87 determines that the signal intensity of digital data S (Pi+K) produced by exciting stimulable phosphor contained in the stimulable phosphor layer region 12 with the laser beam 24 having reference laser power Pi+K and photoelectrically detecting stimulated emission 45 released from the stimulable phosphor layer region 12 has come to be lower than the threshold value T, the signal intensity determining means 87 outputs a correction effecting signal to the data processing means 88, thereby causing the data processing means 88 to correct the summed value of digital data stored in the predetermined memory area of the summed value storing means 89 for each laser power in accordance with the following formula similarly to the embodiment shown in FIGS. 22 and 23 and store the corrected value in the data storing means 86.

$$\Sigma S = \Sigma S(Pi) \times C2(P0/Pi) + \Sigma S(Pi+1) \times C2(P0/Pi+1) + \cdots + \Sigma S(Pi+K) \times C2(P0/Pi+K)$$

In the above formula, $\Sigma S$ is the corrected summed value of digital data and C2 (P0/Pi), C2 (P0/Pi+1) and C2 (P0/Pi+K) are correction coefficients and functions of the reference laser power P0 and the laser power Pi, the reference laser power P0 and the laser power Pi+1, and the reference laser power P0 and the laser power Pi+K.

When the thus corrected summed value of the digital data $\Sigma S$ has been stored in the data storing means 86 in this manner, the control unit 70 completes the production of digital data of the stimulable phosphor layer region 12.

Figure 25:
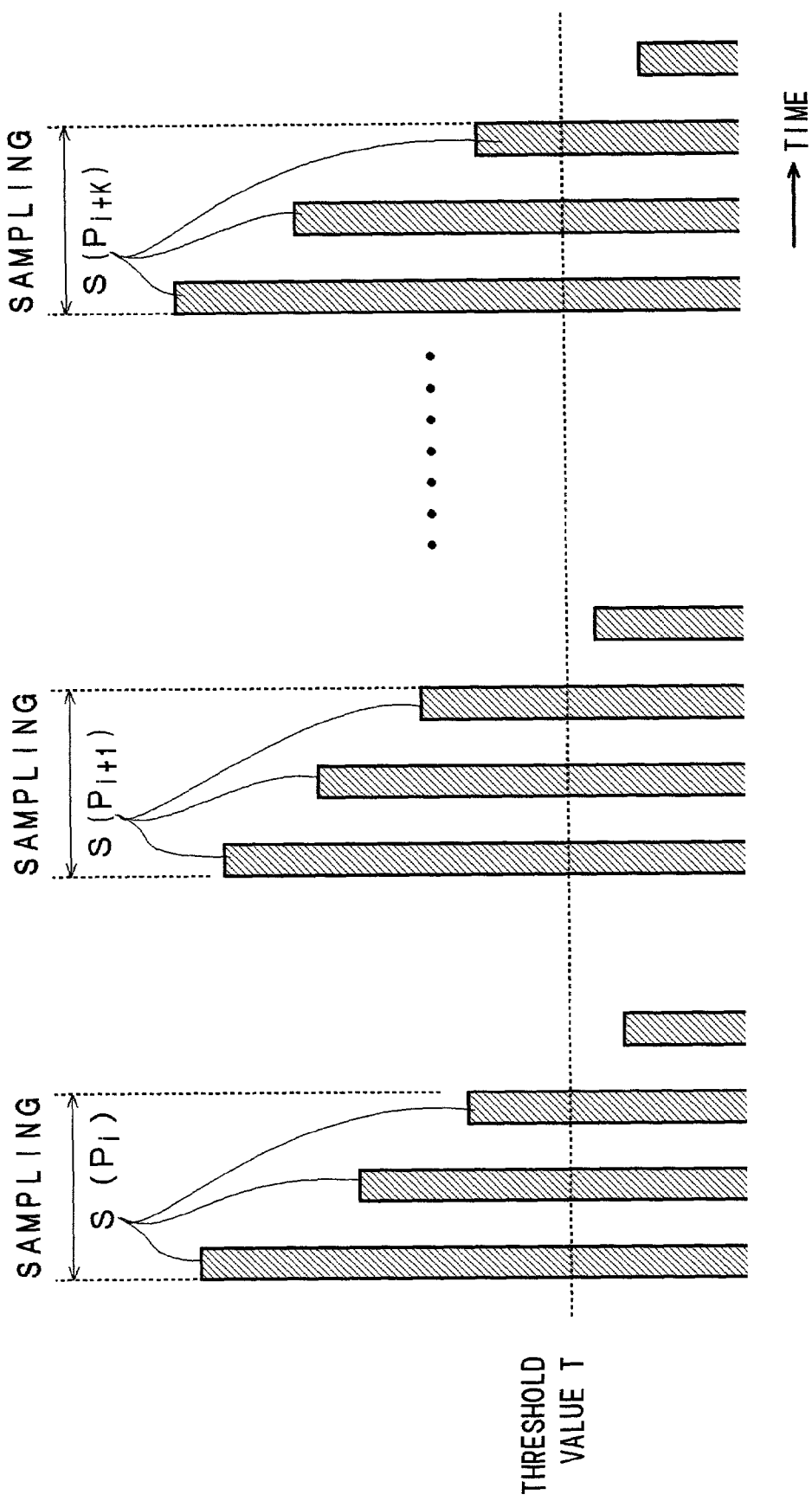
FIG. 25 is a notional view showing the sampling of digital data.

FIG. 25 is a notional view showing the sampling of digital data.

As shown in FIG. 25, the laser power of the laser beam 24 is increased K times and only digital data whose signal intensity is equal to or higher than the threshold value T are sampled by the signal intensity determining means 87.

According to this embodiment, digital data of each of the stimulable phosphor layer regions 12 of the stimulable phosphor sheet 10 are produced by first irradiating each of the stimulable phosphor layer regions 12 with the laser beam 24 having the reference laser power P0 which is relatively low and emitted from the first laser stimulating ray source 21 to excite stimulable phosphor contained therein, photoelectrically detecting stimulated emission 45 released from each of the stimulable phosphor layer regions 12 by the photomultiplier 50 to produce analog data and digitizing the analog data, and the signal intensity of the thus produced digital data S (P0) is compared with the threshold value T by the signal intensity determining means 87. When the signal intensity determining means 87 determines that the signal intensity of the digital data S (P0) is equal to or higher than the threshold value T, it samples the digital data S (P0) at a predetermined cycle and them until the signal intensity of the digital data S (P0) comes to be lower than the threshold value T, thereby storing the summed value in a predetermined memory area of the summed value storing means 89. When the signal intensity determining means 87 determines that the signal intensity of the digital data S (P0) has come to be lower than the threshold value T because stimulated emission 45 is released from the stimulable phosphor layer region 12, whereby radiation energy stored therein is decreased and the intensity of stimulated emission 45 is lowered, it outputs a laser power increasing signal to the control unit 70 K times, thereby causing the control unit 70 to increase the laser power of a laser beam 24 emitted from the first laser stimulating ray source 21 by $\Delta P$ K times. The signal intensity determining means 87 sums digital data produced by exciting stimulable phosphor contained in the stimulable phosphor layer region 12 from which the digital data S (P0) were obtained with a laser beam having distinct laser power levels and photoelectrically detecting stimulated emission 45 released from the stimulable phosphor layer region 12 and stores them in a predetermined memory area of the summed value storing means 89 until the signal intensity of the digital data has come to be lower than the threshold value T. When the operation for storing digital data produced by increasing the laser power of the laser beam 24 K times in the predetermined memory area of the summed value storing means 89 has been completed, the data processing means 88 corrects the summed values of digital data stored in the individual memory areas of the summed value storing means 89 in accordance with the laser power and sums the corrected summed values to produce digital data of the stimulable phosphor layer region 12. Therefore, even in the case where radiation energy stored in a stimulable phosphor region 12 is too small, it is possible to cause stimulable phosphor contained in the stimulable phosphor layer 12 to release substantially all radiation energy stored therein in the form of stimulated emission 45 and to detect stimulated emission 45 with high sensitivity to produce digital data, thereby producing biochemical analysis data having high quantitative characteristics. Further, stimulable phosphor contained in the stimulable phosphor layer region 12 is first excited with a laser beam 24 having the reference laser power P0 which is relatively low and when the signal intensity of the digital data is lower than the threshold value T, since the laser power of a laser beam 24 is increased by $\Delta P$ and stimulable phosphor contained in the stimulable phosphor layer region 12 is excited by the laser beam 24, it is possible to reliably prevent stimulated emission released from stimulable phosphor contained in the stimulable phosphor layer region 12 by exciting the stimulable phosphor with the laser beam 24 from becoming too great to exceed the upper limit of the dynamic range of the photomultiplier 50 and to prevent the signal intensity of digital data produced by detecting the stimulated emission 45 from being saturated, thereby degrading the quantitative characteristics of biochemical analysis data.

Further, according to this embodiment, digital data of each of the stimulable phosphor layer regions 12 of the stimulable phosphor sheet 10 are produced by first irradiating each of the stimulable phosphor layer regions 12 with the laser beam 24 having the reference laser power P0 which is relatively low and emitted from the first laser stimulating ray source 21 to excite stimulable phosphor contained therein, photoelectrically detecting stimulated emission 45 released from each of the stimulable phosphor layer regions 12 by the photomultiplier 50 to produce analog data and digitizing the analog data, and the signal intensity of the thus produced digital data S (P0) is compared with the threshold value T by the signal intensity determining means 87. When the signal intensity determining means 87 determines that the signal intensity of the digital data S (P0) is lower than the threshold value T, the laser power of a laser beam 24 emitted from the first laser stimulating ray source 21 is increased by ΔP and stimulable phosphor contained in the stimulable phosphor layer regions 12 is excited by the laser beam 24. When the signal intensity of digital data produced by photoelectrically detecting stimulated emission 45 released from the stimulable phosphor layer regions 12 has come to be equal to or higher than the threshold value T, the digital data are sampled and stored in a predetermined memory area of the summed value storing means 89 and excitation of stimulable phosphor contained in the stimulable phosphor layer regions 12 with the laser beam having the laser power is continued. When signal intensity of digital data produced by photoelectrically detecting stimulated emission 45 released from the stimulable phosphor layer regions 12 is equal to or higher than the threshold value T, the digital data are added to the digital data stored in the predetermined memory area of the summed value storing means 89. When the signal intensity of digital data produced by exciting stimulable phosphor contained in the stimulable phosphor layer regions 12 with the laser beam having the laser power and photoelectrically detecting stimulated emission 45 released from the stimulable phosphor layer regions 12 has become lower than the threshold value T because stimulated emission has been released from the stimulable phosphor layer region 12 and radiation energy stored in stimulable phosphor layer region 12 has been decreased, a laser power increasing signal is further output to the control unit 70 K times, whereby the laser power of a laser beam 24 emitted from the first laser stimulating ray source 21 is increased by ΔP. Digital data produced by exciting stimulable phosphor contained in the stimulable phosphor layer region 12 with a laser beam having distinct laser power levels and photoelectrically detecting stimulated emission 45 released from the stimulable phosphor layer region 12 are summed until the signal intensity of digital data has come to be lower than the threshold value T and stored in a predetermined memory area of the summed value storing means 89. When an operation for storing digital data produced by increasing the laser power of a laser beam 24 K times have been stored in the predetermined memory area of the summed value storing means 89, the summed values of digital data stored in the individual memory areas of the summed value storing means 89 are corrected in accordance with the laser power of the laser beam 24 and the thus corrected summed values of digital data are summed, thereby producing digital data of the stimulable phosphor layer regions 12. Therefore, even in the case where radiation energy stored in a stimulable phosphor region 12 is too small, it is possible to cause stimulable phosphor contained in the stimulable phosphor layer 12 to release substantially all radiation energy stored therein in the form of stimulated emission 45 and to detect stimulated emission 45 with high sensitivity to produce digital data, thereby producing biochemical analysis data having high quantitative characteristics.

Furthermore, according to this embodiment, since the summed values of digital data produced using laser beams 24 having different laser power are corrected so as to become summed values of digital data that would be obtained by exciting stimulable phosphor contained in the stimulable phosphor layer region 12 with the laser beam 24 having the reference laser power P0, even in the case of increasing the laser power of a laser beam 24 so as to become greater that the reference laser power P0 and exciting stimulable phosphor contained in a stimulable phosphor layer region 12 with the laser beam 24 in order to detect stimulated emission 45 with high sensitivity or release all detectable radiation energy stored in the stimulable phosphor layer region 12 in the form of stimulated emission 45 to be detected, it is possible to produce digital data having signal intensity corresponding to radiation energy stored in the stimulable phosphor layer region 12.

Figure 26:
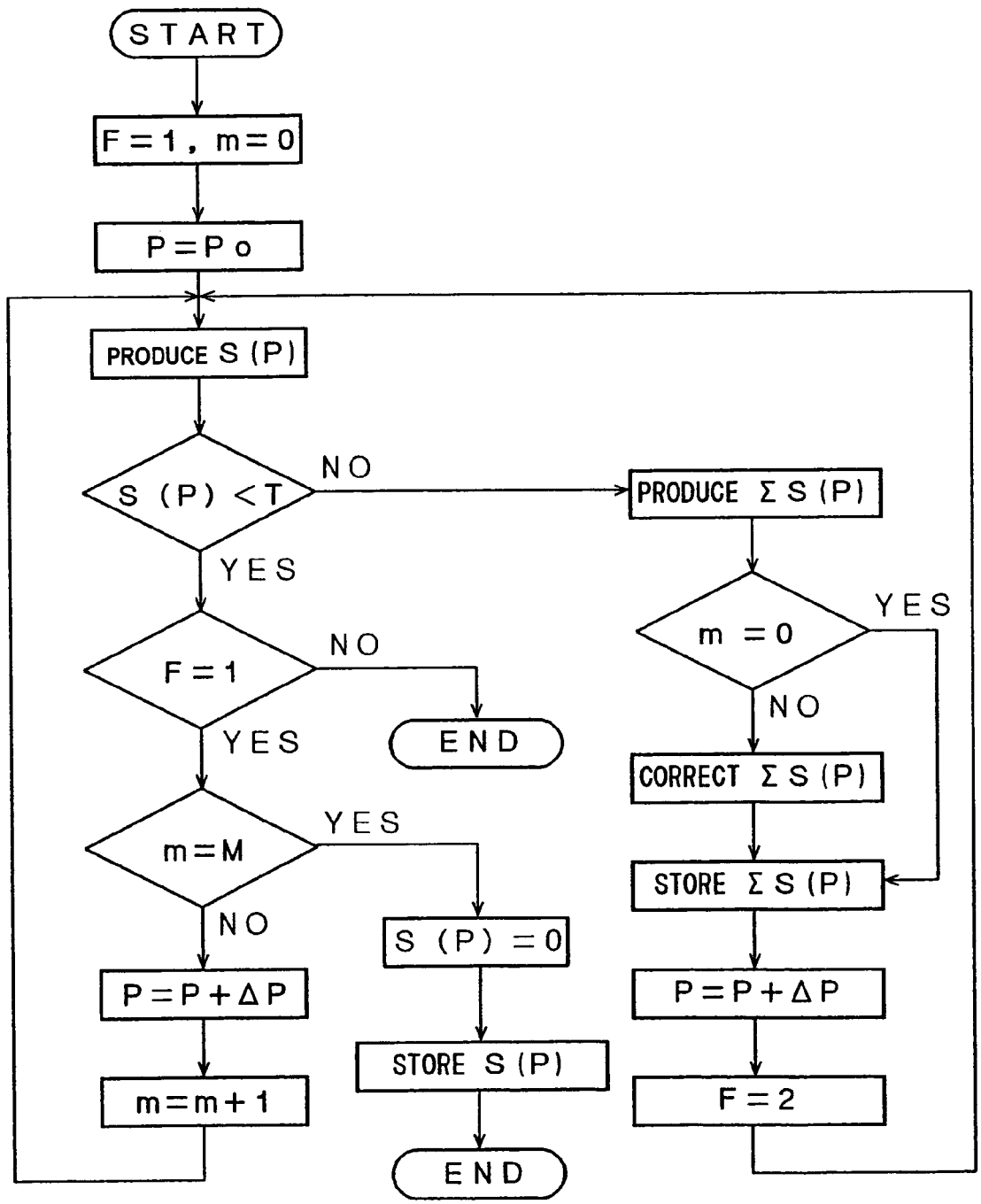
FIG. 26 is a flow chart showing a biochemical analysis data producing operation performed by a signal intensity determining means and a control unit of a scanner which is a further preferred embodiment of the present invention.

FIG. 26 is a flow chart showing a biochemical analysis data producing operation performed by the signal intensity determining means 87 and the control unit 70 of a scanner which is a further preferred embodiment of the present invention.

Similarly to the data processing apparatus 54 of the scanner shown in FIG. 22, a data processing apparatus 54 of a scanner according to this embodiment includes a summed value storing means 89 for storing a summed value of digital data and the signal intensity determining means 87 of the data processing apparatus 54 is constituted so as to temporarily store digital data S (P0) produced by irradiating each of the stimulable phosphor layer regions 12 formed in the support 11 of the stimulable phosphor sheet 10 with a laser beam 24 having the reference laser power P0 to excite stimulable phosphor contained therein, to photoelectrically detect stimulated emission 45 released from each of the stimulable phosphor layer regions 12 by the photomultiplier 50 to produce analog data, and digitizing the analog data, to compare the digital data S (P0) temporarily stored in the temporary memory 85 with the threshold value T, to sample, when it determines that the signal intensity of the digital data S (P0) is equal to or higher than the threshold value T, digital data at a predetermined cycle until the signal intensity of the digital data S (P0) comes to be lower than the threshold value T, to sum the thus sampled digital data, and to store the summed digital data in the summed value storing means 89. The signal intensity determining means 87 of the data processing apparatus 54 is further constituted so as to repeatedly output a laser power increasing signal to the control unit 70 when the signal intensity of the digital data S (P0) has come to be lower than the threshold value T, thereby causing the first laser stimulating ray source 21 to emit a laser beam 24 having greater laser power, to sample digital data at a predetermined cycle and to sum the digital data to store the summed value in the summed value storing means 89 until the signal intensity of digital data cannot come to be equal to or higher than the threshold value even if the laser power increasing signal is output to the control unit 70 and the laser power of a laser beam 24 emitted from the first laser stimulating ray source 21 is increased.

In this embodiment, when the signal intensity determining means 87 of the data processing apparatus 54 determines that the signal intensity of digital data S (P0) produced by irradiating each of the stimulable phosphor layer regions 12 formed in the support 11 of the stimulable phosphor sheet 10 with a laser beam 24 having the reference laser power P0 to excite stimulable phosphor contained therein, photoelectrically detecting stimulated emission 45 released from each of the stimulable phosphor layer regions 12 by the photomultiplier 50 to produce analog data, and digitizing the analog data is lower than the threshold value T, the signal intensity determining means 87 outputs a laser power increasing signal to the control unit 70 up to M times at maximum where M is an integer equal to or greater than 2, thereby causing the control unit 70 to increase the power of a laser beam 24 emitted from the first laser stimulating ray source 21 by ΔP M times at maximum, to temporarily store in the temporary memory 85 digital data S (Pi) produced by exciting stimulable phosphor contained in the stimulable phosphor layer region 12 from which that digital data S (P0) have been obtained with the laser beam 24 thereby exciting stimulable phosphor contained therein, photoelectrically detecting stimulated emission 45 released from the stimulable phosphor layer region 12 to produce analog data and digitizing the analog data to produce digital data, to compare the signal intensity of the digital data S (Pi) temporarily stored in the temporary memory 85 with the threshold value T, to sample, when it determines that the signal intensity of the digital data S (Pi) is equal to or higher than the threshold value T, digital data at a predetermined cycle until the signal intensity of the digital data S (Pi) comes to be lower than the threshold value T, to sum the thus sampled digital data, and to store the summed digital data in the summed value storing means 89. When the signal intensity determining means 87 determines that the signal intensity of the digital data S (Pi) has come to be lower than the threshold value T, it repeatedly outputs a laser power increasing signal to the control unit 70, thereby causing the first laser stimulating ray source 21 to emit a laser beam 24 having greater laser power, to sample digital data at a predetermined cycle and to sum the digital data to store the summed value in the summed value storing means 89 until the signal intensity of digital data cannot come to be equal to or higher than the threshold value even if the laser power increasing signal is output to the control unit 70 and the laser power of a laser beam 24 emitted from the first laser stimulating ray source 21 is increased.

In this embodiment, the control unit 70 is constituted so as to hold the first laser stimulating ray source 21 on and to output a signal intensity determination start signal to of the data processing apparatus 54 at a predetermined cycle.

When digital data S (P0) are produced by irradiating a stimulable phosphor layer region 12 with a laser beam 24 having the reference power P0 and emitted from the first laser stimulating ray source 21 to excite stimulable phosphor contained therein, photoelectrically detecting stimulated emission 45 released from each of the stimulable phosphor layer regions 12 by the photomultiplier 50 to produce analog data, and digitizing the analog data by the A/D converter 53 and temporarily stored in the temporary memory 85 and the signal intensity determination start signal is input from the control unit 70, the signal intensity determining means 87 reads the digital data S (P0) temporarily stored in the temporary memory 85 and compares the signal intensity thereof with the threshold value T.

When the signal intensity determining means 87 determines that the signal intensity of the digital data S (P0) is equal to or higher than the threshold value T, it samples the digital data S (P0) temporarily stored in the temporary memory 85 and stores them in a predetermined memory area of the summed value storing means 89.

Then, each time the signal intensity determination start signal is input from the control unit 70, the signal intensity determining means 87 reads the digital data S (P0) temporarily stored in the temporary memory 85 and compares the signal intensity thereof with the threshold value T. When the signal intensity determining means 87 determines that the signal intensity of the digital data S (P0) is equal to or higher than the threshold value T, it samples the digital data S (P0) and adds them to the digital data S (P0) stored in the predetermined memory area of the summed value storing means 89.

When, as a result of receiving the signal intensity determination start signal from the control unit 70, reading digital data S (P0) temporarily stored in the temporary memory 85 and comparing the signal intensity of the digital data S (P0) with the threshold value T, the signal intensity determining means 87 determines that the signal intensity of the digital data S (P0) has become lower than the threshold value T because stimulated emission has been released from the stimulable phosphor layer region 12 and radiation energy stored in stimulable phosphor layer region 12 has been decreased, the signal intensity determining means 87 outputs a laser power increasing signal to the control unit 70 without sampling the digital data S (P0).

As a result, a laser beam 24 having laser power P1 higher than the reference laser power P0 by ΔP is emitted from the first laser stimulating ray source 21 and the stimulable phosphor layer region 12 from which the digital data S (P0) were obtained is irradiated with the laser beam 24, thereby exciting stimulable phosphor contained therein. Here, P1=P0+ΔP.

Since the stimulable phosphor layer region 12 is irradiated with the laser beam 24 having the laser power P1 higher than the reference laser power P0 by ΔP in this manner, even if the signal intensity of the digital data S (P0) obtained by irradiating the stimulable phosphor layer region 12 with the laser beam 24 having the reference laser power P0 and photoelectrically detecting stimulated emission 45 released from the stimulable phosphor layer region 12 is lower than the threshold value T, the signal intensity of digital data S (P1) obtained by irradiating the stimulable phosphor layer region 12 with the laser beam 24 having the laser power P1 and photoelectrically detecting stimulated emission 45 released from the stimulable phosphor layer region 12 and temporarily stored in the temporary memory 85 is normally equal to or higher than the threshold value T.

Therefore, the signal intensity determining means 87 samples the digital data S (P1) thus produced and temporarily stored in the temporary memory 85 and stores them in a predetermined memory area of the summed value storing means 89 other than the memory area in which the digital data S (P0) are stored.

Then, each time the signal intensity determination start signal is input from the control unit 70, the signal intensity determining means 87 reads the digital data S (P1) temporarily stored in the temporary memory 85 and compares the signal intensity thereof with the threshold value T. When the signal intensity determining means 87 determines that the signal intensity of the digital data S (P1) is equal to or higher than the threshold value T, it samples the digital data S (P1) and adds them to the digital data S (P1) stored in the predetermined memory area of the summed value storing means 89.

In this manner, the signal intensity determining means 87 repeatedly receives the signal intensity determination start signal from the control unit 70, reads the digital data S (P1) temporarily stored in the temporary memory 85 and compares the signal intensity of the digital data S (P1) with the threshold value T. When the signal intensity determining means 87 determines that the signal intensity of the digital data S (P1) is equal to or higher than the threshold value T, it adds the digital data S (P1) to the digital data S (P1) stored in the predetermined memory area of the summed value storing means 89. On the other hand, when the signal intensity determining means 87 determines that the signal intensity of the digital data S (P1) is lower than the threshold value T, it outputs a laser power increasing signal to the control unit 70 without sampling the digital data S (P1).

In the above described manner, the steps of increasing the laser power of a laser beam. 24 emitted from the first laser stimulating ray source 21 and sampling digital data S (Pi) whose signal intensity is equal to or higher than the threshold value T to add them to the digital data S (Pi) stored in the predetermined memory area of the summed value storing means 89 for each laser power are repeated and as a result of increasing the laser power of a laser beam 24 M times at maximum where M is a positive integer, at the time the signal intensity of digital data cannot become equal to or higher than the threshold value T even if the laser power of a laser beam 24 is increased, the signal intensity determining means 87 outputs a correction effecting signal to the data processing means 88, thereby causing the data processing means 88 to correct the summed value of digital data stored in the predetermined memory area of the summed value storing means 89 for each laser power in accordance with the following formula similarly to the embodiment shown in FIGS. 22 and 23 and store the corrected value in the data storing means 86.

$$\Sigma S = \Sigma S(P0) + \Sigma S(P1) \times C2(P0/P1) + \text{- - -} + \Sigma S(PM) \times C2(P0/PM)$$

In the above formula, $\Sigma S$ is the corrected summed value of digital data and C2 (P0/P1) and C2 (P0/PM) are correction coefficients and functions of the reference laser power P0, the laser power P1 and the laser power PM.

In this manner, when the thus corrected summed value of the digital data $\Sigma S$ has been stored in the data storing means 86, the control unit 70 completes the production of digital data of the stimulable phosphor layer region 12.

On the other hand, when the signal intensity determining means 87 determines that the signal intensity of the digital data S (P0) produced by exciting stimulable phosphor contained in the stimulable phosphor layer region 12 with the laser beam 24 having the reference laser power P0 and photoelectrically detecting stimulated emission released from the stimulable phosphor layer region 12 is lower than the threshold value T, it repeatedly outputs a laser power increasing signal to the control unit 70, thereby causing it to sequentially increase the laser power of a laser beam 24 emitted from the first laser stimulating ray source 21.

When, a result of increasing the laser power of the laser beam 24, the signal intensity determining means 87 determines that the signal intensity of digital data S (Pi) produced by exciting stimulable phosphor contained in the stimulable phosphor layer region 12 with the laser beam 24 having laser power Pi and photoelectrically detecting stimulated emission 45 released from the stimulable phosphor layer region 12 and temporarily stored in the temporary memory 85 has come to be equal to or higher than the threshold value T, it samples the digital data S (Pi) and stores them in a predetermined memory area of the summed value storing means 89.

Then, each time the signal intensity determination start signal is input from the control unit 70, the signal intensity determining means 87 reads the digital data S (Pi) temporarily stored in the temporary memory 85 and compares the signal intensity thereof with the threshold value T. When the signal intensity determining means 87 determines that the signal intensity of the digital data S (Pi) is equal to or higher than the threshold value T, it samples the digital data S (Pi) and adds them to the digital data S (Pi) stored in the predetermined memory area of the summed value storing means 89.

As described above, since the intensity of stimulated emission 45 released from the stimulable phosphor layer region 12 is lowered with lapse of time, when the signal intensity determining means 87 determines that the signal intensity of the digital data S (Pi) read from the temporary memory 85 has become lower than the threshold value T because stimulated emission has been released from the stimulable phosphor layer region 12 and radiation energy stored in stimulable phosphor layer region 12 has been decreased, the signal intensity determining means 87 outputs a laser power increasing signal to the control unit 70 without sampling the digital data S (Pi).

Similarly to the case of sampling the digital data S (P0) produced by exciting stimulable phosphor contained in the stimulable phosphor layer region 12 with the laser beam 24 having the reference laser power P0 and photoelectrically detecting stimulated emission 45 released from the stimulable phosphor layer region 12, the laser power of a laser beam 24 emitted from the first laser stimulating ray source 21 is sequentially increased and only digital data S (Pi+m) whose signal intensity is determined to be equal to or higher than the threshold value T are sampled by the signal intensity determining means 87 and added to digital data S (Pi+m) stored in a predetermined memory area of the summed value storing means 89.

As a result, when the signal intensity of digital data produced by exciting stimulable phosphor contained in the stimulable phosphor layer region 12 with a laser beam 24 and photoelectrically detecting stimulated emission released from the stimulable phosphor layer region 12 cannot become equal to or higher than the threshold value T, since it can be considered that radiation energy detectable in the form of stimulated emission 45 no longer remains in the stimulable phosphor layer region 12, the signal intensity determining means 87 outputs a correction effecting signal to the data processing means 88, thereby causing the data processing means 88 to correct the summed value of digital data stored in the predetermined memory area of the summed value storing means 89 for each laser power in accordance with the following formula, similarly to the embodiment shown in FIGS. 22 and 23, and store the corrected value in the data storing means 86.

$$\Sigma S = \Sigma S(Pi) \times C2(P0/Pi) + \Sigma S(Pi+1) \times C2(P0/Pi+1) + \text{- - -} + \Sigma S(Pi+M) \times C2(P0/Pi+M)$$

In the above formula, $\Sigma S$ is the corrected summed value of digital data and C2 (P0/Pi), C2 (P0/Pi+1) and C2 (P0/Pi+M) are correction coefficients and functions of the reference laser power P0 and the laser power Pi, the reference laser power P0 and the laser power Pi+1, and the reference laser power P0 and the laser power Pi+M.

In this manner, when the thus corrected summed value of the digital data $\Sigma S$ has been stored in the data storing means 86, the control unit 70 completes the production of digital data of the stimulable phosphor layer region 12.

According to this embodiment, digital data of each of the stimulable phosphor layer regions 12 of the stimulable phosphor sheet 10 are produced by first irradiating each of the stimulable phosphor layer regions 12 with the laser beam 24 having the reference laser power P0 which is relatively low and emitted from the first laser stimulating ray source 21 to excite stimulable phosphor contained therein, photoelectrically detecting stimulated emission 45 released from each of the stimulable phosphor layer regions 12 by the photomultiplier 50 to produce analog data and digitizing the analog data, and the signal intensity of the thus produced digital data S (P0) is compared with the threshold value T by the signal intensity determining means 87. When the signal intensity determining means 87 determines that the signal intensity of the digital data S (P0) is equal to or higher than the threshold value T, it samples the digital data S (P0) at a predetermined cycle and sums them until the signal intensity of the digital data S (P0) comes to be lower than the threshold value T, thereby storing the summed value in a predetermined memory area of the summed value storing means 89. When the signal intensity determining means 87 determines that the signal intensity of the digital data S (P0) has come to be lower than the threshold value T because stimulated emission 45 is released from the stimulable phosphor layer region 12, whereby radiation energy stored therein is decreased and the intensity of stimulated emission 45 is lowered, it repeatedly outputs a laser power increasing signal to the control unit 70, thereby causing the control unit 70 to sequentially increase the laser power of a laser beam 24 emitted from the first laser stimulating ray source 21 by ΔP. The signal intensity determining means 87 sums digital data produced by exciting stimulable phosphor contained in the stimulable phosphor layer region 12 from which the digital data S (P0) were obtained with a laser beam having distinct laser power levels and photoelectrically detecting stimulated emission 45 released from the stimulable phosphor layer region 12 and stores them in a predetermined memory area of the summed value storing means 89 until the signal intensity of the digital data has come to be lower than the threshold value T. Since stimulated emission 45 is released from the stimulable phosphor layer region 12, whereby radiation energy stored therein decreases and the intensity of stimulated emission 45 is lowered, when the signal intensity determining means 87 determines that the signal intensity of the digital data cannot come to be equal to or higher than the threshold value T even if the laser power of a laser beam 24 emitted from the first laser stimulating ray source 21, the data processing means 88 corrects the summed values of digital data stored in the individual memory areas of the summed value storing means 89 in accordance with the laser power and sums the corrected summed values to produce digital data of the stimulable phosphor layer region 12. Therefore, even in the case where radiation energy stored in a stimulable phosphor region 12 is too small, it is possible to cause stimulable phosphor contained in the stimulable phosphor layer 12 to release substantially all radiation energy stored therein in the form of stimulated emission 45 and to detect stimulated emission 45 with high sensitivity to produce digital data, thereby producing biochemical analysis data having high quantitative characteristics. Further, since stimulable phosphor contained in the stimulable phosphor layer region 12 is first excited with a laser beam 24 having the reference laser power P0 which is relatively low and when the signal intensity of the digital data is lower than the threshold value T, the laser power of a laser beam 24 is increased by ΔP and stimulable phosphor contained in the stimulable phosphor layer region 12, it is possible to reliably prevent stimulated emission released from stimulable phosphor contained in the stimulable phosphor layer region 12 by exciting the stimulable phosphor with the laser beam 24 from becoming too great to exceed the upper limit of the dynamic range of the photomultiplier 50 and to prevent the signal intensity of digital data produced by detecting the stimulated emission 45 from being saturated, thereby degrading the quantitative characteristics of biochemical analysis data.

Furthermore, according to this embodiment, digital data of each of the stimulable phosphor layer regions 12 of the stimulable phosphor sheet 10 are produced by first irradiating each of the stimulable phosphor layer regions 12 with the laser beam 24 having the reference laser power P0 which is relatively low and emitted from the first laser stimulating ray source 21 to excite stimulable phosphor contained therein, photoelectrically detecting stimulated emission 45 released from each of the stimulable phosphor layer regions 12 by the photomultiplier 50 to produce analog data and digitizing the analog data, and the signal intensity of the thus produced digital data S (P0) is compared with the threshold value T by the signal intensity determining means 87. When the signal intensity determining means 87 determines that the signal intensity of the digital data S (P0) is lower than the threshold value T, the laser power of a laser beam 24 emitted from the first laser stimulating ray source 21 is increased by ΔP M times at maximum and stimulable phosphor contained in the stimulable phosphor layer regions 12 is excited by the laser beam 24. When the signal intensity of digital data produced by photoelectrically detecting stimulated emission 45 released from the stimulable phosphor layer regions 12 has come to be equal to or higher than the threshold value T, the digital data are sampled and stored in a predetermined memory area of the summed value storing means 89 and excitation of stimulable phosphor contained in the stimulable phosphor layer regions 12 with the laser beam having the laser power is continued. When signal intensity of digital data produced by photoelectrically detecting stimulated emission 45 released from the stimulable phosphor layer regions 12 is equal to or higher than the threshold value T, the digital data are added to the digital data stored in the predetermined memory area of the summed value storing means 89. When the signal intensity of digital data produced by exciting stimulable phosphor contained in the stimulable phosphor layer regions 12 with the laser beam having the laser power and photoelectrically detecting stimulated emission 45 released from the stimulable phosphor layer regions 12 has become lower than the threshold value T because stimulated emission has been released from the stimulable phosphor layer region 12 and radiation energy stored in stimulable phosphor layer region 12 has been decreased, a laser power increasing signal is further output to the control unit 70, whereby the laser power of a laser beam 24 emitted from the first laser stimulating ray source 21 is increased by ΔP. Digital data produced by exciting stimulable phosphor contained in the stimulable phosphor layer region 12 with the laser beam 24 and photoelectrically detecting stimulated emission 45 released from the stimulable phosphor layer region 12 are summed until the signal intensity of digital data has come to be lower than the threshold value T and stored in a predetermined memory area of the summed value storing means 89. When digital data produced by exciting stimulable phosphor contained in the stimulable phosphor layer region 12 with the laser beam 24 having the laser power and photoelectrically detecting stimulated emission 45 released from the stimulable phosphor layer region 12 has become lower than the threshold value T, the laser power of a laser beam 24 is further increased by $\Delta P$ and digital data are produced by exciting stimulable phosphor contained in the stimulable phosphor layer region 12 with the laser beam 24. The thus produced digital data are summed until the signal intensity of the digital data cannot become equal to or higher than the threshold value T even if the laser power of a laser beam 24 is increased and the summed value of the digital data are stored in a predetermined memory area of the summed value storing means 89. Therefore, since all radiation energy stored in the stimulable phosphor layer region 12 can be completely released and the radiation energy can be detected in the form of stimulated emission 45, even in the case where radiation energy stored in a stimulable phosphor region 12 is too small, it is possible to detect stimulated emission 45 with high sensitivity to produce digital data, thereby producing biochemical analysis data having high quantitative characteristics.

Further, according to this embodiment, since the summed values of digital data produced using laser beams 24 having different laser power are corrected so as to become summed values of digital data that would be obtained by exciting stimulable phosphor contained in the stimulable phosphor layer region 12 with the laser beam 24 having the reference laser power P0, even in the case of increasing the laser power of a laser beam 24 so as to become greater that the reference laser power P0 and exciting stimulable phosphor contained in a stimulable phosphor layer region 12 with the laser beam 24 in order to detect stimulated emission 45 with high sensitivity or release all detectable radiation energy stored in the stimulable phosphor layer region 12 in the form of stimulated emission 45 to be detected, it is possible to produce digital data having signal intensity corresponding to radiation energy stored in the stimulable phosphor layer region 12.

Figure 27:
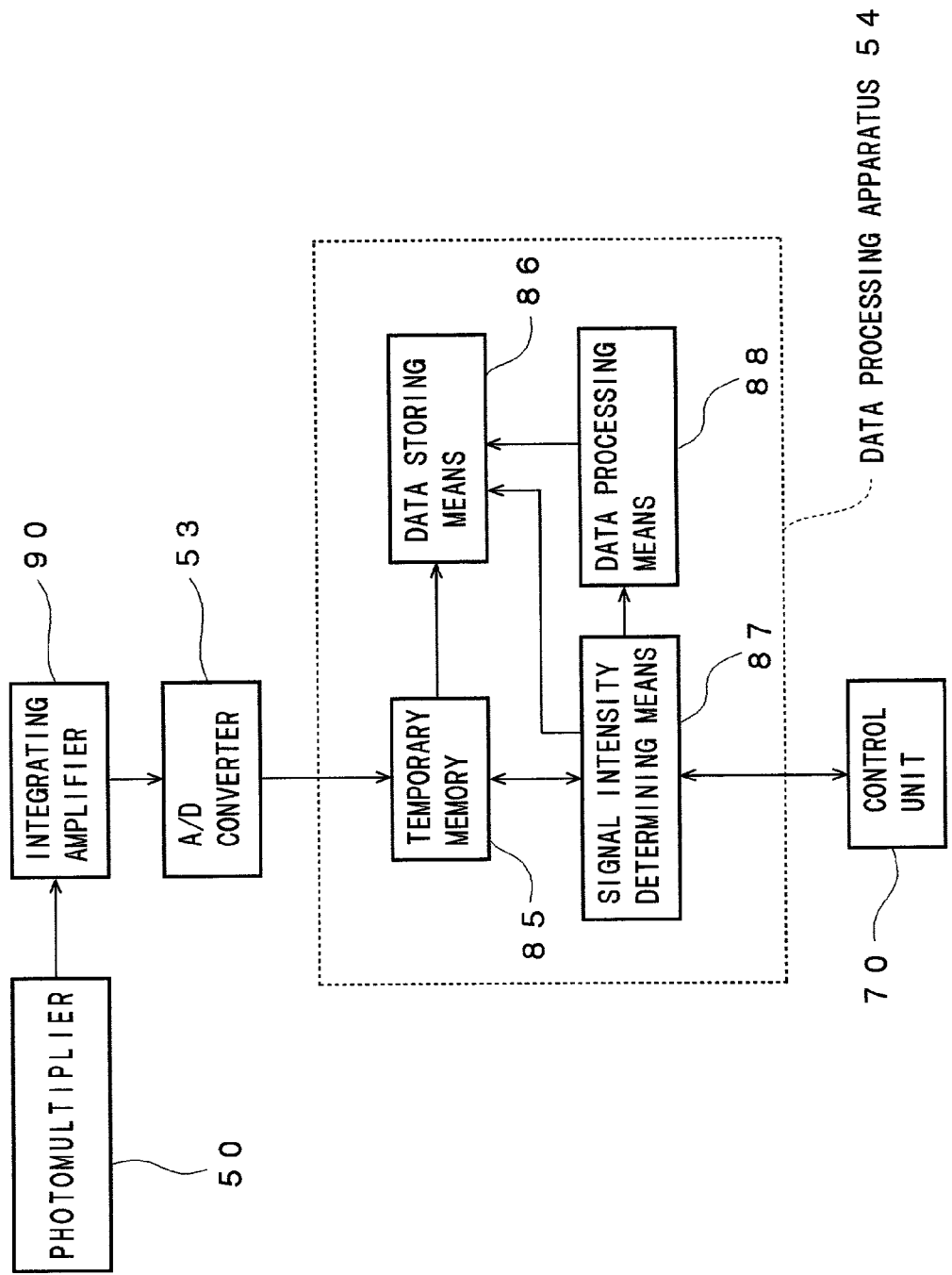
FIG. 27 is a block diagram of a data processing apparatus and its periphery of a scanner which is a further preferred embodiment of the present invention.

FIG. 27 is a block diagram of a data processing apparatus and its periphery of a scanner which is a further preferred embodiment of the present invention.

As shown in FIG. 27, a scanner according to this embodiment includes an integrating amplifier 90 for integrating analog data produced by the photomultiplier 50 and an integrated value of the analog data produced by the integrating amplifier 90 is digitized by the A/D converter 53 to be temporarily stored in the temporary memory 85.

The signal intensity determining means 87 is constituted so as to compare the signal intensity of digital data produced by digitizing the integrated value of analog data with the threshold value T and when it determines that the signal intensity of the digital data is lower than the threshold value T, it outputs a laser power increasing signal to the control unit 70. On the other hand, when the signal intensity determining means 87 determines that the signal intensity of the digital data is equal to or higher than the threshold value T, it transfers digital data temporarily stored in the temporary memory 85 to the data storing means 86 to be stored therein.

Figure 28:
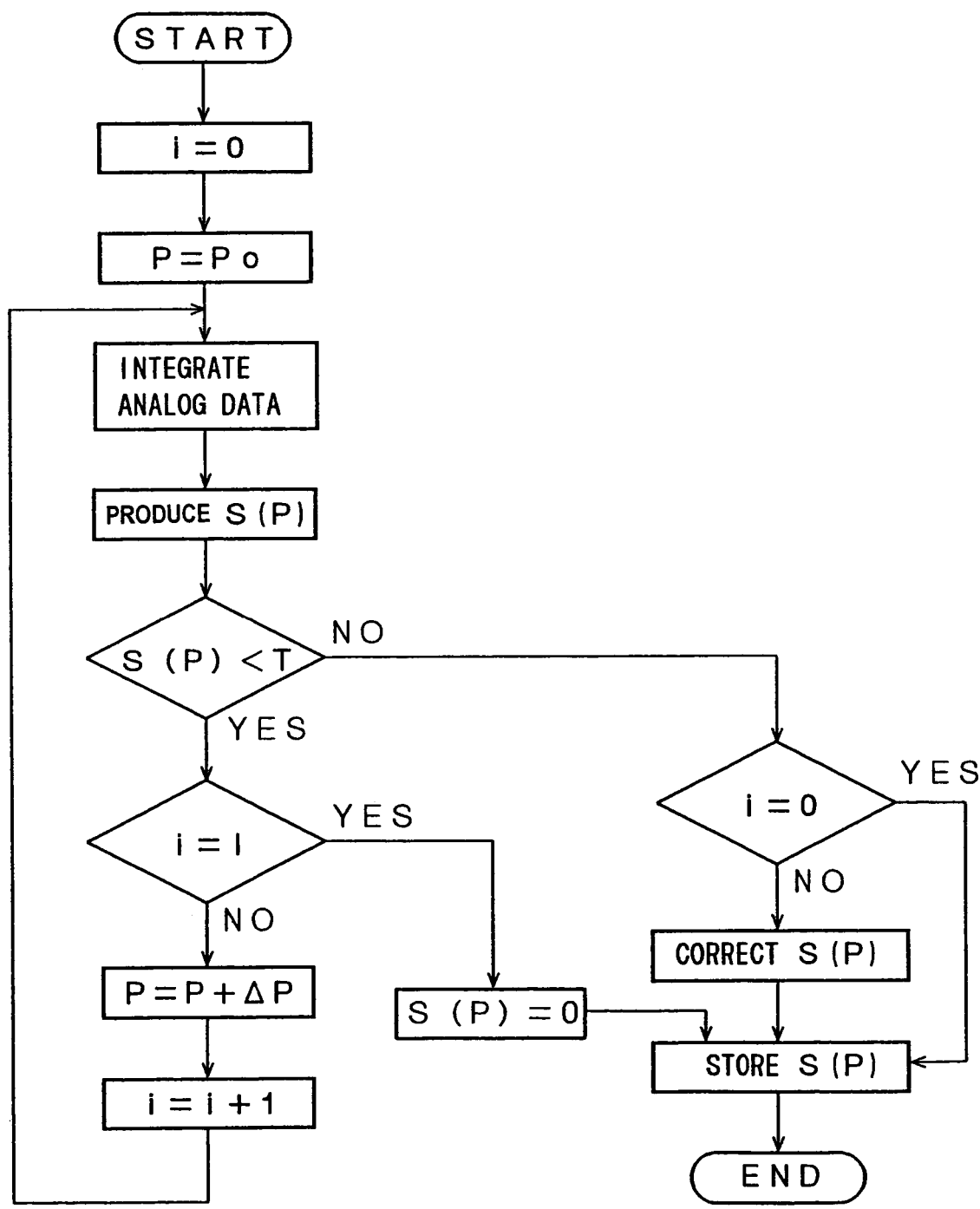
FIG. 28 is a flow chart showing a biochemical analysis data producing operation performed by a signal intensity determining means and a control unit of a scanner which is a further preferred embodiment of the present invention.

FIG. 28 is a flow chart showing a biochemical analysis data producing operation performed by the signal intensity determining means 87 and the control unit 70 of a scanner which is a further preferred embodiment of the present invention.

As shown in FIG. 28, in this embodiment, when radiation data of a radioactive labeling substance recorded in the stimulable phosphor sheet 10 by exposing a number of the stimulable phosphor regions 12 to the radioactive labeling substance selectively contained in a number of the absorptive regions 4 formed in the substrate 2 of the biochemical analysis unit 1 are to be read to produce biochemical analysis data, the control unit 70 outputs a reference drive signal to the first laser stimulating ray source 21 and supplies a reference drive current which is relatively low to the first laser stimulating ray source 21, thereby causing the first laser stimulating ray source 21 to emit a laser beam 24 having a reference power P0 which is relatively low.

A laser beam 24 having the reference power P0 and emitted from the first laser stimulating source 21 passes through the collimator lens 25, thereby being made a parallel beam, and is reflected by the mirror 26.

The laser beam 24 reflected by the mirror 26 passes through the first dichroic mirror 27 and the second dichroic mirror 28 and advances to the mirror 29.

The laser beam 24 advancing to the mirror 29 is reflected by the mirror 29 and advances to the mirror 32 to be reflected thereby.

The laser beam 24 reflected by the mirror 32 passes through the hole 33 of the perforated mirror 34 and advances to the concave mirror 38.

The laser beam 24 advancing to the concave mirror 38 is reflected by the concave mirror 38 and enters the optical head 35.

The laser beam 24 entering the optical head 35 is reflected by the mirror 36 and condensed by the aspherical lens 37 onto the first stimulable phosphor layer region 12 of the stimulable phosphor sheet 10 placed on the glass plate 41 of a stage 40.

As a result, stimulable phosphor contained in the first stimulable phosphor region 12 formed in the support 11 of the stimulable phosphor sheet 10 is excited by the laser beam 24 and stimulated emission 45 is released from the first stimulable phosphor region 12.

The stimulated emission 45 released from the first stimulable phosphor layer region 12 is condensed onto the mirror 36 by the aspherical lens 37 provided in the optical head 35 and reflected by the mirror 36 on the side of the optical path of the laser beam 24, thereby being made a parallel beam to advance to the concave mirror 38.

The stimulated emission 45 advancing to the concave mirror 38 is reflected by the concave mirror 38 and advances to the perforated mirror 34.

As shown in FIG. 7, the stimulated emission 45 advancing to the perforated mirror 34 is reflected downward by the perforated mirror 34 formed as a concave mirror and advances to the filter 52d of the filter unit 48.

Since the filter 52d has a property of transmitting only light having a wavelength corresponding to that of stimulated emission emitted from stimulable phosphor and cutting off light having a wavelength of 640 nm, light having a wavelength of 640 nm corresponding to that of the stimulating ray is cut off by the filter 52d and only light having a wavelength corresponding to that of stimulated emission passes through the filter 52d to be photoelectrically detected by the photomultiplier 50.

Analog data produced by photoelectrically detecting stimulated emission 45 by the photomultiplier 50 are output to the integrating amplifier 90 and integrated thereby.

When a predetermined time, for example, several microseconds, has passed after the first stimulating ray source 21 was turned on, the control unit 70 outputs a drive stop signal to the first stimulating ray source 21, thereby turning it off and outputs an integrated value of the analog data produced by the integrating amplifier 90 to the A/D converter 53.

The integrated value of the analog data is digitized by the A/D converter 53 and digital data S (P0) are output to the temporary memory 85 to be stored therein.

At the same time, the control unit 70 outputs a signal intensity determination start signal to the signal intensity determining means 87 and when the signal intensity determining means 87 receives the signal intensity determination start signal from the control unit 70, it compares the signal intensity of digital data S (P0) stored in the temporary memory 85 with the threshold value T.

When the signal intensity determining means 87 determines that the signal intensity of the digital data S (P0) is equal to or higher than the threshold value T, it can be considered that the digital data S (P0) having sufficiently high signal intensity have been produced even though stimulable phosphor contained in the first stimulable phosphor layer region 12 was excited by the laser beam 24 having the reference laser power P0 which is relatively low and since it can be considered that a large amount of radiation energy is stored in the first stimulable phosphor layer region 12, if stimulable phosphor contained in the first stimulable phosphor layer region 12 is excited by the laser beam 24 having laser power higher than the reference laser power P0, there occurs a risk of the signal intensity of the digital data exceeding the upper limit of the dynamic range of the photomultiplier 50. Therefore, the signal intensity determining means 87 determines the digital data S (P0) produced by exciting stimulable phosphor contained in the first stimulable phosphor layer region 12 by the laser beam 24 having the reference laser power P0 which is relatively low and photoelectrically detecting stimulated emission 45 released from the first stimulable phosphor layer region 12 and temporarily stored in the temporary memory 85 as digital data of the first stimulable phosphor layer region 12 and transfers the digital data S (P0) temporarily stored in the temporary memory 85 to the data storing means 86 to be stored therein.

To the contrary, when the signal intensity determining means 87 determines that the signal intensity of the digital data S (P0) is lower than the threshold value T, it can be considered that since the amount of radiation energy stored in the first stimulable phosphor layer region 12 is small, the intensity of stimulated emission 45 released from the first stimulable phosphor layer region 12 in response to the stimulation with the laser beam 24 having the reference laser power P0 which is relatively low is too low and digital data S (P0) having sufficiently high signal intensity and high quantitative characteristic cannot be obtained. Therefore, the signal intensity determining means 87 outputs a laser power increasing signal to the control unit 70. In this case, the digital data S (P0) is not sampled.

When the laser power increasing signal is input from the signal intensity determining means 87 of the data processing apparatus 54, the control unit 70 outputs a first drive signal and supplies first drive current whose value is higher than that of the reference drive current to the first laser stimulating ray source 21, thereby causing the first laser stimulating ray source 21 to emit a laser beam 24 having first laser power P1 higher than the reference laser power P0 by ΔP.

A laser beam 24 having a wavelength of 640 nm and the first laser power and emitted from the first laser stimulating ray source 21 enters the optical head 35 via the collimator lens 25, the lens 26, the first dichroic mirror 27, the second dichroic mirror 28, the mirror 29, the mirror 32, the hole 33 of the perforated mirror 34 and the concave mirror 38.

The laser beam 24 entering the optical head 35 is reflected by the mirror 36 and condensed by the aspherical lens 37 onto the first stimulable phosphor layer region 12 formed in the support 11 of the stimulable phosphor sheet 10 placed on the glass plate 41 of a stage 40.

When the laser beam 24 impinges on the first stimulable phosphor layer region 12 formed in the support 11 of the stimulable phosphor sheet 10, stimulable phosphor contained in the first stimulable phosphor layer region 12 is excited by the laser beam 24, thereby releasing stimulated emission 45.

Since the laser beam 24 projected on the first stimulable phosphor layer region 12 has the first laser power P1 higher than the reference laser power P0, even when the amount of radiation energy stored in the first stimulable phosphor layer region 12 is small, stimulated emission 45 having high intensity is emitted from the first stimulable phosphor layer region 12.

The stimulated emission 45 released from the first stimulable phosphor layer region 12 is condensed onto the mirror 36 by the aspherical lens 37 provided in the optical head 35 and reflected by the mirror 36 on the side of the optical path of the laser beam 24, thereby being made a parallel beam to advance to the concave mirror 38.

The stimulated emission 45 advancing to the concave mirror 38 is reflected by the concave mirror 38 and advances to the perforated mirror 34.

As shown in FIG. 7, the stimulated emission 45 advancing to the perforated mirror 34 is reflected downward by the perforated mirror 34 formed as a concave mirror and advances to the filter 52d of the filter unit 48.

Since the filter 52d has a property of transmitting only light having a wavelength corresponding to that of stimulated emission emitted from stimulable phosphor and cutting off light having a wavelength of 640 nm, light having a wavelength of 640 nm corresponding to that of the stimulating ray is cut off by the filter 52d and only light having a wavelength corresponding to that of stimulated emission passes through the filter 52d to be photoelectrically detected by the photomultiplier 50.

Analog data produced by photoelectrically detecting stimulated emission 45 by the photomultiplier 50 are output to the integrating amplifier 90 and integrated thereby.

When a predetermined time, for example, several microseconds, has passed after the first stimulating ray source 21 was turned on, the control unit 70 outputs a drive stop signal to the first stimulating ray source 21, thereby turning it off and outputs an integrated value of the analog data produced by the integrating amplifier 90 to the A/D converter 53.

The integrated value of the analog data is digitized by the A/D converter 53 and digital data S (P1) are output to the temporary memory 85 to be stored therein.

The control unit 70 outputs a drive stop signal to the first laser stimulating ray source 21 and outputs a signal intensity determination start signal to the signal intensity determining means 87. When the signal intensity determining means 87 receives the signal intensity determination start signal from the control unit 70, it compares the signal intensity of digital data S (P1) stored in the temporary memory 85 with the threshold value T.

When the signal intensity determining means 87 determines that the signal intensity of the digital data S (P1) is equal to or higher than the threshold value T, it can be considered that since the power of the laser beam was set to be the first laser power P1 higher than the reference laser power P0 by ΔP and stimulable phosphor contained in the first stimulable phosphor layer region 12 was excited by the laser beam 24 having the first laser power P1, the intensity of stimulated emission 45 released from the first stimulable phosphor layer region 12 and photoelectrically detected by the photomultiplier 50 has become sufficiently higher and digital data S (P1) having sufficiently high signal intensity and high quantitative characteristics have been produced. Therefore, if stimulable phosphor contained in the first stimulable phosphor layer region 12 is excited by the laser beam 24 having laser power higher than the first laser power P1, since the intensity of stimulated emission 45 released from the first stimulable phosphor layer region 12 and to be photoelectrically detected by the photomultiplier 50 becomes too high and there occurs a risk of the signal intensity of the digital data exceeding the dynamic range of the photomultiplier 50, the signal intensity determining means 87 determines the digital data S (P1) produced by exciting stimulable phosphor contained in the first stimulable phosphor layer region 12 by the laser beam 24 having the first laser power PI and photoelectrically detecting stimulated emission 45 released from the first stimulable phosphor layer region 12 and temporarily stored in the temporary memory 85 as digital data of the first stimulable phosphor layer region 12.

Since the digital data S (P1) temporarily stored in the temporary memory 85 have been produced by irradiating the first stimulable phosphor layer region 12 with the laser beam 24 having the first laser power P1 higher than the reference laser power P0 to excite stimulable phosphor contained in the first stimulable phosphor layer region 12 and photoelectrically detecting stimulated emission 45 released from the first stimulable phosphor layer region 12, the digital data S (P1) have apparently higher signal intensity than that of the digital data S (P0) produced by irradiating the first stimulable phosphor layer region 12 with the laser beam 24 having the reference laser power P0 to excite stimulable phosphor contained in the first stimulable phosphor layer region 12 and photoelectrically detecting stimulated emission 45 released from the first stimulable phosphor layer region 12 even if same radiation energy is released from the first stimulable phosphor layer region 12. Therefore, since it is necessary to correct the digital data S (P1) so as to become digital data that would be obtained by exciting stimulable phosphor contained in the first stimulable phosphor layer region 12 with the laser beam 24 having the reference laser power P0, the signal intensity determining means 87 outputs a correction effecting signal to the data processing means 88.

When the correction effecting signal is input from the signal intensity determining means 87, the data processing means 88 reads the digital data S (P1) temporarily stored in the temporary memory 85, correct the digital data S (P1) in accordance with the following formula so as to become digital data that would be obtained by exciting stimulable phosphor contained in the first stimulable phosphor layer region 12 with the laser beam 24 having the reference laser power P0 and stores the thus obtained digital data S in the data storing means 88.

$$S = S(P1) \times C1(P0/P1)$$

In this formula, S is digital data to be obtained by correcting the digital data S (P1) and C1 (P0/P1) is a correction coefficient and is a function of the reference laser power P0 and the first laser power P1.

To the contrary, when the signal intensity determining means 87 determines that the signal intensity of the digital data S (P1) is lower than the threshold value T, it can be considered that since the amount of radiation energy stored in the first stimulable phosphor layer region 12 is too small, even though the power of the laser beam 24 was increased from the reference laser power P0 to the first laser power P1 and stimulable phosphor contained in the first stimulable phosphor layer region 12 was excited by the laser beam 24 having the first laser power P1 higher than the reference laser power P0, the intensity of stimulated emission 45 released from the first stimulable phosphor layer region 12 and photoelectrically detected by the photomultiplier 50 is still too low and digital data S (P0) having sufficiently high signal intensity and high quantitative characteristic have not been obtained. Therefore, the signal intensity determining means 87 outputs a laser power increasing signal to the control unit 70.

When the laser power increasing signal is again input from the signal intensity determining means 87 of the data processing apparatus 54, the control unit 70 outputs a second drive signal and supplies second drive current whose value is higher than that of the first drive current to the first laser stimulating ray source 21, thereby causing the first laser stimulating ray source 21 to emit a laser beam 24 having second laser power P2 higher than the first laser power P1 by $\Delta P$ and the first stimulable phosphor layer region 12 is irradiated with the laser beam 24 having the second laser power P2, thereby exciting stimulable phosphor contained therein.

In this manner, the steps of increasing the power of the laser beam 24, exciting stimulable phosphor contained in the first stimulable phosphor layer region 12, photoelectrically detecting stimulated emission 45 released from the first stimulable phosphor layer region 12 by the photomultiplier 50 to produce analog data, integrating the analog data by the integrating amplifier 90, digitizing the integrated value of the analog data by the A/D converter 53 to produce digital data and comparing the signal intensity of the digital data with the threshold value T are repeated up to I times at the maximum where I is an integer greater than 2.

In this embodiment, the step of increasing the power of the laser beam 24 is repeated only I times because some of the stimulable phosphor layer regions 12 store no radiation energy since a number of the stimulable phosphor layer regions 12 formed in the support 11 of the stimulable phosphor sheet 10 are selectively labeled with the radioactive labeling substance and even if the laser beam 24 whose power has been increased is repeatedly projected onto those stimulable phosphor layer regions 12, the signal intensity of digital data cannot become equal to or higher than the threshold value T. Therefore, when the signal intensity of the thus produced digital data is still lower than the threshold value T even though the power of the laser beam 24 was increased I times to produce digital data, the signal intensity determining means 87 determines that digital data of the first stimulable phosphor layer region 12 are zero and stores zero in the data storing means 88 as the digital data of the first stimulable phosphor layer region 12.

To the contrary, when, as the result of increasing the power of the laser beam 24 emitted from the first laser stimulating ray source 21 by $\Delta P$ i times where i is a positive integer less than I and exciting stimulable phosphor contained in the first stimulable phosphor layer region 12, the signal intensity determining means 87 determines that the signal intensity of digital data S (Pi) obtained by photoelectrically detecting stimulated emission 45 released from the first stimulable phosphor layer region 12 by the photomultiplier 50 to produce analog data, integrating the analog data by the integrating amplifier 90 and digitizing the integrated value of the analog data has become equal to or greater than the threshold value T, the signal intensity determining means 87 outputs a correction effecting signal to the data processing means 88 and causes it to correct the digital data S (Pi) similarly to the case of the digital data S (P1) produced using the laser beam 24 having the first laser power P1 and to store the thus corrected digital data in the data storing means 86.

Since radiation energy stored in the stimulable phosphor layer region 12 is released in the form of stimulated emission 45 when it is irradiated with the laser beam 24 and the amount of radiation energy stored in the stimulable phosphor layer region 12 is decreased, the reference laser power P0 and the increment ΔP are experimentally determined in advance so as to minimize the number of repetition of the excitation with the laser beam 24 and stored as set values of the laser power in a memory (not shown) of the control unit 70.

In the above described manner, when digital data have been produced by irradiating the first stimulable phosphor layer region 12 formed in the support 11 of the stimulable phosphor sheet 10 with the laser beam 24 to excite stimulable phosphor contained in the first stimulable phosphor layer region 12, photoelectrically detecting stimulated emission 45 released from the first stimulable phosphor layer region 12 to produce analog data, integrating the analog data and digitizing the integrated value of the analog data and stored in the data storing means 86, the control unit 70 outputs a drive stop signal to the first laser stimulating ray source 21, thereby turning it off and outputs a drive signal to the main scanning stepping motor 65, thereby moving the optical head 35 by one pitch equal to the distance between neighboring stimulable phosphor layer regions 12 of the stimulable phosphor sheet 10 in the main scanning direction.

When the control unit 70 determines based on a detection signal indicating the position of the optical head 35 input from the linear encoder 67 that the optical head 35 has been moved by one pitch equal to the distance between neighboring stimulable phosphor layer regions 12 in the main scanning direction, it outputs a reference drive signal and supplies a reference drive current to the first stimulating ray source 21, thereby causing it to emit a laser beam 24 having the reference laser power P0. As a result, stimulable phosphor contained in a second stimulable phosphor layer region 12 formed in the support 11 of the stimulable phosphor sheet 10 next to the first stimulable phosphor layer region 12 is first excited by the laser beam 24 having the reference laser power P0.

Similarly to the above, the second stimulable phosphor layer region 12 formed in the support 11 of the stimulable phosphor sheet 10 is irradiated with the laser beam 24 for a predetermined time and when the integrated value of analog data are produced by photoelectrically detecting stimulated emission 45 released from the second stimulable phosphor layer region 12 by the photomultiplier 50 to produce analog data and integrating the analog data by the integrating amplifier 90, the control unit 70 outputs a drive stop signal to the first stimulating ray source 21, thereby turning it off, outputs the integrated value of the analog data produced by the integrating amplifier 90 to the A/D converter 53, thereby causing it to digitize them to produce digital data and stores the thus produced digital data in the temporary memory 85. Further, the control unit 70 outputs a signal intensity determination start signal to the signal intensity determining means 87 of the data processing apparatus 54.

When the signal intensity determining means 87 receives the signal intensity determination start signal from the control unit 70, it reads digital data S (P0) produced by photoelectrically detecting stimulated emission 45 released from the second stimulable phosphor layer region 12 and temporarily stored in the temporary memory 85 and compares the signal intensity of the digital data S (P0) with the threshold value T.

Similarly to the case of irradiating the first stimulable phosphor layer region 12 with the laser beam having the reference laser power P0 and producing digital data, when the signal intensity of digital data S (P0) is determined to be equal to or higher than the threshold value T, the digital data S (P0) stored in the temporary memory 85 are determined as digital data of the second stimulable phosphor layer region 12 and stored in the data storing means 86 of the data processing apparatus 54. On the other hand, when the signal intensity of digital data S (P0) is determined to be lower than the threshold value T, the power of the laser beam 24 is increased, whereby stimulable phosphor contained in the second stimulable phosphor layer region 12 second stimulable phosphor layer region 12 is excited by the laser beam and stimulated emission 45 released from the second stimulable phosphor layer region 12 is photoelectrically detected to produce digital data. When the signal intensity of digital data S (P0) is determined to become equal to or higher than the threshold value T, the digital data are determined as digital data of the second stimulable phosphor layer region 12 and corrected by the data processing means 88 in accordance with the power of the laser beam 24 to be stored in the data storing means 86 of the data processing apparatus 54.

In this manner, the on and off operation of the first stimulating ray source 21 is repeated in synchronism with the intermittent movement of the optical head 35 and when the control unit 70 determines based on a detection signal indicating the position of the optical head 35 input from the linear encoder 67 that the optical head 35 has been moved by one scanning line in the main scanning direction and that the stimulable phosphor layer regions 12 included in a first line of the stimulable phosphor layer regions 12 formed in the support 11 of the stimulable phosphor sheet 10 have been scanned with the laser beam 24, it outputs a drive signal to the main scanning stepping motor 65, thereby returning the optical head 35 to its original position and outputs a drive signal to the sub-scanning pulse motor 61, thereby causing it to move the movable base plate 63 by one scanning line in the sub-scanning direction.

When the control unit 70 determines based on a detection signal indicating the position of the optical head 35 input from the linear encoder 67 that the optical head 35 has been returned to its original position and determines that the movable base plate 63 has been moved by one scanning line in the sub-scanning direction, similarly to the manner in which the stimulable phosphor layer regions 12 included in the first line of the stimulable phosphor layer regions 12 formed in the support 11 of the stimulable phosphor sheet 10 were sequentially irradiated with the laser beam 24 emitted from the first laser stimulating ray source 21, the stimulable phosphor layer regions 12 included in a second line of the stimulable phosphor layer regions 12 formed in the support 11 of the stimulable phosphor sheet 10 are sequentially irradiated with the laser beam 24 emitted from the first laser stimulating ray source 21, thereby exciting stimulable phosphor contained in the stimulable phosphor layer regions 12 included in the second line and stimulated emission 45 released from the stimulable phosphor layer regions 12 is sequentially and photoelectrically detected by the photomultiplier 50 to produce analog data. The analog data are integrated by the integrating amplifier 90 and the integrated value of the analog data is digitized by the A/D converter 53 to produce digital data. The thus produced digital data are temporarily stored in the temporary memory 85.

Then, in accordance with the signal intensity of the digital data stored in the temporary memory 85, the digital data stored in the temporary memory 85 are stored as the digital data of the stimulable phosphor layer region 12 in the data storing means 88 of the data processing apparatus 54, or, the steps of increasing the power of the laser beam 24, irradiating each of the stimulable phosphor layer regions 12 included in the second line to excite stimulable phosphor contained therein, photoelectrically detecting stimulated emission 45 from each of the stimulable phosphor layer regions 12 to produce analog data, integrating the analog data and digitizing the integrated value of the analog data to produce digital data are conducted, and when the signal intensity of the digital data is determined to be equal to or higher than the threshold value T, the digital data are stored as the digital data of the stimulable phosphor layer region 12 in the data storing means 88 of the data processing apparatus 54.

When all of the stimulable phosphor layer regions 12 formed in the support 11 of the stimulable phosphor sheet 10 have been scanned with the laser beam 24 in this manner, the first laser stimulating ray source 21 is turned off and the reading operation of radiation data stored in a number of the stimulable phosphor layer regions 12 of the stimulable phosphor sheet 10 is completed.

In this embodiment, digital data of each of the stimulable phosphor layer regions 12 of the stimulable phosphor sheet 10 are produced by first irradiating each of the stimulable phosphor layer regions 12 with the laser beam 24 having the reference laser power P0 which is relatively low and emitted from the first laser stimulating ray source 21 to excite stimulable phosphor contained therein, photoelectrically detecting stimulated emission 45 released from each of the stimulable phosphor layer regions 12 by the photomultiplier 50 to produce analog data, integrating analog data and digitizing the integrated value of the analog data, and the signal intensity of the thus produced digital data S (P0) is compared with the threshold value T by the signal intensity determining means 87. When it is determined that the signal intensity of the digital data S (P0) is equal to or higher than the threshold value T, since it can be considered that large radiation energy is stored in the stimulable phosphor region 12 and if stimulable phosphor contained in the stimulable phosphor region 12 is excited by a laser beam 24 having a laser power higher than the reference laser power P0, there is a risk of the signal strength of digital data exceeding the upper limit of the dynamic range of the photomultiplier 50, the digital data S (P0) produced by exciting stimulable phosphor contained in the stimulable phosphor layer region 12 with the laser beam 24 having the reference laser power P0 which is relatively low, photoelectrically detecting stimulated emission 45 released from the stimulable phosphor layer region 12 to produce analog data, integrating the analog data and digitizing the integrated value of the analog data and temporarily stored in the temporary memory 85 are determined as digital data of the stimulable phosphor layer region 12 and stored in the data storing means 88.

Therefore, according to this embodiment, even in the case where radiation energy stored in a stimulable phosphor layer region 12 is extremely large, it is possible to reliably prevent the intensity of stimulated emission 45 released from the stimulable phosphor layer region 12 from becoming too high and exceeding the upper limit of the dynamic range of the photomultiplier 50 and to photoelectrically detect stimulated emission 45 with high sensitivity by the photomultiplier 50, thereby producing biochemical analysis data.

On the other hand, in this embodiment, when it is determined that the signal intensity of the digital data S (P0) is lower than the threshold value T, since it can be considered that extremely small radiation energy is stored in the stimulable phosphor region 12 and it is extremely difficult for the photomultiplier 50 to photoelectrically detect stimulated emission 45 released from the stimulable phosphor region 12 with high intensity because the intensity of the stimulated emission 45 is too low and to produce digital data having high quantitative characteristics and high signal intensity, only when the signal intensity of digital data S (Pi) produced by increasing the power of a laser beam 24 emitted from the first laser stimulating ray source 21, causing the first laser stimulating ray source 21 to emit a laser beam 24 having laser power Pi higher than the reference power P0 where Pi=P0+ΔP×i and i is a positive integer, exciting stimulable phosphor contained in the stimulable phosphor region 12 by the laser beam 24 having the laser beam Pi, photoelectrically detecting stimulated emission 45 released from the stimulable phosphor region 12 by the photomultiplier 50 to produce analog data, integrating analog data and digitizing the integrated value of the analog data is equal to or higher than the threshold value T, the digital data S (Pi) are determined as digital data of the stimulable phosphor region 12.

Therefore, according to this embodiment, even in the case where radiation energy stored in a stimulable phosphor region 12 is too small, so that the intensity of stimulated emission 45 released from the stimulable phosphor layer region 12 is too low to be photoelectrically detected by the photomultiplier 50 with high sensitivity when the stimulable phosphor layer region 12 is irradiated with a laser beam 24 whose power is selected in such a manner that the signal intensity of digital data produced by irradiating a stimulable phosphor layer regions 12 storing high radiation energy with the laser beam 24 to excite stimulable phosphor contained therein and photoelectrically detecting stimulated emission 45 released from the stimulable phosphor region 12 does not exceed the upper limit of the dynamic range of the photomultiplier 50, stimulated emission 45 released from the stimulable phosphor layer region 12 can be photoelectrically detected with high sensitivity to produce digital data S (Pi), thereby producing biochemical analysis data having high quantitative characteristics.

Further, in this embodiment, when the signal intensity of digital data S (Pi) is equal to or higher than the threshold value T and the digital data S (Pi) are determined as digital data of the stimulable phosphor region 12, the digital data S (Pi) are multiplied by Ci (P0/Pi) which is a function of the power of the laser beam 24 so that the digital data S (Pi) are corrected so as to become digital data that would be obtained by exciting stimulable phosphor contained in the stimulable phosphor layer region 12 with the laser beam 24 having the reference laser power P0 and the thus corrected digital data are stored in the data storing means 86. Therefore, even in the case of increasing the laser power of a laser beam 24 so as to become greater that the reference laser power P0 and exciting stimulable phosphor contained in a stimulable phosphor layer region 12 with the laser beam 24 in order to detect stimulated emission 45 with high sensitivity or release all detectable radiation energy stored in the stimulable phosphor layer region 12 in the form of stimulated emission 45 to be detected, it is possible to produce digital data having signal intensity corresponding to radiation energy stored in the stimulable phosphor layer region 12.

Moreover, according to this embodiment, when the signal intensity of digital data are lower than the threshold value T even if the increase in the power of a laser beam 24 is repeated I times at the maximum where I is an integer equal to or greater than 3, since it is judged that no radiation energy is stored in the stimulable phosphor layer region 12 and digital data S are stored in the data storing means 86 so that S equals to 0, radiation data recorded in a number of the stimulable phosphor layer regions 12 by being selectively labeled with a radioactive labeling substance can be effectively read to produce biochemical analysis data.

Figure 29:
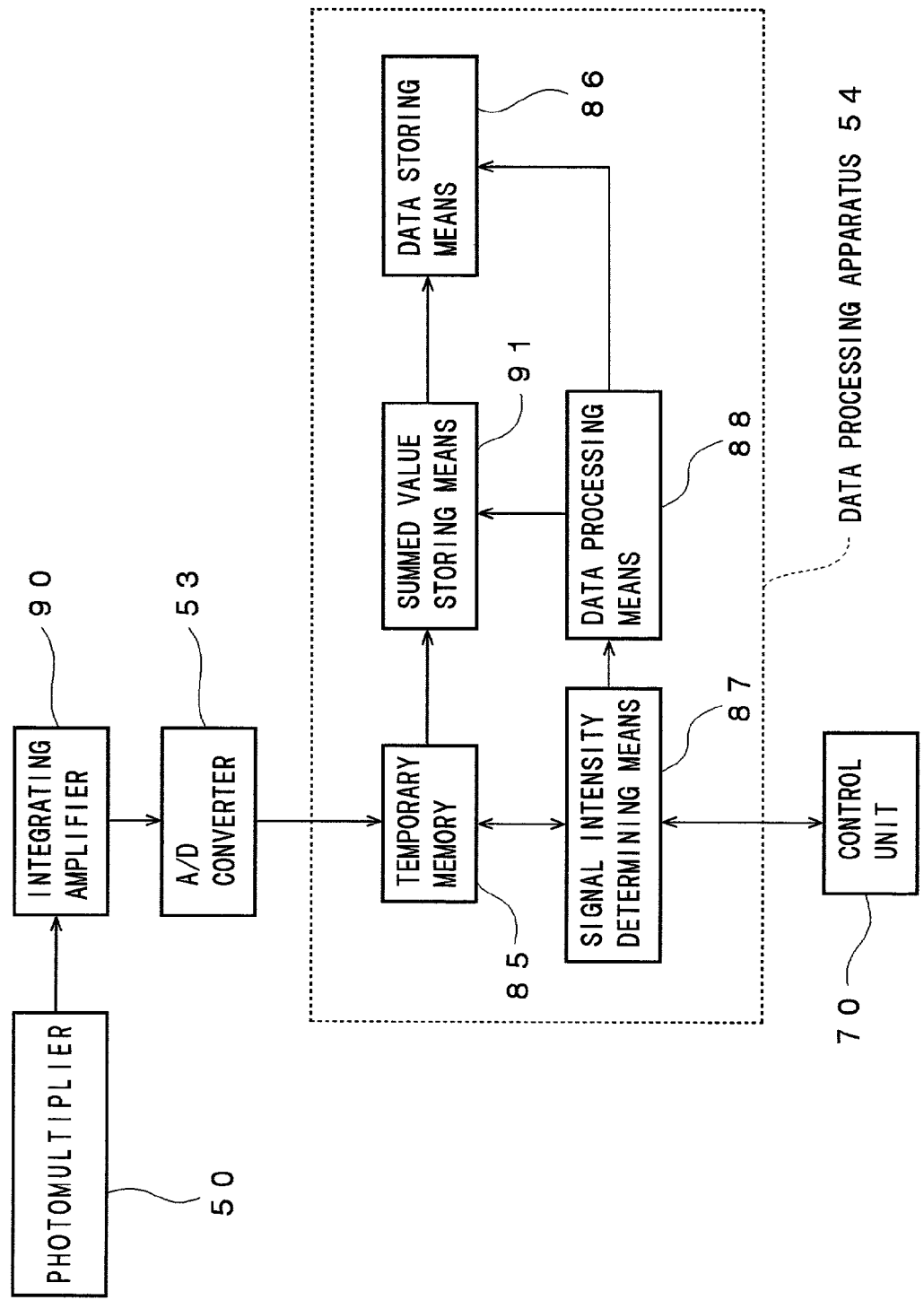
FIG. 29 is a block diagram of a data processing apparatus and its periphery of a scanner which is a further preferred embodiment of the present invention.

FIG. 29 is a block diagram of a data processing apparatus 54 and its periphery of a scanner which is a further preferred embodiment of the present invention.

As shown in FIG. 29, the data processing apparatus 54 of a scanner according to this embodiment further includes a summed value storing means 91 for storing the summed value of digital data.

Figure 30:
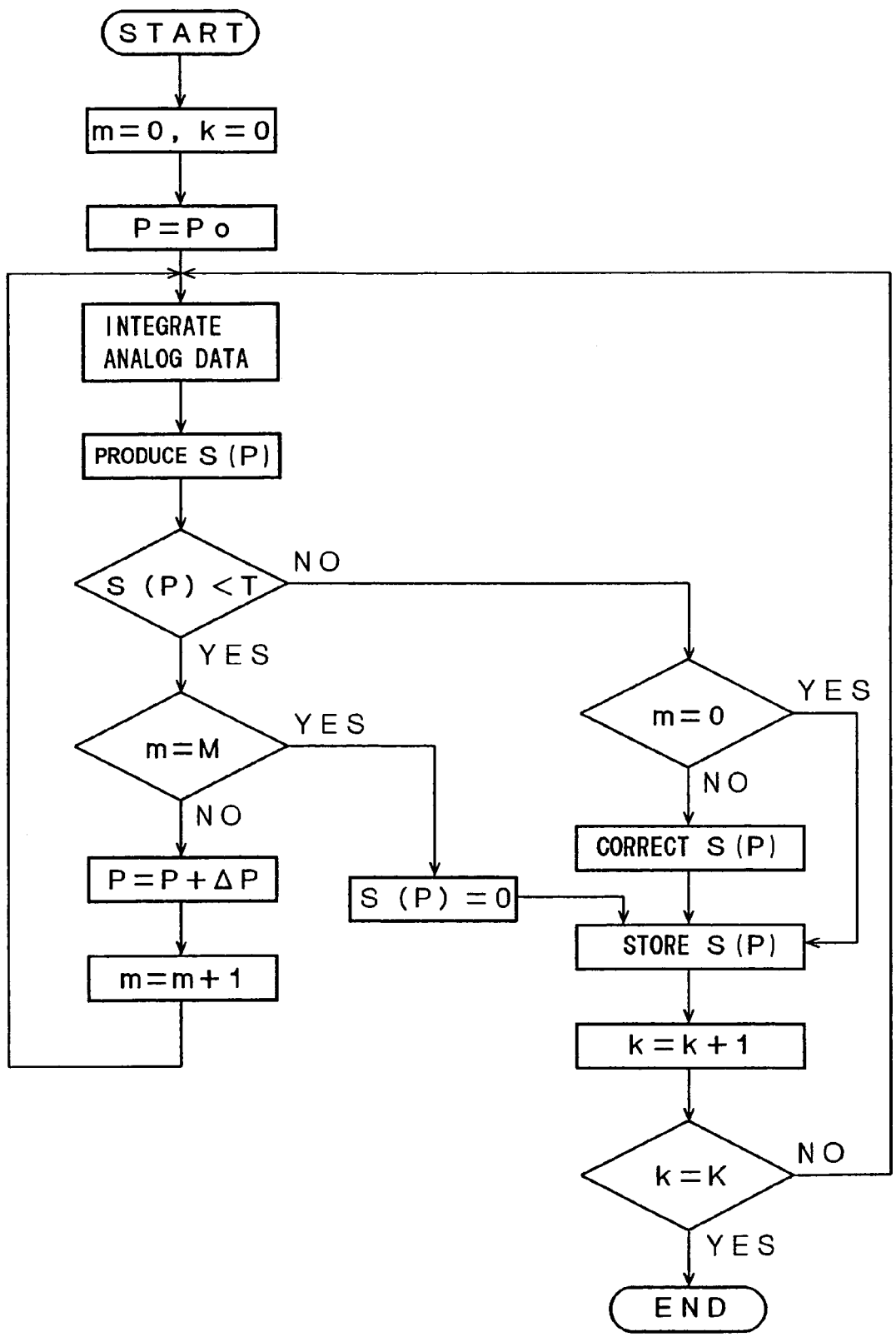
FIG. 30 is a flow chart showing a biochemical analysis data producing operation effected by a signal intensity determining means and a control unit of a scanner which is a further preferred embodiment of the present invention.

FIG. 30 is a flow chart showing a biochemical analysis data producing operation effected by the signal intensity determining means 87 and the control unit 70 of the scanner which is a further preferred embodiment of the present invention.

In this embodiment, the signal intensity determining means 87 of the data processing apparatus 54 is constituted so as to temporarily store digital data S (P0) produced by irradiating each of the stimulable phosphor layer regions 12 formed in the support 11 of the stimulable phosphor sheet 10 with a laser beam 24 having the reference laser power P0 to excite stimulable phosphor contained therein, photoelectrically detecting stimulated emission 45 released from each of the stimulable phosphor layer regions 12 by the photomultiplier 50 to produce analog data, integrating the analog data and digitizing the integrated value of the analog data, to compare the digital data S (P0) temporarily stored in the temporary memory 85 with the threshold value T, to sample the digital data S (P0) when it determines that the signal intensity of the digital data S (P0) is equal to or higher than the threshold value T, to store the digital data S (P0) in a predetermined memory area of the summed value storing means 91, to then output laser power increasing signals to the control unit 70 up to K times at maximum where K is an integer equal to or greater than 2, thereby causing the first laser stimulating ray source 21 to sequentially emit a laser beam 24 having higher laser power to excite stimulable phosphor contained in the stimulable phosphor layer region 12 with the laser beams 24 having distinct laser levels, to sample digital data S (Pk) produced by photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53, to store the digital data S (Pk) in a predetermined memory area of the summed value storing means 89, to output a correction effecting signal to the data processing means 88, thereby causing it to correct the digital data S (Pk) stored in the predetermined memory area of the summed value storing means 89, add the thus corrected digital data to the digital data S (P0) stored in the predetermined memory area of the summed value storing means 89 and store the summed digital data in the data storing means 86 as the digital data of the stimulable phosphor layer region 12. Here, k is a positive integer less than K.

On the other hand, when the signal intensity determining means 87 of the data processing apparatus 54 determines that the signal intensity of digital data S (P0) produced by irradiating each of the stimulable phosphor layer regions 12 formed in the support 11 of the stimulable phosphor sheet 10 with a laser beam 24 having the reference laser power P0 to excite stimulable phosphor contained therein, photoelectrically detecting stimulated emission 45 released from each of the stimulable phosphor layer regions 12 by the photomultiplier 50 to produce analog data, integrating the analog data and digitizing the integrated value of the analog data and temporarily stored in the temporary memory 85 is lower than the threshold value T, the signal intensity determining means 87 outputs laser power increasing signals to the control unit 70 up to M times at maximum where M is an integer equal to or greater than 2, thereby causing the first laser stimulating ray source 21 to sequentially emit a laser beam 24 having higher laser power to excite stimulable phosphor contained in the stimulable phosphor layer region 12 with the laser beams 24, samples digital data S (Pm) produced by exciting stimulable phosphor contained in the stimulable phosphor layer region 12 with the laser beam 24, photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53 when it determines that the signal intensity thereof has come to be equal to or higher than the threshold value T, stores the digital data S (Pm) in a predetermined memory area of the summed value storing means 89, then further outputs laser power increasing signals to the control unit 70 up to K times, thereby causing the first laser stimulating ray source 21 to sequentially emit a laser beam 24 having higher laser power to excite stimulable phosphor contained in the stimulable phosphor layer region 12 with the laser beams 24 having distinct laser power levels, samples digital data S (Pm+k) produced by photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53, stores the digital data S (Pm+k) in a predetermined memory area of the summed value storing means 89, outputs a correction effecting signal to the data processing means 88, thereby causing it to correct the digital data S (Pm+k) stored in the predetermined memory area of the summed value storing means 89, to add the thus corrected digital data to the digital data S (P0) stored in the predetermined memory area of the summed value storing means 89 and store the summed digital data in the data storing means 86 as the digital data of the stimulable phosphor layer region 12. Here, m is a positive integer less than M.

Furthermore, in this embodiment, when the signal intensity determining means 87 of the data processing apparatus 54 determines that the signal intensity of digital data S (P0) produced by irradiating each of the stimulable phosphor layer regions 12 formed in the support 11 of the stimulable phosphor sheet 10 with a laser beam 24 having the reference laser power P0 to excite stimulable phosphor contained therein, photoelectrically detecting stimulated emission 45 released from each of the stimulable phosphor layer regions 12 by the photomultiplier 50 to produce analog data, integrating the analog data and digitizing the integrated value of the analog data and temporarily stored in the temporary memory 85 is lower than the threshold value T, even though the signal intensity determining means 87 output laser power increasing signals to the control unit 70 M times, thereby causing the first laser stimulating ray source 21 to sequentially emit a laser beam 24 having higher laser power and to irradiate the stimulable phosphor layer region 12 with the laser beam 24, if the signal intensity determining means 87 determines that the signal intensity of digital data S (Pm) produced by exciting stimulable phosphor contained in the stimulable phosphor layer region 12, photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53 is still lower than the threshold value T, it determines that digital data of the stimulable phosphor layer region 12 are zero and stores zero in the data storing means 88 as the digital data of the stimulable phosphor layer region 12.

More specifically, the control unit 70 first outputs a reference drive signal to the first laser stimulating ray source 21 and supplies relatively low drive current to the first laser stimulating ray source 21, thereby causing the first laser stimulating ray source 21 to emit a laser beam 24 having the reference laser power P0 which is relatively low. Similarly to the embodiment shown in FIGS. 27 and 28, analog data are produced by photoelectrically detecting stimulated emission 45 released from a stimulable phosphor layer region 12 and the analog data are integrated by the integrating amplifier 90.

When a predetermined time, for example, several microseconds, has passed after the first stimulating ray source 21 was turned on, the control unit 70 outputs a drive stop signal to the first stimulating ray source 21, thereby turning it off and outputs an integrated value of the analog data produced by the integrating amplifier 90 to the A/D converter 53.

The integrated value of the analog data is digitized by the A/D converter 53 and digital data S (P0) are output to the temporary memory 85 to be stored therein.

At the same time, the control unit 70 outputs a signal intensity determination start signal to the signal intensity determining means 87 and when the signal intensity determining means 87 receives the signal intensity determination start signal from the control unit 70, it compares the signal intensity of digital data S (P0) stored in the temporary memory 85 with the threshold value T.

When the signal intensity determining means 87 determines that the signal intensity of the digital data S (P0) is equal to or higher than the threshold value T, it transfers the digital data S (P0) temporarily stored in the temporary memory 85 to the summed value storing means 91 to be stored therein.

In this case, although stimulable phosphor contained in the first stimulable phosphor layer region 12 was excited by the laser beam 24 having the reference laser power P0 which is relatively low, since the signal intensity of the digital data S (P0) is equal to or higher than the threshold value T, it can be considered that the stimulable phosphor layer region 12 stores a sufficient amount of radiation energy detectable in the form of stimulated emission 45.

Therefore, in this embodiment, after the digital data S (P0) have been stored in the predetermined memory area of the summed value storing means 91, the signal intensity determining means 87 further outputs laser power increasing signals to the control unit 70 K times in total, thereby increasing the laser power of a laser beam 24 emitted from the first laser stimulating ray source 21 K times and stores digital data S (Pk) produced by exciting stimulable phosphor contained in the stimulable phosphor layer region 12 from which the digital data S (P0) were obtained, photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53 in a predetermined memory area of the summed value storing means 91. Here, k=1, - - - , K.

However, since the digital data S (P0) were produced by irradiating the stimulable phosphor layer region 12 with the laser beam 24 having the reference laser power and photoelectrically detecting stimulated emission 45 released from the stimulable phosphor layer region 12, while the digital data S (Pk) are produced by irradiating the stimulable phosphor layer region 12 with the laser beam 24 having the laser power Pk and photoelectrically detecting stimulated emission 45 released from the stimulable phosphor layer region 12, when the digital data S (Pk) produced by increasing the power of the laser beam 24 emitted from the first laser stimulating ray source 21 K times are to be added to the digital data S (P0), it is necessary to correct the digital data S (Pk) in accordance with laser power.

Therefore, in this embodiment, the signal intensity determining means 87 stores the digital data S (Pk) in a predetermined memory area of the summed value storing means 91 and outputs a correction effecting signal to the data processing means 88, thereby causing it to correct the digital data S (Pk) in accordance with the following formula and add the corrected digital data to the digital data S (P0) stored in the summed value storing means 91.

$$\Sigma S(Pk) = \Sigma S(Pk-1) + S(Pk) \times C3(P0/Pk)$$

In the above formula, $\Sigma S$ (Pk) is a summed value of digital data obtained by increasing the laser power of the laser beam 24 k times, producing digital data, correcting the digital data and summing the corrected digital data, $\Sigma S$ (Pk–1) is a summed value of digital data obtained by increasing the laser power of the laser beam 24 (k–1) times, producing digital data, correcting the digital data and summing the corrected digital data and C3 (P0/Pk) is a correction coefficient and a function of the reference laser power P0 and the laser power Pk.

On the other hand, when the signal intensity determining means 87 of the data processing apparatus 54 determines that the signal intensity of digital data S (P0) produced by irradiating each of the stimulable phosphor layer regions 12 formed in the support 11 of the stimulable phosphor sheet 10 with a laser beam 24 having the reference laser power P0 to excite stimulable phosphor contained therein, photoelectrically detecting stimulated emission 45 released from each of the stimulable phosphor layer regions 12 by the photomultiplier 50 to produce analog data, integrating the analog data and digitizing the integrated value of the analog data and temporarily stored in the temporary memory 85 is lower than the threshold value T, the signal intensity determining means 87 outputs laser power increasing signals to the control unit 70 up to M times at maximum, thereby causing the first laser stimulating ray source 21 to sequentially emit a laser beam 24 having higher laser power to excite stimulable phosphor contained in the stimulable phosphor layer region 12 with the laser beams 24, and compares digital data produced by exciting stimulable phosphor contained in the stimulable phosphor layer region 12 from which the digital data S (P0) were obtained with the laser beam 24, photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53 with the threshold value T.

When the signal intensity determining means 87 determines that the signal intensity of the digital data S (Pm) produced by exciting stimulable phosphor contained in the stimulable phosphor layer region 12 from which the digital data S (P0) were obtained with the laser beam 24, photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53 has come to be equal to or higher than the threshold value T, the signal intensity determining means 87 stores the digital data S (Pm) in a predetermined memory area of the summed value storing means 91. Here, m=1, - - -, M.

In this case, although the signal intensity of the digital data S (P0) produced by exciting stimulable phosphor contained in the stimulable phosphor layer region 12 with the laser beam 24 having the reference laser power P0 is lower than the threshold value T, since the laser power of the laser beam 24 is increased by ΔP and stimulable phosphor contained in the stimulable phosphor layer region 12 is excited with the laser beam 24 having higher laser power, the signal intensity of the digital data S (Pm) produced by exciting stimulable phosphor contained in the stimulable phosphor layer region 12 with the laser beam 24 having the laser power Pm has come to be equal to or higher than the threshold value T. Therefore, it can be considered that if stimulable phosphor contained in the stimulable phosphor layer region 12 is excited with a laser beam 24 having much higher laser power, radiation energy stored in the stimulable phosphor layer region 12 can be released in the form of stimulated emission 45 and detected.

Therefore, in this embodiment, the signal intensity determining means 87 is constituted so as to output laser power increasing signals to the control unit 70 up to K times in total, thereby increasing the laser power of the laser beam 24 emitted from the first laser stimulating ray source 21 K times, and to store in a predetermined memory area of the summed value storing means 91 digital data S (Pm+k) produced by exciting stimulable phosphor contained in the stimulable phosphor layer region 12 from which the digital data S (Pm) were obtained with the laser beam 24 with the laser beam 24, photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53. Here, k=1, - - -, K.

However, as described above, since the digital data S (Pm) were produced by irradiating the stimulable phosphor layer regions 12 with the laser beam 24 having the laser power Pm and photoelectrically detection stimulated emission 45 released from the stimulable phosphor layer regions 12, while the digital data S (Pm+k) are produced by irradiating the stimulable phosphor layer regions 12 with the laser beam 24 having the laser power Pm+k and photoelectrically detection stimulated emission 45 released from the stimulable phosphor layer regions 12, when the digital data S (Pm+k) produced by increasing the power of the laser beam 24 emitted from the first laser stimulating ray source 21 K times are to be added to the digital data S (Pm), it is necessary to correct the digital data S (Pm+k) in accordance with laser power.

Therefore, in this embodiment, the signal intensity determining means 87 stores the digital data S (Pm+k) in a predetermined memory area of the summed value storing means 91 and outputs a correction effecting signal to the data processing means 88, thereby causing it to correct the digital data S (Pm+k) in accordance with the following formula and add the corrected digital data to the digital data S (Pm) stored in the summed value storing means 91.

$$\Sigma S(Pm+k) = \Sigma S(Pm+k-1) + S(Pm+k) \times C3(Pm/Pm+k)$$

In the above formula, $\Sigma S$ (Pm+k) is a summed value of digital data obtained by increasing the laser power of the laser beam 24 (m+k) times, producing digital data, correcting the digital data and summing the corrected digital data, $\Sigma S$ (Pm+k−1) is a summed value of digital data obtained by increasing the laser power of the laser beam 24 (m+k−1) times, producing digital data, correcting the digital data and summing the corrected digital data and C3 (P0/Pm+k) is a correction coefficient and a function of the laser power Pm and the laser power Pm+k.

To the contrary, when the signal intensity determining means 87 of the data processing apparatus 54 determines that the signal intensity of digital data S (P0) produced by irradiating each of the stimulable phosphor layer regions 12 formed in the support 11 of the stimulable phosphor sheet 10 with a laser beam 24 having the reference laser power P0 to excite stimulable phosphor contained therein, photoelectrically detecting stimulated emission 45 released from each of the stimulable phosphor layer regions 12 by the photomultiplier 50 to produce analog data, integrating the analog data and digitizing the integrated value of the analog data and temporarily stored in the temporary memory 85 is lower than the threshold value T, even though the signal intensity determining means 87 output laser power increasing signals to the control unit 70 M times in total, thereby causing the first laser stimulating ray source 21 to emit a laser beam 24 having laser power higher than the reference laser power P0 by ΔP to irradiate the stimulable phosphor layer region 12 with the laser beam 24, if the signal intensity of digital data S (PM) produced by exciting stimulable phosphor contained in the stimulable phosphor layer region 12 with the laser beam 24, photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53 is still lower than the threshold value T, since it is highly probable that no radiation energy is stored in the stimulable phosphor layer region 12, the signal intensity determining means 87 determines that digital data of the stimulable phosphor layer region 12 are zero and stores zero in the data storing means 86.

According to this embodiment, when the signal intensity of digital data produced by exciting stimulable phosphor contained in a stimulable phosphor layer region 12 with a laser beam 24 having the reference laser power P0, photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53 is equal to or higher than the threshold value T, the laser power of the laser beam 24 is increased by ΔP K times in total, the stimulable phosphor layer regions 12 is irradiated with the laser beam 24 to excite stimulable phosphor contained therein, stimulated emission 45 released from the stimulable phosphor layer region 12 is photoelectrically detected by the photomultiplier 50 to produce analog data, the analog data are integrated by the integrating amplifier 90, the integrated value of the analog data are digitized by the A/D converter 53 to produce digital data and the digital data are corrected in accordance with the laser power to produce digital data of the stimulable phosphor layer regions 12. Therefore, since substantially all radiation energy stored in the stimulable phosphor layer region 12 can be completely released in the form of stimulated emission 45, it is possible to detect stimulated emission 45 with high sensitivity and produce biochemical analysis data having high quantitative characteristics. Further, since stimulable phosphor contained in a stimulable phosphor layer region 12 is first excited with a laser beam 24 having the reference laser power P0 which is relatively low and further excited by increasing the laser power of the laser beam 24 by ΔP, it is possible to reliably prevent stimulated emission released from stimulable phosphor contained in the stimulable phosphor layer region 12 by exciting the stimulable phosphor with the laser beam 24 from becoming too great to exceed the upper limit of the dynamic range of the photomultiplier 50 and to prevent the signal intensity of digital data produced by detecting the stimulated emission 45 from being saturated, thereby degrading the quantitative characteristics of biochemical analysis data.

Furthermore, according to this embodiment, when the signal intensity determining means 87 determines that the signal intensity of digital data S (P0) produced by exciting stimulable phosphor contained in a stimulable phosphor layer regions 12 with the laser beam 24 having the reference laser power P0, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 is lower than the threshold value T, the signal intensity determining means 87 increases the laser power of the laser beam 24 by ΔP M times in total to irradiate the stimulable phosphor layer region 12 therewith, thereby exciting stimulable phosphor contained in the stimulable phosphor layer region 12 and when the signal intensity of digital data produced by photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53 has come to be equal to or higher than the threshold value T, digital data of the stimulable phosphor layer region 12 are produced by increasing the laser power of the laser beam 24 by ΔP K times in total, irradiating the stimulable phosphor layer region 12 with the laser beam 24 to excite stimulable phosphor contained in the stimulable phosphor layer region 12, photoelectrically detecting stimulated emission 45 released from the stimulable phosphor layer region 12 by the photomultiplier 50 to produce analog data, integrating the analog data by the integrating amplifier 90, digitizing the integrated value of the analog data by the A/D converter 53 to produce digital data, correcting the digital data in accordance with the laser power and summing the thus corrected digital data. Therefore, since substantially all radiation energy stored in the stimulable phosphor layer region 12 can be completely released in the form of stimulated emission 45 and digital data can be produced by detecting stimulated emission 45, even in the case where radiation energy stored in a stimulable phosphor region 12 is too small and the intensity of stimulated emission 45 released from the stimulable phosphor layer region 12 is too low, it is possible to detect stimulated emission 45 with high sensitivity and produce biochemical analysis data having high quantitative characteristics.

Moreover, according to this embodiment, when the signal intensity determining means 87 of the data processing apparatus 54 determines that the signal intensity of digital data S (P0) produced by irradiating each of the stimulable phosphor layer regions 12 formed in the support 11 of the stimulable phosphor sheet 10 with a laser beam 24 having the reference laser power P0 to excite stimulable phosphor contained therein, photoelectrically detecting stimulated emission 45 released from each of the stimulable phosphor layer regions 12 by the photomultiplier 50 to produce analog data, integrating the analog data and digitizing the integrated value of the analog data and temporarily stored in the temporary memory 85 is lower than the threshold value T, even though the signal intensity determining means 87 output laser power increasing signals to the control unit 70 M times, thereby causing the first laser stimulating ray source 21 to sequentially emit a laser beam 24 having higher laser power and to irradiate the stimulable phosphor layer region 12 with the laser beam 24, if the signal intensity determining means 87 determines that the signal intensity of digital data S (Pm) produced by exciting stimulable phosphor contained in the stimulable phosphor layer region 12, photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53 is still lower than the threshold value T, it determines that digital data of the stimulable phosphor layer region 12 are zero and stores zero in the data storing means 88 as the digital data of the stimulable phosphor layer region 12. Therefore, it is possible to efficiently read radiation data recorded in a number of the stimulable phosphor layer regions 12 by selectively labeling with the radioactive labeling substance to produce biochemical analysis data.

Figure 31:
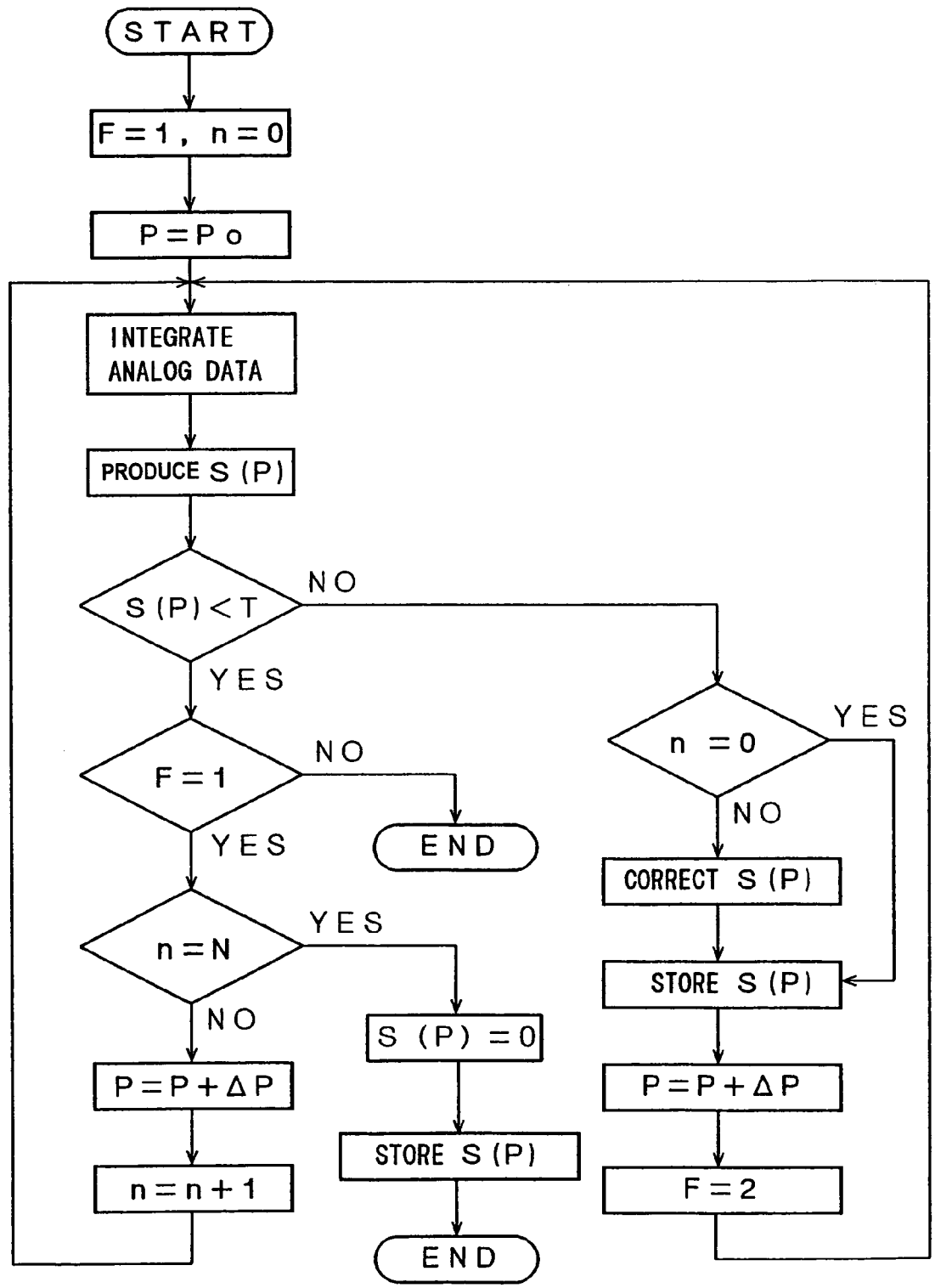
FIG. 31 is a flow chart showing a biochemical analysis data producing operation performed by a signal intensity determining means and a control unit of a scanner which is a further preferred embodiment of the present invention.

FIG. 31 is a flow chart showing a biochemical analysis data producing operation performed by the signal intensity determining means 87 and the control unit 70 of a scanner which is a further preferred embodiment of the present invention.

As shown in FIG. 31, when the signal intensity determining means 87 of the data processing apparatus 54 according to this embodiment determines that the signal intensity of digital data S (P0) produced by exciting stimulable phosphor contained in a stimulable phosphor layer regions 12 with the laser beam 24 having the reference laser power P0, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 is equal to or higher than the threshold value T, the signal intensity determining means 87 further increases the laser power of the laser beam 24 emitted from the first laser stimulating ray source 21 by ΔP to irradiate the stimulable phosphor layer region 12 therewith, thereby exciting stimulable phosphor contained in the stimulable phosphor layer region 12 and adopts digital data produced by photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53 as digital data of the stimulable phosphor layer region 12 when the signal intensity thereof is equal to or higher than the threshold value T, while it terminates irradiation of the stimulable phosphor layer region 12 with the laser beam 24 when the signal intensity of digital data produced by increasing the laser power of the laser beam 24 cannot become to be equal to or higher than the threshold value T.

Further, as shown in FIG. 31, when the signal intensity determining means 87 of the data processing apparatus 54 according to this embodiment determines that the signal intensity of digital data S (P0) produced by exciting stimulable phosphor contained in a stimulable phosphor layer regions 12 with the laser beam 24 having the reference laser power P0, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 is lower than the threshold value T, the signal intensity determining means 87 increases the laser power of the laser beam 24 emitted from the first laser stimulating ray source 21 by $\Delta P$ N times where N is an integer equal to or greater than 2 to irradiate the stimulable phosphor layer region 12 therewith, thereby exciting stimulable phosphor contained in the stimulable phosphor layer region 12. When the signal intensity determining means 87 determines that the signal intensity of digital data produced by photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 has come to be equal to or higher than the threshold value T, the signal intensity determining means 87 further increases the laser power of the laser beam 24 emitted from the first laser stimulating ray source 21 by $\Delta P$ to irradiate the stimulable phosphor layer region 12 therewith, thereby exciting stimulable phosphor contained in the stimulable phosphor layer region 12 and adopts digital data produced by photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53 as digital data of the stimulable phosphor layer region 12 when the signal intensity thereof is equal to or higher than the threshold value T, while it terminates irradiation of the stimulable phosphor layer region 12 with the laser beam 24 when the signal intensity of digital data produced by increasing the laser power of the laser beam 24 emitted from the first laser stimulating ray source 21 cannot come to be equal to or higher than the threshold value T.

As shown in FIG. 31, when the signal intensity determining means 87 of the data processing apparatus 54 according to this embodiment determines that the signal intensity of digital data S (P0) produced by exciting stimulable phosphor contained in a stimulable phosphor layer regions 12 with the laser beam 24 having the reference laser power P0, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 is lower than the threshold value T, the signal intensity determining means 87 increases the laser power of the laser beam 24 emitted from the first laser stimulating ray source 21 by $\Delta P$ N times where N is an integer equal to or greater than 2 to irradiate the stimulable phosphor layer region 12 therewith, thereby exciting stimulable phosphor contained in the stimulable phosphor layer region 12. Nevertheless, when the signal intensity determining means 87 determines that the signal intensity of digital data produced by photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 cannot come to be equal to or higher than the threshold value T, it determines that no radiation energy is stored in the stimulable phosphor layer regions 12 and terminates irradiation of the stimulable phosphor layer regions 12 with the laser beam 24.

More specifically, the control unit 70 first outputs a reference drive signal to the first laser stimulating ray source 21 and supplies relatively low drive current to the first laser stimulating ray source 21, thereby causing the first laser stimulating ray source 21 to emit a laser beam 24 having the reference laser power P0 which is relatively low. Similarly to the embodiment shown in FIGS. 27 and 28, analog data are produced by photoelectrically detecting stimulated emission 45 released from a stimulable phosphor layer region 12 and the analog data are integrated by the integrating amplifier 90.

When a predetermined time, for example, several microseconds, has passed after the first stimulating ray source 21 was turned on, the control unit 70 outputs a drive stop signal to the first stimulating ray source 21, thereby turning it off and outputs an integrated value of the analog data produced by the integrating amplifier 90 to the A/D converter 53.

The integrated value of the analog data is digitized by the A/D converter 53 and digital data S (P0) are output to the temporary memory 85 to be stored therein.

At the same time, the control unit 70 outputs a signal intensity determination start signal to the signal intensity determining means 87 and when the signal intensity determining means 87 receives the signal intensity determination start signal from the control unit 70, it compares the signal intensity of digital data S (P0) stored in the temporary memory 85 with the threshold value T.

When the signal intensity determining means 87 determines that the signal intensity of the digital data S (P0) is equal to or higher than the threshold value T, it transfers the digital data S (P0) temporarily stored in the temporary memory 85 to the data storing means 86 to be stored therein.

In this case, although stimulable phosphor contained in the first stimulable phosphor layer region 12 is excited by the laser beam 24 having the reference laser power P0 which is relatively low, since the signal intensity of the digital data S (P0) is equal to or higher than the threshold value T, it can be considered that the stimulable phosphor layer region 12 stores a sufficient amount of radiation energy detectable in the form of stimulated emission 45.

Therefore, in this embodiment, after the digital data S (P0) have been stored in the predetermined memory area of the summed value storing means 89, the signal intensity determining means 87 further outputs laser power increasing signals to the control unit 70.

As a result, a laser beam 24 having laser power P1 greater than the reference laser power P0 by $\Delta P$ is emitted from the first laser stimulating ray source 21 and projected onto the stimulable phosphor layer region 12 from which the digital data S (P0) were obtained, thereby exciting stimulable phosphor contained in the stimulable phosphor layer region 12. Stimulated emission 45 released from the stimulable phosphor layer region 12 is photoelectrically detected by the photomultiplier 50 to produce analog data and the analog data are integrated by the integrating amplifier 90. Here, P1=P0+$\Delta P$.

When a predetermined time, for example, several microseconds, has passed after the first stimulating ray source 21 was turned on, the control unit 70 outputs a drive stop signal to the first stimulating ray source 21, thereby turning it off and outputs an integrated value of the analog data produced by the integrating amplifier 90 to the A/D converter 53.

The integrated value of the analog data is digitized by the A/D converter 53 and digital data S (P1) are output to the temporary memory 85 to be stored therein. Then, the signal intensity of the digital data S (P1) stored in the temporary memory 85 is compared with the threshold value T by the signal intensity determining means 87.

When the signal intensity determining means 87 determines that the signal intensity of the digital data S (P1) is equal to or higher than the threshold value T, it transfers the digital data S (P1) stored in the temporary memory 85 to the summed value storing means 91 and the digital data S (P1) are stored in a predetermined memory area of the summed value storing means 91. At the same time, the signal intensity determining means 87 outputs a correction effecting signal to the data processing means 88, thereby causing the data processing means 88 to correct the digital data S (P1) in accordance with the following formula and add the corrected digital data to the digital data S (P0) stored in the summed value storing means 91.

$$\Sigma S(P1)=S(P0)+S(P1)\times C3(P0/P1)$$

In this formula, $\Sigma S$ (P1) is a summed value of digital data to be obtained by correcting digital data S (P1) produced by increasing the laser power of the laser beam 24 by $\Delta P$ and adding the corrected digital data to the digital data S (P0) and C3 (P0/P1) is a correction coefficient and a function of the reference laser power P0 and the laser power P1.

In this manner, the laser power of the laser beam 24 emitted from the first laser stimulating ray source 21 is sequentially increased by $\Delta P$ and digital data S (Pi) are produced by irradiating the stimulable phosphor layer region 12 from which the digital data S (P1) were obtained with the laser beam 24 to excite stimulable phosphor contained in the stimulable phosphor layer region 12, photoelectrically detecting stimulated emission 45 released from the stimulable phosphor layer region 12 by the photomultiplier 50 to produce analog data, integrating the analog data by the integrating amplifier 90 and digitizing the integrated value of the analog data by the A/D converter 53. When the signal intensity determining means 87 determines that the signal intensity of the digital data S (Pi) is equal to or higher than the threshold value T, the data processing means 88 corrects the digital data S (Pi) in accordance with the following formula and adds the corrected digital data to digital data S (Pi-1) stored in the summed value storing means 89.

$$\Sigma S(Pi)=\Sigma S(Pi-1)+S(Pi)\times C3(P0/Pi)$$

In this formula, $\Sigma S$ (Pi) is a summed value of digital data obtained by increasing the laser power of the laser beam 24 i times, producing digital data, correcting the digital data and summing the corrected digital data, $\Sigma S$ (Pi-1) is a summed value of digital data obtained by increasing the laser power of the laser beam 24 (i-1) times, producing digital data, correcting the digital data and summing the corrected digital data and C3 (P0/Pi) is a correction coefficient and a function of the reference laser power P0 and the laser power Pi.

The laser power of the laser beam 24 emitted from the first laser stimulating ray source 21 is sequentially increased by $\Delta P$ in this manner and the signal intensity determining means 87 determines that the signal intensity of the digital data S (Pj) produced by irradiating the stimulable phosphor layer region 12 from which the digital data S (P1) were obtained with the laser beam 24 to excite stimulable phosphor contained therein, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 has come to be lower than the threshold value T, since it can be considered that radiation energy detectable in the form of stimulated emission 45 no longer remains in the stimulable phosphor layer region 12, the signal intensity determining means 87 outputs a data production completion signal to the data processing means 88, thereby causing the data processing means 88 to transfer the summed value $\Sigma S$ (Pj-1) of digital data stored in a predetermined memory area of the summed value storing means 91 to the data storing means 86 to be stored therein as digital data of the stimulable phosphor layer region 12.

To the contrary, when the signal intensity determining means 87 determines that the signal intensity of the digital data S (P0) produced by exciting stimulable phosphor contained in the stimulable phosphor layer region 12 with the laser beam 24 having the reference laser power P0, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 is lower than the threshold value T, the signal intensity determining means 87 outputs laser power increasing signals to the control unit 70 N times at maximum, thereby causing the control unit 1 to increase the laser power of a laser beam 24 emitted from the first laser stimulating ray source 21 to emit a laser beam 24 by $\Delta P$ N times, and compares the signal intensity of digital data produced by exciting stimulable phosphor contained in the stimulable phosphor layer region 12 from which the digital data S (P0) were obtained with the laser beam 24, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 with the threshold value T.

When the signal intensity determining means 87 determines that the signal intensity of digital data S (Pn) produced by exciting stimulable phosphor contained in the stimulable phosphor layer region 12 from which the digital data S (P0) were obtained with the laser beam 24, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 has come to be equal to or higher than the threshold value T, the signal intensity determining means 87 stores the digital data S (Pn) in a predetermined memory area of the summed value storing means 91. Here, n=1, - - -, N.

In this case, although the signal intensity of the digital data S (P0) produced by exciting stimulable phosphor contained in the stimulable phosphor layer region 12 with the laser beam 24 having the reference laser power P0 is lower than the threshold value T, since the laser power of the laser beam 24 is increased by $\Delta P$ and stimulable phosphor contained in the stimulable phosphor layer region 12 is excited with the laser beam 24 having higher laser power, the signal intensity of the digital data S (Pn) produced by exciting stimulable phosphor contained in the stimulable phosphor layer region 12 with the laser beam 24 having the laser power Pn has come to be equal to or higher than the threshold value T. Therefore, it can be considered that if stimulable phosphor contained in the stimulable phosphor layer region 12 with a laser beam 24 having much higher laser power, radiation energy stored in the stimulable phosphor layer region 12 can be released in the form of stimulated emission 45 and detected.

Therefore, the signal intensity determining means 87 outputs a laser power increasing signal to the control unit 70, thereby increasing the laser power of the laser beam 24 emitted from the first laser stimulating ray source 21 by ΔP.

Similarly to the case where the signal intensity of the digital data S (P0) produced by exciting stimulable phosphor contained in the stimulable phosphor layer region 12 with the laser beam 24 having the reference laser power P0, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 is determined to be equal to or higher than the threshold value T, the signal intensity determining means 87 and the data processing means 88 of the data processing apparatus 54 repeat the production of digital data, correction of the digital data and storage of the digital data in the summed value storing means 91 until the signal intensity of digital data S (Pi) produced by exciting stimulable phosphor contained in the stimulable phosphor layer region 12 with a laser beam 24 having greater laser power has come to be lower than the threshold value T and when the signal intensity determining means 87 determines that the signal intensity of digital data S (Pi) has come to be lower than the threshold value T, it outputs a data production completion signal to the data processing means 88, thereby causing the data processing means 88 to transfer the summed value ΣS (Pj−1) of digital data stored in a predetermined memory area of the summed value storing means 91 to the data storing means 86 to be stored therein as digital data of the stimulable phosphor layer region 12.

To the contrary, when the signal intensity determining means 87 determines that the signal intensity of digital data S (P0) produced by exciting stimulable phosphor contained in the stimulable phosphor layer region 12 with the laser beam 24 having the reference laser power P0, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 is lower than the threshold value T, even though the signal intensity determining means 87 output laser power increasing signals to the control unit 70 N times in total, thereby causing the first laser stimulating ray source 21 to emit laser beams 24 whose laser powers were increased by ΔP and the stimulable phosphor layer region 12 was irradiated with the laser beams 24, if the signal intensity determining means 87 determines that the signal intensity of the digital data S (PN) produced by exciting stimulable phosphor contained in the stimulable phosphor layer region 12 with the laser beam 24 having laser power PN, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 is still lower than the threshold value T, since it is highly probable that no radiation energy is stored in the stimulable phosphor layer region 12, the signal intensity determining means 87 determines that digital data of the stimulable phosphor layer region 12 are zero and stores zero in the data storing means 86.

According to this embodiment, when the signal intensity determining means 87 of the data processing apparatus 54 determines that the signal intensity of digital data S (P0) produced by exciting stimulable phosphor contained in a stimulable phosphor layer regions 12 with the laser beam 24 having the reference laser power P0, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 is equal to or higher than the threshold value T, digital data are produced by sequentially increasing the laser power of the laser beam 24 emitted from the first laser stimulating ray source 21 by ΔP, irradiating the stimulable phosphor layer region 12 with the laser beam 24 to excite stimulable phosphor contained in the stimulable phosphor layer region 12, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 and the thus produced digital data are corrected in accordance with the laser power of the laser beam 24 used fro producing the digital data and summed to produce digital data of the stimulable phosphor layer region 12 until the signal intensity of the digital data has come to be lower than the threshold value since radiation energy stored in the stimulable phosphor layer region 12 is reduced and the intensity of stimulated emission 45 is decreased. Therefore, since substantially all radiation energy stored in the stimulable phosphor layer region 12 can be completely released in the form of stimulated emission 45, it is possible to detect stimulated emission 45 with high sensitivity and produce biochemical analysis data having high quantitative characteristics. Moreover, since stimulable phosphor contained in a stimulable phosphor layer region 12 is first excited with a laser beam 24 having the reference laser power P0 which is relatively low and further excited by increasing the laser power of the laser beam 24 by ΔP, it is possible to reliably prevent stimulated emission released from stimulable phosphor contained in the stimulable phosphor layer region 12 by exciting the stimulable phosphor with the laser beam 24 from becoming too great to exceed the upper limit of the dynamic range of the photomultiplier 50 and to prevent the signal intensity of digital data produced by detecting the stimulated emission 45 from being saturated, thereby degrading the quantitative characteristics of biochemical analysis data.

Furthermore, according to this embodiment, when the signal intensity determining means 87 of the data processing apparatus 54 determines that the signal intensity of digital data S (P0) produced by exciting stimulable phosphor contained in a stimulable phosphor layer regions 12 with the laser beam 24 having the reference laser power P0, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 is lower than the threshold value T, the laser power of the laser beam emitted from the first laser stimulating ray source 21 is increased by ΔP N times at maximum and the stimulable phosphor layer region 12 is irradiated with the laser beam 24, thereby exciting stimulable phosphor contained therein. When the signal intensity determining means 87 determines that the signal intensity of digital data S (Pn) produced by photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 has come to be equal to or higher than the threshold value T, digital data are produced by sequentially increasing the laser power of the laser beam 24 emitted from the first laser stimulating ray source 21 by ΔP, irradiating the stimulable phosphor layer region 12 with the laser beam 24 to excite stimulable phosphor contained in the stimulable phosphor layer region 12, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 and the thus produced digital data are corrected in accordance with the laser power of the laser beam 24 used fro producing the digital data and summed to produce digital data of the stimulable phosphor layer region 12 until the signal intensity of the digital data has come to be lower than the threshold value because radiation energy stored in the stimulable phosphor layer region 12 is reduced and the intensity of stimulated emission 45 is decreased. Therefore, since all radiation energy stored in each of a number of the stimulable phosphor layer regions 12 can be completely released in the form of stimulated emission 45 and digital data of the stimulable phosphor layer region 12 can be produced by detecting stimulated emission 45, even in the case where radiation energy stored in a stimulable phosphor region 12 is too small and the intensity of stimulated emission 45 released from the stimulable phosphor layer region 12 when stimulable phosphor contained in the stimulable phosphor layer region 12 is excited is too low, it is possible to produce biochemical analysis data having high quantitative characteristics by detecting stimulated emission 45 with high sensitivity.

Moreover, according to this embodiment, when the signal intensity determining means 87 of the data processing apparatus 54 determines that the signal intensity of digital data S (P0) produced by exciting stimulable phosphor contained in a stimulable phosphor layer regions 12 with the laser beam 24 having the reference laser power P0, photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 is lower than the threshold value T, the laser power of the laser beam emitted from the first laser stimulating ray source 21 are increased by ΔP N times in total and the stimulable phosphor layer region 12 is irradiated with the laser beam 24, thereby exciting stimulable phosphor contained therein. Nevertheless, when the signal intensity of digital data S (PN) produced by photoelectrically detecting stimulated emission 45 released from the stimulable phosphor layer regions 12 by the photomultiplier 50 to produce analog data, integrating the analog data by the integrating amplifier 90 and digitizing the integrated value of the analog data by the A/D converter 53 has not come to be equal to or higher than the threshold value T, since it is judged that no radiation energy is stored in the stimulable phosphor layer regions 12 and the signal intensity determining means 87 determines that digital data of the stimulable phosphor layer region 12 are zero and stores the thus determined digital data in the data storing means 88, it is possible to efficiently read radiation data recorded in a number of the stimulable phosphor layer regions 12 by selectively labeling with the radioactive labeling substance to produce biochemical analysis data.

Figure 32:
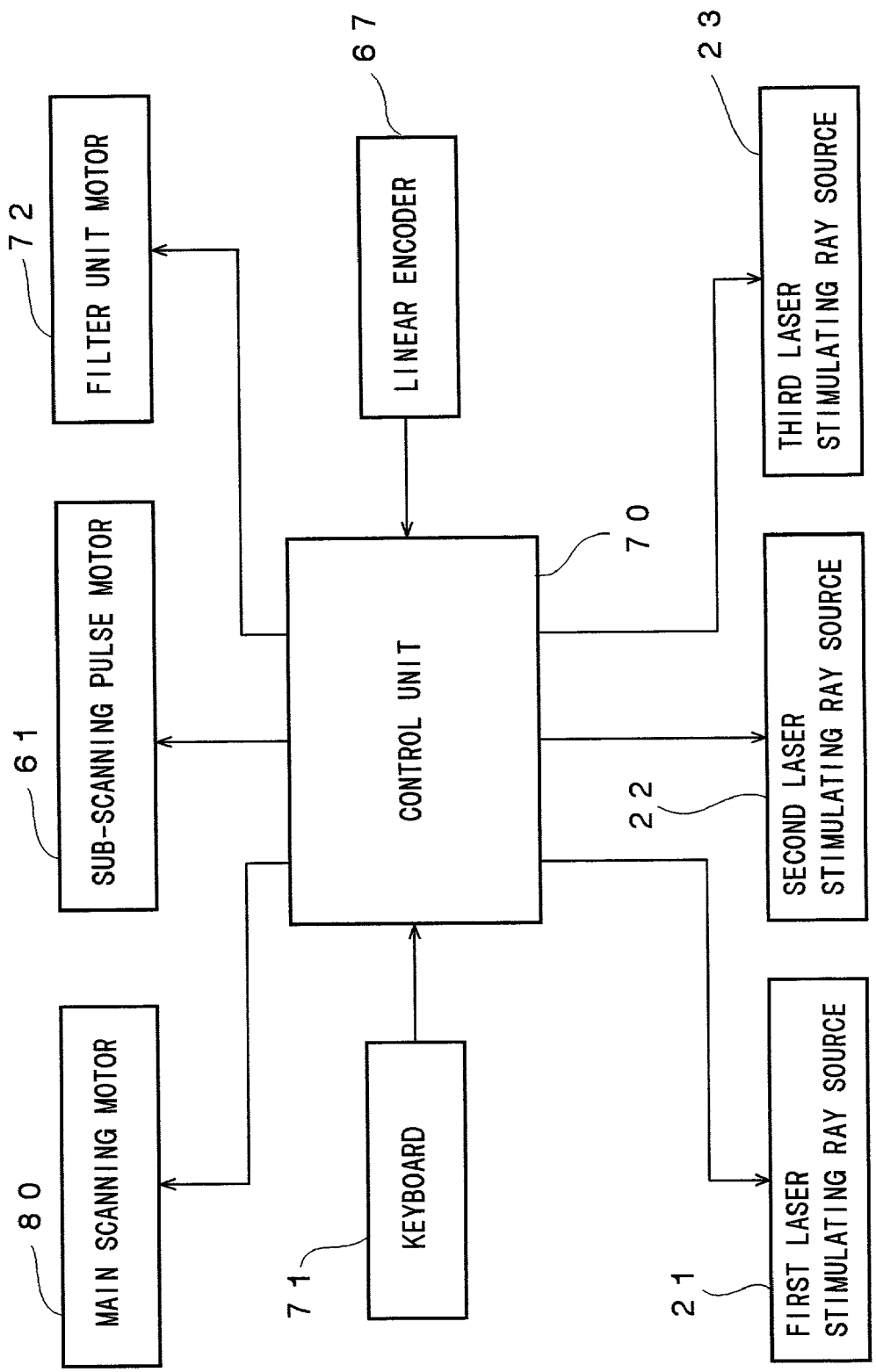
FIG. 32 is a block diagram of a control system, an input system, a drive system and a detection system of a scanner which is a further preferred embodiment of the present invention.

FIG. 32 is a block diagram of a control system, an input system, a drive system and a detection system of a scanner which is a further preferred embodiment of the present invention.

As shown in FIG. 32, a scanner according to this embodiment has the same configuration as that of the scanner shown in FIGS. 6 to 13 except that it is provided with a main scanning motor 80 for continuously moving the endless belt 66 to which the optical head 35 is fixed at a constant speed in the main scanning direction indicated by the arrow X in FIG. 12 instead of the main scanning stepping motor 65.

In this embodiment, the control unit 70 is adapted for selectively outputting a drive signal to the first laser stimulating ray source 21, the second laser stimulating ray source 22 or the third laser stimulating ray source 23 in accordance with a detection signal indicating the position of the optical head 35 input from the linear encoder 67.

The thus constituted scanner reads radiation data recorded in a stimulable phosphor sheet 10 by exposing a number of the stimulable phosphor layer regions 12 to a radioactive labeling substance contained in a number of the absorptive regions 4 formed in the biochemical analysis unit 1 and produces biochemical analysis data in the following manner.

A stimulable phosphor sheet 10 is first set on the glass plate 41 of the stage 40 by a user.

An instruction signal indicating that radiation data recorded in the stimulable phosphor layer 12 formed in the support 11 of the stimulable phosphor sheet 10 are to be read is then input by the user through the keyboard 71.

The instruction signal input through the keyboard 71 is input to the control unit 70 and when the control unit 70 receives the instruction signal, it outputs a drive signal to the filter unit motor 72 in accordance with the instruction signal, thereby moving the filter unit 48 so as to locate the filter member 51d provided with the filter 52d having a property of transmitting only light having a wavelength corresponding to that of stimulated emission emitted from stimulable phosphor but cutting off light having a wavelength of 640 nm in the optical path of stimulated emission 45.

The control unit 70 further outputs a drive signal to the main scanning motor 80 to move the optical head 35 in the main scanning direction and when it determines based on a detection signal indicating the position of the optical head 35 input from the linear encoder 67 that the optical head 35 has reached a position where a laser beam 24 can be projected onto a first stimulable phosphor layer region 12 among a number of the stimulable phosphor layer regions 12 formed in the support 11 of the stimulable phosphor sheet 10, it outputs a drive stop signal to the main scanning stepping motor 65 and a drive signal to the first stimulating ray source 21, thereby actuating it to emit a laser beam 24 having a wavelength of 640 nm.

A laser beam 24 emitted from the first laser stimulating source 21 passes through the collimator lens 25, thereby being made a parallel beam, and is reflected by the mirror 26.

The laser beam 24 reflected by the mirror 26 passes through the first dichroic mirror 27 and the second dichroic mirror 28 and advances to the mirror 29.

The laser beam 24 advancing to the mirror 29 is reflected by the mirror 29 and advances to the mirror 32 to be reflected thereby.

The laser beam 24 reflected by the mirror 32 passes through the hole 33 of the perforated mirror 34 and advances to the concave mirror 38.

The laser beam 24 advancing to the concave mirror 38 is reflected by the concave mirror 38 and enters the optical head 35.

The laser beam 24 entering the optical head 35 is reflected by the mirror 36 and condensed by the aspherical lens 37 onto the first stimulable phosphor layer region 12 of the stimulable phosphor sheet 10 placed on the glass plate 41 of a stage 40.

As a result, stimulable phosphor contained in the first stimulable phosphor layer region 12 formed in the stimulable phosphor sheet 10 is excited by the laser beam 24, thereby releasing stimulated emission 45 from the first stimulable phosphor layer region 12.

The stimulated emission 45 released from the first stimulable phosphor layer region 12 is condensed onto the mirror 36 by the aspherical lens 37 provided in the optical head 35 and reflected by the mirror 36 on the side of the optical path of the laser beam 24, thereby being made a parallel beam to advance to the concave mirror 38.

The stimulated emission 45 advancing to the concave mirror 38 is reflected by the concave mirror 38 and advances to the perforated mirror 34.

As shown in FIG. 7, the stimulated emission 45 advancing to the perforated mirror 34 is reflected downward by the perforated mirror 34 formed as a concave mirror and advances to the filter 52d of the filter unit 48.

Since the filter 52d has a property of transmitting only light having a wavelength corresponding to that of stimulated emission emitted from stimulable phosphor and cutting off light having a wavelength of 640 nm, light having a wavelength of 640 nm corresponding to that of the stimulating ray is cut off by the filter 52d and only light having a wavelength corresponding to that of stimulated emission passes through the filter 52d to be photoelectrically detected by the photomultiplier 50.

Analog data produced by photoelectrically detecting stimulated emission 45 with the photomultiplier 50 are converted by an A/D converter 53 into digital data and the digital data are fed to a data processing apparatus 54.

Since the main scanning motor 80 is constituted so as to continuously move the endless belt 66 to which the optical head 35 is fixed at a constant speed in the main scanning direction indicated by the arrow X in FIG. 12, the optical head 35 is continuously moved at a constant speed in the main scanning direction, whereby the laser beam 24 emitted from the first laser stimulating ray source 21 continuously moves on the first stimulable phosphor layer region 12 and excites stimulable phosphor contained in the first stimulable phosphor layer region 12.

The control unit 70 outputs a drive stop signal to the first laser stimulating ray source 21 based on a detection signal indicating the position of the optical head 35 input from the linear encoder 67 immediately before the optical head 35 has reached a position where the first stimulable phosphor layer region 12 cannot be irradiated with the laser beam 24 and turns off the first laser stimulating ray source 21.

The speed of the endless belt 66 driven by the main scanning motor 80 is set in such a manner that even in the case where radiation energy stored in a stimulable phosphor layer region 12 is too small, digital data having sufficiently high signal intensity can be produced by moving the laser beam 24 emitted from the first laser stimulating ray source 21 on a stimulable phosphor layer region 12 to excite stimulable phosphor contained therein and photoelectrically detecting stimulated emission 45 released from the stimulable phosphor layer region 12 by the photomultiplier 50.

The optical head 35 is further moved in the main scanning direction indicated by the arrow X in FIG. 6 and when the control unit 70 determines based on a detection signal indicating the position of the optical head 35 input from the linear encoder 67 that the optical head 35 has reached a position where a laser beam 24 can be projected onto a second stimulable phosphor layer region 12 next to the first stimulable phosphor layer region 12, it outputs a drive signal to the first stimulating ray source 21 to turn it on, thereby causing the first laser stimulating ray source 21 to emit a laser beam 24 having a wavelength of 640 nm.

A laser beam 24 emitted from the first laser stimulating source 21 passes through the collimator lens 25, thereby being made a parallel beam, and is reflected by the mirror 26.

The laser beam 24 reflected by the mirror 26 passes through the first dichroic mirror 27 and the second dichroic mirror 28 and advances to the mirror 29.

The laser beam 24 advancing to the mirror 29 is reflected by the mirror 29 and advances to the mirror 32 to be reflected thereby.

The laser beam 24 reflected by the mirror 32 passes through the hole 33 of the perforated mirror 34 and advances to the concave mirror 38.

The laser beam 24 advancing to the concave mirror 38 is reflected by the concave mirror 38 and enters the optical head 35.

The laser beam 24 entering the optical head 35 is reflected by the mirror 36 and condensed by the aspherical lens 37 onto the second stimulable phosphor layer region 12 of the stimulable phosphor sheet 10 placed on the glass plate 41 of a stage 40.

As a result, stimulable phosphor contained in the second stimulable phosphor layer region 12 is excited, whereby stimulated emission 45 is released from the second stimulable phosphor layer region 12 and similarly to the stimulated emission 45 released from the first stimulable phosphor layer region 12, the stimulated emission 45 is photoelectrically detected by the photomultiplier 50 to produce analog data.

The analog data produced by the photomultiplier 50 are output to the A/D converter 53 to be converted to digital data and the digital data are output to the data processing apparatus 54.

The control unit 70 outputs a drive stop signal to the first laser stimulating ray source 21 based on a detection signal indicating the position of the optical head 35 input from the linear encoder 67 immediately before the optical head 35 has reached a position where the second stimulable phosphor layer region 12 cannot be irradiated with the laser beam 24 and turns off the first laser stimulating ray source 21.

In this manner, the stimulable phosphor layer regions 12 included in a first line of the stimulable phosphor layer regions 12 formed in the support 11 of the stimulable phosphor sheet 10 are sequentially irradiated with the laser beam 24 by continuously moving the optical head 35 at a constant speed in the main scanning direction and repeating the on and off operation of the first laser stimulating ray source 21 based on a detection signal indicating the position of the optical head 35 input from the linear encoder 67, stimulated emission 45 released from the stimulable phosphor layer regions 12 included in a first line of the stimulable phosphor layer regions 12 is photoelectrically detected by photomultiplier 50 to produce analog data and the analog data are digitized by the A/D converter 53, thereby producing and forwarding digital data to the data processing apparatus 54.

When the control unit 70 determines based on a detection signal indicating the position of the optical head 35 input from the linear encoder 67 that the optical head 35 has been moved by one scanning line in the main scanning direction and that the stimulable phosphor layer regions 12 included in the first line of the stimulable phosphor layer regions 12 formed in the support 11 of the stimulable phosphor sheet 10 have been scanned with the laser beam 24, it outputs a drive signal to the main scanning motor 78, thereby returning the optical head 35 to its original position and outputs a drive signal to the sub-scanning pulse motor 61, thereby causing it to move the movable base plate 63 by one scanning line in the sub-scanning direction.

When the control unit 70 determines based on a detection signal indicating the position of the optical head 35 input from the linear encoder 67 that the optical head 35 has been returned to its original position and determines that the movable base plate 63 has been moved by one scanning line in the sub-scanning direction, similarly to the manner that the stimulable phosphor layer regions 12 included in the first line of the stimulable phosphor layer regions 12 formed in the support 11 of the stimulable phosphor sheet 10 were sequentially irradiated with the laser beam 24 emitted from the first laser stimulating ray source 21, the stimulable phosphor layer regions 12 included in a second line of the stimulable phosphor layer regions 12 formed in the support 11 of the stimulable phosphor sheet 10 are sequentially irradiated with the laser beam 24 emitted from the first laser stimulating ray source 21, thereby exciting stimulable phosphor contained in the stimulable phosphor layer regions 12 included in the second line and stimulated emission 45 released from the stimulable phosphor layer regions 12 is sequentially and photoelectrically detected by the photomultiplier 50 to produce analog data.

The analog data produced by photoelectrically detecting stimulated emission 45 by the photomultiplier 50 are converted by the A/D converter 53 to digital data and the digital data are forwarded to the data processing apparatus 54.

When all of the stimulable phosphor layer regions 12 formed in the support 11 of the stimulable phosphor sheet 10 have been scanned with the laser beam 24 to excite stimulable phosphor contained in the stimulable phosphor layer regions 12 and digital data produced by photoelectrically detecting stimulated emission 45 released from the stimulable phosphor layer regions 12 by the photomultiplier 50 to produce analog data and digitizing the analog data by the A/D converter 53 have been forwarded to the data processing apparatus 54, the control unit 70 outputs a drive stop signal to the first laser stimulating ray source 21, thereby turning it off.

In the above described manner, radiation data recorded in a number of the stimulable phosphor layer regions 12 formed in the support 11 of the stimulable phosphor sheet 10 are read and biochemical analysis data are produced.

According to this embodiment, only when the optical head 35 is located at positions where one of the stimulable phosphor layer regions 12 formed in the support 11 of the stimulable phosphor sheet 10 can be sequentially irradiated with a laser beam 24 emitted from the first laser stimulating ray source 21, the first laser stimulating ray source 21 is activated, thereby irradiating the stimulable phosphor layer region 12 with the laser beam 24. Therefore, since it is possible to reliably prevent the laser beam 24 from entering a neighboring stimulable phosphor layer region 12 to be next stimulated as the laser beam 24 is scanned and thus prevent stimulable phosphor contained in the neighboring stimulable phosphor layer region 12 from being excited to release radiation energy stored therein, biochemical analysis data having an excellent quantitative characteristic can be produced.

Figure 33:
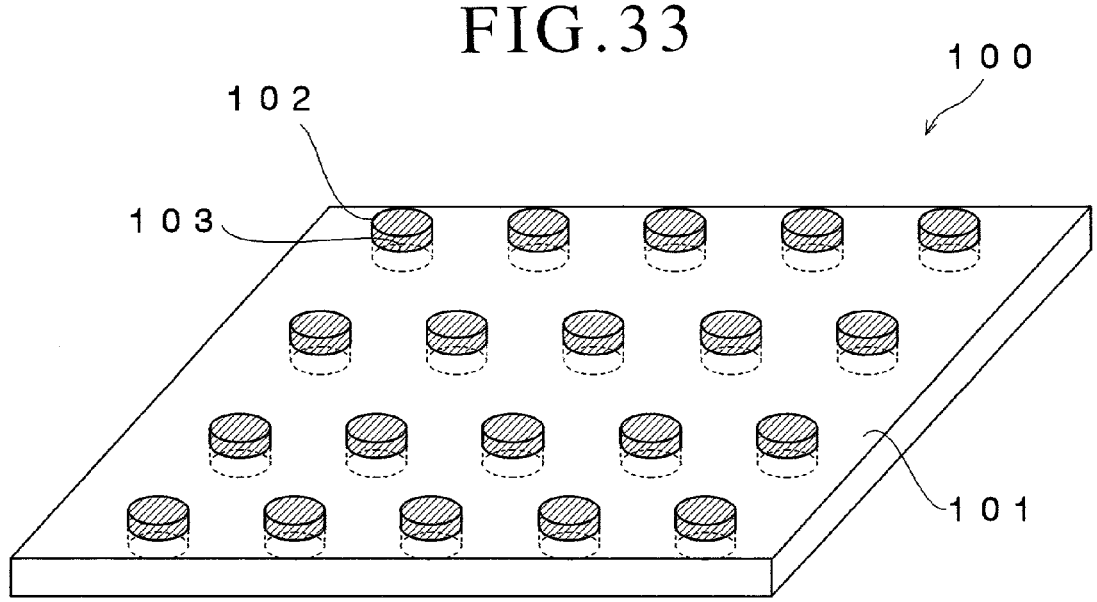
FIG. 33 is a schematic perspective view showing a stimulable phosphor sheet used for a method for producing biochemical analysis data which is a further preferred embodiment of the present invention.

FIG. 33 is a schematic perspective view showing a stimulable phosphor sheet used for a method for producing biochemical analysis data which is a further preferred embodiment of the present invention, As shown in FIG. 33, a stimulable phosphor sheet 100 according to this embodiment includes a support 101 made of silicon nitride and the support 101 is formed with a number of substantially circular through-holes 103 in the same pattern as that of a number of the through-holes, namely, a number of the absorptive regions 4 formed in the substrate 2 of the biochemical analysis unit 1 so that each of them has the same size as that of the absorptive region 4 and a number of stimulable phosphor layer regions 102 are formed by charging BaFX system stimulable phosphor (where X is at least one halogen atom selected from the group consisting of Cl, Br and I) capable of absorbing and storing radiation energy in the through-holes 103.

Therefore, although not accurately shown in FIG. 33, in this embodiment, substantially circular stimulable phosphor layer regions 102 having a size of about 0.07 $cm^2$ are regularly formed in the manner of a matrix of 120 columns× 160 lines in the support 11 and, therefore, 19,200 stimulable phosphor layer regions 102 are dot-like formed.

In this embodiment, the stimulable phosphor is charged in the through-holes so that the surfaces of the stimulable phosphor layer regions 102 are located above the surface of the support 101.

Figure 34:
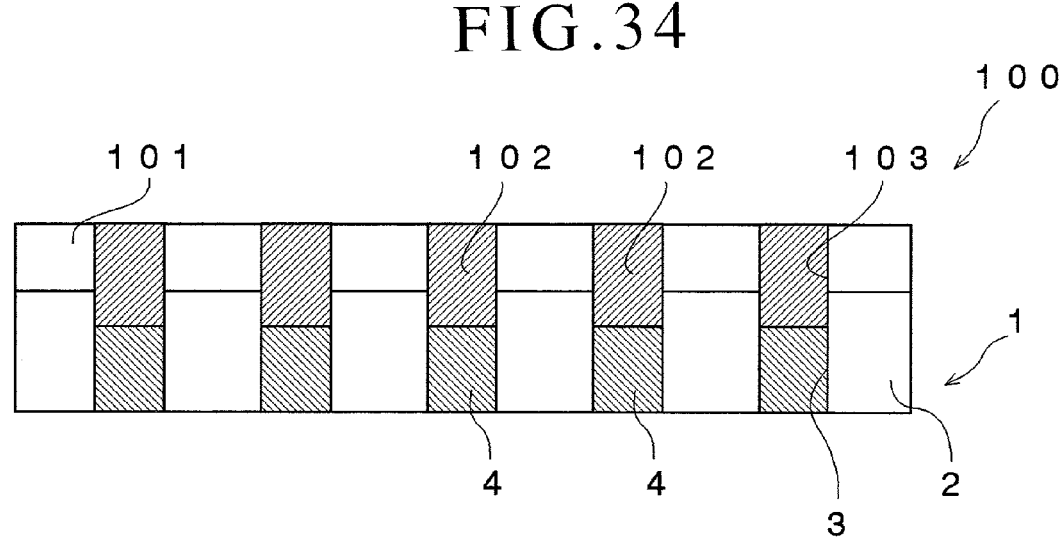
FIG. 34 is a schematic-cross-sectional view showing a method for exposing a number of stimulable phosphor layer regions formed in a support of a stimulable phosphor sheet to a radioactive labeling substance contained in a number of absorptive regions formed in a substrate of a biochemical analysis unit.

FIG. 34 is a schematic cross-sectional view showing a method for exposing a number of the stimulable phosphor layer regions 102 formed in the support 101 of the stimulable phosphor sheet 100 to a radioactive labeling substance contained in a number of the absorptive regions 4 formed in the substrate 2 of the biochemical analysis unit 1.

As shown in FIG. 34, when a number of the stimulable phosphor layer regions 102 formed in the support 101 of the stimulable phosphor sheet 100 are to be exposed to a radioactive labeling substance contained in a number of the absorptive regions 4 formed in the substrate 2 of the biochemical analysis unit 1, the stimulable phosphor sheet 100 is superposed on the biochemical analysis unit 1 in such a manner that a number of the stimulable phosphor layer regions 102 formed in the support 101 of the stimulable phosphor sheet 100 are located in the corresponding through-holes 3 formed in the substrate 2 of the biochemical analysis unit 1 and face the corresponding absorptive regions 4.

In this manner, each of the stimulable phosphor layer regions 102 formed in the support 101 of the stimulable phosphor sheet 100 is kept to face the corresponding absorptive region 4 formed in the substrate 2 of the biochemical analysis unit 1 for a predetermined time period, whereby a number of the stimulable phosphor layer regions 102 formed in the support 101 of the stimulable phosphor sheet 100 are exposed to the radioactive labeling substance selectively contained in a number of the absorptive regions 4 formed in the substrate 2 of the biochemical analysis unit 1.

During the exposure operation, electron beams (β rays) are released from the radioactive labeling substance contained in the absorptive regions 4 of the biochemical analysis unit 1. However, since a number of the absorptive regions 4 of the biochemical analysis unit 1 are formed spaced apart from each other in the substrate 2 made of stainless steel and the substrate 2 made of stainless steel capable of attenuating radiation energy is present around each of the absorptive regions 4, electron beams (β rays) released from the radioactive labeling substance contained in the absorptive regions 4 of the biochemical analysis unit 1 can be efficiently prevented from scattering in the substrate 2 of the biochemical analysis unit 1. Further, since a number of the stimulable phosphor layer regions 102 of the stimulable phosphor sheet 100 are formed by charging stimulable phosphor in a number of the through-holes 103 formed in the support 101 made of silicon nitride and the support 101 made of silicon nitride capable of attenuating radiation energy is present around each of the stimulable phosphor layer regions 102, electron beams (β rays) released from the radioactive labeling substance contained in the absorptive regions 4 of the biochemical analysis unit 1 can be efficiently prevented from scattering in the support 101 of the stimulable phosphor sheet 100. Therefore, it is possible to selectively expose only the stimulable phosphor layer region 102 each of the absorptive regions 4 faces to the electron beams (β rays) released from the radioactive labeling substance contained in each of the absorptive regions 4.

Therefore, according to this embodiment, it is possible to prevent noise caused by the scattering of electron beams (β rays) from being generated in biochemical analysis data produced by photoelectrically detecting stimulated emission 45 released from the stimulable phosphor layer regions 102 of the stimulable phosphor sheet 100 in response to the stimulation with the laser beam 24 and to produce biochemical analysis data having a high quantitative accuracy.

In this manner, radiation data of the radioactive labeling substance are recorded in a number of the stimulable phosphor layer regions 102 formed in the support 101 of the stimulable phosphor sheet 100.

The radiation data recorded in a number of the stimulable phosphor layer regions 102 of the stimulable phosphor sheet 100 are read using the scanner shown in FIGS. 6 to 13, the scanner shown in FIGS. 20 and 21, the scanner shown in FIG. 22, the scanner shown in FIG. 24, the scanner shown in FIG. 26, the scanner shown in FIGS. 27 and 28, the scanner shown in FIGS. 29 and 30, the scanner shown in FIG. 31 or the scanner shown in FIG. 32, thereby producing biochemical analysis data.

Figure 35:
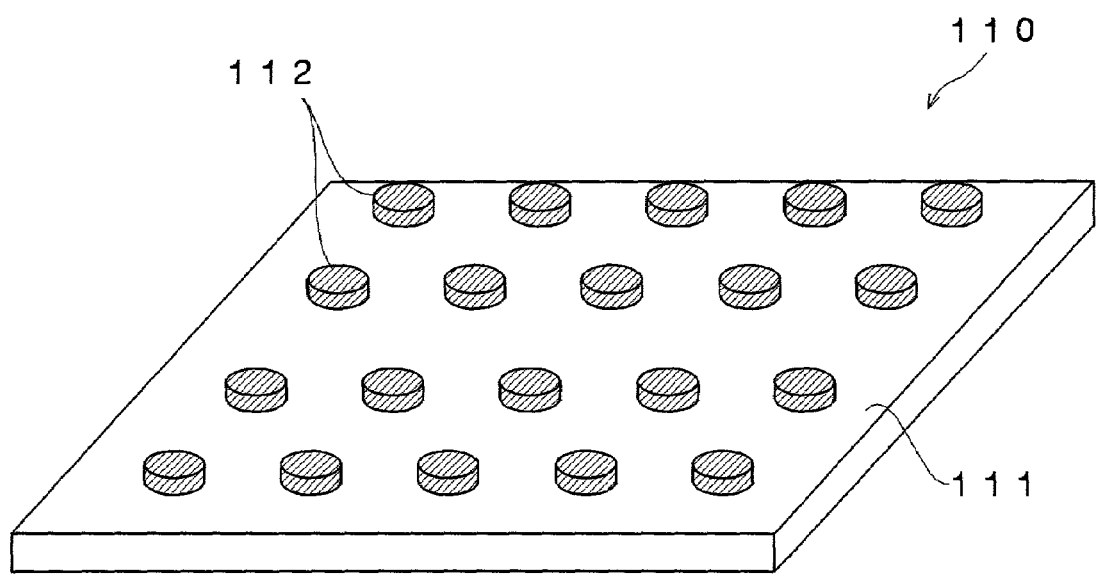
FIG. 35 is a schematic perspective view showing a stimulable phosphor sheet used for a method for producing biochemical analysis data which is a further preferred embodiment of the present invention.

FIG. 35 is a schematic perspective view showing a stimulable phosphor sheet used for a method for producing biochemical analysis data which is a further preferred embodiment of the present invention, As shown in FIG. 35, a stimulable phosphor sheet 110 according to this embodiment includes a support 111 made of made of polyethylene terephthalate and a number of stimulable phosphor layer regions 112 containing BaFX system stimulable phosphor (where X is at least one halogen atom selected from the group consisting of Cl, Br and I) capable of absorbing and storing radiation energy are formed on the surface of the support 111 in a regular pattern.

A number of the stimulable phosphor layer regions 112 are formed on the surface of the support 111 in the same pattern as that of a number of the through-holes, namely, a number of the absorptive regions 4 formed in the substrate 2 of the biochemical analysis unit 1 so that each of them has the same size as that of the absorptive region 4 and a substantially circular shape and, therefore, in this embodiment, substantially circular stimulable phosphor layer regions 112 having a size of about 0.07 cm$^2$ are regularly formed in the manner of a matrix of 120 columns×160 lines on the surface of the support 111 and, therefore, 19,200 stimulable phosphor layer regions 112 are dot-like formed, although not accurately shown in FIG. 35.

Figure 36:
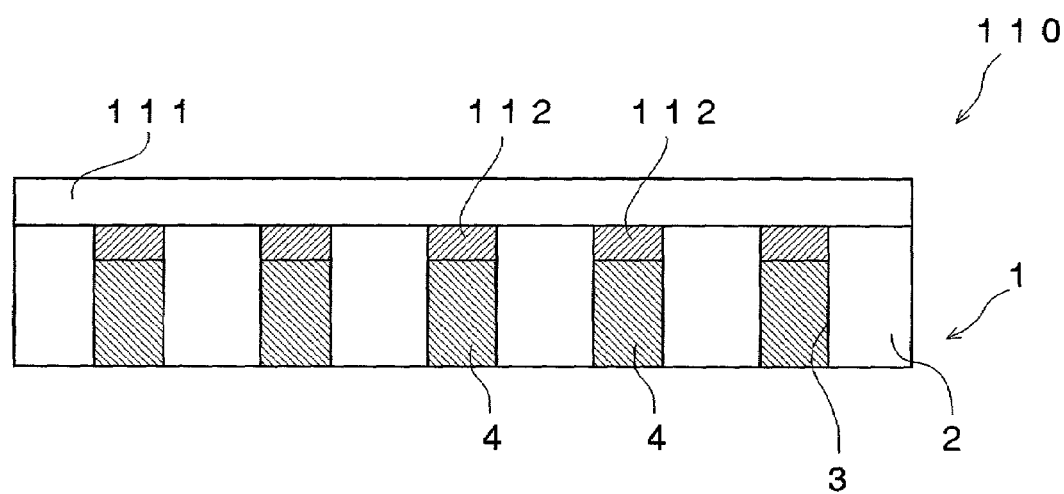
FIG. 36 is a schematic cross-sectional view showing a method for exposing a number of stimulable phosphor layer regions formed on a surface of the support of a stimulable phosphor sheet to a radioactive labeling substance contained in a number of absorptive regions formed in the substrate of the biochemical analysis unit.

FIG. 36 is a schematic cross-sectional view showing a method for exposing a number of the stimulable phosphor layer regions 112 formed on the surface of the support 111 of the stimulable phosphor sheet 110 to a radioactive labeling substance contained in a number of the absorptive regions 4 formed in the substrate 2 of the biochemical analysis unit 1.

As shown in FIG. 35, when a number of the stimulable phosphor layer regions 112 formed on the surface of the support 111 of the stimulable phosphor sheet 110 are to be exposed to a radioactive labeling substance contained in a number of the absorptive regions 4 formed in the substrate 2 of the biochemical analysis unit 1, the stimulable phosphor sheet 110 is superposed on the biochemical analysis unit 1 in such a manner that a number of the stimulable phosphor layer regions 112 formed in the support 111 of the stimulable phosphor sheet 110 are located in the corresponding through-holes 3 formed in the substrate 2 of the biochemical analysis unit 1.

In this manner, each of the stimulable phosphor layer regions 112 formed on the surface of the support 111 of the stimulable phosphor sheet 110 is kept to face the corresponding absorptive region 4 formed in the substrate 2 of the biochemical analysis unit 1 for a predetermined time period, whereby a number of the stimulable phosphor layer regions 112 formed on the surface of the support 111 of the stimulable phosphor sheet 110 are exposed to the radioactive labeling substance selectively contained in a number of the absorptive regions 4 formed in the substrate 2 of the biochemical analysis unit 1.

During the exposure operation, electron beams (β rays) are released from the radioactive labeling substance contained in the absorptive regions 4 of the biochemical analysis unit 1. However, since a number of the absorptive regions 4 of the biochemical analysis unit 1 are formed spaced apart from each other in the substrate 2 made of stainless steel and the substrate 2 made of stainless steel capable of attenuating radiation energy is present around each of the absorptive regions 4, electron beams (β rays) released from the radioactive labeling substance contained in the absorptive regions 4 of the biochemical analysis unit 1 can be efficiently prevented from scattering in the substrate 2 of the biochemical analysis unit 1. Further, since the stimulable phosphor sheet 110 is superposed on the biochemical analysis unit 1 so that a number of the stimulable phosphor layer regions 112 formed in the support 111 of the stimulable phosphor sheet 110 are located in the corresponding through-holes 3 formed in the substrate 2 of the biochemical analysis unit 1, electron beams (β rays) released from the radioactive labeling substance contained in the absorptive regions 4 of the biochemical analysis unit 1 enter only the stimulable phosphor layer region 12 the absorptive region 4 faces and since the support 111 of the stimulable phosphor sheet 110 is made of polyethylene terephthalate capable of capable of attenuating radiation energy, electron beams (β rays) released from the radioactive labeling substance contained in the absorptive regions 4 of the biochemical analysis unit 1 can be efficiently prevented from scattering in the support 111 of the stimulable phosphor sheet 110. Therefore, it is possible to selectively expose only the stimulable phosphor layer region 112 each of the absorptive regions 4 faces to the electron beams (β rays) released from the radioactive labeling substance contained in each of the absorptive regions 4.

Therefore, according to this embodiment, it is possible to prevent noise caused by the scattering of electron beams (β rays) from being generated in biochemical analysis data produced by photoelectrically detecting stimulated emission 45 released from the stimulable phosphor layer regions 112 of the stimulable phosphor sheet 110 in response to the stimulation with the laser beam 24 and to produce biochemical analysis data having a high quantitative accuracy.

In this manner, radiation data of the radioactive labeling substance are recorded in a number of the stimulable phosphor layer regions 112 formed on the surface of the support 111 of the stimulable phosphor sheet 110.

The radiation data recorded in a number of the stimulable phosphor layer regions 112 of the stimulable phosphor sheet 110 are read using the scanner shown in FIGS. 6 to 13, the scanner shown in FIGS. 20 and 21, the scanner shown in FIG. 22, the scanner shown in FIG. 24, the scanner shown in FIG. 26, the scanner shown in FIGS. 27 and 28, the scanner shown in FIGS. 29 and 30, the scanner shown in FIG. 31 or the scanner shown in FIG. 32, thereby producing biochemical analysis data.

Figure 37:
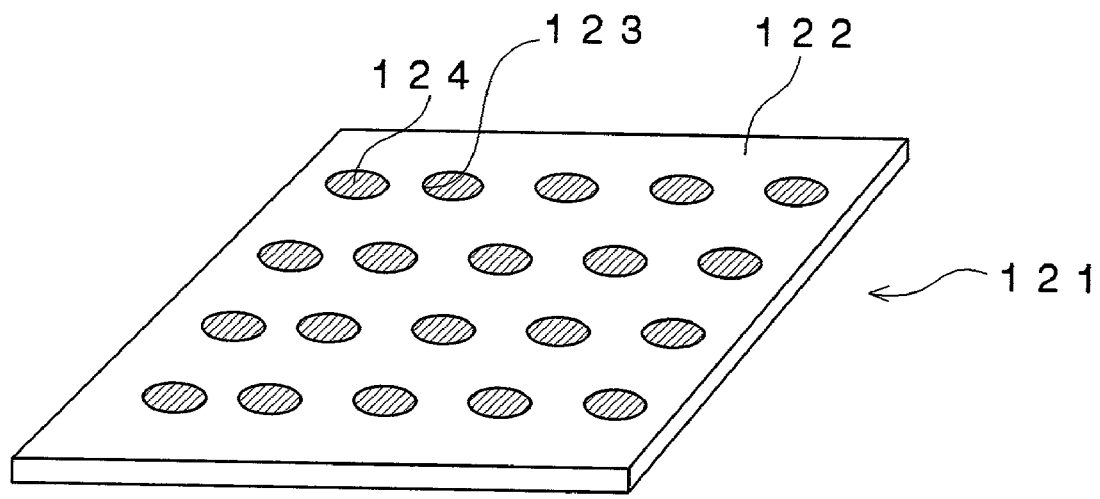
FIG. 37 is a schematic perspective view showing a biochemical analysis unit used in a biochemical analysis data producing method which is a further preferred embodiment of the present invention.

FIG. 37 is a schematic perspective view showing a biochemical analysis unit used in a biochemical analysis data producing method which is a further preferred embodiment of the present invention.

As shown in FIG. 37, a biochemical analysis unit 121 includes a substrate 122 formed of stainless steel and formed with a number of substantially circular through-holes 123 at a high density, and a number of absorptive regions 124 are dot-like formed by charging nylon-6 in the through-holes 123.

Although not accurately shown in FIG. 37, in this embodiment, the through-holes 123 are formed in the substrate 122 so that substantially circular absorptive regions 124 having a size of about 0.07 cm$^2$ are regularly formed in the manner of a matrix of 120 columns×160 lines and, therefore, 19,200 absorptive regions 124 are formed.

A number of absorptive regions 124 are formed by charging absorptive material in the through-holes 123 formed in the substrate 122 in such a manner that the surfaces of the absorptive regions 124 coincide with that of the substrate 122.

Figure 38:
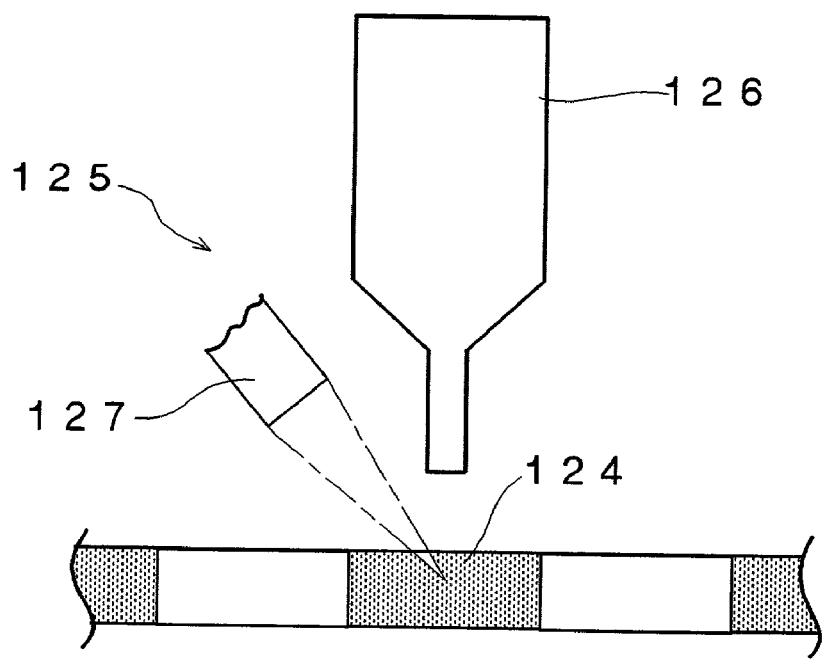
FIG. 38 is a schematic front view showing a spotting device.

FIG. 38 is a schematic front view showing a spotting device.

As shown in FIG. 38, when biochemical analysis is performed, a solution containing specific binding substances such as a plurality of cDNAs whose sequences are known but differ from each other are spotted using a spotting device 125 onto a number of the absorptive regions 124 of the biochemical analysis unit 121 and the specific binding substances are fixed therein.

As shown in FIG. 38, the spotting device 125 includes an injector 126 for ejecting a solution of specific binding substances toward the biochemical analysis unit 121 and a CCD camera 127 and is constituted so that the solution of specific binding substances such as cDNAs are spotted from the injector 126 when the tip end portion of the injector 126 and the center of the absorptive region 124 into which the solution containing specific binding substances is to be spotted are determined to coincide with each other as a result of viewing them using the CCD camera 127, thereby ensuring that the solution of specific binding substances can be accurately spotted into a number of the absorptive regions 124 of the biochemical analysis unit 121.

Figure 39:
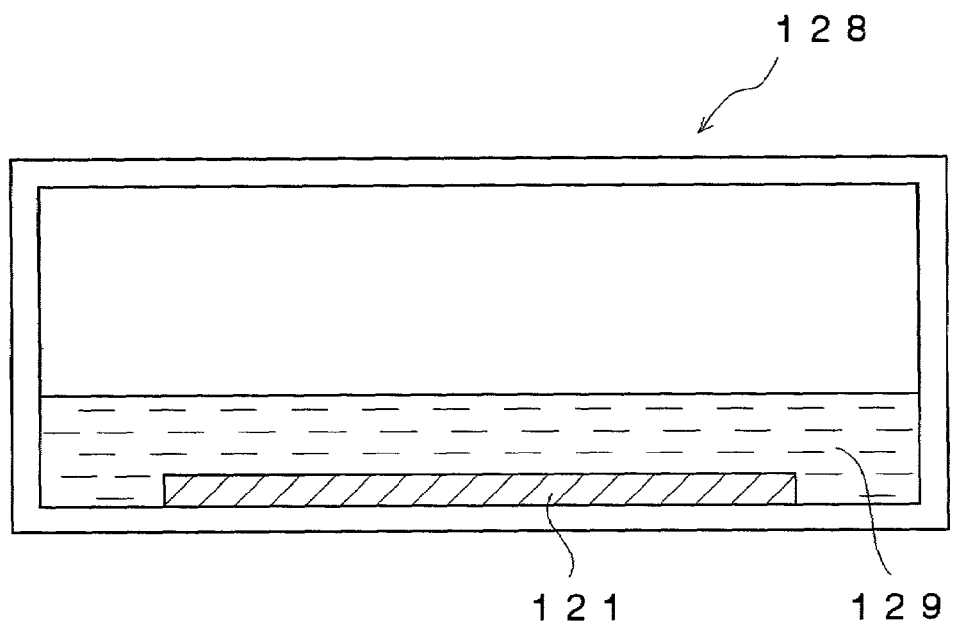
FIG. 39 is a schematic longitudinal cross sectional view showing a hybridization reaction vessel.

FIG. 39 is a schematic longitudinal cross sectional view showing a hybridization reaction vessel.

As shown in FIG. 39, a hybridization reaction vessel 128 is formed to have a substantially rectangular cross section and accommodates a hybridization solution 129 containing a substance derived from a living organism labeled with a labeling substance as a probe therein.

In this embodiment, a hybridization solution 129 containing a substance derived from a living organism labeled with a radioactive labeling substance and a substance derived from a living organism labeled with a fluorescent substance such as a fluorescent dye is prepared and accommodated in the hybridization reaction vessel 128.

When hybridization is to be performed, the biochemical analysis unit 121 containing specific binding substances such as a plurality of cDNAs spotted into a number of absorptive regions 124 is set in the hybridization reaction vessel 128.

As a result, specific binding substances spotted in a number of the absorptive regions 124 of the biochemical analysis unit 121 can be selectively hybridized with a substance derived from a living organism labeled with a radioactive labeling substance and a substance derived from a living organism labeled with a fluorescent substance such as a fluorescent dye.

In this manner, radiation data of a radioactive labeling substance and fluorescence data of a fluorescent substance such as a fluorescent dye are recorded in a number of absorptive regions 124 formed in the biochemical analysis unit 121. Fluorescence data recorded in the biochemical analysis unit 121 are read by a scanner described later, thereby producing biochemical analysis data.

On the other hand, radiation data of the radioactive labeling substance recorded in a number of absorptive regions 124 formed in the biochemical analysis unit 121 are transferred onto a stimulable phosphor layer of a stimulable phosphor sheet and read by the scanner described later, thereby producing biochemical analysis data.

Figure 40:
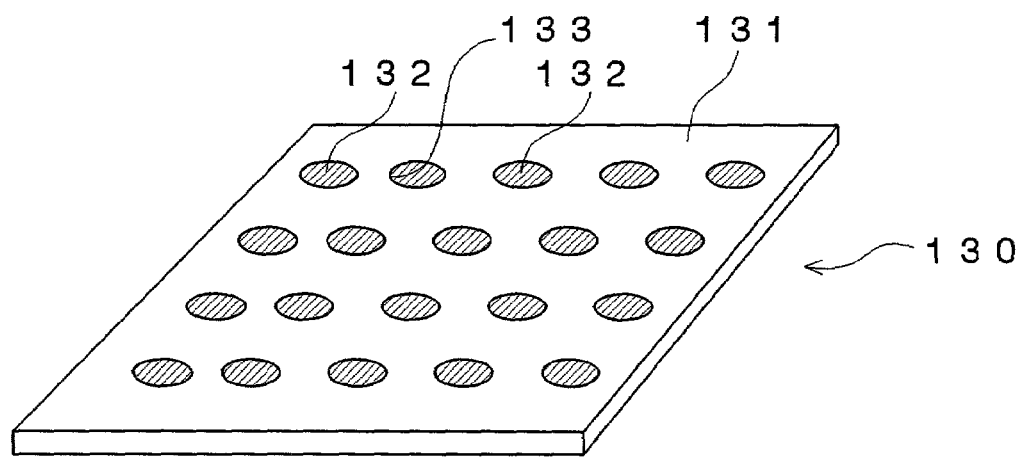
FIG. 40 is a schematic perspective view showing a stimulable phosphor sheet used for a biochemical analysis data producing method which is a further preferred embodiment of the present invention.

FIG. 40 is a schematic perspective view showing a stimulable phosphor sheet used for a biochemical analysis data producing method which is a further preferred embodiment of the present invention.

As shown in FIG. 40, a stimulable phosphor sheet 130 according to this embodiment includes a support 131 made of stainless steel and regularly formed with a number of substantially circular through-holes 133 and a number of stimulable phosphor layer regions 132 are dot-like formed by charging stimulable phosphor in the through-holes 133.

A number of the through-holes 133 are formed in the support 131 in the same pattern as that of a number of the absorptive regions 124 formed in the substrate 122 of the biochemical analysis unit 121 and each of them has the same size as that of the absorptive region 124 formed in the substrate 122 of the biochemical analysis unit 121.

Therefore, although not accurately shown in FIG. 40, in this embodiment, substantially circular stimulable phosphor layer regions 132 having a size of about 0.07 cm$^2$ are regularly formed in the manner of a matrix of 120 columns× 160 lines in the support 131 and, therefore, 19,200 stimulable phosphor layer regions 132 are dot-like formed.

Further, in this embodiment, the stimulable phosphor sheet 130 is formed by charging stimulable phosphor in the through-holes 133 formed in the support 131 so that the surface of the support 131 and the surfaces of the stimulable phosphor layer regions 132 lie at the same height level.

Figure 41:
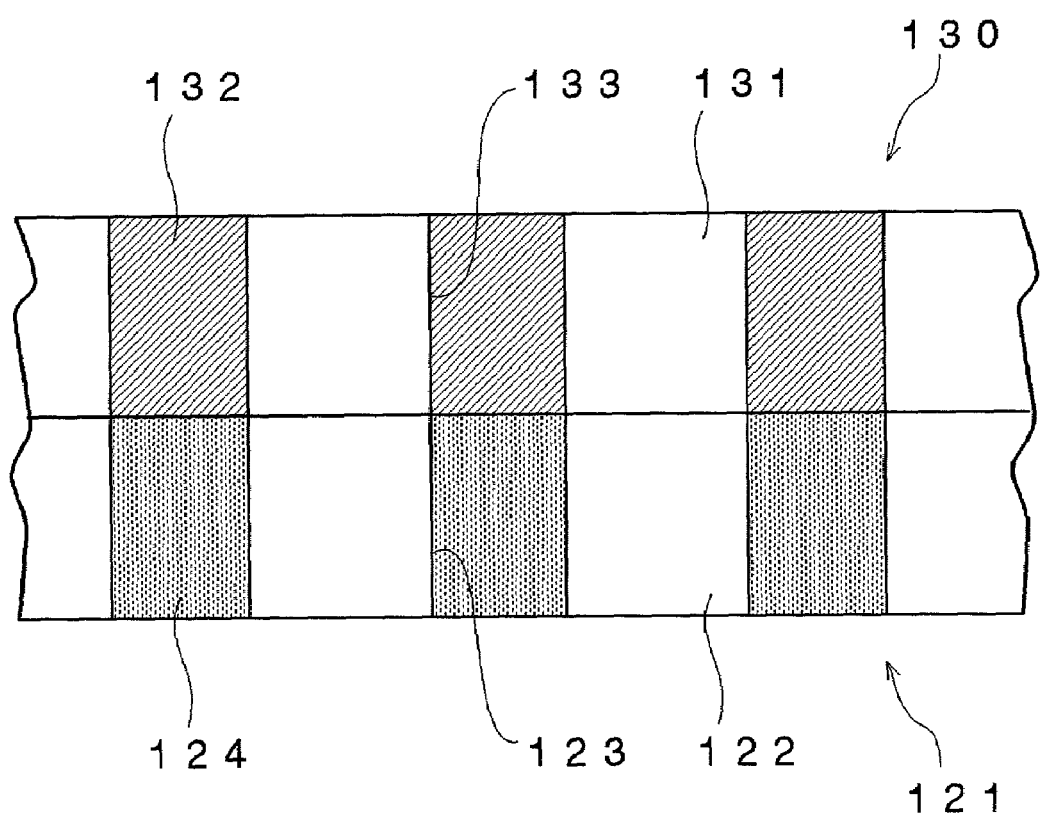
FIG. 41 is a schematic cross-sectional view showing a method for exposing a number of stimulable phosphor layer regions formed in a support of a stimulable phosphor sheet to a radioactive labeling substance contained in a number of absorptive regions formed in a substrate of a biochemical analysis unit.

FIG. 41 is a schematic cross-sectional view showing a method for exposing a number of the stimulable phosphor layer regions 132 formed in the support 131 of the stimulable phosphor sheet 130 to a radioactive labeling substance contained in a number of the absorptive regions 124 formed in the substrate 122 of the biochemical analysis unit 121.

As shown in FIG. 41, when the stimulable phosphor layer regions 132 formed in the support 131 of a stimulable phosphor sheet 130 are to be exposed, the stimulable phosphor sheet 130 is superposed on the biochemical analysis unit 121 in such a manner that a number of the stimulable phosphor layer regions 132 formed in the support 131 of the stimulable phosphor sheet 130 face the corresponding absorptive regions 124 formed in the biochemical analysis unit 121.

In this embodiment, since the biochemical analysis unit 121 is formed by charging nylon-6 in a number of the through-holes 123 formed in the substrate 122 made of stainless steel, the biochemical analysis unit 121 hardly stretches or shrinks even when it is subjected to liquid processing such as hybridization and, therefore, it is possible to easily and accurately superpose the stimulable phosphor sheet 130 on the biochemical analysis unit 121 so that each of the stimulable phosphor layer regions 132 formed in the support 131 of the stimulable phosphor sheet 130 accurately faces the corresponding absorptive region 124 formed in the substrate 122 of the biochemical analysis unit 121, thereby exposing the stimulable phosphor layer regions 132.

In this manner, each of the stimulable phosphor layer regions 132 formed in the support 131 of the stimulable phosphor sheet 130 is kept to face the corresponding absorptive region 124 formed in the substrate 122 of the biochemical analysis unit 121 for a predetermined time period, whereby a number of the stimulable phosphor layer regions 132 formed in the support 131 of the stimulable phosphor sheet 130 are exposed to the radioactive labeling substance contained in a number of the absorptive regions 124 formed in the substrate 122 of the biochemical analysis unit 121.

During the exposure operation, electron beams (β rays) are released from the radioactive labeling substance contained in the absorptive regions 124 of the biochemical analysis unit 121. However, since a number of the absorptive regions 124 of the biochemical analysis unit 121 are formed spaced apart from each other in the substrate 122 made of stainless steel and the substrate 122 made of stainless steel capable of attenuating radiation energy is present around each of the absorptive regions 124, electron beams (β rays) released from the radioactive labeling substance contained in the absorptive regions 124 of the biochemical analysis unit 121 can be efficiently prevented from scattering in the substrate 122 of the biochemical analysis unit 121. Further, since a number of the stimulable phosphor layer regions 132 of the stimulable phosphor sheet 130 are formed by charging stimulable phosphor in a number of the through-holes 133 formed in the support 131 made of stainless steel and the support 131 made of stainless steel capable of attenuating radiation energy is present around each of the stimulable phosphor layer regions 132, electron beams (β rays) released from the radioactive labeling substance contained in the absorptive regions 124 of the biochemical analysis unit 121 can be efficiently prevented from scattering in the support 131 of the stimulable phosphor sheet 130. Therefore, it is possible to selectively expose only the stimulable phosphor layer region 132 each of the absorptive regions 124 faces to the electron beams (β rays) released from the radioactive labeling substance contained in each of the absorptive regions 124.

In this manner, radiation data of a radioactive labeling substance are recorded in a number of the stimulable phosphor layer regions 132 formed in the support 131 of the stimulable phosphor sheet 130.

Figure 42:
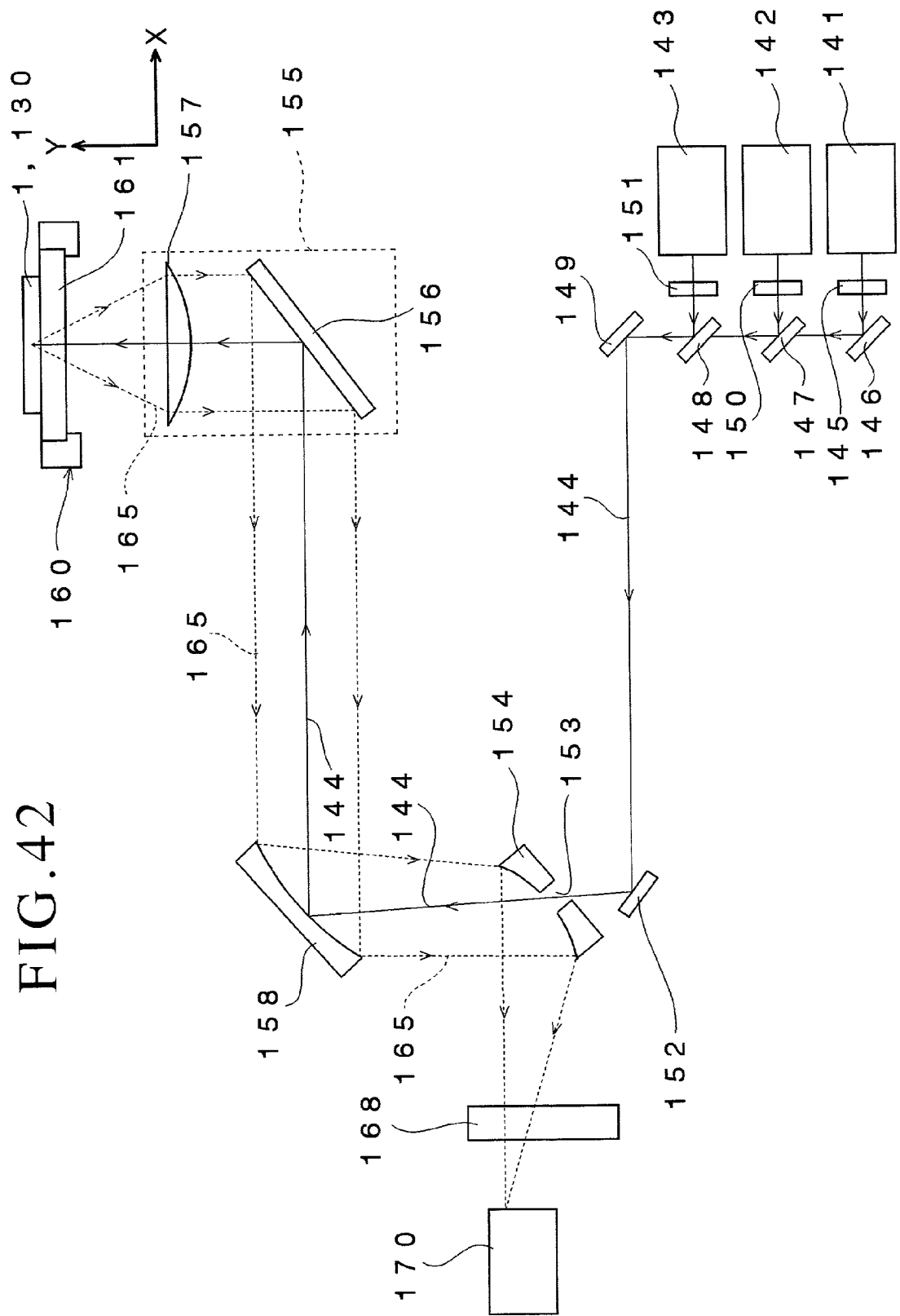
FIG. 42 is a schematic view showing a scanner for reading radiation data of a radioactive labeling substance recorded in a number of stimulable phosphor layer regions formed in a support of a stimulable phosphor sheet and fluorescence data recorded in a number of absorptive regions formed in a substrate of a biochemical analysis unit and producing biochemical analysis data.
Figure 43:
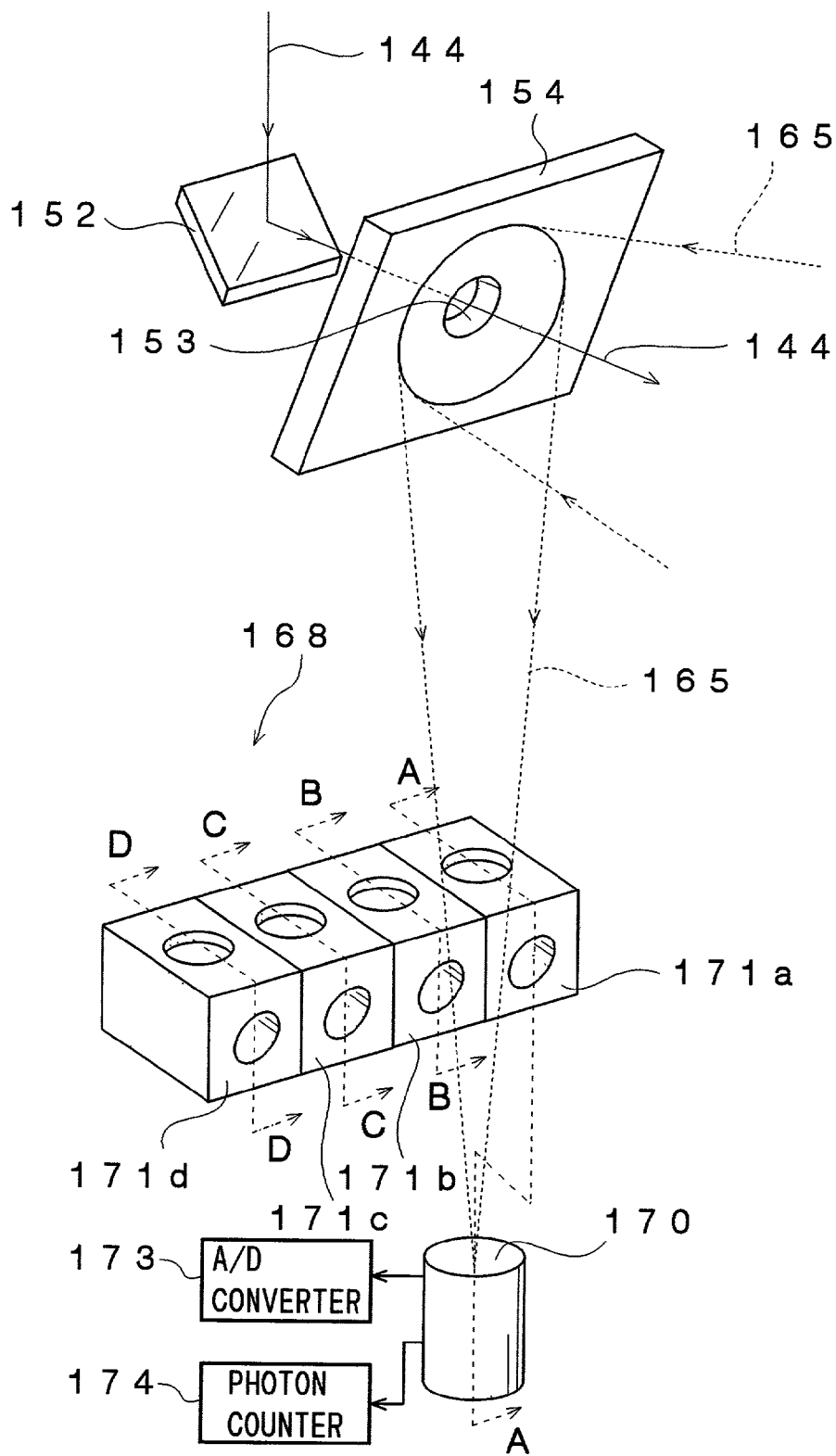
FIG. 43 is a schematic perspective view showing details in the vicinity of a photomultiplier.

FIG. 42 is a schematic view showing a scanner for reading radiation data of a radioactive labeling substance recorded in a number of the stimulable phosphor layer regions 132 formed in the support 131 of the stimulable phosphor sheet 130 and fluorescence data recorded in a number of the absorptive regions 124 formed in the substrate 121 of the biochemical analysis unit 121 and producing biochemical analysis data, and FIG. 43 is a schematic perspective view showing details in the vicinity of a photomultiplier.

The scanner shown in FIG. 42 is constituted so as to read radiation data of a radioactive labeling substance recorded in a number of the stimulable phosphor layer regions 132 formed in the support 131 of the stimulable phosphor sheet 130 and fluorescence data recorded in a number of the absorptive regions 124 formed in the substrate 121 of the biochemical analysis unit 121 and includes a first laser stimulating ray source 141 for emitting a laser beam having a wavelength of 640 nm, a second laser stimulating ray source 142 for emitting a laser beam having a wavelength of 532 nm and a third laser stimulating ray source 143 for emitting a laser beam having a wavelength of 473 nm.

In this embodiment, the first laser stimulating ray source 141 is constituted by a semiconductor laser beam source and the second laser stimulating ray source 142 and the third laser stimulating ray source 143 are constituted by a second harmonic generation element.

A laser beam 144 emitted from the first laser stimulating source 141 passes through a collimator lens 145, thereby being made a parallel beam, and is reflected by a mirror 146. A first dichroic mirror 147 for transmitting light having a wavelength of 640 nm but reflecting light having a wavelength of 532 nm and a second dichroic mirror 148 for transmitting light having a wavelength equal to and longer than 532 nm but reflecting light having a wavelength of 473 nm are provided in the optical path of the laser beam 144 emitted from the first laser stimulating ray source 141. The laser beam 144 emitted from the first laser stimulating ray source 141 and reflected by the mirror 146 passes through the first dichroic mirror 147 and the second dichroic mirror 148 and advances to a mirror 149.

On the other hand, the laser beam 144 emitted from the second laser stimulating ray source 142 passes through a collimator lens 150, thereby being made a parallel beam, and is reflected by the first dichroic mirror 147, thereby changing its direction by 90 degrees. The laser beam 144 then passes through the second dichroic mirror 148 and advances to the mirror 149.

Further, the laser beam 144 emitted from the third laser stimulating ray source 143 passes through a collimator lens 151, thereby being made a parallel beam, and is reflected by the second dichroic mirror 148, thereby changing its direction by 90 degrees. The laser beam 144 then advances to the mirror 149.

The laser beam 144 advancing to the mirror 149 is reflected by the mirror 149 and advances to a mirror 142 to be reflected thereby.

A perforated mirror 154 formed with a hole 153 at the center portion thereof is provided in the optical path of the laser beam 144 reflected by the mirror 152. The laser beam 144 reflected by the mirror 152 passes through the hole 153 of the perforated mirror 154 and advances to a concave mirror 158.

The laser beam 144 advancing to the concave mirror 158 is reflected by the concave mirror 158 and enters an optical head 155.

The optical head 155 includes a mirror 156 and an aspherical lens 157. The laser beam 144 entering the optical head 155 is reflected by the mirror 156 and condensed by the aspherical lens 157 onto the stimulable phosphor sheet 130 or the biochemical analysis unit 121 placed on the glass plate 161 of a stage 160.

When the laser beam 144 impinges on the stimulable phosphor layer region 132 of the stimulable phosphor sheet 130, stimulable phosphor contained in the stimulable phosphor layer region 132 formed in the support 131 of the stimulable phosphor 130 is excited, thereby releasing stimulated emission 165. On the other hand, when the laser beam 144 impinges on the absorptive region 124 formed in the substrate 122 of the biochemical analysis unit 121, a fluorescent dye or the like contained in the absorptive region 124 is excited, thereby releasing fluorescence emission 165.

The stimulated emission 165 released from the stimulable phosphor layer region 132 of the stimulable phosphor 130 or the fluorescence emission 165 released from the absorptive region 124 of the biochemical analysis unit 121 is condensed onto the mirror 156 by the aspherical lens 157 provided in the optical head 155 and reflected by the mirror 156 on the side of the optical path of the laser beam 144, thereby being made a parallel beam to advance to the concave mirror 158.

The stimulated emission 165 or the fluorescence emission 165 advancing to the concave mirror 158 is reflected by the concave mirror 158 and advances to the perforated mirror 154.

As shown in FIG. 43, the stimulated emission 165 or the fluorescence emission 165 advancing to the perforated mirror 154 is reflected downward by the perforated mirror 154 formed as a concave mirror and advances to a filter unit 168, whereby light having a predetermined wavelength is cut. The stimulated emission 165 or the fluorescence emission 165 then impinges on a photomultiplier 170, thereby being photoelectrically detected.

As shown in FIG. 43, the filter unit 168 is provided with four filter members 171a, 171b, 171c and 171d and is constituted to be laterally movable in FIG. 43 by a motor (not shown).

The filter 171a is used for reading fluorescence emission 165 by stimulating a fluorescent substance such as a fluorescent dye contained in a number of the absorptive regions 124 formed in the substrate 122 of the biochemical analysis unit 121 using the first laser stimulating ray source 141 and is provided with a filter (not shown) having a property of cutting off light having a wavelength of 640 nm but transmitting light having a wavelength longer than 640 nm.

The filter 171b is used for reading fluorescence emission 45 by stimulating a fluorescent substance such as a fluorescent dye contained in a number of the absorptive regions 4 formed in the substrate 2 of the biochemical analysis unit 1 using the second laser stimulating ray source 22 and is provided with a filter (not shown) having a property of cutting off light having a wavelength of 532 nm but transmitting light having a wavelength longer than 532 nm.

The filter 171c is used for reading fluorescence emission 165 by stimulating a fluorescent substance such as a fluorescent dye contained in a number of the absorptive regions 124 formed in the substrate 122 of the biochemical analysis unit 121 using the third laser stimulating ray source 143 and is provided a filter (not shown) having a property of cutting off light having a wavelength of 473 nm but transmitting light having a wavelength longer than 473 nm.

The filter 171d is used for reading stimulated emission released from stimulable phosphor contained in the stimulable phosphor layer 12 formed in the support 11 of the stimulable phosphor sheet 10 upon being stimulated using the first laser stimulating ray source 1 and is provided with a filter (not shown) having a property of transmitting only light having a wavelength corresponding to that of stimulated emission emitted from stimulable phosphor and cutting off light having a wavelength of 640 nm.

Therefore, in accordance with the kind of a stimulating ray source to be used, one of these filter members 171a, 171b, 171c, 171d is selectively positioned in front of the photomultiplier 170, thereby enabling the photomultiplier 170 to photoelectrically detect only light to be detected.

Analog data produced by photoelectrically detecting stimulated emission 165 by the photomultiplier 170 are output to a photon counter 174 and the number of photons contained in stimulated emission 165 detected by the photomultiplier 170 is counted by the photon counter 174 based on the analog data, thereby producing biochemical analysis data from radiation data recorded in the individual stimulable phosphor layer regions 132.

On the other hand, analog data produced by photoelectrically detecting fluorescence emission 165 by the photomultiplier 170 are output to an A/D converter 173 and digitized by the A/D converter 173, thereby producing biochemical analysis data.

Although not shown in FIG. 42, the optical head 155 is constituted to be movable by a scanning mechanism in a main scanning direction indicated by an arrow X and a sub-scanning direction perpendicular to the main scanning direction and indicated by an arrow Y in FIG. 42 so that all of the stimulable phosphor layer regions 132 formed in the support 131 of the stimulable phosphor sheet 130 or all of the absorptive regions 124 formed in the substrate 122 of the biochemical analysis unit 121 can be scanned by the laser beam 144.

Figure 44:
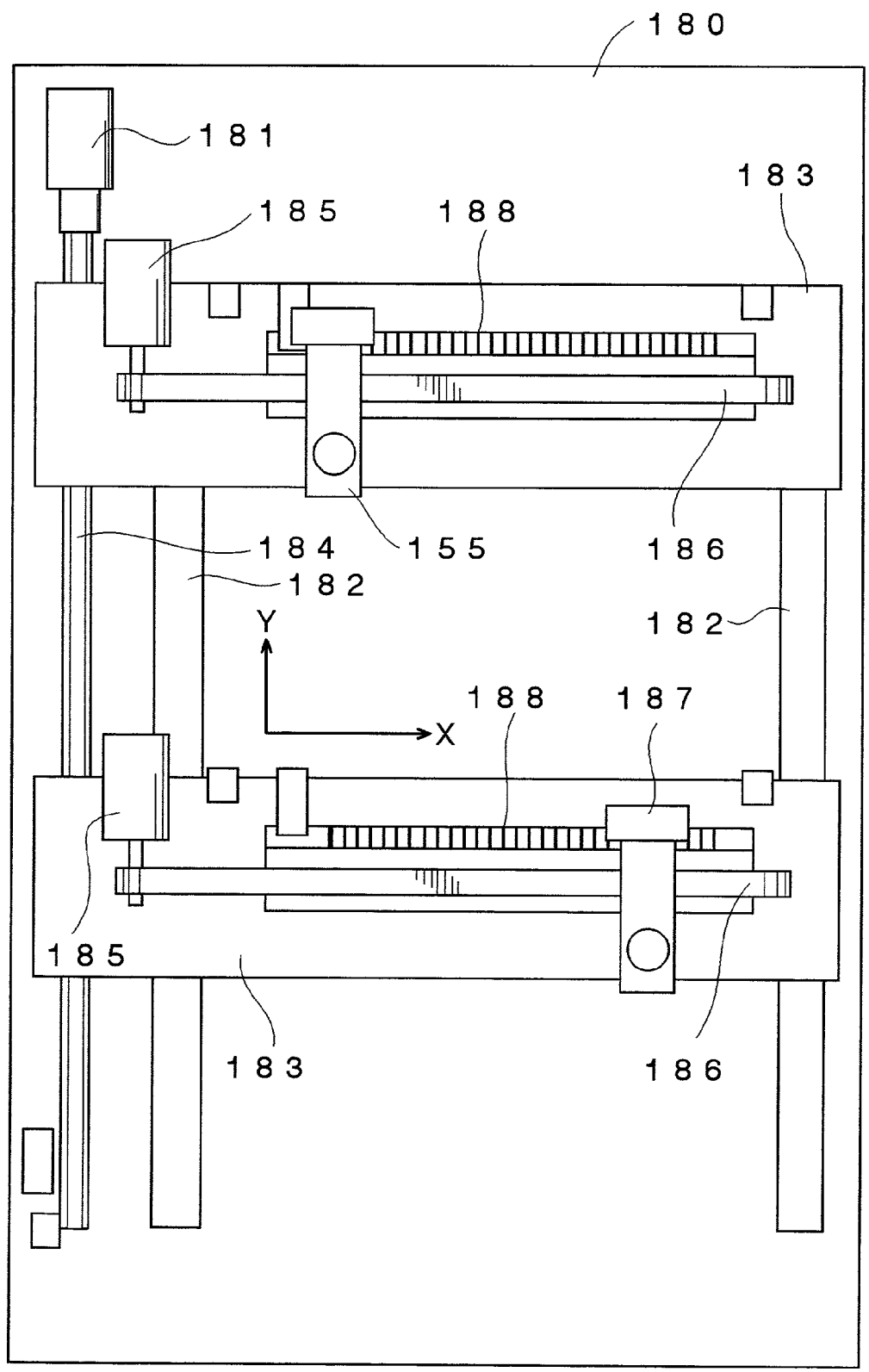
FIG. 44 is a schematic plan view showing a scanning mechanism of an optical head.

FIG. 44 is a schematic plan view showing the scanning mechanism of the optical head 155.

In FIG. 44, optical systems other than the optical head 155 and the paths of the laser beam 144 and stimulated emission 165 or fluorescence emission 165 are omitted for simplification.

As shown in FIG. 44, the scanning mechanism of the optical head 155 includes a base plate 180, and a sub-scanning pulse motor 181 and a pair of rails 182, 182 are fixed on the base plate 180. A movable base plate 183 is further provided so as to be movable in the sub-scanning direction indicated by an arrow Y in FIG. 44.

The movable base plate 183 is formed with a threaded hole (not shown) and a threaded rod 184 rotated by the sub-scanning pulse motor 181 is engaged with the inside of the hole.

A main scanning stepping motor 185 is provided on the movable base plate 183. The main scanning stepping motor 185 is adapted for intermittently driving an endless belt 186 by a pitch equal to the distance between neighboring absorptive regions 124 formed in the biochemical analysis unit 121, namely, the distance between neighboring stimulable phosphor layer regions 132 formed in the stimulable phosphor sheet 130.

The optical head 155 is fixed to the endless belt 186 and when the endless belt 186 is driven by the main scanning stepping motor 185, the optical head 155 is moved in the main scanning direction indicated by an arrow X in FIG. 44.

In FIG. 44, the reference numeral 187 designates a linear encoder for detecting the position of the optical head 155 in the main scanning direction and the reference numeral 188 designates slits of the linear encoder 187.

Therefore, the optical head 155 is moved in the main scanning direction indicated by the arrow X and the sub-scanning direction indicated by the arrow Y in FIG. 44 by intermittently driving the endless belt 186 in the main scanning direction by the main scanning stepping motor 185 and intermittently moving the movable base plate 183 in the sub-scanning direction by the sub-scanning pulse motor 181, thereby scanning all of the stimulable phosphor layer regions 132 formed in the support 131 of the stimulable phosphor sheet 130 or all of the absorptive regions 124 formed in the substrate 122 of the biochemical analysis unit 121 with the laser beam 144.

Figure 45:
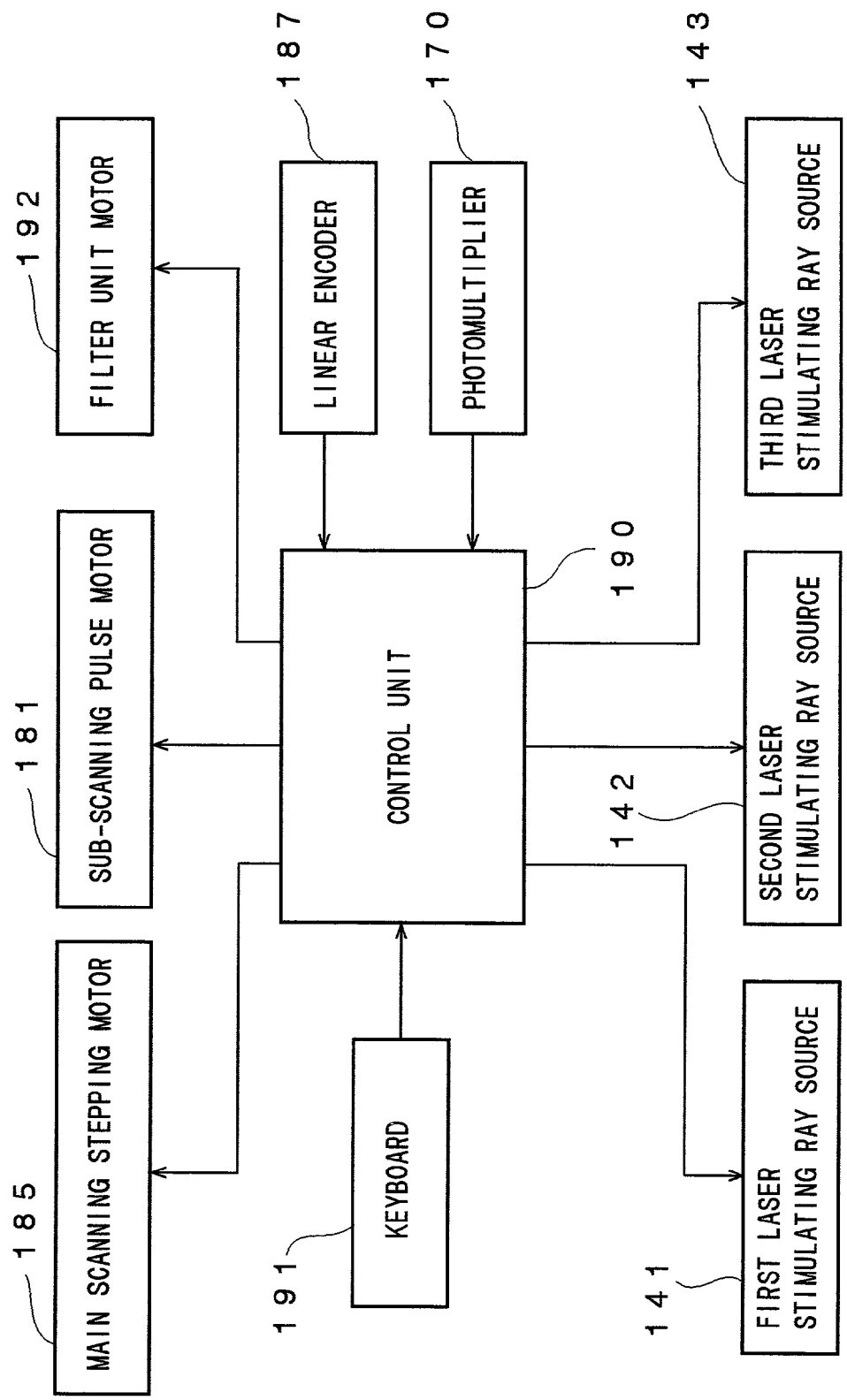
FIG. 45 is a block diagram of a control system, an input system, a drive system and a detection system of a scanner which is a further preferred embodiment of the present invention.

FIG. 45 is a block diagram of a control system, an input system, a drive system and a detection system of the scanner according to this embodiment.

As shown in FIG. 45, the control system of the scanner includes a control unit 190 for controlling the overall operation of the scanner and the input system of the scanner includes a keyboard 191 which can be operated by a user and through which various instruction signals can be input.

As shown in FIG. 45, the drive system of the scanner includes the main scanning stepping motor 185 for moving the optical head 155 in the main scanning direction, the sub-scanning pulse motor 181 for moving the optical head 155 in the sub-scanning direction and a filter unit motor 192 for moving the filter unit 168 provided with the four filter members 171a, 171b, 171c and 171d.

The control unit 70 is adapted for selectively outputting a drive signal to the first laser stimulating ray source 141, the second laser stimulating ray source 142 or the third laser stimulating ray source 143 and outputting a drive signal to the filter unit motor 192.

As shown in FIG. 45, the detection system of the scanner includes the photomultiplier 170 and the linear encoder 187.

In this embodiment, the control unit 190 is adapted to control the on and off operation of the first laser stimulating ray source 141, the second laser stimulating ray source 142 or the third laser stimulating ray source 143 in accordance with a detection signal indicating the position of the optical head 155 input from the linear encoder 187 and to also control a drive current value supplied to the first laser stimulating ray source 141, the second laser stimulating ray source 142 or the third laser stimulating ray source 143, thereby controlling the power of a laser beam 144 emitted from the first laser stimulating ray source 141, the second laser stimulating ray source 142 or the third laser stimulating ray source 143.

The thus constituted scanner according to this embodiment reads radiation data recorded in a number of the stimulable phosphor regions 132 formed in the support 131 of the stimulable phosphor sheet 130 in the following manner to produce biochemical analysis data.

The stimulable phosphor sheet 130 is placed on the glass plate 161 of the stage 160 by the user.

An instruction signal indicating that the stimulable phosphor layer regions 132 formed in the support 131 of the stimulable phosphor sheet 130 are to be scanned with a laser beam 144 is then input by the user through the keyboard 191.

The instruction signal input through the keyboard 191 is output to the control unit 190 and when the control unit 190 receives the instruction signal, it outputs a drive signal to the filter unit motor 192 in accordance with the instruction signal, thereby moving the filter unit 168 to locate the filter member 171d provided with a filter having a property of transmitting only light having a wavelength corresponding to that of stimulated emission emitted from stimulable phosphor and cutting off light having a wavelength of 640 nm in the optical path of stimulated emission 165 to be released from the stimulable phosphor layer regions 132.

The control unit 190 further outputs a drive signal to the main scanning stepping motor 185 to move the optical head 155 in the main scanning direction and when it determines based on a detection signal indicating the position of the optical head 155 input from the linear encoder 187 that the optical head 155 has reached a position where a laser beam 144 can be projected onto a first stimulable phosphor layer region 132 among a number of the stimulable phosphor layer regions 132 formed in the support 131 of the stimulable phosphor sheet 130, it outputs a drive stop signal to the main scanning stepping motor 185. At the same time, the control unit 190 outputs a drive signal to the first stimulating ray source 141 and supplies drive current to the first stimulating ray source 141, thereby actuating it to emit a laser beam 144 having a wavelength of 640 nm.

In this embodiment, the control unit 190 is constituted so as to increase a drive current value supplied to the first laser stimulating ray source 21 in accordance with an exponential function, thereby increasing the laser power of a laser beam 144 emitted from the first laser stimulating ray source 21 in accordance with an exponential function.

Figure 46A:
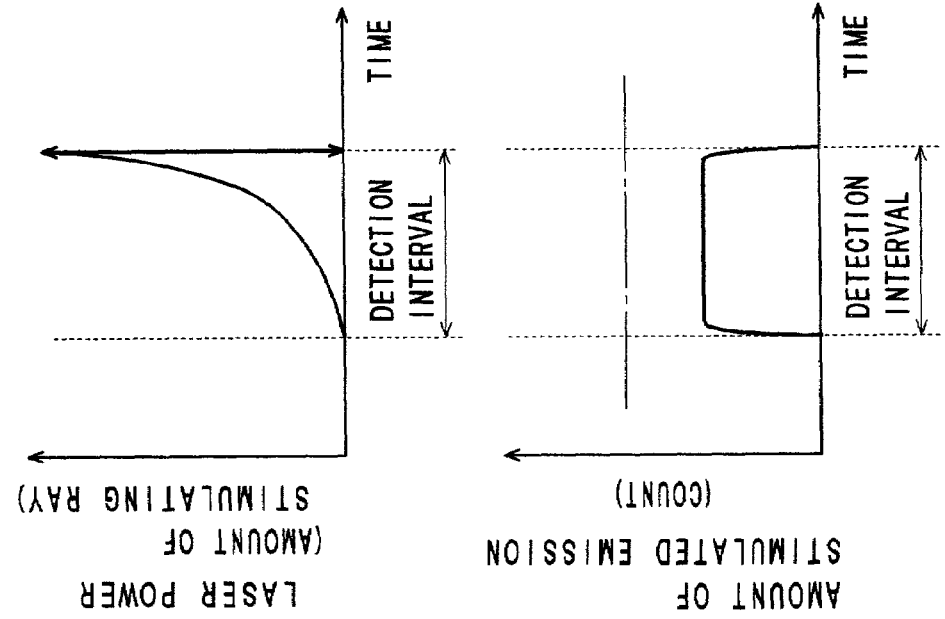
FIG. 46 is a graph showing the relationship between the laser power of a laser beam emitted from a first laser stimulating ray source and the number of photons counted by a photon counter based on analog data produced by irradiating a stimulable phosphor layer region with a laser beam to excite stimulable phosphor contained in the stimulable phosphor layer region and photoelectrically detecting stimulated emission released from the stimulable phosphor layer region by a photomultiplier.
Figure 46B:
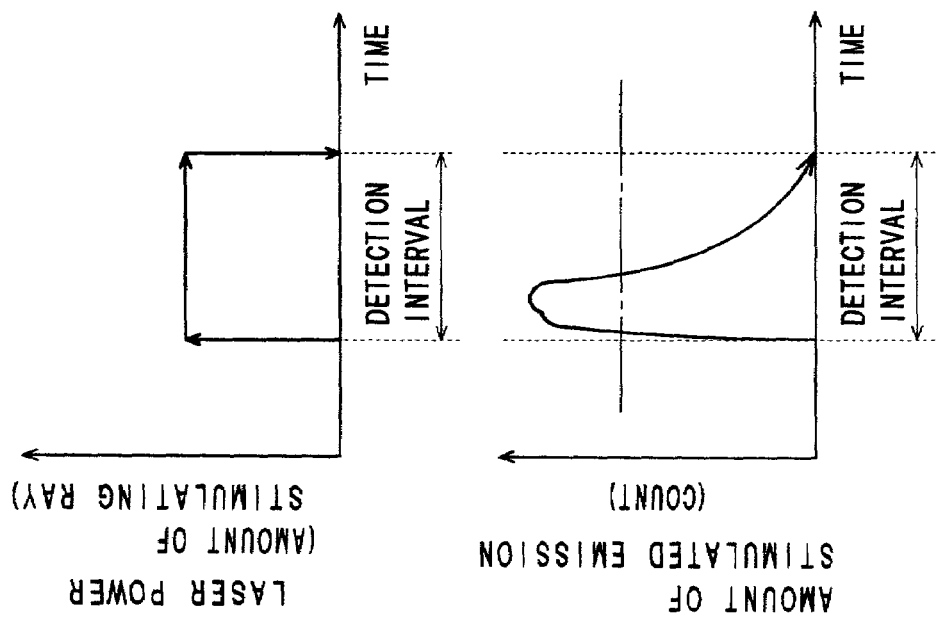

FIG. 46 is a graph showing the relationship between the laser power of a laser beam 144 emitted from the first laser stimulating ray source 141 and the number of photons counted by the photon counter 174 based on analog data produced by irradiating a stimulable phosphor layer region 132 with a laser beam 144 to excite stimulable phosphor contained in the stimulable phosphor layer region 132 and photoelectrically detecting stimulated emission 165 released from the stimulable phosphor layer region 132 by the photomultiplier 170.

As shown in FIG. 46 (A), in the case where the laser power of a laser beam 144 emitted from the first laser stimulating ray source 21 is constant, the amount of stimulated emission 165 released from stimulable phosphor contained in a stimulable phosphor layer region 132 in response to the excitation with the laser beam 144 is extremely great immediately after the stimulable phosphor layer region 132 is irradiated with the laser beam 144 and, therefore, the number of photons counted, based on analog data produced by exciting stimulable phosphor contained in the stimulable phosphor layer region 132 with the laser beam 144 and photoelectrically detecting stimulated emission 165 released from the stimulable phosphor layer region 132 by the photomultiplier 170, by the photon counter 174 is extremely large immediately after the stimulable phosphor layer region 132 is irradiated with the laser beam 144. However, the number of photons counted by the photon counter 174 drastically decreases with the lapse of time in accordance with an exponential function. This is because stimulable phosphor releases radiation energy stored therein in the form of stimulated emission 165 when it is irradiated with the laser beam 144 and radiation energy stored in the stimulable phosphor drastically decreases in accordance with an exponential function as it releases stimulated emission 165.

Therefore, in the case where the laser power (stimulation amount) of a laser beam 144 emitted from the first laser stimulating ray source 141 is held constant and stimulable phosphor contained in a stimulable phosphor layer region 132 of the stimulable phosphor sheet 130 is excited by the laser beam 144, the amount of stimulated emission 165 detected by the photomultiplier 170 is too large immediately after the stimulable phosphor layer region 132 is irradiated with the laser beam 144 and exceeds the upper limit of the dynamic range of the photomultiplier 170. It is therefore extremely difficult for the photon counter 174 to count the number of photons contained in the stimulated emission 165 photoelectrically detected by the photomultiplier 170, while it is extremely difficult to detect stimulated emission 165 with high sensitivity since the amount of stimulated emission 165 released from a stimulable phosphor layer region 132 drastically decreases in accordance with an exponential function with the lapse of time.

However, in this embodiment, since the control unit 190 increases the value of drive current to be supplied to the first laser stimulating ray source 141 in accordance with an exponential function, thereby controlling the power of a laser beam 144 emitted from the first laser stimulating ray source 141 to be increased in accordance with an exponential function, as shown in FIG. 46 (B), it is possible to control the amount of stimulated emission 165 released from stimulable phosphor contained in a stimulable phosphor layer region 132 in response to the excitation with the laser beam 144 to be substantially constant. Therefore, since the number of photons counted by the photon counter 174 based on analog data produced by exciting stimulable phosphor contained in the stimulable phosphor layer region 132 of the stimulable phosphor sheet 130 with the laser beam 144 and photoelectrically detecting stimulated emission 165 released from the stimulable phosphor layer region 132 by the photomultiplier 170 can be controlled to be substantially constant, it is possible to reliably prevent the amount of stimulated emission 165 to be detected by the photomultiplier 170 from exceeding the upper limit of the dynamic range of the photomultiplier 170 and, therefore, biochemical analysis data having high quantitative characteristics can be produced by photoelectrically detecting stimulated emission 165 released from the stimulable phosphor layer region 132 with high sensitivity.

A laser beam 144 emitted from the first laser stimulating source 141 passes through the collimator lens 145, thereby being made a parallel beam, and is reflected by the mirror 146.

The laser beam 144 reflected by the mirror 146 passes through the first dichroic mirror 147 and the second dichroic mirror 148 and advances to the mirror 149.

The laser beam 144 advancing to the mirror 149 is reflected by the mirror 149 and advances to the mirror 152 to be reflected thereby.

The laser beam 144 reflected by the mirror 152 passes through the hole 153 of the perforated mirror 154 and advances to the concave mirror 158.

The laser beam 144 advancing to the concave mirror 158 is reflected by the concave mirror 158 and enters the optical head 155.

The laser beam 144 entering the optical head 155 is reflected by the mirror 156 and condensed by the aspherical lens 157 onto the first stimulable phosphor layer region 132 of the stimulable phosphor sheet 130 placed on the glass plate 161 of a stage 160.

In this embodiment, since the stimulable phosphor layer regions 132 are formed by embedding stimulable phosphor in the through-holes 133 formed in the support 131 made of stainless steel capable of attenuating light energy, it is possible to effectively prevent the laser beam 144 from scattering in each of the stimulable phosphor layer regions 132 and entering the neighboring stimulable phosphor layer regions 132 to excite stimulable phosphor contained in the neighboring stimulable phosphor layer regions 132.

When the laser beam 144 impinges onto the first stimulable phosphor layer region 132 formed in the support 131 of the stimulable phosphor sheet 130, stimulable phosphor contained in the first stimulable phosphor layer region 132 formed in the stimulable phosphor sheet 130 is excited by the laser beam 144, thereby releasing stimulated emission 165 from the first stimulable phosphor layer region 132.

Further, in this embodiment, since the support 131 of the stimulable phosphor sheet 130 made of stainless steel capable of attenuating light energy, stimulated emission 165 released from the first stimulable phosphor layer region 132 can be effectively prevented from scattering in the support 131.

The stimulated emission 165 released from the first stimulable phosphor layer region 132 is condensed onto the mirror 156 by the aspherical lens 157 provided in the optical head 155 and reflected by the mirror 156 on the side of the optical path of the laser beam 144, thereby being made a parallel beam to advance to the concave mirror 158.

The stimulated emission 165 advancing to the concave mirror 158 is reflected by the concave mirror 158 and advances to the perforated mirror 154.

As shown in FIG. 43, the stimulated emission 165 advancing to the perforated mirror 154 is reflected downward by the perforated mirror 154 formed as a concave mirror and advances to the filter member 171d of the filter unit 168.

Since the filter member 171d is provided with the filter (not shown) having a property of transmitting only light having a wavelength corresponding to that of stimulated emission emitted from stimulable phosphor and cutting off light having a wavelength of 640 nm, light having a wavelength of 640 nm corresponding to that of the stimulating ray is cut off by the filter of the filter member 171d and only light having a wavelength corresponding to that of stimulated emission 165 released from the first stimulable phosphor layer region 132 passes through the filter of the filter member 171d to be photoelectrically detected by the photomultiplier 170.

Analog data produced by the photomultiplier 170 are output to the photon counter 174 and the number of photons contained in the stimulated emission 165 detected by the photomultiplier 170 is counted by the photon counter 174 based on the analog data, whereby biochemical analysis data are produced from radiation data recorded in the first stimulable phosphor layer region 132 of the stimulable phosphor sheet 130.

When a predetermined time, for example, several microseconds has passed after the first stimulating ray source 141 was turned on, the control unit 190 outputs a drive stop signal to the first stimulating ray source 141, thereby turning it off and outputs a drive signal to the main scanning stepping motor 185, thereby moving the optical head 155 by one pitch equal to the distance between neighboring stimulable phosphor layer regions 132 formed in the support 131 of the stimulable phosphor sheet 130.

When the control unit 190 determines based on a detection signal indicating the position of the optical head 155 input from the linear encoder 187 that the optical head 155 has been moved by one pitch equal to the distance between neighboring stimulable phosphor layer regions 132, it outputs a drive signal to the first stimulating ray source 141 to turn it on, thereby causing the laser beam 144 to excite stimulable phosphor contained in a second stimulable phosphor layer region 132 formed in the support 131 of the stimulable phosphor sheet 130 next to the first stimulable phosphor layer region 132.

Similarly to the above, the second stimulable phosphor layer region 132 formed in the support 131 of the stimulable phosphor sheet 130 is irradiated with the laser beam 144 for a predetermined time, while the value of drive current supplied to the first laser stimulating ray source 141 is controlled by the control unit 190 so as to be increased in accordance with an exponential function and stimulable phosphor contained in the second stimulable phosphor layer region 132 is excited, thereby releasing stimulated emission 165. the stimulated emission 165 is photoelectrically detected by the photomultiplier 170, thereby producing analog data. When the number of photons contained in the stimulated emission 165 detected by the photomultiplier 170 is counted by the photon counter 174, whereby biochemical analysis data are produced from radiation data recorded in the second stimulable phosphor layer region 132, the control unit 190 outputs a drive stop signal to the first stimulating ray source 141, thereby turning it off and outputs a drive signal to the main scanning stepping motor 185, thereby moving the optical head 155 by one pitch equal to the distance between neighboring stimulable phosphor layer regions 132.

In this manner, the on and off operation of the first stimulating ray source 141 is repeated in synchronism with the intermittent movement of the optical head 155 and when the control unit 190 determines based on a detection signal indicating the position of the optical head 155 input from the linear encoder 187 that the optical head 155 has been moved by one scanning line in the main scanning direction and that the stimulable phosphor layer regions 132 included in a first line of the stimulable phosphor layer regions 132 formed in the support 131 of the stimulable phosphor sheet 130 have been scanned with the laser beam 144, it outputs a drive signal to the main scanning stepping motor 185, thereby returning the optical head 155 to its original position and outputs a drive signal to the sub-scanning pulse motor 181, thereby causing it to move the movable base plate 183 by one scanning line in the sub-scanning direction.

When the control unit 190 determines based on a detection signal indicating the position of the optical head 155 input from the linear encoder 187 that the optical head 155 has been returned to its original position and determines that the movable base plate 183 has been moved by one scanning line in the sub-scanning direction, then, similarly to the manner in which the stimulable phosphor layer regions 132 included in the first line of the stimulable phosphor layer regions 132 formed in the support 131 of the stimulable phosphor sheet 130 were sequentially irradiated with the laser beam 144 emitted from the first laser stimulating ray source 141, the stimulable phosphor layer regions 132 included in a second line of the stimulable phosphor layer regions 132 formed in the support 131 of the stimulable phosphor sheet 130 are sequentially irradiated with the laser beam 144 emitted from the first laser stimulating ray source 141, thereby exciting stimulable phosphor contained in the stimulable phosphor layer regions 132 included in the second line and stimulated emission 165 released from the stimulable phosphor layer regions 132 is sequentially and photoelectrically detected by the photomultiplier 170.

Analog data produced by the photomultiplier 170 are output to the photon counter 174 and the number of photons contained in the stimulated emission 165 detected by the photomultiplier 170 is counted by the photon counter 174 based on the analog data, whereby biochemical analysis data are produced from radiation data recorded in the second stimulable phosphor layer region 132 of the stimulable phosphor sheet 130.

All of the stimulable phosphor layer regions 132 formed in the support 131 of the stimulable phosphor sheet 130 are scanned with the laser beam 144 in this manner and stimulated emission 165 released from stimulable phosphor contained in the individual stimulable phosphor layer regions 132 is photoelectrically detected by the photomultiplier 170, thereby producing analog data. When the number of photons contained in the stimulated emission 165 detected by the photomultiplier 170 have been counted by the photon counter 174 based on the thus produced analog data and biochemical analysis data have been produced from radiation data recorded in the individual stimulable phosphor layer regions 132 formed in the support 131 of the stimulable phosphor sheet 130, the control unit 190 outputs a drive stop signal to the first laser stimulating ray source 141, thereby turning off the first laser stimulating ray source 141 and the production of biochemical analysis data is completed.

On the other hand, when fluorescence data of a fluorescent substance recorded in a number of the absorptive regions 4 formed in the substrate 2 of the biochemical analysis unit 1 are to be read to produce biochemical analysis data, the biochemical analysis unit 1 is first set by the user on the glass plate 161 of the stage 160.

An instruction signal identifying the kind of a fluorescent substance such as a fluorescent dye labeling a substance derived from a living organism is then input by the user through the keyboard 191.

When the kind of fluorescent substance is input by the user through the keyboard 191, the control unit 190 selects a laser stimulating ray source for emitting a laser beam 144 of a wavelength capable of efficiently stimulating the input fluorescent substance from among the first laser stimulating ray source 141, the second laser stimulating ray source 142 and the third laser stimulating ray source 143 and selects the filter member for cutting light having a wavelength of the laser beam 144 to be used for stimulating the input fluorescent substance and transmitting light having a longer wavelength than that of the laser beam to be used for stimulation from among the three filter members 171a, 171b and 171c.

Similarly to the case where radiation data recorded in a number of the stimulable phosphor layer regions 132 of the stimulable phosphor sheet 130 are read, all of the absorptive regions 4 formed in the substrate 2 of the biochemical analysis unit 1 are scanned by the laser beam 144, thereby stimulating a fluorescent substance contained in the absorptive regions 4, fluorescence emission 165 released from the fluorescent substance is photoelectrically detected by the photomultiplier 170 to produce analog data and the analog data are digitized by the A/D converter 53 to produce biochemical analysis data.

In the case where the laser power (stimulation amount) of a laser beam 144 emitted from the first laser stimulating ray source 141 is held constant and stimulable phosphor contained in a stimulable phosphor layer region 132 of the stimulable phosphor sheet 130 is excited by the laser beam 144, the amount of stimulated emission 165 detected by the photomultiplier 170 is too large immediately after the stimulable phosphor layer region 132 is irradiated with the laser beam 144 and exceeds the upper limit of the dynamic range of the photomultiplier 170 and it is therefore extremely difficult for the photon counter 174 to count the number of photons contained in the stimulated emission 165 photoelectrically detected by the photomultiplier 170, while it is extremely difficult to detect stimulated emission 165 with high sensitivity since the amount of stimulated emission 165 released from a stimulable phosphor layer region 132 drastically decreases in accordance with an exponential function with the lapse of time. However, in this embodiment, since the control unit 190 increases the value of drive current to be supplied to the first laser stimulating ray source 141 in accordance with an exponential function, thereby controlling the power of a laser beam 144 emitted from the first laser stimulating ray source 141 to be increased in accordance with an exponential function, as shown in FIG. 46 (B), it is possible to control the amount of stimulated emission 165 released from stimulable phosphor contained in a stimulable phosphor layer region 132 in response to the excitation with the laser beam 144 to be substantially constant. Therefore, since the number of photons counted, based on analog data produced by exciting stimulable phosphor contained in the stimulable phosphor layer region 132 of the stimulable phosphor sheet 130 with the laser beam 144 and photoelectrically detecting stimulated emission 165 released from the stimulable phosphor layer region 132 by the photomultiplier 170, by the photon counter 174 can be controlled to be substantially constant, it is possible to reliably prevent the amount of stimulated emission 165 to be detected by the photomultiplier 170 from exceeding the upper limit of the dynamic range of the photomultiplier 170 and, therefore, biochemical analysis data having high quantitative characteristics can be produced by photoelectrically detecting stimulated emission 165 released from the stimulable phosphor layer region 132 with high sensitivity.

The present invention has thus been shown and described with reference to specific embodiments. However, it should be noted that the present invention is in no way limited to the details of the described arrangements but changes and modifications may be made without departing from the scope of the appended claims.

For example, in the above described embodiments, as specific binding substances, cDNAs each of which has a known base sequence and is different from the others are used. However, specific binding substances usable in the present invention are not limited to cDNAs but all specific binding substances capable of specifically binding with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, can be employed in the present invention as a specific binding substance.

Further, in the above described embodiments, specific binding substances are hybridized with substances derived from a living organism labeled with a radioactive labeling substance and a fluorescent substance. However, it is not absolutely necessary to hybridize substances derived from a living organism with specific binding substances and substances derived from a living organism may be specifically bound with specific binding substances by means of antigen-antibody reaction, receptor-ligand reaction or the like instead of hybridization.

Furthermore, in the embodiment shown in FIGS. 6 to 13, the embodiment shown in FIG. 18, the embodiment shown in FIG. 19, the embodiment shown in FIGS. 21 and 22, the embodiment shown in FIGS. 22 to 25, the embodiment shown in FIG. 26, the embodiment shown in FIGS. 27 and 28, the embodiment shown in FIGS. 29 and 30, the embodiment shown in FIG. 31 and the embodiment shown in FIG. 32, a number of the stimulable phosphor layer regions 12 formed in the support 11 of the stimulable phosphor sheet 10 are scanned with the laser beam 24 having a wavelength of 640 nm emitted from the first laser stimulating ray source 21 and radiation data recorded in a number of the stimulable phosphor layer regions 12 of the stimulable phosphor sheet 10 are read, thereby producing biochemical analysis data, and in the embodiment shown in FIGS. 42 to 46, a number of the stimulable phosphor layer regions 132 formed in the support 131 of the stimulable phosphor sheet 130 are scanned with the laser beam 144 having a wavelength of 640 nm emitted from the first laser stimulating ray source 141 and radiation data recorded in a number of the stimulable phosphor layer regions 132 of the stimulable phosphor sheet 130 are read, thereby producing biochemical analysis data. However, similarly to the embodiment shown in FIGS. 15 to 17, it is possible to provide a fourth laser stimulating ray source 55 for emitting a laser beam 24 having a wavelength of 980 nm in the scanner instead of the first laser stimulating ray source 21 for emitting a laser beam 24 having a wavelength of 640 nm or in addition to the first laser stimulating ray source 21 for emitting a laser beam 24 having a wavelength of 640 nm, to scan a number of the stimulable phosphor layer regions 15 formed in the support 16 of the stimulable phosphor sheet 15 and to read chemiluminescent data recorded in a number of the stimulable phosphor layer regions 15 of the stimulable phosphor sheet 15, thereby producing biochemical analysis data.

Moreover, in the embodiment shown in FIG. 33, the embodiment shown in FIG. 35 and the embodiment shown in FIG. 40, the stimulable phosphor layer regions 102, 112, 132 of the stimulable phosphor sheet 100, 110, 130 are formed of BaFX system stimulable phosphor (where X is at least one halogen atom selected from the group consisting of Cl, Br and I) capable of absorbing and storing radiation energy. However, it is possible to form the stimulable phosphor layer regions 102, 112, 132 of the stimulable phosphor sheet 100, 110, 130 of SrS system stimulable phosphor capable of absorbing and storing light energy so as to store the energy of chemiluminescent emission and record chemiluminescent data therein.

Further, in the embodiment shown in FIGS. 6 to 13, the embodiment shown in FIGS. 15 to 17, the embodiment shown in FIG. 18, the embodiment shown in FIG. 19, the embodiment shown in FIGS. 21 and 22, the embodiment shown in FIGS. 22 to 25, the embodiment shown in FIG. 26, the embodiment shown in FIGS. 27 and 28, the embodiment shown in FIGS. 29 and 30, the embodiment shown in FIG. 31 and the embodiment shown in FIGS. 42 to 46, the on and off operation of the laser stimulating ray source 21, 55, 141 is controlled by the control unit 70, 190 in synchronism with the intermittent movement of the optical head 35, 155. However, if the moving speed of the optical head 35, 155 in the main scanning direction is determined so that the laser beam 24, 144 quickly passes portions between neighboring stimulable phosphor layer regions 12, 17, 102, 112, 132 in the main scanning direction, biochemical analysis data may be produced by merely intermittently moving the optical head 35, 155 while the laser stimulating ray source 21, 55, 141 is kept on, thereby sequentially scanning a number of the stimulable phosphor layer regions 12, 17, 102, 112, 132 with the laser beam 24, 144 and photoelectrically detecting stimulated emission 45, 165 released from the stimulable phosphor layer regions 12, 17, 102, 112, 132.

Furthermore, in the embodiment shown in FIG. 18, although biochemical analysis data of the individual stimulable phosphor layer regions 12 are produced by controlling the on and off operation of the first laser stimulating ray source 21 in synchronism with the intermittent movement of the optical head 35, integrating analog data produced by the photomultiplier 50 by the integrating amplifier 75 and digitizing an integrated value of the analog data by the A/D converter 53, it is possible, similarly to the embodiment shown in FIG. 19, to further provide a summing means 77 and to sum digital data produced by digitizing the integrated value of the analog data by the A/D converter 53, thereby producing biochemical analysis data of the individual stimulable phosphor layer regions 12.

Moreover, in the embodiment shown in FIG. 19, although biochemical analysis data of the individual stimulable phosphor layer regions 12 are produced by controlling the on and off operation of the first laser stimulating ray source 21 in synchronism with the intermittent movement of the optical head 35, digitizing analog data produced by the photomultiplier 50 by the A/D converter 53 to produce digital data and summing the digital data by the summing means 77, it is possible, similarly to the embodiment shown in FIG. 18, to further provide an integrating amplifier 75, to integrate analog data produced by the photomultiplier 50 by the integrating amplifier 75, to digitize an integrated value of the analog data by the A/D converter 53 to produce digital data and to sum the digital data, thereby producing biochemical analysis data of the individual stimulable phosphor layer regions 12.

Further, in the embodiment shown in FIG. 32, biochemical analysis data of the individual stimulable phosphor layer regions 12 are produced by controlling the on and off operation of the first laser stimulating ray source 21, while continuously moving the optical head 35 in the main scanning direction, and digitizing analog data produced by the photomultiplier 50. However, similarly to the embodiment shown in FIG. 18, it is possible to further provide an integrating amplifier 75, to integrate analog data produced by the photomultiplier 50 by the integrating amplifier 75, to digitize an integrated value of the analog data by the A/D converter 53 to produce digital data and to sum the digital data, thereby producing biochemical analysis data of the individual stimulable phosphor layer regions 12 and similarly to the embodiment shown in FIG. 19, it is also possible to further provide a summing means 77, to digitize analog data produced by the photomultiplier 50 by the A/D converter 53 to produce digital data and to sum the digital data by the summing means 77, thereby producing biochemical analysis data of the individual stimulable phosphor layer regions 12. Moreover, it is possible to provide an integrating amplifier 75 for integrating analog data as well as a summing means 77 for summing digital data in the scanner shown in FIG. 32, to integrate analog data produced by the photomultiplier 50, to digitize an integrated value of the analog data by the A/D converter 53 to produce digital data and to sum the digital data by the summing means 77, thereby producing biochemical analysis data of the individual stimulable phosphor layer regions 12.

Furthermore, in the embodiment shown in FIGS. 20 and 21, the embodiment shown in FIGS. 22 to 25, the embodiment shown in FIG. 26, the embodiment shown in FIGS. 27 and 28, the embodiment shown in FIGS. 29 and 30 and the embodiment shown in FIG. 31, although the laser power of the laser beam 24 emitted from the first laser stimulating ray source 21 is increased by the increment ΔP, it is not absolutely necessary to determine the increment ΔP to be constant. The laser power of the laser beam 24 emitted from the first laser stimulating ray source 21 may be increased in such a manner that the increment ΔP becomes greater every time the laser power of the laser beam 24 is to be increased or the laser power of the laser beam 24 emitted from the first laser stimulating ray source 21 may be increased in such a manner that the increment ΔP becomes smaller every time the laser power of the laser beam 24 is to be increased.

Moreover, in the embodiment shown in FIGS. 20 and 21 and the embodiment shown in FIGS. 27 and 28, when the signal intensity of digital data is lower than the threshold value T, the laser power of the laser beam 24 emitted from the first laser stimulating ray source 21 is repeatedly increased by the increment ΔP until the signal intensity of digital data has come to be equal to or higher than the threshold value T. However, when it is determined that the signal intensity of digital data is lower than the threshold value T and the laser power of the laser beam 24 emitted from the first laser stimulating ray source 21 is increased, the thus produced digital data P1 may be adopted as biochemical analysis data of the stimulable phosphor layer region irrespective of the signal intensity of the digital data P1.

Further, in the embodiment shown in FIGS. 22 to 25, the embodiment shown in FIG. 26, the embodiment shown in FIGS. 27 and 26 and the embodiment shown in FIG. 31, when the signal intensity of the summed value ΣS (P0) of digital data P0 is lower than the threshold value T, the laser power of the laser beam 24 emitted from the first laser stimulating ray source 21 is repeatedly increased by the increment ΔP until the signal intensity of the summed value of digital data has come to be equal to or higher than the threshold value T. However, when it is determined that the signal intensity of the summed value ΣS (P0) of digital data P0 is lower than the threshold value T and the laser power of the laser beam 24 emitted from the first laser stimulating ray source 21 is increased, the summed value ΣS (P1) of digital data P1 may be adopted as biochemical analysis data of the stimulable phosphor layer region irrespective of the signal intensity of the summed value ΣS (P1) of the digital data P1.

Furthermore, in the embodiment shown in FIGS. 42 to 46, analog data produced by photoelectrically detecting stimulated emission 165 released from a stimulable phosphor layer region 132 of the stimulable phosphor sheet 130 by the photomultiplier 170 are output to the photon counter 174 and the number of photons contained in the stimulated emission 165 detected by the photomultiplier 170 is counted by the photon counter 174 based on the analog data, thereby producing biochemical analysis data of the stimulable phosphor layer region 132 from radiation data recorded in the stimulable phosphor layer region 132 of the stimulable phosphor sheet 130. However, it is possible to output the analog data produced by the photomultiplier 170 to the A/D converter 173 and digitize the analog data by the A/D converter 173, thereby producing biochemical analysis data of the stimulable phosphor layer region 132.

Moreover, in the embodiment shown in FIGS. 42 to 46, the value of drive current to be supplied to the first laser stimulating ray source 141 is increased with the lapse of time in accordance with an exponential function, thereby increasing the laser power of the laser beam 144 emitted from the first laser stimulating ray source 141 and projected onto a stimulable phosphor layer region 132 of the stimulable phosphor sheet 130 with the lapse of time in accordance with the exponential function. However, it is sufficient to control the first laser stimulating ray source 141 so that the laser power of the laser beam 144 emitted from the first laser stimulating ray source 141 and projected onto a stimulable phosphor layer region 132 of the stimulable phosphor sheet 130 is increased with the lapse of time and it is not absolutely necessary to control the first laser stimulating ray source 141 so that the laser power of the laser beam 144 emitted from the first laser stimulating ray source 141 and projected onto a stimulable phosphor layer region 132 of the stimulable phosphor sheet 130 is increased with the lapse of time in accordance with an exponential function.

Further, in the embodiment shown in FIGS. 6 to 13, the embodiment shown in FIGS. 15 to 17 and the embodiment shown in FIGS. 42 to 46, although the position of the optical head 35, 155 in the main scanning direction is detected using the linear encoder 67, 187, the position of the optical head 35, 155 in the main scanning direction can be detected by detecting the rotation position of the main scanning stepping motor 65, 185.

Furthermore, in the embodiment shown in FIGS. 6 to 13, the scanner is constituted so as to read radiation data recorded in a number of the stimulable phosphor layer regions 12, 102, 112 formed in the support 11, 101, 111 of the stimulable phosphor sheet 10, 100, 110 and fluorescent data of a fluorescent substance such as a fluorescent dye recorded in a number of absorptive regions 4 formed in the substrate 2 of the biochemical analysis unit 1, thereby producing biochemical analysis data and includes the first laser stimulating ray source 21 for emitting a laser beam 24 having a wavelength of 640 nm, the second laser stimulating ray source 22 for emitting a laser beam 24 having a wavelength of 532 nm and the third laser stimulating ray source 23 for emitting a laser beam 24 having a wavelength of 473 nm. However, it is sufficient for the scanner to be constituted so as to read radiation data recorded in a number of the stimulable phosphor layer regions 12, 102, 112 formed in the support 11, 101, 111 of the stimulable phosphor sheet 10, 100, 110, thereby producing biochemical analysis data and it is not absolutely necessary for the scanner to be constituted so as to read fluorescent data of a fluorescent substance such as a fluorescent dye recorded in a number of absorptive regions 4 formed in the substrate 2 of the biochemical analysis unit 1, thereby producing biochemical analysis data. Therefore, it is sufficient for the scanner to include the first laser stimulating ray source 21 for emitting a laser beam 24 having a wavelength of 640 nm and it is not absolutely necessary for the scanner to include the second laser stimulating ray source 22 for emitting a laser beam 24 having a wavelength of 532 nm and the third laser stimulating ray source 23 for emitting a laser beam 24 having a wavelength of 473 nm.

Moreover, in the embodiment shown in FIGS. 15 to 17, the scanner is constituted so as to read radiation data recorded in a number of the stimulable phosphor layer regions 17 formed in the support 16 of the stimulable phosphor sheet 15 and fluorescent data of a fluorescent substance such as a fluorescent dye recorded in a number of absorptive regions 4 formed in the substrate 2 of the biochemical analysis unit 1, thereby producing biochemical analysis data and includes the first laser stimulating ray source 21 for emitting a laser beam 24 having a wavelength of 640 nm, the second laser stimulating ray source 22 for emitting a laser beam 24 having a wavelength of 532 nm and the fourth laser stimulating ray source 55 for emitting a laser beam 24 having a wavelength of 980 nm. However, it is sufficient for the scanner to be constituted so as to read radiation data recorded in a number of the stimulable phosphor layer regions 17 formed in the support 16 of the stimulable phosphor sheet 15, thereby producing biochemical analysis data and it is not absolutely necessary for the scanner to be constituted so as to read fluorescent data of a fluorescent substance such as a fluorescent dye recorded in a number of absorptive regions 4 formed in the substrate 2 of the biochemical analysis unit 1, thereby producing biochemical analysis data. Therefore, it is sufficient for the scanner to include the fourth laser stimulating ray source 55 for emitting a laser beam 24 having a wavelength of 980 nm and it is not absolutely necessary for the scanner to include the first laser stimulating ray source 21 for emitting a laser beam 24 having a wavelength of 640 nm and the second laser stimulating ray source 22 for emitting a laser beam 24 having a wavelength of 532 nm.

Further, in the embodiment shown in FIGS. 42 to 46, the scanner is constituted so as to read radiation data recorded in a number of the stimulable phosphor layer regions 132 formed in the support 131 of the stimulable phosphor sheet 130 and fluorescent data of a fluorescent substance such as a fluorescent dye recorded in a number of absorptive regions 124 formed in the substrate 122 of the biochemical analysis unit 121, thereby producing biochemical analysis data and includes the first laser stimulating ray source 141 for emitting a laser beam 144 having a wavelength of 640 nm, the second laser stimulating ray source 142 for emitting a laser beam 144 having a wavelength of 532 nm and the third laser stimulating ray source 143 for emitting a laser beam 144 having a wavelength of 473 nm. However, it is sufficient for the scanner to be constituted so as to read radiation data recorded in a number of the stimulable phosphor layer regions 132 formed in the support 131 of the stimulable phosphor sheet 130, thereby producing biochemical analysis data and it is not absolutely necessary for the scanner to be constituted so as to read fluorescent data of a fluorescent substance such as a fluorescent dye recorded in a number of absorptive regions 124 formed in the substrate 122 of the biochemical analysis unit 121, thereby producing biochemical analysis data. Therefore, it is sufficient for the scanner to include the first laser stimulating ray source 141 for emitting a laser beam 144 having a wavelength of 640 nm and it is not absolutely necessary for the scanner to include the second laser stimulating ray source 142 for emitting a laser beam 144 having a wavelength of 532 nm and the third laser stimulating ray source 143 for emitting a laser beam 144 having a wavelength of 473 nm.

Furthermore, the scanner includes the semiconductor laser stimulating ray source for emitting a laser beam 24 having a wavelength of 640 nm as the first laser stimulating ray source 21 in the embodiment shown in FIGS. 6 to 13, the embodiment shown in FIGS. 15 to 17 and the embodiment shown in FIG. 32 and the semiconductor laser stimulating ray source for emitting a laser beam 144 having a wavelength of 640 nm as the first laser stimulating ray source 141 in the embodiment shown in FIGS. 42 to 46. However, instead of the semiconductor laser stimulating ray source 21, 141, the scanner may include a semiconductor laser stimulating ray source for emitting a laser beam 24, 144 having a wavelength of 635 nm or a He—Ne laser stimulating ray source for emitting laser beam 24, 144 having a wavelength of 633 nm.

Moreover, in the above described embodiments, although the scanner includes the stimulating ray sources 21, 22, 23, 55, 141, 142, 143 for emitting a laser beam 24, 144, it is not absolutely necessary to employ a laser stimulating ray source as a stimulating ray source and an LED (light emitting diode) light source may be employed as a stimulating ray source instead of a laser stimulating ray source. Further, it is possible to employ a halogen lamp as a stimulating ray source and to provide a spectral filter to cut wavelength components which cannot contribute to the excitation of stimulable phosphor.

Furthermore, in the embodiment shown in FIGS. 6 to 13, the embodiment shown in FIGS. 15 to 17, the embodiment shown in FIG. 18, the embodiment shown in FIG. 11, the embodiment shown in FIGS. 21 and 22, the embodiment shown in FIGS. 22 to 25, the embodiment shown in FIG. 26, the embodiment shown in FIGS. 27 and 28, the embodiment shown in FIGS. 29 and 30, the embodiment shown in FIG. 31, the embodiment shown in FIG. 32 and the embodiment shown in FIGS. 42 to 46, the scanner is constituted so that all of the stimulable phosphor layer regions 12, 17, 102, 112, 132 of the stimulable phosphor sheet 10, 15, 100, 110, 130 or all of the absorptive regions 4, 124 of the biochemical analysis unit 1, 121 are scanned with a laser beam 24, 144 to excite stimulable phosphor or a fluorescent substance such as a fluorescent dye by moving the optical head 35, 155 using a scanning mechanism in the main scanning direction indicated by the arrow X direction and the sub-scanning direction indicated by the arrow Y in FIG. 6, 15 or 42. However, all of the stimulable phosphor layer regions 12, 17, 102, 112, 132 of the stimulable phosphor sheet 10, 15, 100, 110, 132 or all of the absorptive regions 4, 124 of the biochemical analysis unit 1, 121 may be scanned with a laser beam 24, 144 to excite stimulable phosphor or a fluorescent substance such as a fluorescent dye by moving the stage 40, 160 in the main scanning direction indicated by the arrow X direction and the sub-scanning direction indicated by the arrow Y in FIG. 6, 15 or 42, while holding the optical head 35, 155 stationary, or moving the optical head 35, 155 in the main scanning direction indicated by the arrow X direction or the sub-scanning direction indicated by the arrow Y in FIG. 6, 15 or 42 and moving the stage 40, 160 in the sub-scanning direction indicated by the arrow Y or the main scanning direction indicated by the arrow X in FIG. 6,15 or 42. In the case where the stage 40, 160 is constituted so as to be moved in the main scanning direction, it is possible to detect the position of the stage relative to the optical head 35, 155 by providing a linear encoder in a moving mechanism of the stage 40, 160 or to detect the position of the stage relative to the optical head 35, 155 by detecting the rotational position of a motor for driving the stage 40, 160 by a rotary encoder.

Further, in the above described embodiments, the scanner employs the photomultiplier 50, 170 as a light detector to photoelectrically detect fluorescent light or stimulated. However, it is sufficient for the light detector used in the present invention to be able to photoelectrically detect fluorescent light or stimulated emission and it is possible to employ a light detector such as a CCD instead of the photomultiplier 50, 170.

Furthermore, in the above described embodiments, the absorptive regions 4, 124 of the biochemical analysis unit 1, 121 are formed by charging nylon-6 in a number of the through-holes 3, 123 formed in the substrate 2, 122. However, absorptive material for forming the absorptive regions 4, 124 of the biochemical analysis unit 1, 121 is not limited to nylon-6 and other kinds of absorptive materials can be employed instead for forming the absorptive regions 4, 124 of the biochemical analysis unit 1, 121. A porous material or a fiber material may be preferably used as the absorptive material for forming the absorptive regions 4, 124 of the biochemical analysis unit 1, 121 and the absorptive regions 4, 124 of the biochemical analysis unit 1, 121 may be formed by combining a porous material and a fiber material. A porous material for forming the absorptive regions 4, 124 of the biochemical analysis unit 1, 121 may be any type of an organic material or an inorganic material and may be an organic/inorganic composite material. An organic porous material used for forming the absorptive regions 4, 124 of the biochemical analysis unit 1, 121 is not particularly limited but a carbon porous material such as an activated carbon or a porous material capable of forming a membrane filter can be preferably used. Illustrative examples of porous materials capable of forming a membrane filter include nylons such as nylon-6, nylon-6,6, nylon-4,10; cellulose derivatives such as nitrocellulose, acetyl cellulose, butyric-acetyl cellulose; collagen; alginic acids such as alginic acid, calcium alginate, alginic acid/poly-L-lysine polyionic complex; polyolefins such as polyethylene, polypropylene; polyvinyl chloride; polyvinylidene chloride; polyfluoride such as polyvinylidene fluoride, polytetrafluoride; and copolymers or composite materials thereof. An inorganic porous material used for forming the absorptive regions 4, 121 of the biochemical analysis unit 1, 121 is not particularly limited. Illustrative examples of inorganic porous materials preferably usable in the present invention include metals such as platinum, gold, iron, silver, nickel, aluminum and the like; metal oxides such as alumina, silica, titania, zeolite and the like; metal salts such as hydroxy apatite, calcium sulfate and the like; and composite materials thereof. A fiber material used for forming the absorptive regions 4, 124 of the biochemical analysis unit 1, 121 is not particularly limited. Illustrative examples of fiber materials preferably usable in the present invention include nylons such as nylon-6, nylon-6,6, nylon-4,10; and cellulose derivatives such as nitrocellulose, acetyl cellulose, butyric-acetyl cellulose.

Moreover, in the above described embodiments, although the substrate 2, 122 of the biochemical analysis unit 1, 121 is made of stainless steel, it is not absolutely necessary to make the substrate 2, 122 of the biochemical analysis unit 1, 121 of stainless steel and the substrate 2, 122 of the biochemical analysis unit 1, 121 can be made of other kinds of materials. The substrate 2, 122 of the biochemical analysis unit 1, 121 is preferably formed of material capable of attenuating radiation energy but the material for forming the substrate 2, 122 of the biochemical analysis unit 1, 121 is not particularly limited. The substrate 2, 122 of the biochemical analysis unit 1, 121 can be formed of either inorganic compound material or organic compound material and is preferably formed of metal material, ceramic material or plastic material. Illustrative examples of inorganic compound materials include metals such as gold, silver, copper, zinc, aluminum, titanium, tantalum, chromium, steel, nickel, cobalt, lead, tin, selenium and the like; alloys such as brass, stainless, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. High molecular compounds are preferably used as organic compound material and illustrative examples thereof include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifluoroethylene; polycarbonate; polyesters such as polyethylene naphthalate, polyethylene terephthalate and the like; nylons such as nylon-6, nylon-6,6, nylon-4,10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials.

Further, in the above described embodiments, although 19,200 of substantially circular absorptive regions 4, 124 having a size of about 0.07 cm$^2$ are regularly formed in the biochemical analysis unit 1, 121 in the manner of a matrix of 120 columns×160 lines, the number or size of the absorptive regions 4, 124 may be arbitrarily selected in accordance with the purpose. Preferably, 10 or more of the absorptive regions 4, 124 having a size of 5 cm$^2$ or less are formed in the biochemical analysis unit 1, 121 at a density of 10/cm$^2$ or less.

Furthermore, in the above described embodiments, although 19,200 of substantially circular absorptive regions 4, 124 having a size of about 0.07 cm$^2$ are regularly formed in the biochemical analysis unit 1, 121 in the manner of a matrix of 120 columns×160 lines, it is not absolutely necessary to regularly form the absorptive regions 4, 124 in the biochemical analysis unit 1, 121.

Moreover, in the above described embodiments, although 19,200 of substantially circular absorptive regions 4, 124 having a size of about 0.07 cm$^2$ are regularly formed in the biochemical analysis unit 1, 121 in the manner of a matrix of 120 columns×160 lines, the shape of each of the absorptive regions 4, 124 is not limited to substantially a circular shape and may be arbitrarily selected.

Furthermore, the support 11 of the stimulable phosphor sheet 10 is made of oxygen free copper in the embodiment shown in FIG. 4, the support 16, 131 of the stimulable phosphor sheet 15, 130 is made of stainless steel in the embodiment shown in FIG. 14 and the embodiment shown in FIG. 40, the support 101 of the stimulable phosphor sheet 100 is made of silicon nitride in the embodiment shown in FIG. 33 and the support 111 of the stimulable phosphor sheet 110 is made of polyethylene terephthalate in the embodiment shown in FIG. 35. However, it is not absolutely necessary to make the support 11, 16, 101, 111, 131 of the stimulable phosphor sheet 10, 15, 100, 110, 130 of oxygen free copper, stainless steel, silicon nitride or polyethylene terephthalate and the support 11, 16, 101, 111, 131 of the stimulable phosphor sheet 10, 15, 100, 110, 130 may be made of other kinds of materials. The support 11, 16, 101, 111, 131 of the stimulable phosphor sheet 10, 15, 100, 110, 130 is preferably made of material capable of attenuating radiation energy but the material for forming the support 11, 16, 101, 111, 131 of the stimulable phosphor sheet 10, 15, 100, 110, 130 is not particularly limited. The support 11, 16, 101, 111, 131 of the stimulable phosphor sheet 10, 15, 100, 110, 130 can be formed of either inorganic compound material or organic compound material and is preferably formed of metal material, ceramic material or plastic material. Illustrative examples of inorganic compound materials include metals such as gold, silver, copper, zinc, aluminum, titanium, tantalum, chromium, steel, nickel, cobalt, lead, tin, selenium and the like; alloys such as brass, stainless, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. High molecular compounds are preferably used as organic compound material and illustrative examples thereof include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifluoroethylene; polycarbonate; polyesters such as polyethylene naphthalate, polyethylene terephthalate and the like; nylons such as nylon-6, nylon-6,6, nylon-4,10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials.

Further, in the embodiment shown in FIG. 4, the embodiment shown in FIG. 14, the embodiment shown in FIG. 33 and the embodiment shown in FIG. 35, correspondingly to the absorptive regions 4 formed in the substrate 2 of the biochemical analysis unit 1 shown in FIG. 1, 19,200 substantially circular stimulable phosphor layer regions 12, 17, 102, 112 having a size of about 0.07 cm$^2$ are regularly formed in the stimulable phosphor sheet 10, 15, 100, 110 in the manner of a matrix of 120 columns×160 lines, and in the embodiment shown in FIG. 40, correspondingly to the absorptive regions 124 formed in the substrate 122 of the biochemical analysis unit 121 shown in FIG. 37, 19,200 substantially circular stimulable phosphor layer regions 132 having a size of about 0.07 cm$^2$ are regularly formed in the stimulable phosphor sheet 130 in the manner of a matrix of 120 columns×160 lines. However, the shape of each of the stimulable phosphor layer regions 12, 17, 102, 112, 132 is not limited to substantially a circular shape and may be arbitrarily selected.

Furthermore, in the embodiment shown in FIG. 4, the embodiment shown in FIG. 14, the embodiment shown in FIG. 33 and the embodiment shown in FIG. 35, correspondingly to the absorptive regions 4 formed in the substrate 2 of the biochemical analysis unit 1 shown in FIG. 1, 19,200 substantially circular stimulable phosphor layer regions 12, 17, 102, 112 having a size of about 0.07 cm$^2$ are regularly formed in the stimulable phosphor sheet 10, 15, 100, 110 in the manner of a matrix of 120 columns×160 lines, and in the embodiment shown in FIG. 40, correspondingly to the absorptive regions 124 formed in the substrate 122 of the biochemical analysis unit 121 shown in FIG. 37, 19,200 substantially circular stimulable phosphor layer regions 132 having a size of about 0.07 cm$^2$ are regularly formed in the stimulable phosphor sheet 130 in the manner of a matrix of 120 columns×160 lines. However, the number or size of the stimulable phosphor layer regions 12, 17, 102, 112, 132 may be arbitrarily selected in accordance with the purpose. Preferably, 10 or more of the stimulable phosphor layer regions 12, 17, 102, 112, 132 having a size of 5 cm$^2$ or less are formed in the stimulable phosphor sheet 10, 15, 100, 110, 130 at a density of 10/cm$^2$ or less.

Moreover, in the embodiment shown in FIG. 4, the embodiment shown in FIG. 14, the embodiment shown in FIG. 33 and the embodiment shown in FIG. 35, correspondingly to the absorptive regions 4 formed in the substrate 2 of the biochemical analysis unit 1 shown in FIG. 1, 19,200 substantially circular stimulable phosphor layer regions 12, 17, 102, 112 having a size of about 0.07 cm$^2$ are regularly formed in the stimulable phosphor sheet 10, 15, 100, 110 in the manner of a matrix of 120 columns×160 lines, and in the embodiment shown in FIG. 40, correspondingly to the absorptive regions 124 formed in the substrate 122 of the biochemical analysis unit 121 shown in FIG. 37, 19,200 substantially circular stimulable phosphor layer regions 132 having a size of about 0.07 cm$^2$ are regularly formed in the stimulable phosphor sheet 130 in the manner of a matrix of 120 columns×160 lines. However, it is sufficient for the stimulable phosphor layer regions 12, 17, 102, 112, 132 to be formed in the same pattern as that of the absorptive regions 4, 124 of the corresponding biochemical analysis unit 1, 121 and it is not absolutely necessary to regularly form the stimulable phosphor layer regions 12, 17, 102, 112, 132.

Further, in the above described embodiments, although each of the stimulable phosphor layer regions 12, 17, 102, 112, 132 of the stimulable phosphor sheet 10, 15, 100, 110, 130 has the same size as that of each of the absorptive regions 4, 124 of the corresponding biochemical analysis unit 1, 121, it is not absolutely necessary to form each of the stimulable phosphor layer regions 12, 17, 102, 112, 132 of the stimulable phosphor sheet 10, 15, 100, 110, 130 so as to have the same size as that of each of the absorptive regions 4, 124 of the corresponding biochemical analysis unit 1, 121 and each of the stimulable phosphor layer regions 12, 17, 102, 112, 132 of the stimulable phosphor sheet 10, 15, 100, 110, 130 is preferably formed so as to have a size equal to or larger than each of the absorptive regions 4, 124 of the corresponding biochemical analysis unit 1, 121.

Furthermore, in the above described embodiments, a number of the absorptive regions 4, 124 are two-dimensionally formed in the substrate 2, 122 of the biochemical analysis unit 1, 121 and a number of the stimulable phosphor layer regions 12, 17, 102, 112, 132 are two-dimensionally formed in the support 11, 16, 101, 11, 131 of the stimulable phosphor sheet 10, 15, 100, 110, 130. However, a number of the absorptive regions 4, 124 and a number of the stimulable phosphor layer regions 12, 17, 102, 112, 132 may be formed one-dimensionally.

Moreover, a hybridization reaction solution 9 containing a substance derived from a living organism labeled with a radioactive labeling substance, a substance derived from a living organism labeled with a fluorescent substance such as a fluorescent dye and a substance derived from a living organism labeled with a labeling substance which generates chemiluminescent emission when it contacts a chemiluminescent substrate is prepared in the embodiment shown in FIGS. 1 to 18 and a hybridization reaction solution 129 containing a substance derived from a living organism labeled with a radioactive labeling substance and a substance derived from a living organism labeled with a fluorescent substance such as a fluorescent dye is prepared in the embodiment shown in FIGS. 37 to 46. However, it is sufficient for hybridization reaction solution 9, 129 to contain at least one labeling substance of a substance derived from a living organism labeled with a radioactive labeling substance and a substance derived from a living organism labeled with a labeling substance which generates chemiluminescent emission when it contacts a chemiluminescent substrate.

Furthermore, in the above-described embodiments, a solution containing specific binding substances such as cDNAs are spotted using the spotting device 5, 125 including an injector 6, 126 and a CCD camera 7, 127 so that when the tip end portion of the injector 6, 126 and the center of the absorptive region 4, 124 into which a solution containing specific binding substances is to be spotted are determined to coincide with each other as a result of viewing them using the CCD camera 7, 127, the solution containing the specific binding substances such as cDNA is spotted from the injector 6, 126. However, the solution containing specific binding substances such as cDNAs can be spotted by detecting the positional relationship between a number of the absorptive regions 4, 124 formed in the biochemical analysis unit 1, 121 and the tip end portion of the injector 6, 126 in advance and two-dimensionally moving the biochemical analysis unit 1, 121 or the tip end portion of the injector 6, 126 so that the tip end portion of the injector 6, 126 coincides with each of the absorptive regions 4, 124.

Furthermore, in the present invention, the respective means need not necessarily be physical means and arrangements whereby the functions of the respective means are accomplished by software fall within the scope of the present invention. In addition, the function of a single means may be accomplished by two or more physical means and the functions of two or more means may be accomplished by a single physical means.

According to the present invention, it is possible to provide a biochemical analysis data producing method and a scanner therefor, which can produce biochemical analysis data having excellent quantitative characteristics with high resolution even in the case of forming at a high density on the surface of a carrier such as a membrane filter a plurality of spot-like regions containing specific binding substances which can specifically bind with a substance derived from a living organism and whose sequence, base length, composition and the like are known, selectively labeling the plurality of spot-like regions with a radioactive labeling substance, thereby recording radiation data therein, exposing the stimulable phosphor layer of a stimulable phosphor sheet to the radioactive labeling substance selectively contained in the plurality of spot-like regions and recording radiation data in the stimulable phosphor layer of the stimulable phosphor sheet or in the case of forming at a high density on the surface of a carrier such as a membrane filter a plurality of spot-like regions containing specific binding substances which can specifically bind with a substance derived from a living organism and whose sequence, base length, composition and the like are known, selectively labeling the plurality of spot-like regions with a labeling substance which generates chemiluminescent emission when it contacts a chemiluminescent substrate, thereby recording chemiluminescent data therein, causing the plurality of spot-like regions to come into contact with a chemiluminescent substrate and to release chemiluminescent emission, exposing the stimulable phosphor layer of a stimulable phosphor sheet to the chemiluminescent emission selectively released from the plurality of spot-like regions and recording chemiluminescent data in the stimulable phosphor layer of the stimulable phosphor sheet.

The invention claimed is:

1. A biochemical analysis data producing method comprising:
   superposing a biochemical analysis unit including a substrate and a plurality of absorptive regions at least one dimensionally formed in the substrate in a predetermined pattern to be apart from each other and containing specimen selectively labeled with a radioactive labeling substance, and a stimulable phosphor sheet including a support and a plurality of stimulable phosphor layer regions formed in the support in substantially the same pattern as that of the plurality of absorptive regions of the biochemical analysis unit so that corresponding absorptive regions of the biochemical analysis unit and stimulable phosphor layer regions face to each other,
   exposing the plurality of stimulable phosphor layer regions of the stimulable phosphor sheet with the radioactive labeling substance selectively contained in the plurality of absorptive regions of the biochemical analysis unit thereby selectively storing radiation energy in the plurality of stimulable phosphor layer regions of the stimulable phosphor sheet,
   intermittently moving the stimulable phosphor sheet and a stimulating ray relative to each other at least one dimensionally;
   sequentially irradiating the plurality of stimulable phosphor layer regions with a stimulating ray having reference excitation power which is relatively low, to excite stimulable phosphor contained in the individual stimulable phosphor layer regions, so that energy of the stimulating ray projected onto the plurality of stimulable phosphor layer regions per unit area is higher than that projected on regions other than the plurality of stimulable phosphor layer regions, thereby exciting stimulable phosphor contained in the plurality of stimulable phosphor layer regions, and photoelectrically detecting stimulated emission released from the stimulable phosphor layer to produce analog data, digitizing the analog data to produce digital data, comparing signal intensity of the digital data with a threshold value, and irradiating, when the signal intensity of the digital data is lower than the threshold value, the stimulable phosphor layer region from which the digital data were obtained with a stimulating ray having excitation power higher than the reference excitation power to excite stimulable phosphor contained therein, and wherein the stimulating ray is on and off controlled in such a manner that only the plurality of stimulable phosphor layer regions are irradiated with the stimulating ray and regions other than the plurality of stimulable phosphor layer regions are not irradiated with the stimulating ray, wherein a plurality of holes are formed in the support of the stimulable phosphor sheet so as to be spaced apart from each other and the plurality of stimulable phosphor layer regions of the stimulable phosphor sheet are formed by charging stimulable phosphor in the holes, and wherein the support of the stimulable phosphor sheet has a property of reducing the energy of radiation and/or the energy of light to ⅕ or less when the radiation and/or light travels in the support by a distance equal to that between neighboring stimulable phosphor layer regions.

2. A biochemical analysis data producing method in accordance with claim 1 wherein the stimulable phosphor sheet and the stimulating ray are intermittently moved relative to each other in the main scanning direction and the individual stimulable phosphor regions are irradiated with the stimulating ray for a predetermined time.

3. A biochemical analysis data producing method in accordance with claim 2, further comprising:
   photoelectrically detecting stimulated emission to produce analog data
   integrating the analog data and
   digitizing an integrated value of the analog data to produce biochemical analysis data.

4. A biochemical analysis data producing method in accordance with claim 2 further comprising:
   intermittently moving the stimulable phosphor sheet and the stimulating ray relative to each other at least one-dimensionally;
   sequentially irradiating the plurality of stimulable phosphor layer regions with a stimulating ray having reference excitation power which is relatively low for a predetermined time to excite stimulable phosphor contained in the individual stimulable phosphor layer regions;
   photoelectrically detecting stimulated emission released from the individual stimulable phosphor layer regions to produce analog data
   integrating the analog data to produce an integrated value of the analog data, digitizing the integrated value of the analog data to produce digital data
   comparing signal intensity of the thus produced digital data with a threshold value;
   irradiating, when the signal intensity of the digital data is lower than the threshold value, the stimulable phosphor layer region from which the digital data were obtained with the stimulating ray having excitation power higher than the reference excitation power to excite stimulable phosphor contained therein, and
   photoelectrically detecting stimulated emission released from the stimulable phosphor layer region.

5. A biochemical analysis data producing method in accordance with claim 4 further comprising:
   adopting, when the signal intensity of the digital data produced by irradiating the stimulable phosphor layer region with the stimulating ray having the reference excitation power to excite stimulable phosphor contained in the stimulable phosphor layer region;
   photoelectrically detecting stimulated emission to produce analog data;
   integrating the analog data to produce an integrated value of the analog data and
   digitizing the integrated value of the analog data is equal to or higher than the threshold value, the thus produced digital data as biochemical analysis data of the stimulable phosphor layer region.

6. A biochemical analysis data producing method in accordance with claim 5 further comprising:
   when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is lower than the threshold value;
   irradiating the stimulable phosphor layer region from which the digital data were obtained with a stimulating ray having excitation power higher than the reference excitation power to excite stimulable phosphor contained therein;
   photoelectrically detecting stimulated emission released from the stimulable phosphor layer region to produce analog data;
   integrating the analog data to produce an integrated value of the analog data;
   digitizing the integrated value of the analog data to produce digital data, and
   adopting the thus produced digital data as biochemical analysis data of the stimulable phosphor layer region.

7. A biochemical analysis data producing method in accordance with claim 6, further comprising:
   multiplying digital data produced by irradiating the stimulable phosphor layer region with the stimulating ray having different excitation power to excite stimulable phosphor contained in the stimulable phosphor layer region;
   photoelectrically detecting stimulated emission released from the stimulable phosphor to produce analog data;
   integrating the analog data to produce an integrated value of the analog data and
   digitizing the integrated value of the analog data by a correction coefficient determined in accordance with the excitation power of the stimulating ray projected onto the stimulable phosphor layer region and producing biochemical analysis data of the stimulable phosphor layer region.

8. A biochemical analysis data producing method in accordance with claim 5 further comprising:

when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data;

integrating the analog data to produce an integrated value of the analog data and digitizing the integrated value of the analog data is lower than the threshold value irradiating the stimulable phosphor layer region from which the digital data were obtained with a stimulating ray having excitation power higher than the reference excitation power to excite stimulable phosphor contained therein;

photoelectrically detecting stimulated emission released from the stimulable phosphor layer region to produce analog data;

integrating the analog data to produce an integrated value of the analog data, digitizing the integrated value of the analog data to produce digital data comparing signal intensity of the thus obtained digital data with the threshold value, and adopting the digital data as biochemical analysis data of the stimulable phosphor layer region when the signal intensity of the digital data is equal to or higher than the threshold value.

9. A biochemical analysis data producing method in accordance with claim 8 further comprising:

when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data;

integrating the analog data to produce an integrated value of the analog data and digitizing the integrated value of the analog data is lower than the threshold value;

irradiating the stimulable phosphor layer region from which the digital data were obtained with a stimulating ray having excitation power higher than the reference excitation power to excite stimulable phosphor contained therein;

photoelectrically detecting stimulated emission released from the stimulable phosphor layer region to produce analog data;

integrating the analog data to produce an integrated value of the analog data;

digitizing the integrated value of the analog data to produce digital data;

comparing signal intensity of the thus obtained digital data with the threshold value;

sequentially increasing, when the signal intensity of the digital data is lower than the threshold value, the excitation power of the stimulating ray I times at maximum where I is a positive integer;

irradiating the stimulable phosphor layer region from which the digital data were obtained with the stimulating ray to excite stimulable phosphor contained therein;

photoelectrically detecting the stimulated emission released from the stimulable phosphor by the light detector to produce analog data;

integrating the analog data to produce an integrated value of the analog data;

digitizing the integrated value of the analog data, and adopting the thus produced digital data as biochemical analysis data of the stimulable phosphor layer region when the signal intensity of the digital data is equal to or higher than the threshold value, or determining biochemical analysis data of the stimulable phosphor layer region to be zero when the signal intensity of the digital data is still lower than the threshold value even though the digital data were produced by sequentially increasing the excitation power of the stimulating ray I times in total;

irradiating the stimulable phosphor layer region from which the digital data were obtained with the stimulating ray, photoelectrically detecting stimulated emission released from the stimulable phosphor layer region by the light detector to produce analog data;

integrating the analog data to produce an integrated value of the analog data, and digitizing the integrated value of the analog data.

10. A biochemical analysis data producing method in accordance with claim 9 further comprising:

multiplying digital data produced by irradiating the stimulable phosphor layer region with the stimulating ray having different excitation power to excite stimulable phosphor contained in the stimulable phosphor layer region;

photoelectrically detecting stimulated emission released from the stimulable phosphor to produce analog data;

integrating the analog data to produce an integrated value of the analog data and digitizing the integrated value of the analog data by a correction coefficient determined in accordance with the excitation power of the stimulating ray projected onto the stimulable phosphor layer region and producing biochemical analysis data of the stimulable phosphor layer region.

11. A biochemical analysis data producing method in accordance with claim 8 further comprising:

multiplying digital data produced by irradiating the stimulable phosphor layer region with the stimulating ray having different excitation power to excite stimulable phosphor contained in the stimulable phosphor layer region;

photoelectrically detecting stimulated emission released from the stimulable phosphor to produce analog data;

integrating the analog data to produce an integrated value of the analog data and digitizing the integrated value of the analog data by a correction coefficient determined in accordance with the excitation power of the stimulating ray projected onto the stimulable phosphor layer region and producing biochemical analysis data of the stimulable phosphor layer region.

12. A biochemical analysis data producing method in accordance with claim 5 further comprising:

when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is lower than the threshold value;

irradiating the stimulable phosphor layer region from which the digital data were obtained with a stimulating ray having excitation power higher than the reference excitation power to excite stimulable phosphor contained therein;

photoelectrically detecting stimulated emission released from the stimulable phosphor layer region to produce analog data;

integrating the analog data to produce an integrated value of the analog data, digitizing the integrated value of the analog data to produce digital data;

comparing signal intensity of the thus obtained digital data with the threshold value, sequentially increasing, when the signal intensity of the digital data is lower than the threshold value, the excitation power of the stimulating ray I times at maximum where I is a positive integer irradiating the stimulable phosphor layer region from which the digital data were obtained with the stimulating ray to excite stimulable phosphor contained therein photoelectrically detecting the stimulated emission released from the stimulable phosphor by the light detector to produce analog data;

integrating the analog data to produce an integrated value of the analog data, digitizing the integrated value of the analog data, and adopting the thus produced digital data as biochemical analysis data of the stimulable phosphor layer region when the signal intensity of the digital data is equal to or higher than the threshold value, or determining biochemical analysis data of the stimulable phosphor layer region to be zero when the signal intensity of the digital data is still lower than the threshold value even though the digital data were produced by sequentially increasing the excitation power of the stimulating ray I times in total;

irradiating the stimulable phosphor layer region from which the digital data were obtained with the stimulating ray;

photoelectrically detecting stimulated emission released from the stimulable phosphor layer region by the light detector to produce analog data integrating the analog data to produce an integrated value of the analog data, and digitizing the integrated value of the analog data.

13. A biochemical analysis data producing method in accordance with claim 12 further comprising:

multiplying digital data produced by irradiating the stimulable phosphor layer region with the stimulating ray having different excitation power to excite stimulable phosphor contained in the stimulable phosphor layer region;

photoelectrically detecting stimulated emission released from the stimulable phosphor to produce analog data;

integrating the analog data to produce an integrated value of the analog data and digitizing the integrated value of the analog data by a correction coefficient determined in accordance with the excitation power of the stimulating ray projected onto the stimulable phosphor layer region and producing biochemical analysis data of the stimulable phosphor layer region.

14. A biochemical analysis data producing method in accordance with claim 4 further comprising when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is lower than the threshold value;

irradiating the stimulable phosphor layer region from which the digital data were obtained with a stimulating ray having excitation power higher than the reference excitation power to excite stimulable phosphor contained therein;

photoelectrically detecting stimulated emission released from the stimulable phosphor layer region to produce analog data;

integrating the analog data to produce an integrated value of the analog data;

digitizing the integrated value of the analog data to produce digital data, and adopting the thus produced digital data as biochemical analysis data of the stimulable phosphor layer region.

15. A biochemical analysis data producing method in accordance with claim 14 further comprising:

multiplying digital data produced by irradiating the stimulable phosphor layer region with the stimulating ray having different excitation power to excite stimulable phosphor contained in the stimulable phosphor layer region;

photoelectrically detecting stimulated emission released from the stimulable phosphor to produce analog data;

integrating the analog data to produce an integrated value of the analog data and digitizing the integrated value of the analog data by a correction coefficient determined in accordance with the excitation power of the stimulating ray projected onto the stimulable phosphor layer region and producing biochemical analysis data of the stimulable phosphor layer region.

16. A biochemical analysis data producing method in accordance with claim 4 further comprising:

when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is lower than the threshold value;

irradiating the stimulable phosphor layer region from which the digital data were obtained with a stimulating ray having excitation power higher than the reference excitation power to excite stimulable phosphor contained therein;

photoelectrically detecting stimulated emission released from the stimulable phosphor layer region to produce analog data;

integrating the analog data to produce an integrated value of the analog data;

digitizing the integrated value of the analog data to produce digital data;

comparing signal intensity of the thus obtained digital data with the threshold value, and adopting the digital data as biochemical analysis data of the stimulable phosphor layer region when the signal intensity of the digital data is equal to or higher than the threshold value.

17. A biochemical analysis data producing method in accordance with claim 16
when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data;
integrating the analog data to produce an integrated value of the analog data and
digitizing the integrated value of the analog data is lower than the threshold value, irradiating the stimulable phosphor layer region from which the digital data were obtained with a stimulating ray having excitation power higher than the reference excitation power to excite stimulable phosphor contained therein;
photoelectrically detecting stimulated emission released from the stimulable phosphor layer region to produce analog data;
integrating the analog data to produce an integrated value of the analog data;
digitizing the integrated value of the analog data to produce digital data;
comparing signal intensity of the thus obtained digital data with the threshold value;
sequentially increasing, when the signal intensity of the digital data is lower than the threshold value, the excitation power of the stimulating ray I times at maximum where I is a positive integer;
irradiating the stimulable phosphor layer region from which the digital data were obtained with the stimulating ray to excite stimulable phosphor contained therein;
photoelectrically detecting the stimulated emission released from the stimulable phosphor by the light detector to produce analog data;
integrating the analog data to produce an integrated value of the analog data;
digitizing the integrated value of the analog data, and adopting the thus produced digital data as biochemical analysis data of the stimulable phosphor layer region when the signal intensity of the digital data is equal to or higher than the threshold value, or determining biochemical analysis data of the stimulable phosphor layer region to be zero when the signal intensity of the digital data is still lower than the threshold value even though the digital data were produced by sequentially increasing the excitation power of the stimulating ray I times in total;
irradiating the stimulable phosphor layer region from which the digital data were obtained with the stimulating ray;
photoelectrically detecting stimulated emission released from the stimulable phosphor layer region by the light detector to produce analog data;
integrating the analog data to produce an integrated value of the analog data, and
digitizing the integrated value of the analog data.

18. A biochemical analysis data producing method in accordance with claim 17 further comprising:
multiplying digital data produced by irradiating the stimulable phosphor layer region with the stimulating ray having different excitation power to excite stimulable phosphor contained in the stimulable phosphor layer region;
photoelectrically detecting stimulated emission released from the stimulable phosphor to produce analog data;
integrating the analog data to produce an integrated value of the analog data and digitizing the integrated value of the analog data by a correction coefficient determined in accordance with the excitation power of the stimulating ray projected onto the stimulable phosphor layer region and producing biochemical analysis data of the stimulable phosphor layer region.

19. A biochemical analysis data producing method in accordance with claim 16 further comprising:
multiplying digital data produced by irradiating the stimulable phosphor layer region with the stimulating ray having different excitation power to excite stimulable phosphor contained in the stimulable phosphor layer region;
photoelectrically detecting stimulated emission released from the stimulable phosphor to produce analog data;
integrating the analog data to produce an integrated value of the analog data and digitizing the integrated value of the analog data by a correction coefficient determined in accordance with the excitation power of the stimulating ray projected onto the stimulable phosphor layer region and producing biochemical analysis data of the stimulable phosphor layer region.

20. A biochemical analysis data producing method in accordance with claim 4 further comprising:
when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data, integrating the analog data to produce an integrated value of the analog data and digitizing the integrated value of the analog data is lower than the threshold value;
irradiating the stimulable phosphor layer region from which the digital data were obtained with a stimulating ray having excitation power higher than the reference excitation power to excite stimulable phosphor contained therein;
photoelectrically detecting stimulated emission released from the stimulable phosphor layer region to produce analog data;
integrating the analog data to produce an integrated value of the analog data
digitizing the integrated value of the analog data to produce digital data
comparing signal intensity of the thus obtained digital data with the threshold value
sequentially increasing, when the signal intensity of the digital data is lower than the threshold value, the excitation power of the stimulating ray I times at maximum where I is a positive integer
irradiating the stimulable phosphor layer region from which the digital data were obtained with the stimulating ray to excite stimulable phosphor contained therein;
photoelectrically detecting the stimulated emission released from the stimulable phosphor by the light detector to produce analog data, integrating the analog data to produce an integrated value of the analog data, digitizing the integrated value of the analog data, and adopting the thus produced digital data as biochemical analysis data of the stimulable phosphor layer region when the signal intensity of the digital data is equal to or higher than the threshold value, or determining biochemical analysis data of the stimulable phosphor layer region to be zero when the signal intensity of the digital data is still lower than the threshold value even though the digital data were produced by sequentially increasing the excitation power of the stimulating ray I times in total;

irradiating the stimulable phosphor layer region from which the digital data were obtained with the stimulating ray, photoelectrically detecting stimulated emission released from the stimulable phosphor layer region by the light detector to produce analog data integrating the analog data to produce an integrated value of the analog data, and digitizing the integrated value of the analog data.

21. A biochemical analysis data producing method in accordance with claim 20, further comprising:

multiplying digital data produced by irradiating the stimulable phosphor layer region with the stimulating ray having different excitation power to excite stimulable phosphor contained in the stimulable phosphor layer region;

photoelectrically detecting stimulated emission released from the stimulable phosphor to produce analog data;

integrating the analog data to produce an integrated value of the analog data and digitizing the integrated value of the analog data by a correction coefficient determined in accordance with the excitation power of the stimulating ray projected onto the stimulable phosphor layer region and producing biochemical analysis data of the stimulable phosphor layer region.

22. A biochemical analysis data producing method in accordance with claim 4 further comprising:

when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data;

integrating the analog data to produce an integrated value of the analog data and digitizing the integrated value of the analog data is equal to or higher than the threshold value;

storing the thus produced digital data in a digital memory, irradiating the stimulable phosphor layer region from which the digital data were obtained with a stimulating ray having excitation power greater than the reference excitation power to excite stimulable phosphor contained therein;

photoelectrically detecting stimulated emission to produce analog data;

integrating the analog data to produce an integrated value of the analog data and digitizing the integrated value of the analog data to produce digital data;

storing the thus produced digital data in the digital memory, sequentially increasing the excitation power of the stimulating ray K times in total where K is a positive integer;

irradiating the stimulable phosphor layer region from which the digital data were obtained with the stimulating ray having excitation power greater than the reference excitation power to excite stimulable phosphor contained therein;

photoelectrically detecting stimulated emission to produce analog data;

integrating the analog data to produce an integrated value of the analog data and digitizing the integrated value of the analog data to produce digital data;

storing the thus produced digital data in the digital memory;

summing the digital data stored in the digital memory to produce summed digital data, and adopting the summed digital data as biochemical analysis data of the stimulable phosphor layer region.

23. A biochemical analysis data producing method in accordance with claim 22 further comprising:

when the signal intensity of digital data produced by irradiating the stimulable phosphor layer region with the stimulating ray having the reference excitation power to excite stimulable phosphor contained therein, photoelectrically detecting stimulated emission released from the stimulable phosphor layer region to produce analog data;

integrating the analog data to produce an integrated value of the analog data and digitizing the integrated value of the analog data is lower than the threshold value;

irradiating the stimulable phosphor layer region from which the digital data were obtained with a stimulating ray having excitation power greater than the reference excitation power to excite stimulable phosphor contained therein;

photoelectrically detecting stimulated emission released from the stimulable phosphor layer region to produce analog data;

integrating the analog data to produce an integrated value of the analog data;

digitizing the analog data to produce digital data, comparing the signal intensity of the thus produced digital data with the threshold value;

sequentially increasing, when the signal intensity of the digital data is lower than the threshold value, the excitation power of the stimulating ray M times at maximum where M is a positive integer, irradiating the stimulable phosphor layer region from which the digital data were obtained with the stimulating ray to excite stimulable phosphor contained therein;

photoelectrically detecting stimulated emission released from the stimulable phosphor layer region to produce analog data;

integrating the analog data to produce an integrated value of the analog data;

digitizing the analog data to produce digital data;

comparing the signal intensity of the thus produced digital data with the threshold value;

storing the digital data in the digital memory when the signal intensity of the digital data has become to be equal to or higher than the threshold value;

further sequentially increasing the excitation power of the stimulating ray K times in total, irradiating the stimulable phosphor layer region from which the digital data were obtained with the stimulating ray to excite stimulable phosphor contained therein;

photoelectrically detecting stimulated emission released from the stimulable phosphor layer region to produce analog data;

integrating the analog data to produce an integrated value of the analog data;

digitizing the analog data to produce digital data, storing the thus produced digital data in the digital memory;
summing the digital data stored in the digital data, and
adopting the thus summed digital data as biochemical analysis data of the stimulable phosphor layer region, or determining biochemical analysis data of the stimulable phosphor layer region to be zero when the signal intensity of the digital data is still lower than the threshold value even though the digital data were produced by sequentially increasing the excitation power of the stimulating ray M times in total;
irradiating the stimulable phosphor layer region from which the digital data were obtained with the stimulating ray;
photoelectrically detecting stimulated emission released from the stimulable phosphor layer region to produce analog data;
integrating the analog data to produce an integrated value of the analog data and
digitizing the integrated value of the analog data.

24. A biochemical analysis data producing method in accordance with claim 23 further comprising:
multiplying summed digital data produced by irradiating the stimulable phosphor layer region with a stimulating ray having different excitation power to excite stimulable phosphor contained in the stimulable phosphor layer region;
photoelectrically detecting stimulated emission released from the stimulable phosphor to produce analog data;
integrating the analog data to produce an integrated value of the analog data;
digitizing the integrated value of the analog data to produce digital data and
summing the digital data by a correction coefficient determined in accordance with the excitation power of the stimulating ray projected onto the stimulable phosphor layer region to correct the summed digital data and calculating a total of the thus corrected summed digital data to produce biochemical analysis data of the stimulable phosphor layer region.

25. A biochemical analysis data producing method in accordance with claim 22 further comprising:
multiplying summed digital data produced by irradiating the stimulable phosphor layer region with a stimulating ray having different excitation power to excite stimulable phosphor contained in the stimulable phosphor layer region;
photoelectrically detecting stimulated emission released from the stimulable phosphor to produce analog data;
integrating the analog data to produce an integrated value of the analog data;
digitizing the integrated value of the analog data to produce digital data and
summing the digital data by a correction coefficient determined in accordance with the excitation power of the stimulating ray projected onto the stimulable phosphor layer region to correct the summed digital data and calculating a total of the thus corrected summed digital data to produce biochemical analysis data of the stimulable phosphor layer region.

26. A biochemical analysis data producing method in accordance with claim 4 further comprising:
when the signal intensity of digital data produced by irradiating the stimulable phosphor layer region with the stimulating ray having the reference excitation power to excite stimulable phosphor contained therein, photoelectrically detecting stimulated emission released from the stimulable phosphor layer region to produce analog data;
integrating the analog data to produce an integrated value of the analog data and
digitizing the integrated value of the analog data is equal to or higher than the threshold value;
storing the thus produced digital data in the digital memory;
irradiating the stimulable phosphor layer region from which the digital data were obtained with a stimulating ray having excitation power greater than the reference excitation power to excite stimulable phosphor contained therein;
photoelectrically detecting stimulated emission released from the stimulable phosphor layer region to produce analog data;
integrating the analog data to produce an integrated value of the analog data;
digitizing the analog data to produce digital data;
storing the thus produced digital data in the digital memory;
sequentially increasing the excitation power of the stimulating ray;
irradiating the stimulable phosphor layer region from which the digital data were obtained with the stimulating ray having excitation power greater than the reference excitation power to excite stimulable phosphor contained therein;
photoelectrically detecting stimulated emission released from the stimulable phosphor layer region to produce analog data
integrating the analog data to produce an integrated value of the analog data;
digitizing the analog data to produce digital data, storing the thus produced digital data in the digital memory;
summing the digital data stored in the digital memory so far to calculate summed digital data when the signal intensity of digital data produced by irradiating the stimulable phosphor layer region from which the digital data were obtained with the stimulating ray to excite stimulable phosphor contained therein;
photoelectrically detecting stimulated emission released from the stimulable phosphor layer region to produce analog data;
integrating the analog data to produce an integrated value of the analog data and
digitizing the analog data cannot come to be equal to or higher than the threshold value even if the excitation power of the stimulating ray is increased, and
adopting the summed digital data as biochemical analysis data of the stimulable phosphor layer region.

27. A biochemical analysis data producing method in accordance with claim 26 further comprising: when the signal intensity of the digital data produced by irradiating the stimulable phosphor layer region with the stimulating ray having the reference excitation power to excite stimulable phosphor contained in the stimulable phosphor layer region, photoelectrically detecting stimulated emission to produce analog data;
integrating the analog data to produce an integrated value of the analog data and digitizing the integrated value of the analog data is equal to or higher than the threshold value;
storing the thus produced digital data in a digital memory;
irradiating the stimulable phosphor layer region from which the digital data were obtained with a stimulating ray having excitation power greater than the reference excitation power to excite stimulable phosphor contained therein;

photoelectrically detecting stimulated emission to produce analog data;

integrating the analog data to produce an integrated value of the analog data and digitizing the integrated value of the analog data to produce digital data;

comparing the signal intensity of the thus produced digital data with the threshold value;

sequentially increasing, when the signal intensity of the digital data is lower than the threshold value, the excitation power of the stimulating ray N times at maximum where N is a positive integer;

irradiating the stimulable phosphor layer region from which the digital data were obtained with the stimulating ray having excitation power greater than the reference excitation power to excite stimulable phosphor contained therein;

photoelectrically detecting stimulated emission to produce analog data;

integrating the analog data to produce an integrated value of the analog data and digitizing the integrated value of the analog data to produce digital data;

storing, when the signal intensity of the thus produced digital data has come to be equal to or higher than the threshold value, the digital data in a digital memory;

further sequentially increasing the excitation power of the stimulating ray;

irradiating the stimulable phosphor layer region from which the digital data were obtained with the stimulating ray, to excite stimulable phosphor contained therein;

photoelectrically detecting stimulated emission to produce analog data;

integrating the analog data to produce an integrated value of the analog data and digitizing the integrated value of the analog data to produce digital data;

summing the digital data to produce summed digital data;

storing the thus summed digital data in the digital memory;

calculating, when the signal intensity of the thus produced digital data cannot come to be equal to or higher than the threshold value even if the excitation power of the stimulating ray is increased, a total of the summed digital data stored in the digital memory so far to produce the total of the summed digital dada, and adopting the thus calculated total of the summed digital data as biochemical analysis data of the stimulable phosphor layer region, or determining digital data of the stimulable phosphor layer region to be zero when the signal intensity of the digital data is still lower than the threshold value even though the excitation power of the stimulating ray was sequentially increased N times in total to irradiate the stimulable phosphor layer region from which the digital data were obtained with the stimulating ray and stimulated emission released from the stimulable phosphor layer region was photoelectrically detected by the light detector.

28. A biochemical analysis data producing method in accordance with claim 27 further comprising:

multiplying summed digital data produced by irradiating the stimulable phosphor layer region with a stimulating ray having different excitation power to excite stimulable phosphor contained in the stimulable phosphor layer region;

photoelectrically detecting stimulated emission released from the stimulable phosphor to produce analog data;

integrating the analog data to produce an integrated value of the analog data;

digitizing the integrated value of the analog data to produce digital data and summing the digital data by a correction coefficient determined in accordance with the excitation power of the stimulating ray projected onto the stimulable phosphor layer region to correct the summed digital data and calculating a total of the thus corrected summed digital data to produce biochemical analysis data of the stimulable phosphor layer region.

29. A biochemical analysis data producing method in accordance with claim 26 further comprising:

multiplying summed digital data produced by irradiating the stimulable phosphor layer region with a stimulating ray having different excitation power to excite stimulable phosphor contained in the stimulable phosphor layer region;

photoelectrically detecting stimulated emission released from the stimulable phosphor to produce analog data;

integrating the analog data to produce an integrated value of the analog data;

digitizing the integrated value of the analog data to produce digital data and summing the digital data by a correction coefficient determined in accordance with the excitation power of the stimulating ray projected onto the stimulable phosphor layer region to correct the summed digital data and calculating a total of the thus corrected summed digital data to produce biochemical analysis data of the stimulable phosphor layer region.

30. A biochemical analysis data producing method in accordance with claim 4, wherein the stimulable phosphor sheet and the stimulating ray are intermittently moved relative to each other in the main scanning direction by a pitch equal to a distance between neighboring stimulable phosphor layer regions in the main scanning direction.

31. A biochemical analysis data producing method in accordance with claim 4, wherein the plurality of stimulable phosphor layer regions of the stimulable phosphor sheet are two-dimensionally formed in the support so as to be spaced apart from each other and the biochemical analysis data producing method comprises:

moving the stimulable phosphor sheet and the stimulating ray relative to each other in the main scanning direction and a sub-scanning direction perpendicular to the main scanning direction;

sequentially irradiating the plurality of stimulable phosphor layer regions with the stimulating ray to excite stimulable phosphor contained in the individual stimulable phosphor layer regions, and photoelectrically detecting stimulated emission released from the individual stimulable phosphor layer regions, thereby producing biochemical analysis data.

32. A biochemical analysis data producing method in accordance with claim 4, wherein a plurality of holes are formed in the support of the stimulable phosphor sheet so as to be spaced apart from each other and the plurality of stimulable phosphor layer regions of the stimulable phosphor sheet are formed by charging stimulable phosphor in the holes.

33. A biochemical analysis data producing method in accordance with claim 4, wherein the support of the stimulable phosphor sheet is formed with 10 or more stimulable phosphor layer regions.

34. A biochemical analysis data producing method in accordance with claim 4, wherein each of the plurality of stimulable phosphor layer regions is formed in the stimulable phosphor sheet to have a size of less than 5 mm$^2$.

35. A biochemical analysis data producing method in accordance with claim 4, wherein the plurality of stimulable phosphor layer regions are formed in the stimulable phosphor sheet at a density of 10 or more per cm$^2$.

36. A biochemical analysis data producing method in accordance with claim 4, wherein the support of the stimulable phosphor sheet has a property of attenuating radiation energy and/or light energy.

37. A biochemical analysis data producing method in accordance with claim 36, wherein the support of the stimulable phosphor sheet has a property of reducing the energy of radiation and/or the energy of light to $\frac{1}{5}$ or less when the radiation and/or light travels in the support by a distance equal to that between neighboring stimulable phosphor layer regions.

38. A biochemical analysis data producing method in accordance with claim 2 further comprising:
   intermittently moving the stimulable phosphor sheet and the stimulating ray relative to each other at least one-dimensionally;
   sequentially irradiating the plurality of stimulable phosphor layer regions with the stimulating ray for a predetermined time and
   increasing the excitation power of the stimulating ray with the lapse of time to excite stimulable phosphor contained in the individual stimulable phosphor layer regions.

39. A biochemical analysis data producing method in accordance with claim 38, wherein the excitation power of the stimulating ray is controlled so as to be increased with the lapse of time in accordance with an exponential function.

40. A biochemical analysis data producing method in accordance with claim 39 further comprising:
   photoelectrically detecting stimulated emission released from the stimulable phosphor layer region to produce analog data and counting the number of photons contained in the stimulated emission based on the thus produced analog data, thereby producing biochemical analysis data of the stimulable phosphor layer region.

41. A biochemical analysis data producing method in accordance with claim 38 further comprising:
   photoelectrically detecting stimulated emission released from the stimulable phosphor layer region to produce analog data and
   counting the number of photons contained in the stimulated emission based on the thus produced analog data, thereby producing biochemical analysis data of the stimulable phosphor layer region.

42. A biochemical analysis data producing method in accordance with claim 38, wherein the stimulating ray is on and off controlled in such a manner that only the plurality of stimulable phosphor layer regions are irradiated with the stimulating ray and regions other than the plurality of stimulable phosphor layer regions are not irradiated with the stimulating ray.

43. A biochemical analysis data producing method in accordance with claim 38, wherein the stimulable phosphor sheet and the stimulating ray are intermittently moved relative to each other in the main scanning direction by a pitch equal to a distance between neighboring stimulable phosphor layer regions in the main scanning direction.

44. A biochemical analysis data producing method in accordance with claim 38, wherein the plurality of stimulable phosphor layer regions of the stimulable phosphor sheet are two-dimensionally formed in the support so as to be spaced apart from each other and the biochemical analysis data producing method comprises:
   moving the stimulable phosphor sheet and the stimulating ray relative to each other in the main scanning direction and a sub-scanning direction perpendicular to the main scanning direction;
   sequentially irradiating the plurality of stimulable phosphor layer regions with the stimulating ray to excite stimulable phosphor contained in the individual stimulable phosphor layer regions, and
   photoelectrically detecting stimulated emission released from the individual stimulable phosphor layer regions, thereby producing biochemical analysis data.

45. A biochemical analysis data producing method in accordance with claim 38, wherein a plurality of holes are formed in the support of the stimulable phosphor sheet so as to be spaced apart from each other and the plurality of stimulable phosphor layer regions of the stimulable phosphor sheet are formed by charging stimulable phosphor in the holes.

46. A biochemical analysis data producing method in accordance with claim 38, wherein the support of the stimulable phosphor sheet is formed with 10 or more stimulable phosphor layer regions.

47. A biochemical analysis data producing method in accordance with claim 38, wherein each of the plurality of stimulable phosphor layer regions is formed in the stimulable phosphor sheet to have a size of less than 5 mm$^2$.

48. A biochemical analysis data producing method in accordance with claim 38, wherein the plurality of stimulable phosphor layer regions are formed in the stimulable phosphor sheet at a density of 10 or more per cm$^2$.

49. A biochemical analysis data producing method in accordance with claim 38, wherein the support of the stimulable phosphor sheet has a property of attenuating radiation energy and/or light energy.

50. A biochemical analysis data producing method in accordance with claim 49, wherein the support of the stimulable phosphor sheet has a property of reducing the energy of radiation and/or the energy of light to $\frac{1}{5}$ or less when the radiation and/or light travels in the support by a distance equal to that between neighboring stimulable phosphor layer regions.

51. A biochemical analysis data producing method in accordance with claim 2, wherein the stimulating ray is on and off controlled in such a manner that only the plurality of stimulable phosphor layer regions are irradiated with the stimulating ray and regions other than the plurality of stimulable phosphor layer regions are not irradiated with the stimulating ray.

52. A biochemical analysis data producing method in accordance with claim 4, wherein the stimulating ray is on and off controlled in such a manner that only the plurality of stimulable phosphor layer regions are irradiated with the stimulating ray and regions other than the plurality of stimulable phosphor layer regions are not irradiated with the stimulating ray.

53. A biochemical analysis data producing method in accordance with claim 2, wherein the stimulable phosphor sheet and the stimulating ray are intermittently moved relative to each other in the main scanning direction by a pitch equal to a distance between neighboring stimulable phosphor layer regions in the main scanning direction.

54. A biochemical analysis data producing method in accordance with claim 2, wherein the stimulable phosphor sheet is constantly irradiated with the stimulating ray while the stimulable phosphor sheet and the stimulating ray are intermittently moved relative to each other in the main scanning direction.

55. A biochemical analysis data producing method in accordance with claim 2, wherein the plurality of stimulable phosphor layer regions of the stimulable phosphor sheet are two-dimensionally formed in the support so as to be spaced apart from each other and the biochemical analysis data producing method comprises:
  moving the stimulable phosphor sheet and the stimulating ray relative to each other in the main scanning direction and a sub-scanning direction perpendicular to the main scanning direction;
  sequentially irradiating the plurality of stimulable phosphor layer regions with the stimulating ray to excite stimulable phosphor contained in the individual stimulable phosphor layer regions, and
  photoelectrically detecting stimulated emission released from the individual stimulable phosphor layer regions, thereby producing biochemical analysis data.

56. A biochemical analysis data producing method in accordance with claim 2, wherein a plurality of holes are formed in the support of the stimulable phosphor sheet so as to be spaced apart from each other and the plurality of stimulable phosphor layer regions of the stimulable phosphor sheet are formed by charging stimulable phosphor in the holes.

57. A biochemical analysis data producing method in accordance with claim 2, wherein the support of the stimulable phosphor sheet is formed with 10 or more stimulable phosphor layer regions.

58. A biochemical analysis data producing method in accordance with claim 2, wherein each of the plurality of stimulable phosphor layer regions is formed in the stimulable phosphor sheet to have a size of less than 5 mm$^2$.

59. A biochemical analysis data producing method in accordance with claim 2, wherein the plurality of stimulable phosphor layer regions are formed in the stimulable phosphor sheet at a density of 10 or more per cm$^2$.

60. A biochemical analysis data producing method in accordance with claim 2, wherein the support of the stimulable phosphor sheet has a property of attenuating radiation energy and/or light energy.

61. A biochemical analysis data producing method in accordance with claim 60, wherein the support of the stimulable phosphor sheet has a property of reducing the energy of radiation and/or the energy of light to 1/5 or less when the radiation and/or light travels in the support by a distance equal to that between neighboring stimulable phosphor layer regions.

62. A biochemical analysis data producing method in accordance with claim 2, further comprising:
  photoelectrically detecting stimulated emission to produce analog data,
  digitizing the analog data to produce digital data and
  summing the digital data to produce biochemical analysis data.

63. A biochemical analysis data producing method in accordance with claim 1, further comprising:
  when the signal intensity of the digital data produced by irradiating the stimulable phosphor layer region with the stimulating ray having the reference excitation power is equal to or higher than the threshold value, adopting the thus produced digital data as biochemical analysis data of the stimulable phosphor layer region.

64. A biochemical analysis data producing method in accordance with claim 63 further comprising:
  when the signal intensity of the digital data produced by irradiating the stimulable phosphor layer region with the stimulating ray having the reference excitation power is lower than the threshold value, irradiating the stimulable phosphor layer region from which the digital data were obtained with the stimulating ray having excitation power higher than the reference excitation power to excite stimulable phosphor contained therein;
  photoelectrically detecting stimulated emission released from the stimulable phosphor layer region to produce analog data and
  digitizing the analog data to produce digital data and adopting the digital data as biochemical analysis data of the stimulable phosphor layer region.

65. A biochemical analysis data producing method in accordance with claim 64 further comprising:
  when the signal intensity of the digital data produced by irradiating the stimulable phosphor layer region with the stimulating ray having the reference excitation power is lower than the threshold value;
  irradiating the stimulable phosphor layer region from which the digital data were obtained with a stimulating ray having excitation power higher than the reference excitation power to excite stimulable phosphor contained therein;
  photoelectirically detecting stimulated emission released from the stimulable phosphor layer region to produce analog data, digitizing the analog data to produce digital data;
  comparing signal intensity of the thus obtained digital data with the threshold value;
  sequentially increasing, when the signal intensity of the digital data is lower than the threshold value, the excitation power of the stimulating ray I times at maximum where I is a positive integer, irradiating the stimulable phosphor layer region from which the digital data were obtained with the stimulating ray to excite stimulable phosphor contained therein;
  photoelectrically detecting the stimulated emission released from the stimulable phosphor by the light detector, and
  adopting the digital data as biochemical analysis data of the stimulable phosphor layer region when the signal intensity of the digital data is equal to or higher than the threshold value, or determining biochemical analysis data of the stimulable phosphor layer region to be zero when the signal intensity of the digital data is still lower than the threshold value even though the excitation power of the stimulating ray was sequentially increased I times in total to irradiate the stimulable phosphor layer region from which the digital data were obtained with the stimulating ray and stimulated emission released from the stimulable phosphor layer region was photoelectrically detected by the light detector.

66. A biochemical analysis data producing method in accordance with claim 65 further comprising:
  multiplying digital data produced by irradiating the stimulable phosphor layer region with the stimulating ray having different excitation power to excite stimulable phosphor contained in the stimulable phosphor layer region;
  photoelectrically detecting stimulated emission released from the stimulable phosphor to produce analog data, and digitizing the analog data by a correction coefficient determined in accordance with the excitation power of the stimulating ray projected onto the stimulable phosphor layer region and producing biochemical analysis data of the stimulable phosphor layer region.

67. A biochemical analysis data producing method in accordance with claim 64 further comprising:
multiplying digital data produced by irradiating the stimulable phosphor layer region with the stimulating ray having different excitation power to excite stimulable phosphor contained in the stimulable phosphor layer region
photoelectrically detecting stimulated emission released from the stimulable phosphor to produce analog data, and
digitizing the analog data by a correction coefficient determined in accordance with the excitation power of the stimulating ray projected onto the stimulable phosphor layer region and producing biochemical analysis data of the stimulable phosphor layer region.

68. A biochemical analysis data producing method in accordance with claim 63 further comprising:
when the signal intensity of the digital data produced by irradiating the stimulable phosphor layer region with the stimulating ray having the reference excitation power is lower than the threshold value, irradiating the stimulable phosphor layer region from which the digital data were obtained with a stimulating ray having excitation power higher than the reference excitation power to excite stimulable phosphor contained therein;
photoelectrically detecting stimulated emission released from the stimulable phosphor layer region to produce analog data, digitizing the analog data to produce digital data;
comparing signal intensity of the thus obtained digital data with the threshold value, and
adopting the digital data as biochemical analysis data of the stimulable phosphor layer region when the signal intensity of the digital data is equal to or higher than the threshold value.

69. A biochemical analysis data producing method in accordance with claim 68 further comprising:
multiplying digital data produced by irradiating the stimulable phosphor layer region with the stimulating ray having different excitation power to excite stimulable phosphor contained in the stimulable phosphor layer region;
photoelectrically detecting stimulated emission released from the stimulable phosphor to produce analog data, and
digitizing the analog data by a correction coefficient determined in accordance with the excitation power of the stimulating ray projected onto the stimulable phosphor layer region and producing biochemical analysis data of the stimulable phosphor layer region.

70. A biochemical analysis data producing method in accordance with claim 63 further comprising:
when the signal intensity of the digital data produced by irradiating the stimulable phosphor layer region with the stimulating ray having the reference excitation power is lower than the threshold value;
irradiating the stimulable phosphor layer region from which the digital data were obtained with a stimulating ray having excitation power higher than the reference excitation power to excite stimulable phosphor contained therein;
photoelectrically detecting stimulated emission released from the stimulable phosphor layer region to produce analog data;
digitizing the analog data to produce digital data;
comparing signal intensity of the thus obtained digital data with the threshold value, sequentially increasing, when the signal intensity of the digital data is lower than the threshold value, the excitation power of the stimulating ray I times at maximum where I is a positive integer, irradiating the stimulable phosphor layer region from which the digital data were obtained with the stimulating ray to excite stimulable phosphor contained therein;
photoelectrically detecting the stimulated emission released from the stimulable phosphor by the light detector, and
adopting the digital data as biochemical analysis data of the stimulable phosphor layer region when the signal intensity of the digital data is equal to or higher than the threshold value, or determining biochemical analysis data of the stimulable phosphor layer region to be zero when the signal intensity of the digital data is still lower than the threshold value even though the excitation power of the stimulating ray was sequentially increased I times in total to irradiate the stimulable phosphor layer region from which the digital data were obtained with the stimulating ray and stimulated emission released from the stimulable phosphor layer region was photoelectrically detected by the light detector.

71. A biochemical analysis data producing method in accordance with claim 70 further comprising:
multiplying digital data produced by irradiating the stimulable phosphor layer region with the stimulating ray having different excitation power to excite stimulable phosphor contained in the stimulable phosphor layer region;
photoelectrically detecting stimulated emission released from the stimulable phosphor to produce analog data, and
digitizing the analog data by a correction coefficient determined in accordance with the excitation power of the stimulating ray projected onto the stimulable phosphor layer region and producing biochemical analysis data of the stimulable phosphor layer region.

72. A biochemical analysis data producing method in accordance with claim 1 further comprising
when the signal intensity of the digital data produced by irradiating the stimulable phosphor layer region with the stimulating ray having the reference excitation power is lower than the threshold value, irradiating the stimulable phosphor layer region from which the digital data were obtained with the stimulating ray having excitation power higher than the reference excitation power to excite stimulable phosphor contained therein;
photoelectirically detecting stimulated emission released from the stimulable phosphor layer region to produce analog data and digitizing the analog data to produce digital data and
adopting the digital data as biochemical analysis data of the stimulable phosphor layer region.

73. A biochemical analysis data producing method in accordance with claim 72 further comprising:
multiplying digital data produced by irradiating the stimulable phosphor layer region with the stimulating ray having different excitation power to excite stimulable phosphor contained in the stimulable phosphor layer region;

photoelectrically detecting stimulated emission released from the stimulable phosphor to produce analog data, and digitizing the analog data by a correction coefficient determined in accordance with the excitation power of the stimulating ray projected onto the stimulable phosphor layer region and producing biochemical analysis data of the stimulable phosphor layer region.

74. A biochemical analysis data producing method in accordance with claim 1 further comprising:

when the signal intensity of the digital data produced by irradiating the stimulable phosphor layer region with the stimulating ray having the reference excitation power is lower than the threshold value, irradiating the stimulable phosphor layer region from which the digital data were obtained with a stimulating ray having excitation power higher than the reference excitation power to excite stimulable phosphor contained therein, photoelectrically detecting stimulated emission released from the stimulable phosphor layer region to produce analog data;

digitizing the analog data to produce digital data, comparing signal intensity of the thus obtained digital data with the threshold value, and adopting the digital data as biochemical analysis data of the stimulable phosphor layer region when the signal intensity of the digital data is equal to or higher than the threshold value.

75. A biochemical analysis data producing method in accordance with claim 74 further comprising:

multiplying digital data produced by irradiating the stimulable phosphor layer region with the stimulating ray having different excitation power to excite stimulable phosphor contained in the stimulable phosphor layer region;

photoelectrically detecting stimulated emission released from the stimulable phosphor to produce analog data, and digitizing the analog data by a correction coefficient determined in accordance with the excitation power of the stimulating ray projected onto the stimulable phosphor layer region and producing biochemical analysis data of the stimulable phosphor layer region.

76. A biochemical analysis data producing method in accordance with claim 1 further comprising:

when the signal intensity of the digital data produced by irradiating the stimulable phosphor layer region with the stimulating ray having the reference excitation power is lower than the threshold value, irradiating the stimulable phosphor layer region from which the digital data were obtained with a stimulating ray having excitation power higher than the reference excitation power to excite stimulable phosphor contained therein;

photoelectrically detecting stimulated emission released from the stimulable phosphor layer region to produce analog data digitizing the analog data to produce digital data, comparing signal intensity of the thus obtained digital data with the threshold value, sequentially increasing, when the signal intensity of the digital data is lower than the threshold value, the excitation power of the stimulating ray I times at maximum where I is a positive integer;

irradiating the stimulable phosphor layer region from which the digital data were obtained with the stimulating ray to excite stimulable phosphor contained therein;

photoelectrically detecting the stimulated emission released from the stimulable phosphor by the light detector, and adopting the digital data as biochemical analysis data of the stimulable phosphor layer region when the signal intensity of the digital data is equal to or higher than the threshold value, or determining biochemical analysis data of the stimulable phosphor layer region to be zero when the signal intensity of the digital data is still lower than the threshold value even though the excitation power of the stimulating ray was sequentially increased I times in total to irradiate the stimulable phosphor layer region from which the digital data were obtained with the stimulating ray and stimulated emission released from the stimulable phosphor layer region was photoelectrically detected by the light detector.

77. A biochemical analysis data producing method in accordance with claim 76 further comprising:

multiplying digital data produced by irradiating the stimulable phosphor layer region with the stimulating ray having different excitation power to excite stimulable phosphor contained in the stimulable phosphor layer region;

photoelectrically detecting stimulated emission released from the stimulable phosphor to produce analog data, and digitizing the analog data by a correction coefficient determined in accordance with the excitation power of the stimulating ray projected onto the stimulable phosphor layer region and producing biochemical analysis data of the stimulable phosphor layer region.

78. A biochemical analysis data producing method in accordance with claim 1 further comprising:

when the signal intensity of the digital data produced by irradiating the stimulable phosphor layer region with the stimulating ray having the reference excitation power is equal to or higher than the threshold value;

continuing to irradiate the stimulable phosphor layer region with the stimulating ray;

summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value and adopting the summed digital data as biochemical analysis data of the stimulable phosphor layer region.

79. A biochemical analysis data producing method in accordance with claim 78 further comprising:

when the signal intensity of the digital data produced by irradiating the stimulable phosphor layer region with the stimulating ray having the reference excitation power is lower than the threshold value, irradiating the stimulable phosphor layer region from which the digital data were obtained with a stimulating ray having excitation power higher than the reference excitation power to excite stimulable phosphor contained therein;

photoelectrically detecting stimulated emission released from the stimulable phosphor layer region to produce analog data;

digitizing the analog data to produce digital data, comparing signal intensity of the thus obtained digital data with the threshold value;
sequentially increasing, when the signal intensity of the digital data is lower than the threshold value, the excitation power of the stimulating ray j times at maximum where j is a positive integer
irradiating the stimulable phosphor layer region from which the digital data were obtained with the stimulating ray to excite stimulable phosphor contained therein;
photoelectrically detecting the stimulated emission released from the stimulable phosphor by the light detector to produce analog data, digitizing the analog data to produce digital data;
continuing, when the signal intensity of the thus obtained digital data has come to be equal to or higher than the threshold value, to irradiate the stimulable phosphor layer region with the stimulating ray
summing digital data produced by photoelectrically detecting stimulated emission released from stimulable phosphor contained in the stimulable phosphor layer region to produce analog data and
digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value and adopting the summed digital data as biochemical analysis data of the stimulable phosphor layer region, or determining biochemical analysis data of the stimulable phosphor layer region to be zero when the signal intensity of the digital data is still lower than the threshold value even though the excitation power of the stimulating ray was sequentially increased j times in total to irradiate the stimulable phosphor layer region from which the digital data were obtained with the stimulating ray and stimulated emission released from the stimulable phosphor layer region was photoelectrically detected by the light detector.

80. A biochemical analysis data producing method in accordance with claim 79 further comprising:
multiplying summed digital data produced by irradiating the stimulable phosphor layer region with the stimulating ray having different excitation power to excite stimulable phosphor contained in the stimulable phosphor layer region, photoelectrically detecting stimulated emission released from the stimulable phosphor to produce analog data;
digitizing the analog data to produce digital data and summing the digital data by a correction coefficient determined in accordance with the excitation power of the stimulating ray projected onto the stimulable phosphor region to correct the summed digital data and
calculating a total of the thus corrected summed digital data to produce biochemical analysis data of the stimulable phosphor layer.

81. A biochemical analysis data producing method in accordance with claim 78 further comprising:
multiplying summed digital data produced by irradiating the stimulable phosphor layer region with the stimulating ray having different excitation power to excite stimulable phosphor contained in the stimulable phosphor layer region;
photoelectrically detecting stimulated emission released from the stimulable phosphor to produce analog data
digitizing the analog data to produce digital data and summing the digital data by a correction coefficient determined in accordance with the excitation power of the stimulating ray projected onto the stimulable phosphor region to correct the summed digital data and
calculating a total of the thus corrected summed digital data to produce biochemical analysis data of the stimulable phosphor layer.

82. A biochemical analysis data producing method in accordance with claim 1 further comprising:
when the signal intensity of the digital data produced by irradiating the stimulable phosphor layer region with the stimulating ray having the reference excitation power is equal to or higher than the threshold value;
continuing to irradiate the stimulable phosphor layer region with the stimulating ray, summing digital data produced by photoelectrically detecting stimulated emission released from stimulable phosphor contained in the stimulable phosphor layer region to produce analog data and
digitizing the analog data to store the summed digital data in a digital memory until the signal intensity of digital data produced by photoelectrically detecting stimulated emission released from stimulable phosphor contained in the stimulable phosphor layer region to produce analog data and
digitizing the analog data has come to be lower than the threshold value, irradiating, when the signal intensity of digital data produced by photoelectrically detecting stimulated emission released from stimulable phosphor contained in the stimulable phosphor layer region to produce analog data and digitizing the analog data has come to be lower than the threshold value, the stimulable phosphor layer region from which the digital data were obtained with a stimulating ray having excitation power higher than the reference excitation power to excite stimulable phosphor contained therein;
photoelectrically detecting stimulated emission released from the stimulable phosphor layer region to produce analog data, digitizing the analog data to produce digital data, comparing signal intensity of the thus obtained digital data with the threshold value;
continuing to irradiate the stimulable phosphor layer region with the stimulating ray;
summing digital data produced by photoelectrically detecting stimulated emission released from stimulable phosphor contained in the stimulable phosphor layer region to produce analog data and
digitizing the analog data to store the summed digital data in a digital memory until the signal intensity of digital data become to be lower than the threshold value, further sequentially increasing the excitation power of the stimulating ray k times at maximum where k is a positive integer
irradiating the stimulable phosphor layer region from which the digital data were obtained with the stimulating ray to excite stimulable phosphor contained therein;
photoelectrically detecting the stimulated emission released from the stimulable phosphor by the light detector to produce analog data, digitizing the analog data to produce digital data
summing the digital data
storing the summed digital data in the digital memory
calculating a total of the summed digital value, and adopting the thus calculated total of the summed digital value as biochemical analysis data of the stimulable phosphor layer region.

83. A biochemical analysis data producing method in accordance with claim 82 further comprising:

when the signal intensity of the digital data produced by irradiating the stimulable phosphor layer region with the stimulating ray having the reference excitation power is lower than the threshold value;

irradiating the stimulable phosphor layer region from which the digital data were obtained with a stimulating ray having excitation power higher than the reference excitation power to excite stimulable phosphor contained therein, photoelectrically detecting stimulated emission released from the stimulable phosphor layer region to produce analog data; digitizing the analog data to produce digital data comparing signal intensity of the thus obtained digital data with the threshold value sequentially increasing, when the signal intensity of the digital data is lower than the threshold value, the excitation power of the stimulating ray m times at maximum where m is a positive integer;

irradiating the stimulable phosphor layer region from which the digital data were obtained with the stimulating ray to excite stimulable phosphor contained therein, photoelectrically detecting the stimulated emission released from the stimulable phosphor by the light detector to produce analog data, digitizing the analog data to produce digital data;

continuing, when the signal intensity of the thus obtained digital data has come to be equal to or higher than the threshold value, to irradiate the stimulable phosphor layer region with the stimulating ray summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value, further sequentially increasing the excitation power of the stimulating ray m times at maximum, irradiating the stimulable phosphor layer region from which the digital data were obtained with the stimulating ray to excite stimulable phosphor contained therein;

photoelectrically detecting the stimulated emission released from the stimulable phosphor by the light detector to produce analog data, digitizing the analog data to produce digital data;

summing the digital data;

storing the summed digital data in the digital memory;

calculating a total of the summed digital value, and adopting the thus calculated total of the digital data as biochemical analysis data of the stimulable phosphor layer region, or determining biochemical analysis data of the stimulable phosphor layer region to be zero when the signal intensity of the digital data is still lower than the threshold value even though the excitation power of the stimulating ray was sequentially increased m times in total to irradiate the stimulable phosphor layer region from which the digital data were obtained with the stimulating ray and stimulated emission released from the stimulable phosphor layer region was photoelectrically detected by the light detector.

84. A biochemical analysis data producing method in accordance with claim 83 further comprising:

multiplying summed digital data produced by irradiating the stimulable phosphor layer region with the stimulating ray having different excitation power to excite stimulable phosphor contained in the stimulable phosphor layer region photoelectrically detecting stimulated emission released from the stimulable phosphor to produce analog data;

digitizing the analog data to produce digital data and summing the digital data by a correction coefficient determined in accordance with the excitation power of the stimulating ray projected onto the stimulable phosphor region to correct the summed digital data and calculating a total of the thus corrected summed digital data to produce biochemical analysis data of the stimulable phosphor layer.

85. A biochemical analysis data producing method in accordance with claim 82 further comprising:

multiplying summed digital data produced by irradiating the stimulable phosphor layer region with the stimulating ray having different excitation power to excite stimulable phosphor contained in the stimulable phosphor layer region, photoelectrically detecting stimulated emission released from the stimulable phosphor to produce analog data, digitizing the analog data to produce digital data and summing the digital data by a correction coefficient determined in accordance with the excitation power of the stimulating ray projected onto the stimulable phosphor region to correct the summed digital data and calculating a total of the thus corrected summed digital data to produce biochemical analysis data of the stimulable phosphor layer.

86. A biochemical analysis data producing method in accordance with claim 1 further comprising:

when the signal intensity of the digital data produced by irradiating the stimulable phosphor layer region with the stimulating ray having the reference excitation power is equal to or higher than the threshold value continuing to irradiate the stimulable phosphor layer region with the stimulating ray;

summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value;

irradiating, when the signal intensity of digital data produced by photoelectrically detecting stimulated emission released from stimulable phosphor contained in the stimulable phosphor layer region to produce analog data and digitizing the analog data has come to be lower than the threshold value, the stimulable phosphor layer region from which the digital data were obtained with a stimulating ray having excitation power higher than the reference excitation power to excite stimulable phosphor contained therein, photoelectrically detecting stimulated emission released from the stimulable phosphor layer region to produce analog data, digitizing the analog data to produce digital data;

comparing signal intensity of the thus obtained digital data with the threshold value;

continuing to irradiate the stimulable phosphor layer region with the stimulating ray summing digital data produced by photoelectrically detecting stimulated emission released from stimulable phosphor contained in the stimulable phosphor layer region to produce analog data and digitizing the analog data to store the summed digital data in a digital memory until the signal intensity of digital data comes to be lower than the threshold value, calculating, when the signal intensity of digital data cannot come to be equal to or higher than the threshold value even if the excitation power of the stimulating ray is increased, a total of the summed digital data stored in the digital memory so far, and adopting it as the biochemical analysis data of the stimulable phosphor layer region.

87. A biochemical analysis data producing method in accordance with claim 86 further comprising:

when the signal intensity of the digital data produced by irradiating the stimulable phosphor layer region with the stimulating ray having the reference excitation power is lower than the threshold value irradiating the stimulable phosphor layer region from which the digital data were obtained with a stimulating ray having excitation power higher than the reference excitation power to excite stimulable phosphor contained therein, photoelectrically detecting stimulated emission released from the stimulable phosphor layer region to produce analog data;

digitizing the analog data to produce digital data;

comparing signal intensity of the thus obtained digital data with the threshold value;

sequentially increasing, when the signal intensity of the digital data is lower than the threshold value, the excitation power of the stimulating ray n times at maximum where n is a positive integer irradiating the stimulable phosphor layer region from which the digital data were obtained with the stimulating ray to excite stimulable phosphor contained therein photoelectrically detecting the stimulated emission released from the stimulable phosphor by the light detector to produce analog data digitizing the analog data to produce digital data, continuing, when the signal intensity of the thus obtained digital data has come to be equal to or higher than the threshold value, to irradiate the stimulable phosphor layer region with the stimulating ray summing digital data produced by photoelectrically detecting stimulated emission released from stimulable phosphor contained in the stimulable phosphor layer region to produce analog data and digitizing the analog data to store the summed digital data in a digital memory until the signal intensity of digital data produced by photoelectrically detecting stimulated emission released from stimulable phosphor contained in the stimulable phosphor layer region to produce analog data and digitizing the analog data has come to be lower than the threshold value;

further sequentially increasing the excitation power of the stimulating ray n times at maximum;

irradiating the stimulable phosphor layer region from which the digital data were obtained with the stimulating ray to excite stimulable phosphor contained therein photoelectrically detecting the stimulated emission released from the stimulable phosphor by the light detector to produce analog data digitizing the analog data to produce digital data, summing the digital data;

storing the summed digital data in the digital memory;

calculating, when the signal intensity of digital data cannot come to be equal to or higher than the threshold value even if the excitation power of the stimulating ray is increased, a total of the summed digital data stored in the digital memory so far, and adopting it as the biochemical analysis data of the stimulable phosphor layer region, or determining biochemical analysis data of the stimulable phosphor layer region to be zero when the signal intensity of the digital data is still lower than the threshold value even though the excitation power of the stimulating ray was sequentially increased n times in total to irradiate the stimulable phosphor layer region from which the digital data were obtained with the stimulating ray and stimulated emission released from the stimulable phosphor layer region was photoelectrically detected by the light detector.

88. A biochemical analysis data producing method in accordance with claim 87 further comprising:

multiplying summed digital data produced by irradiating the stimulable phosphor layer region with the stimulating ray having different excitation power to excite stimulable phosphor contained in the stimulable phosphor layer region photoelectrically detecting stimulated emission released from the stimulable phosphor to produce analog data;

digitizing the analog data to produce digital data and summing the digital data by a correction coefficient determined in accordance with the excitation power of the stimulating ray projected onto the stimulable phosphor region to correct the summed digital data and calculating a total of the thus corrected summed digital data to produce biochemical analysis data of the stimulable phosphor layer.

89. A biochemical analysis data producing method in accordance with claim 86 further comprising:

multiplying summed digital data produced by irradiating the stimulable phosphor layer region with the stimulating ray having different excitation power to excite stimulable phosphor contained in the stimulable phosphor layer region;

photoelectrically detecting stimulated emission released from the stimulable phosphor to produce analog data;

digitizing the analog data to produce digital data and summing the digital data by a correction coefficient determined in accordance with the excitation power of the stimulating ray projected onto the stimulable phosphor region to correct the summed digital data and calculating a total of the thus corrected summed digital data to produce biochemical analysis data of the stimulable phosphor layer.

90. A biochemical analysis data producing method in accordance with claim 1, wherein the stimulating ray is on and off controlled in such a manner that only the plurality of stimulable phosphor layer regions are irradiated with the stimulating ray and regions other than the plurality of stimulable phosphor layer regions are not irradiated with the stimulating ray.

91. A biochemical analysis data producing method in accordance with claim 1, wherein the stimulable phosphor sheet and the stimulating ray are intermittently moved relative to each other in the main scanning direction by a pitch equal to a distance between neighboring stimulable phosphor layer regions in the main scanning direction.

92. A biochemical analysis data producing method in accordance with claim 1, wherein the stimulable phosphor sheet and the stimulating ray are continuously moved relative to each other in the main scanning direction and the stimulating ray is on and off controlled in such a manner that substantially only the plurality of stimulable phosphor layer regions are irradiated with the stimulating ray and regions other than the plurality of stimulable phosphor layer regions are not irradiated with the stimulating ray.

93. A biochemical analysis data producing method in accordance with claim 1, wherein the plurality of stimulable phosphor layer regions of the stimulable phosphor sheet are two-dimensionally formed in the support so as to be spaced apart from each other and the biochemical analysis data producing method comprises:
  moving the stimulable phosphor sheet and the stimulating ray relative to each other in the main scanning direction and a sub-scanning direction perpendicular to the main scanning direction
  sequentially irradiating the plurality of stimulable phosphor layer regions with the stimulating ray to excite stimulable phosphor contained in the individual stimulable phosphor layer regions, and
  photoelectrically detecting stimulated emission released from the individual stimulable phosphor layer regions, thereby producing biochemical analysis data.

94. A biochemical analysis data producing method in accordance with claim 1, wherein the plurality of stimulable phosphor layer regions of the stimulable phosphor sheet are two-dimensionally formed in the support so as to be spaced apart from each other and the biochemical analysis data producing method comprises:
  moving the stimulable phosphor sheet and the stimulating ray relative to each other in the main scanning direction and a sub-scanning direction perpendicular to the main scanning direction
  sequentially irradiating the plurality of stimulable phosphor layer regions with the stimulating ray to excite stimulable phosphor contained in the individual stimulable phosphor layer regions, and
  photoelectrically detecting stimulated emission released from the individual stimulable phosphor layer regions, thereby producing biochemical analysis data.

95. A biochemical analysis data producing method in accordance with claim 1, wherein a plurality of holes are formed in the support of the stimulable phosphor sheet so as to be spaced apart from each other and the plurality of stimulable phosphor layer regions of the stimulable phosphor sheet are formed by charging stimulable phosphor in the holes.

96. A biochemical analysis data producing method in accordance with claim 1, wherein the plurality of stimulable phosphor layer regions are formed on a surface of the support of the stimulable phosphor sheet.

97. A biochemical analysis data producing method in accordance with claim 1, wherein the support of the stimulable phosphor sheet is formed with 10 or more stimulable phosphor layer regions.

98. A biochemical analysis data producing method in accordance with claim 1, wherein the support of the stimulable phosphor sheet is formed with 10 or more stimulable phosphor layer regions.

99. A biochemical analysis data producing method in accordance with claim 1, wherein each of the plurality of stimulable phosphor layer regions is formed in the stimulable phosphor sheet to have a size of less than 5 mm$^2$.

100. A biochemical analysis data producing method in accordance with claim 1, wherein each of the plurality of stimulable phosphor layer regions is formed in the stimulable phosphor sheet to have a size of less than 5 mm$^2$.

101. A biochemical analysis data producing method in accordance with claim 1, wherein the plurality of stimulable phosphor layer regions are formed in the stimulable phosphor sheet at a density of 10 or more per cm$^2$.

102. A biochemical analysis data producing method in accordance with claim 1, wherein the plurality of stimulable phosphor layer regions are formed in the stimulable phosphor sheet at a density of 10 or more per cm$^2$.

103. A biochemical analysis data producing method in accordance with claim 1, wherein the support of the stimulable phosphor sheet has a property of attenuating radiation energy and/or light energy.

104. A biochemical analysis data producing method in accordance with claim 1, wherein the support of the stimulable phosphor sheet has a property of attenuating radiation energy and/or light energy.

105. A biochemical analysis data producing method in accordance with claim 104, wherein the support of the stimulable phosphor sheet has a property of reducing the energy of radiation and/or the energy of light to ⅕ or less when the radiation and/or light travels in the support by a distance equal to that between neighboring stimulable phosphor layer regions.

* * * * *